US008563289B2

(12) United States Patent  
Svendsen et al.

(10) Patent No.: US 8,563,289 B2  
(45) Date of Patent: Oct. 22, 2013

(54) PROTEASE VARIANTS

(75) Inventors: Allan Svendsen, Hoersholm (DK); Stefan Minning, Ballerup (DK)

(73) Assignee: Novozymes A/S, Bagsvaerd (DK)

( * ) Notice: Subject to any disclaimer, the term of this patent is extended or adjusted under 35 U.S.C. 154(b) by 494 days.

(21) Appl. No.: 12/758,943

(22) Filed: Apr. 13, 2010

(65) Prior Publication Data

US 2010/0196990 A1    Aug. 5, 2010

Related U.S. Application Data

(63) Continuation of application No. 10/588,555, filed as application No. PCT/DK2005/000097 on Feb. 14, 2005, now abandoned.

(60) Provisional application No. 60/558,191, filed on Mar. 31, 2004.

(30) Foreign Application Priority Data

Feb. 13, 2004  (DK) ................................ 2004 00226

(51) Int. Cl.
    *C12N 9/64*    (2006.01)
    *C07H 21/04*   (2006.01)
    *C11D 3/386*   (2006.01)

(52) U.S. Cl.
    USPC ................ 435/226; 536/23.2; 510/306

(58) Field of Classification Search
    None
    See application file for complete search history.

(56) References Cited

U.S. PATENT DOCUMENTS

| | | | |
|---|---|---|---|
| 4,266,031 A | 5/1981 | Tang et al. | |
| 6,682,924 B1 | 1/2004 | Sierkstra | |
| 7,521,204 B2 | 4/2009 | Andersen et al. | |

FOREIGN PATENT DOCUMENTS

| | | |
|---|---|---|
| EP | 0 369 817 B1 | 5/1990 |
| EP | 0 482 879 A2 | 4/1992 |
| EP | 2 042 593 A2 | 4/2009 |
| WO | 88/08033 A1 | 10/1988 |
| WO | WO 88/08028 A1 | 10/1988 |
| WO | 91/13553 A1 | 9/1991 |
| WO | WO 98/12307 | 3/1998 |
| WO | WO 01/16285 | 3/2001 |
| WO | 03/093453 A2 | 11/2003 |

OTHER PUBLICATIONS

A_Geneseq_201215 database Acc#AAE00011 from Norregaard-Madsen et al, WO200116285 Mar. 8, 2001. Alignment with Seq ID No. 2_Gly30Ala.*
Wishart et al, A single mutation converts a novel phosphotyrosine binding domain into a dual-specificity phosphatase. J Biol Chem. Nov. 10, 1995;270(45):26782-26785.*
Whisstock et al, Prediction of protein function from protein sequence and structure. Q Rev Biophys. Aug. 2003;36(3):307-40. Review.*
Svendsen et al, Eur J Biochem. Feb. 15, 1992;204(1):165-71. Isolation and amino acid sequence of a glutamic acid specific endopeptidase from *Bacillus licheniformis*.*
Gray et al., Nucleic Acids Research, vol. 15, No. 16, p. 6757 (1987).
Jackson et al., Journal of Bacteriology, vol. 167, No. 2, pp. 726-728 (1986).
Lee et al., Journal of Bacteriology, vol. 169, No. 9, pp. 3904-3909 (1987).
Rebrikov et al., Journal of Protein Chemistry, vol. 18, No. 1, pp. 21-27 (1999).
Rieneck et al., Biochimica Biophysica Acta, vol. 1350, pp. 128-132 (1997).
Rufo et al., Journal of Bacteriology, vol. 172, No. 2, pp. 1019-1023 (1990).
Sloma et al., Database UniProt, Accession No. P39790 (1990).
Barbosa et al., Protein Engineering, vol. 9, No. 7, pp. 591-601 (1996).
Goodenough, Molecular Biotechnology, vol. 4, pp. 151-166 (1995).
Kuranova et al., Journal of Crystal Growth, vol. 196, No. 2-4, pp. 313-318 (1999).
Miltogina et al., Russian Journal of Bioorganic Chemistry, vol. 29, No. 6, pp. 511-522 (2003).
Strausberg et al., Bio-Technology, vol. 13, pp. 669-673 (1995).
Cavarelli et al, Structure, vol. 5, (6), pp. 813-824 (1997).
Galye et al, J. Biol Chem. vol. 268, (29), 22105-22111 (1993).
Kakudo et al, The Journal of Biological Chemistry, vol. 267 (33), pp. 23782-23788 (1992).
Meijers et al., Biochemistry, vol. 43, pp. 2784-2791 (2004).
Okamoto et al, Applied Microbiology Biotechnology, vol. 48, pp. 27-33 (1997).
Prasad et al, Acta Crystallographica D60, pp. 256-259 (2004).
Rao et al, Microbiology and Molecular Biology Reviews, vol. 62, (3), pp. 597-635 (1998).
Whisstock et al, Quarterly Reviews Biophysics vol. 36, (3), pp. 307-340 (2003).
Ostergaard et al., Issued Patents Database US 6,558,939 Seq ID No. 10. Alignment with Seq ID No. 2 (2003).
Sloma et al, J. Bacteriol. 172: 1024-1029 (1990).
Uniprot Database Acc. No. MPR-BACSU 1995 Alignment with Seq No. 2.(1990).
Svendsen et al, Eur. J. Biochem. vol. 204, 165-171 (1992).
Liu et al, Journal of Virology, vol. 74, (13), pp. 5949-5956 (2000).

* cited by examiner

*Primary Examiner* — Sheridan Swope
(74) *Attorney, Agent, or Firm* — Kristin J. McNamara

(57) ABSTRACT

The present invention relates to methods for producing variants of a parent RP-II protease and the variants having altered properties as compared to the parent RP-II protease.

13 Claims, 4 Drawing Sheets

```
       [N-term][]                [ 2 ]    [ 3 ]     [ 4]
         + +    9             22  26     31   36     41 44
BLC   1 SVIGSDDRTRVTNTTAYPYRAIVHISSSIGSCTGWMIGPKTVATA 45

[]       []     [ 7]           [ 8   ]   {     }
         *  50      56     62 65          77       83 86  90
BLC  46 GHCIYDTSSGSFAGTATVSPGRNGTSYPYGSVKSTRYFIPSGWRS 90

[ 9]    {   }    []              [ 11   ]
                *  99 102 106 110 114             126   131
BLC  91 GNTNYDYGAIELSEPIGNTVGYFGYSYTTSSLVGTTVTISGYPGD 135

[    12    ]     [13]          [ 14   ]
                142         151 156    +   *  171    177
BLC 136 KTAGTQWQHSGPIAISETYKLQYAMDTYGGQSGSPVFEQSSSRTN 180

[    15    ]       [ 16]   {          }
                182          192    201  208         219
BLC 181 CSGPCSLAVHTNGVYGGSSYNRGTRITKEVFDNLTNWKNSAQ 222
```

* Active site residue (47, 96, 167)
+ Calcium coordination residue (3, 5, 161)
[] Short strands: 1 (residues 9-10), 5 (residues 50-51), 6 (residues 56-57), 10 (residues 114-115)
[ ] Long strands: 2 (residues 22-26), 3 (residues 31-36), 4 (residues 41-44), 7 (residues 62-65), 8 (residues 77-83), 9 (residues 99-102), 11 (residues 126-131), 12 (residues 142-151), 13 (residues 156-159), 14 (residues 171-177), 15 (residues 182-192), 16 (residues 201-205)
{ } Helix (86-90, 106-110, 208-219)

Fig. 1

```
BLC       .SVIGSDDRTRVTNTTAYPYRAIVHISSS******IGSCTGWMIGPKTVA  43
CDJ31     .SVIGSDERTRVTNTTAYPYRAIVHISSS******IGSCTGSLIGPKTVA
AC116     .SVIGSDERTRVTDTTAFPYRAIVHISSS******IGSCTGWLIGPKTVA

MIP       .VVIGDDGRTKVANTRVAPYNSIAYITFG******GSSCTGTLIAPNKIL
JA96      .VVIGDDGRTKVTNTRVAPYNSIAYITFG******GSSCTGTLIAPNKIL
BO32      .VVIGDDGRTKVANTRVAPYNSIAYTTFG******GSSCTGTLIAPNKIL
                                    abcdef .
MPR       . SIIGTDERTRISSTTSFPYRATVQLSIKYPNTSSTYGCTGFLVNPNTVV
AA513     .VVIGDDGRRQVQNTSFMPFRALTYIEFG**NLTSTWSCSGGVIGTDLVV BLC       TAGHCIYDTSSGSFAGTATVSPGRNGTSYPYGSVKSTRYFIPSGWR*SGN  92
CDJ31     TAGHCIYDTASGSFAGTATVSPGRNGSTYPYGSVTSTRYFIPSGYR*SGN
AC116     TAGHCVYDTASRSFAGTATVSPGRNGSAYPYGSVTSTRYFIPSGWQ*SGN
                                                      a.
MIP       TNGHCVYNTASRSYSAKGSVYPGMNDSTAVNGSANMTEFYVPSGYINTGA
JA96      TNGHCVYNTATRSYSAKGSVYPGMNDSTAVNGSANMTEFYVPSGYINTGA
BO32      TNGHCVYNTASRSYSAKGSVYPGMNDSTAVNGSANMTEFYVPSGYINTGA
                                                      a.
MPR       TAGHCVY*SQDHGWASTITAAPGRNGSSYPYGTYSGTMFYSVKGWTESKD
AA513     TNAHCV***EGSVLAGTVVPGMNNSQWAYGHYRVTQIIYPDQYRNNGA BLC       TNYDYGAIELS***EPIGNTVGYFGYSYT*TSSLVGTTVTISGYPGDK  136
CDJ31     SNYDYGAIELS*****QPIGNTVGYFGYSYT*TSSLVGSSVTIIGYPGDK
AC116     SNYDYAAIELS*****QPIGNTVGYFGYSYT*ASSLAGAGVTISGYPGDK MIP       SQYDFAVIKTD***TNIGNTVGYRSIRQVTNLTGTTIKISGYPGDK
JA96      SQYDFAVIKTD***TNIGNTVGYRSIRQVTNLTGTTIKISGYPGDK
BO32      SQYDFAVIKTD*****TNIGNTVGYRSIRQ**VTNLTGTTIKISGYPGDK
                  abcde                   a .
MPR       TNYDYGAIKLN*****GSPGNTVGWYGYRTTNSSSPVGLSSSVTGFPCDK
AA513     SEFDYAILRVAPDSDGRHIGNRAGILSFTETGTVN*ENTFLRTYGYPGDK BLC       T****AGTQWQHSGPIAISET*YKLQYAMDTYGGQSGSPVFEQSSSRTNC  181
CDJ31     T****SGTQWQMSGNIAVSET*YKLQYAIDTYGGQSGSPVYEASSSRTNC
AC116     T****TGTQWQMSGTIAVSET*YKLQYAIDTYGGQSGSPVYEKSSSRTNC
               abcd .
MIP       MRSTGKVSQWEMSGSVTREDT*NLAYYTIDTFSGNSGSAMLDQ*******
JA96      MRSTGKVSQWEMSGPVTREDT*NLAYYTIDTFSGNSGSAMLDQ*******
BO32      MRSTGKISQWEMSGPVTREDT*NLAYYMIDTFSGNSGSAMLDQ*******
               abcd .          a .
MPR       T****FGTMWSDTKPIRSAET*YKLTYTTDTYGCQSGSPVYRNYSD****
AA513     ISETKLISLWGMVGRSDAFLHRDLLFYNMDTYFGQSGSPVLN********

BLC       NGPCSLAVHTNG**VYGGSSYNRGTRITKEVFDNLTNWKNSAQ  222
CDJ31     SGPCSLAVHTNG**VYGGSSYNRGTRITKEVFDNLTNWKNSAQ
AC116     SGPCSLAVHTNG**VYGGSSYNRGTRITKEVFDNFTSWKNSAQ
```

Fig. 2

```
MIP     *NQQIVGVHNAG***YSNGTINGGPKATAAFVEFINYAKAQ**
JA96    *NQQIVGVHNAG***YSNGTINGGPKATAAFVEFINYAKAQ**
BO32    *NQQIVGVHNAG***YSNGTINGGPKATAAFVEFINYAKAQ**
                     ab
MPR     TGQTAIAIHTN*****GGSSYNLGTRVTNDVFNNIQYWANQ**
AA513   SVDSMVAVHNAGYIVGGNREINGGPKIRRDFTNLFNQMN****.
```

Fig. 2 continued

SEQUENCE LISTING

<160> NUMBER OF SEQ ID NOS: 18

<210> SEQ ID NO 1
<211> LENGTH: 948
<212> TYPE: DNA
<213> ORGANISM: Bacillus licheniformis
<220> FEATURE:
<221> NAME/KEY: CDS
<222> LOCATION: (1)..(948)
<220> FEATURE:
<221> NAME/KEY: sig_peptide
<222> LOCATION: (1)..(90)
<220> FEATURE:
<221> NAME/KEY: pro_peptide
<222> LOCATION: (91)..(282)
<220> FEATURE:
<221> NAME/KEY: mat_peptide
<222> LOCATION: (283)..(948)

<400> SEQUENCE: 1

```
ttg gtt agt aaa aag agt gtt aaa cga ggt ttg atc aca ggt ctc att      48
Leu Val Ser Lys Lys Ser Val Lys Arg Gly Leu Ile Thr Gly Leu Ile
            -90                 -85                 -80 ggt att tct att tat tct tta ggt atg cac ccg gcc caa gcc gcg cca      96
Gly Ile Ser Ile Tyr Ser Leu Gly Met His Pro Ala Gln Ala Ala Pro
        -75                 -70                 -65 tcg cct cat act cct gtt tca agc gat cct tca tac aaa gcg gaa aca     144
Ser Pro His Thr Pro Val Ser Ser Asp Pro Ser Tyr Lys Ala Glu Thr
    -60                 -55                 -50 tcg gtt act tat gac cca cac att aag agc gat caa tac ggc ttg tat     192
Ser Val Thr Tyr Asp Pro His Ile Lys Ser Asp Gln Tyr Gly Leu Tyr
-45                 -40                 -35 tca aaa gcg ttt aca ggc acc ggc aaa gtg aat gaa aca aag gaa aaa     240
Ser Lys Ala Phe Thr Gly Thr Gly Lys Val Asn Glu Thr Lys Glu Lys
-30                 -25                 -20                 -15 gcg gaa aaa aag tca ccc gcc aaa gct cct tac agc att aaa tcg gtg     288
Ala Glu Lys Lys Ser Pro Ala Lys Ala Pro Tyr Ser Ile Lys Ser Val
                -10                  -5                  -1   1 att ggt tct gat gat cgg aca agg gtc acc aac aca acc gca tat ccg     336
Ile Gly Ser Asp Asp Arg Thr Arg Val Thr Asn Thr Thr Ala Tyr Pro
              5                  10                  15 tac aga gcg atc gtt cat att tca agc agc atc ggt tca tgc acc gga     384
Tyr Arg Ala Ile Val His Ile Ser Ser Ser Ile Gly Ser Cys Thr Gly
         20                  25                  30 tgg atg atc ggt ccg aaa acc gtc gca aca gcc gga cac tgc atc tat     432
Trp Met Ile Gly Pro Lys Thr Val Ala Thr Ala Gly His Cys Ile Tyr
35                  40                  45                  50 gac aca tca agc ggt tca ttt gcc ggt aca gcc act gtt tcg ccg gga     480
Asp Thr Ser Ser Gly Ser Phe Ala Gly Thr Ala Thr Val Ser Pro Gly
                55                  60                  65
```

| | | | | | | | | | | | | | | | |
|---|---|---|---|---|---|---|---|---|---|---|---|---|---|---|---|
| cgg | aac | ggg | aca | agc | tat | cct | tac | ggc | tca | gtt | aaa | tcg | acg | cgc | tac | 528 |
| Arg | Asn | Gly | Thr | Ser | Tyr | Pro | Tyr | Gly | Ser | Val | Lys | Ser | Thr | Arg | Tyr | |
| | | | 70 | | | | 75 | | | | | 80 | | | | |
| ttt | att | ccg | tca | gga | tgg | aga | agc | gga | aac | acc | aat | tac | gat | tac | gga | 576 |
| Phe | Ile | Pro | Ser | Gly | Trp | Arg | Ser | Gly | Asn | Thr | Asn | Tyr | Asp | Tyr | Gly | |
| | | 85 | | | | | 90 | | | | | 95 | | | | |
| gca | atc | gaa | cta | agc | gaa | ccg | atc | ggc | aat | act | gtc | gga | tac | ttc | gga | 624 |
| Ala | Ile | Glu | Leu | Ser | Glu | Pro | Ile | Gly | Asn | Thr | Val | Gly | Tyr | Phe | Gly | |
| | 100 | | | | | 105 | | | | | 110 | | | | | |
| tac | tcg | tac | act | act | tca | tca | ctt | gtt | ggg | aca | act | gtt | acc | atc | agc | 672 |
| Tyr | Ser | Tyr | Thr | Thr | Ser | Ser | Leu | Val | Gly | Thr | Thr | Val | Thr | Ile | Ser | |
| 115 | | | | | 120 | | | | | 125 | | | | | 130 | |
| ggc | tac | cca | ggc | gat | aaa | aca | gca | ggc | aca | caa | tgg | cag | cat | tca | gga | 720 |
| Gly | Tyr | Pro | Gly | Asp | Lys | Thr | Ala | Gly | Thr | Gln | Trp | Gln | His | Ser | Gly | |
| | | | | 135 | | | | | 140 | | | | | 145 | | |
| ccg | att | gcc | atc | tcc | gaa | acg | tat | aaa | ttg | cag | tac | gca | atg | gac | acg | 768 |
| Pro | Ile | Ala | Ile | Ser | Glu | Thr | Tyr | Lys | Leu | Gln | Tyr | Ala | Met | Asp | Thr | |
| | | | 150 | | | | | 155 | | | | | 160 | | | |
| tac | gga | gga | caa | agc | ggt | tca | ccg | gta | ttc | gaa | caa | agc | agc | tcc | aga | 816 |
| Tyr | Gly | Gly | Gln | Ser | Gly | Ser | Pro | Val | Phe | Glu | Gln | Ser | Ser | Ser | Arg | |
| | | 165 | | | | | 170 | | | | | 175 | | | | |
| acg | aac | tgt | agc | ggt | ccg | tgc | tcg | ctt | gcc | gta | cac | aca | aat | gga | gta | 864 |
| Thr | Asn | Cys | Ser | Gly | Pro | Cys | Ser | Leu | Ala | Val | His | Thr | Asn | Gly | Val | |
| | 180 | | | | | 185 | | | | | 190 | | | | | |
| tac | ggc | ggc | tcc | tcg | tac | aac | aga | ggc | acc | cgg | att | aca | aaa | gag | gtg | 912 |
| Tyr | Gly | Gly | Ser | Ser | Tyr | Asn | Arg | Gly | Thr | Arg | Ile | Thr | Lys | Glu | Val | |
| 195 | | | | | 200 | | | | | 205 | | | | | 210 | |
| ttc | gac | aat | ttg | acc | aac | tgg | aaa | aac | agc | gca | caa | | | | | 948 |
| Phe | Asp | Asn | Leu | Thr | Asn | Trp | Lys | Asn | Ser | Ala | Gln | | | | | |
| | | | | 215 | | | | | 220 | | | | | | | |

```
<210> SEQ ID NO 2
<211> LENGTH: 316
<212> TYPE: PRT
<213> ORGANISM: Bacillus licheniformis

<400> SEQUENCE: 2
```

| | | | | | | | | | | | |
|---|---|---|---|---|---|---|---|---|---|---|---|
| Leu | Val | Ser | Lys | Lys | Ser | Val | Lys | Arg | Gly | Leu | Ile | Thr | Gly | Leu | Ile |
| | | | | -90 | | | | | -85 | | | | | -80 | |

| | | | | | | | | | | | |
|---|---|---|---|---|---|---|---|---|---|---|---|
| Gly | Ile | Ser | Ile | Tyr | Ser | Leu | Gly | Met | His | Pro | Ala | Gln | Ala | Ala | Pro |
| | | | -75 | | | | | -70 | | | | | -65 | | |

| | | | | | | | | | | | |
|---|---|---|---|---|---|---|---|---|---|---|---|
| Ser | Pro | His | Thr | Pro | Val | Ser | Ser | Asp | Pro | Ser | Tyr | Lys | Ala | Glu | Thr |
| | | | -60 | | | | | -55 | | | | -50 | | | |

| | | | | | | | | | | | |
|---|---|---|---|---|---|---|---|---|---|---|---|
| Ser | Val | Thr | Tyr | Asp | Pro | His | Ile | Lys | Ser | Asp | Gln | Tyr | Gly | Leu | Tyr |
| | -45 | | | | | -40 | | | | | -35 | | | | |

| | | | | | | | | | | | |
|---|---|---|---|---|---|---|---|---|---|---|---|
| Ser | Lys | Ala | Phe | Thr | Gly | Thr | Gly | Lys | Val | Asn | Glu | Thr | Lys | Glu | Lys |
| -30 | | | | -25 | | | | | -20 | | | | | | -15 |

| | | | | | | | | | | | |
|---|---|---|---|---|---|---|---|---|---|---|---|
| Ala | Glu | Lys | Lys | Ser | Pro | Ala | Lys | Ala | Pro | Tyr | Ser | Ile | Lys | Ser | Val |
| | | | | -10 | | | | -5 | | | | | -1 | 1 | |

| | | | | | | | | | | | |
|---|---|---|---|---|---|---|---|---|---|---|---|
| Ile | Gly | Ser | Asp | Asp | Arg | Thr | Arg | Val | Thr | Asn | Thr | Thr | Ala | Tyr | Pro |
| | | | | 5 | | | | | 10 | | | | 15 | | |

| | | | | | | | | | | | |
|---|---|---|---|---|---|---|---|---|---|---|---|
| Tyr | Arg | Ala | Ile | Val | His | Ile | Ser | Ser | Ser | Ile | Gly | Ser | Cys | Thr | Gly |
| | 20 | | | | | 25 | | | | | 30 | | | | |

| | | | | | | | | | | | |
|---|---|---|---|---|---|---|---|---|---|---|---|
| Trp | Met | Ile | Gly | Pro | Lys | Thr | Val | Ala | Thr | Ala | Gly | His | Cys | Ile | Tyr |
| 35 | | | | | 40 | | | | | 45 | | | | | 50 |

| | | | | | | | | | | | |
|---|---|---|---|---|---|---|---|---|---|---|---|
| Asp | Thr | Ser | Ser | Gly | Ser | Phe | Ala | Gly | Thr | Ala | Thr | Val | Ser | Pro | Gly |
| | | | | 55 | | | | | 60 | | | | | 65 | |

| | | | | | | | | | | | |
|---|---|---|---|---|---|---|---|---|---|---|---|
| Arg | Asn | Gly | Thr | Ser | Tyr | Pro | Tyr | Gly | Ser | Val | Lys | Ser | Thr | Arg | Tyr |
| | | | 70 | | | | | 75 | | | | | 80 | | |

```
Phe Ile Pro Ser Gly Trp Arg Ser Gly Asn Thr Asn Tyr Asp Tyr Gly
        85                  90                  95

Ala Ile Glu Leu Ser Glu Pro Ile Gly Asn Thr Val Gly Tyr Phe Gly
        100                 105                 110

Tyr Ser Tyr Thr Thr Ser Ser Leu Val Gly Thr Val Thr Ile Ser
115                 120                 125                 130

Gly Tyr Pro Gly Asp Lys Thr Ala Gly Thr Gln Trp Gln His Ser Gly
                135                 140                 145

Pro Ile Ala Ile Ser Glu Thr Tyr Lys Leu Gln Tyr Ala Met Asp Thr
            150                 155                 160

Tyr Gly Gly Gln Ser Gly Ser Pro Val Phe Glu Gln Ser Ser Ser Arg
        165                 170                 175

Thr Asn Cys Ser Gly Pro Cys Ser Leu Ala Val His Thr Asn Gly Val
        180                 185                 190

Tyr Gly Gly Ser Ser Tyr Asn Arg Gly Thr Arg Ile Thr Lys Glu Val
195                 200                 205                 210

Phe Asp Asn Leu Thr Asn Trp Lys Asn Ser Ala Gln
                215                 220

<210> SEQ ID NO 3
<211> LENGTH: 1026
<212> TYPE: DNA
<213> ORGANISM: Bacillus halmapalus AA513
<220> FEATURE:
<221> NAME/KEY: CDS
<222> LOCATION: (1)..(1026)
<220> FEATURE:
<221> NAME/KEY: sig_peptide
<222> LOCATION: (1)..(78)
<220> FEATURE:
<221> NAME/KEY: pro_peptide
<222> LOCATION: (79)..(360)
<220> FEATURE:
<221> NAME/KEY: mat_peptide
<222> LOCATION: (361)..(1026)

<400> SEQUENCE: 3 atg aaa cta cta tta aaa ctt act ttt gta tgc ata ttt atg tta          45
Met Lys Leu Leu Leu Lys Leu Thr Phe Val Cys Ile Phe Met Leu
-120                -115                -110 agt ggg att cta tcc cca gta aac gca act caa gct gag act ctt act     93
Ser Gly Ile Leu Ser Pro Val Asn Ala Thr Gln Ala Glu Thr Leu Thr
-105                -100                -95                 -90 aaa tta aat aaa ata agt cag aag cag gaa cca tca tat aaa cta gat    141
Lys Leu Asn Lys Ile Ser Gln Lys Gln Glu Pro Ser Tyr Lys Leu Asp
            -85                 -80                 -75 gaa gaa atg gat tat gtt cta att gat ttg gaa aca caa tct gaa tcg    189
Glu Glu Met Asp Tyr Val Leu Ile Asp Leu Glu Thr Gln Ser Glu Ser
        -70                 -65                 -60 att att tcg ata gga gat aat acc gat ttg gga gat caa tcg ttt act    237
Ile Ile Ser Ile Gly Asp Asn Thr Asp Leu Gly Asp Gln Ser Phe Thr
    -55                 -50                 -45 tct tta ggg aag gtg gga cat gga gaa ctt gag aaa att aac tta gaa    285
Ser Leu Gly Lys Val Gly His Gly Glu Leu Glu Lys Ile Asn Leu Glu
    -40                 -35                 -30 gaa ttt cgt aat cct aat tta aca gta gta gac ccg tta aca cgt aag    333
Glu Phe Arg Asn Pro Asn Leu Thr Val Val Asp Pro Leu Thr Arg Lys
-25                 -20                 -15                 -10 cct att gaa caa aaa atc agc cct ttt gtt gtt ata ggc gat gat ggg    381
Pro Ile Glu Gln Lys Ile Ser Pro Phe Val Val Ile Gly Asp Asp Gly
            -5                  -1  1               5
```

| | | | | | | | | | | | | | | | |
|---|---|---|---|---|---|---|---|---|---|---|---|---|---|---|---|
| aga | aga | caa | gtt | caa | aat | act | tct | ttc | atg | cca | ttt | cgt | gca | ctt | act | 429 |
| Arg | Arg | Gln | Val | Gln | Asn | Thr | Ser | Phe | Met | Pro | Phe | Arg | Ala | Leu | Thr |
| | | 10 | | | | 15 | | | | 20 | | | | | |

```
aga aga caa gtt caa aat act tct ttc atg cca ttt cgt gca ctt act       429
Arg Arg Gln Val Gln Asn Thr Ser Phe Met Pro Phe Arg Ala Leu Thr
        10                  15                  20 tat att gag ttt gga aac ctt aca agt aca tgg agt tgt tct gga ggt       477
Tyr Ile Glu Phe Gly Asn Leu Thr Ser Thr Trp Ser Cys Ser Gly Gly
 25                  30                  35 gtg att gga aca gat tta gtt gtt act aat gca cat tgt gta gaa ggt       525
Val Ile Gly Thr Asp Leu Val Val Thr Asn Ala His Cys Val Glu Gly
 40                  45                  50                  55 tct gtg tta gca ggt act gta gtt cct ggt atg aac aat agt cag tgg       573
Ser Val Leu Ala Gly Thr Val Val Pro Gly Met Asn Asn Ser Gln Trp
                 60                  65                  70 gca tat ggg cat tat agg gtt act cag att atc tac cct gat caa tac       621
Ala Tyr Gly His Tyr Arg Val Thr Gln Ile Ile Tyr Pro Asp Gln Tyr
                 75                  80                  85 aga aat aac ggt gct tca gag ttt gat tat gct ata ctt aga gta gca       669
Arg Asn Asn Gly Ala Ser Glu Phe Asp Tyr Ala Ile Leu Arg Val Ala
             90                  95                 100 cct gac tct gat gga cgt cat att gga aac aga gct gga att tta tct       717
Pro Asp Ser Asp Gly Arg His Ile Gly Asn Arg Ala Gly Ile Leu Ser
105                 110                 115 ttt aca gaa aca gga act gtt aac gaa aat act ttt cta aga acg tat       765
Phe Thr Glu Thr Gly Thr Val Asn Glu Asn Thr Phe Leu Arg Thr Tyr
120                 125                 130                 135 gga tac ccc ggt gat aaa ata tca gag aca aaa tta att tct ttg tgg       813
Gly Tyr Pro Gly Asp Lys Ile Ser Glu Thr Lys Leu Ile Ser Leu Trp
                140                 145                 150 gga atg gtt ggt cga tct gat gca ttt ttg cat cga gac cta ctg ttc       861
Gly Met Val Gly Arg Ser Asp Ala Phe Leu His Arg Asp Leu Leu Phe
                155                 160                 165 tac aat atg gac acc tat ttt ggt caa tca ggt tct cct gta tta aac       909
Tyr Asn Met Asp Thr Tyr Phe Gly Gln Ser Gly Ser Pro Val Leu Asn
                170                 175                 180 agc gta gat tca atg gtt gcg gtt cat aat gca ggg tat atc gtt ggt       957
Ser Val Asp Ser Met Val Ala Val His Asn Ala Gly Tyr Ile Val Gly
185                 190                 195 ggt aat agg gaa att aat ggt ggt cct aaa atc aga aga gat ttt aca      1005
Gly Asn Arg Glu Ile Asn Gly Gly Pro Lys Ile Arg Arg Asp Phe Thr
200                 205                 210                 215 aac tta ttt aat caa atg aac                                          1026
Asn Leu Phe Asn Gln Met Asn
                220
```

<210> SEQ ID NO 4
<211> LENGTH: 342
<212> TYPE: PRT
<213> ORGANISM: Bacillus halmapalus AA513

<400> SEQUENCE: 4

```
Met  Lys  Leu  Leu  Leu  Lys  Leu  Thr  Phe  Val  Cys  Ile  Phe  Met  Leu
-120                 -115                 -110

Ser  Gly  Ile  Leu  Ser  Pro  Val  Asn  Ala  Thr  Gln  Ala  Glu  Thr  Leu  Thr
-105                 -100                  -95                  -90

Lys  Leu  Asn  Lys  Ile  Ser  Gln  Lys  Gln  Glu  Pro  Ser  Tyr  Lys  Leu  Asp
                -85                  -80                  -75

Glu  Glu  Met  Asp  Tyr  Val  Leu  Ile  Asp  Leu  Glu  Thr  Gln  Ser  Glu  Ser
                 -70                  -65                  -60

Ile  Ile  Ser  Ile  Gly  Asp  Asn  Thr  Asp  Leu  Gly  Asp  Gln  Ser  Phe  Thr
                 -55                  -50                  -45
```

```
Ser Leu Gly Lys Val Gly His Gly Glu Leu Glu Lys Ile Asn Leu Glu
    -40             -35                 -30
Glu Phe Arg Asn Pro Asn Leu Thr Val Val Asp Pro Leu Thr Arg Lys
-25                 -20                 -15                 -10
Pro Ile Glu Gln Lys Ile Ser Pro Phe Val Val Ile Gly Asp Asp Gly
                -5               -1   1                  5
Arg Arg Gln Val Gln Asn Thr Ser Phe Met Pro Phe Arg Ala Leu Thr
            10                  15                  20
Tyr Ile Glu Phe Gly Asn Leu Thr Ser Thr Trp Ser Cys Ser Gly Gly
        25                  30                  35
Val Ile Gly Thr Asp Leu Val Val Thr Asn Ala His Cys Val Glu Gly
40                  45                  50                  55
Ser Val Leu Ala Gly Thr Val Val Pro Gly Met Asn Asn Ser Gln Trp
                60                  65                  70
Ala Tyr Gly His Tyr Arg Val Thr Gln Ile Ile Tyr Pro Asp Gln Tyr
            75                  80                  85
Arg Asn Asn Gly Ala Ser Glu Phe Asp Tyr Ala Ile Leu Arg Val Ala
            90                  95                  100
Pro Asp Ser Asp Gly Arg His Ile Gly Asn Arg Ala Gly Ile Leu Ser
            105                 110                 115
Phe Thr Glu Thr Gly Thr Val Asn Glu Asn Thr Phe Leu Arg Thr Tyr
120                 125                 130                 135
Gly Tyr Pro Gly Asp Lys Ile Ser Glu Thr Lys Leu Ile Ser Leu Trp
                140                 145                 150
Gly Met Val Gly Arg Ser Asp Ala Phe Leu His Arg Asp Leu Leu Phe
            155                 160                 165
Tyr Asn Met Asp Thr Tyr Phe Gly Gln Ser Gly Ser Pro Val Leu Asn
            170                 175                 180
Ser Val Asp Ser Met Val Ala Val His Asn Ala Gly Tyr Ile Val Gly
            185                 190                 195
Gly Asn Arg Glu Ile Asn Gly Gly Pro Lys Ile Arg Arg Asp Phe Thr
200                 205                 210                 215
Asn Leu Phe Asn Gln Met Asn
                220

<210> SEQ ID NO 5
<211> LENGTH: 942
<212> TYPE: DNA
<213> ORGANISM: Bacillus licheniformis AC116
<220> FEATURE:
<221> NAME/KEY: CDS
<222> LOCATION: (1)..(942)
<220> FEATURE:
<221> NAME/KEY: sig_peptide
<222> LOCATION: (1)..(87)
<220> FEATURE:
<221> NAME/KEY: pro_peptide
<222> LOCATION: (88)..(276)
<220> FEATURE:
<221> NAME/KEY: mat_peptide
<222> LOCATION: (277)..(942)

<400> SEQUENCE: 5 atg gcg aaa aat ggt gtt tca cgc gtt ttc att gcc gga ctc atc gga    48
Met Ala Lys Asn Gly Val Ser Arg Val Phe Ile Ala Gly Leu Ile Gly
        -90                 -85                 -80 att tct att ttt tct tcg ggc att tac tct gca caa gct gca tca tcg    96
Ile Ser Ile Phe Ser Ser Gly Ile Tyr Ser Ala Gln Ala Ala Ser Ser
    -75                 -70                 -65
```

```
ccg cat acc cca gtc tcc agc gac cct tcg tac aag ccc ggc tcc acc      144
Pro His Thr Pro Val Ser Ser Asp Pro Ser Tyr Lys Pro Gly Ser Thr
-60             -55                 -50                 -45 tat gat ccc aac ata aaa att gac aat aac ggc gca tat tcg aaa gcc      192
Tyr Asp Pro Asn Ile Lys Ile Asp Asn Asn Gly Ala Tyr Ser Lys Ala
                -40                 -35                 -30 ttc gaa gga acc gga aca ccc ggc ggc tcc gtt cag gcc aaa ccg aaa      240
Phe Glu Gly Thr Gly Thr Pro Gly Gly Ser Val Gln Ala Lys Pro Lys
            -25                 -20                 -15 aaa gaa tcg ccc gcc ggc ccg cct tac agc cct aaa tcg gta atc ggc      288
Lys Glu Ser Pro Ala Gly Pro Pro Tyr Ser Pro Lys Ser Val Ile Gly
        -10                 -5                  -1  1 tca gat gaa cgg aca agg gtg act gat aca acg gcc ttt cca tac aga      336
Ser Asp Glu Arg Thr Arg Val Thr Asp Thr Thr Ala Phe Pro Tyr Arg
5               10                  15                  20 gca atc gtc cat att tca agc agc atc ggc tca tgc aca ggc tgg ctg      384
Ala Ile Val His Ile Ser Ser Ser Ile Gly Ser Cys Thr Gly Trp Leu
                25                  30                  35 atc gga ccg aaa acg gta gca acg gcc ggg cac tgc gtc tat gac acg      432
Ile Gly Pro Lys Thr Val Ala Thr Ala Gly His Cys Val Tyr Asp Thr
            40                  45                  50 gca agc cga tca ttc gcg gga acc gcc acc gtt tcc ccg gga cga aac      480
Ala Ser Arg Ser Phe Ala Gly Thr Ala Thr Val Ser Pro Gly Arg Asn
        55                  60                  65 ggt tca gct tac cct tac gga tct gtt aca tcg acc cgc tat ttc atc      528
Gly Ser Ala Tyr Pro Tyr Gly Ser Val Thr Ser Thr Arg Tyr Phe Ile
    70                  75                  80 ccg tcg ggt tgg cag agc gga aat tcc aat tat gac tac gca gcg atc      576
Pro Ser Gly Trp Gln Ser Gly Asn Ser Asn Tyr Asp Tyr Ala Ala Ile
85                  90                  95                  100 gag ctc agc cag ccg atc ggc aat acc gtc gga tat ttc gga tat tca      624
Glu Leu Ser Gln Pro Ile Gly Asn Thr Val Gly Tyr Phe Gly Tyr Ser
                105                 110                 115 tac acc gct tca tcg ctt gca gga gca ggc gtg acc atc agc gga tat      672
Tyr Thr Ala Ser Ser Leu Ala Gly Ala Gly Val Thr Ile Ser Gly Tyr
            120                 125                 130 cca gga gac aaa aca aca ggc acc cag tgg caa atg tcc gga acg atc      720
Pro Gly Asp Lys Thr Thr Gly Thr Gln Trp Gln Met Ser Gly Thr Ile
        135                 140                 145 gct gtt tca gaa acg tat aaa ctg caa tat gcg atc gac aca tac gga      768
Ala Val Ser Glu Thr Tyr Lys Leu Gln Tyr Ala Ile Asp Thr Tyr Gly
    150                 155                 160 ggt caa agc ggt tcc ccg gta tat gag aaa agc agt tca agg aca aac      816
Gly Gln Ser Gly Ser Pro Val Tyr Glu Lys Ser Ser Ser Arg Thr Asn
165                 170                 175                 180 tgc agc ggc cca tgc tcg ctg gcc gtt cat acg aac ggc gtg tac gga      864
Cys Ser Gly Pro Cys Ser Leu Ala Val His Thr Asn Gly Val Tyr Gly
                185                 190                 195 gga tcc tct tac aac aga ggc acc cgc att acg aaa gaa gta ttt gat      912
Gly Ser Ser Tyr Asn Arg Gly Thr Arg Ile Thr Lys Glu Val Phe Asp
            200                 205                 210 aat ttc aca agc tgg aaa aac agc gca cag                              942
Asn Phe Thr Ser Trp Lys Asn Ser Ala Gln
        215                 220

<210> SEQ ID NO 6
<211> LENGTH: 314
<212> TYPE: PRT
<213> ORGANISM: Bacillus licheniformis AC116
```

<400> SEQUENCE: 6

```
Met Ala Lys Asn Gly Val Ser Arg Val Phe Ile Ala Gly Leu Ile Gly
    -90                 -85                 -80
Ile Ser Ile Phe Ser Ser Gly Ile Tyr Ser Ala Gln Ala Ala Ser Ser
    -75                 -70                 -65
Pro His Thr Pro Val Ser Ser Asp Pro Ser Tyr Lys Pro Gly Ser Thr
-60                 -55                 -50                 -45
Tyr Asp Pro Asn Ile Lys Ile Asp Asn Asn Gly Ala Tyr Ser Lys Ala
                -40                 -35                 -30
Phe Glu Gly Thr Gly Thr Pro Gly Gly Ser Val Gln Ala Lys Pro Lys
            -25                 -20                 -15
Lys Glu Ser Pro Ala Gly Pro Tyr Ser Pro Lys Ser Val Ile Gly
        -10                 -5              -1   1
Ser Asp Glu Arg Thr Arg Val Thr Asp Thr Thr Ala Phe Pro Tyr Arg
5                   10                  15                  20
Ala Ile Val His Ile Ser Ser Ser Ile Gly Ser Cys Thr Gly Trp Leu
                25                  30                  35
Ile Gly Pro Lys Thr Val Ala Thr Ala Gly His Cys Val Tyr Asp Thr
            40                  45                  50
Ala Ser Arg Ser Phe Ala Gly Thr Ala Thr Val Ser Pro Gly Arg Asn
        55                  60                  65
Gly Ser Ala Tyr Pro Tyr Gly Ser Val Thr Ser Thr Arg Tyr Phe Ile
70                  75                  80
Pro Ser Gly Trp Gln Ser Gly Asn Ser Asn Tyr Asp Tyr Ala Ala Ile
85                  90                  95                  100
Glu Leu Ser Gln Pro Ile Gly Asn Thr Val Gly Tyr Phe Gly Tyr Ser
                105                 110                 115
Tyr Thr Ala Ser Ser Leu Ala Gly Ala Gly Val Thr Ile Ser Gly Tyr
            120                 125                 130
Pro Gly Asp Lys Thr Thr Gly Thr Gln Trp Gln Met Ser Gly Thr Ile
        135                 140                 145
Ala Val Ser Glu Thr Tyr Lys Leu Gln Tyr Ala Ile Asp Thr Tyr Gly
    150                 155                 160
Gly Gln Ser Gly Ser Pro Val Tyr Glu Lys Ser Ser Ser Arg Thr Asn
165                 170                 175                 180
Cys Ser Gly Pro Cys Ser Leu Ala Val His Thr Asn Gly Val Tyr Gly
                185                 190                 195
Gly Ser Ser Tyr Asn Arg Gly Thr Arg Ile Thr Lys Glu Val Phe Asp
            200                 205                 210
Asn Phe Thr Ser Trp Lys Asn Ser Ala Gln
        215                 220
```

<210> SEQ ID NO 7
<211> LENGTH: 909
<212> TYPE: DNA
<213> ORGANISM: Bacillus pumilus BO32
<220> FEATURE:
<221> NAME/KEY: CDS
<222> LOCATION: (1)..(909)
<220> FEATURE:
<221> NAME/KEY: sig_peptide
<222> LOCATION: (1)..(78)
<220> FEATURE:
<221> NAME/KEY: pro_peptide
<222> LOCATION: (79)..(264)
<220> FEATURE:
<221> NAME/KEY: mat_peptide
<222> LOCATION: (265)..(909)

<400> SEQUENCE: 7

```
atg atg aaa aag gtg aaa atg tta ctc cct tct cta ctt gtt ttt ggt      48
Met Met Lys Lys Val Lys Met Leu Leu Pro Ser Leu Leu Val Phe Gly
        -85                 -80                 -75 gct tta agt gtg cct agt ttt gcc cat gcc gca tct gat tca gtg cta      96
Ala Leu Ser Val Pro Ser Phe Ala His Ala Ala Ser Asp Ser Val Leu
        -70                 -65                 -60 acg tct gat tat gac atg gtg act tct gat gga aag gtg atc tct tca     144
Thr Ser Asp Tyr Asp Met Val Thr Ser Asp Gly Lys Val Ile Ser Ser
        -55                 -50                 -45 agt gat ttc cac aat gat acg aaa tcc ccc tca tcc ttt gat aaa gtg     192
Ser Asp Phe His Asn Asp Thr Lys Ser Pro Ser Ser Phe Asp Lys Val
-40                 -35                 -30                 -25 gat gat cta tct tca act gtt ggt gaa aaa gta aaa cca cta tca aaa     240
Asp Asp Leu Ser Ser Thr Val Gly Glu Lys Val Lys Pro Leu Ser Lys
        -20                 -15                 -10 tat tta aaa gac ttt caa aca aaa gtc gtc att gga gac gat ggt aga     288
Tyr Leu Lys Asp Phe Gln Thr Lys Val Val Ile Gly Asp Asp Gly Arg
        -5                  -1  1                5 aca aaa gta gca aat aca aga gtg gca cca tat aat tca att gct tat     336
Thr Lys Val Ala Asn Thr Arg Val Ala Pro Tyr Asn Ser Ile Ala Tyr
        10                  15                  20 act acg ttt ggc ggc tcc agc tgc acg ggg acc ctg att gcc cct aac     384
Thr Thr Phe Gly Gly Ser Ser Cys Thr Gly Thr Leu Ile Ala Pro Asn
25                  30                  35                  40 aaa att ttg aca aac gga cac tgc gtg tac aat aca gca tcc aga agt     432
Lys Ile Leu Thr Asn Gly His Cys Val Tyr Asn Thr Ala Ser Arg Ser
                    45                  50                  55 tat agt gca aaa gga tcg gtg tat cca ggc atg aat gat agt act gcg     480
Tyr Ser Ala Lys Gly Ser Val Tyr Pro Gly Met Asn Asp Ser Thr Ala
            60                  65                  70 gtg aat ggc tca gca aat atg aca gag ttc tat gta cca agc ggg tat     528
Val Asn Gly Ser Ala Asn Met Thr Glu Phe Tyr Val Pro Ser Gly Tyr
        75                  80                  85 atc aat aca ggt gcg agc caa tat gat ttt gcc gtg atc aaa aca gat     576
Ile Asn Thr Gly Ala Ser Gln Tyr Asp Phe Ala Val Ile Lys Thr Asp
        90                  95                  100 acg aac att ggc aat aca gtt ggt tac cgt tcc atc cgt cag gtg aca     624
Thr Asn Ile Gly Asn Thr Val Gly Tyr Arg Ser Ile Arg Gln Val Thr
105                 110                 115                 120 aac tta act ggg aca acg att aaa att tct gga tat cca ggt gat aaa     672
Asn Leu Thr Gly Thr Thr Ile Lys Ile Ser Gly Tyr Pro Gly Asp Lys
            125                 130                 135 atg aga tca act ggc aag atc tcg cag tgg gag atg tca ggt cct gtg     720
Met Arg Ser Thr Gly Lys Ile Ser Gln Trp Glu Met Ser Gly Pro Val
        140                 145                 150 aca aga gaa gat acg aat ctc gca tac tat atg att gat aca ttt agt     768
Thr Arg Glu Asp Thr Asn Leu Ala Tyr Tyr Met Ile Asp Thr Phe Ser
        155                 160                 165 gga aat tca ggc tca gcg atg cta gat caa aat cag caa att gtt ggg     816
Gly Asn Ser Gly Ser Ala Met Leu Asp Gln Asn Gln Gln Ile Val Gly
        170                 175                 180 gtt cat aac gca ggg tat tca aac ggt acg att aat ggc ggt cca aaa     864
Val His Asn Ala Gly Tyr Ser Asn Gly Thr Ile Asn Gly Gly Pro Lys
185                 190                 195                 200 gcg aca gct gcc ttt gtt gaa ttt atc aac tat gca aaa gcg caa         909
Ala Thr Ala Ala Phe Val Glu Phe Ile Asn Tyr Ala Lys Ala Gln
                    205                 210                 215
```

<210> SEQ ID NO 8
<211> LENGTH: 303
<212> TYPE: PRT
<213> ORGANISM: Bacillus pumilus BO32

<400> SEQUENCE: 8

```
Met Met Lys Lys Val Lys Met Leu Leu Pro Ser Leu Leu Val Phe Gly
            -85                 -80                 -75

Ala Leu Ser Val Pro Ser Phe Ala His Ala Ala Ser Asp Ser Val Leu
        -70                 -65                 -60

Thr Ser Asp Tyr Asp Met Val Thr Ser Asp Gly Lys Val Ile Ser Ser
        -55                 -50                 -45

Ser Asp Phe His Asn Asp Thr Lys Ser Pro Ser Ser Phe Asp Lys Val
-40                 -35                 -30                 -25

Asp Asp Leu Ser Ser Thr Val Gly Glu Lys Val Lys Pro Leu Ser Lys
            -20                 -15                 -10

Tyr Leu Lys Asp Phe Gln Thr Lys Val Val Ile Gly Asp Asp Gly Arg
            -5                  -1  1               5

Thr Lys Val Ala Asn Thr Arg Val Ala Pro Tyr Asn Ser Ile Ala Tyr
    10                  15                  20

Thr Thr Phe Gly Gly Ser Ser Cys Thr Gly Thr Leu Ile Ala Pro Asn
25                  30                  35                  40

Lys Ile Leu Thr Asn Gly His Cys Val Tyr Asn Thr Ala Ser Arg Ser
                45                  50                  55

Tyr Ser Ala Lys Gly Ser Val Tyr Pro Gly Met Asn Asp Ser Thr Ala
                60                  65                  70

Val Asn Gly Ser Ala Asn Met Thr Glu Phe Tyr Val Pro Ser Gly Tyr
            75                  80                  85

Ile Asn Thr Gly Ala Ser Gln Tyr Asp Phe Ala Val Ile Lys Thr Asp
        90                  95                  100

Thr Asn Ile Gly Asn Thr Val Gly Tyr Arg Ser Ile Arg Gln Val Thr
105                 110                 115                 120

Asn Leu Thr Gly Thr Thr Ile Lys Ile Ser Gly Tyr Pro Gly Asp Lys
            125                 130                 135

Met Arg Ser Thr Gly Lys Ile Ser Gln Trp Glu Met Ser Gly Pro Val
            140                 145                 150

Thr Arg Glu Asp Thr Asn Leu Ala Tyr Tyr Met Ile Asp Thr Phe Ser
        155                 160                 165

Gly Asn Ser Gly Ser Ala Met Leu Asp Gln Asn Gln Ile Val Gly
        170                 175                 180

Val His Asn Ala Gly Tyr Ser Asn Gly Thr Ile Asn Gly Gly Pro Lys
185                 190                 195                 200

Ala Thr Ala Ala Phe Val Glu Phe Ile Asn Tyr Ala Lys Ala Gln
                205                 210                 215
```

<210> SEQ ID NO 9
<211> LENGTH: 954
<212> TYPE: DNA
<213> ORGANISM: Bacillus licheniformis CDJ31
<220> FEATURE:
<221> NAME/KEY: CDS
<222> LOCATION: (1)..(954)
<220> FEATURE:
<221> NAME/KEY: sig_peptide
<222> LOCATION: (1)..(84)
<220> FEATURE:
<221> NAME/KEY: pro_peptide
<222> LOCATION: (85)..(288)

```
<220> FEATURE:
<221> NAME/KEY: mat_peptide
<222> LOCATION: (289)..(954)

<400> SEQUENCE: 9 atg aaa aaa agt gtg aca cgc gta tta atg gcc ggt ctt att gga ata      48
Met Lys Lys Ser Val Thr Arg Val Leu Met Ala Gly Leu Ile Gly Ile
    -95                 -90                 -85 tct att tat tct atg ggc atc gac tcc gct caa gct gca tca tcg ccg      96
Ser Ile Tyr Ser Met Gly Ile Asp Ser Ala Gln Ala Ala Ser Ser Pro
-80                 -75                 -70                 -65 cat act cct gtc tct agc gat cct tca tac aag ccc gac tca tcc gca     144
His Thr Pro Val Ser Ser Asp Pro Ser Tyr Lys Pro Asp Ser Ser Ala
                -60                 -55                 -50 agc tat gat cct gct att aaa acc aac aaa aac ggc gcc tat tca aaa     192
Ser Tyr Asp Pro Ala Ile Lys Thr Asn Lys Asn Gly Ala Tyr Ser Lys
            -45                 -40                 -35 gca ttt gaa ggt aca gga aaa cta gac gct ccc ctt tat cag gaa aaa     240
Ala Phe Glu Gly Thr Gly Lys Leu Asp Ala Pro Leu Tyr Gln Glu Lys
        -30                 -25                 -20 agc aaa cca acc aaa aaa tcc cct gcc gga cca cgt tac agc ccc aaa     288
Ser Lys Pro Thr Lys Lys Ser Pro Ala Gly Pro Arg Tyr Ser Pro Lys
    -15                 -10                 -5                  -1 tcc gtg att ggt tct gat gaa cgg acg aga gtg aca aac act acc gca     336
Ser Val Ile Gly Ser Asp Glu Arg Thr Arg Val Thr Asn Thr Thr Ala
1                   5                   10                  15 tat cca tac aga gcg atc gtg cat att tca agc agc atc ggg tct tgc     384
Tyr Pro Tyr Arg Ala Ile Val His Ile Ser Ser Ser Ile Gly Ser Cys
                20                  25                  30 acc ggc tcc ctg atc ggt ccg aaa acg gtg gca acg gcc gga cac tgc     432
Thr Gly Ser Leu Ile Gly Pro Lys Thr Val Ala Thr Ala Gly His Cys
            35                  40                  45 att tat gac aca gcg agc ggg tca ttc gcc gga acc gct acc gtt tct     480
Ile Tyr Asp Thr Ala Ser Gly Ser Phe Ala Gly Thr Ala Thr Val Ser
        50                  55                  60 ccg gga cgg aac ggt tca aca tat ccg tac gga tca gtt aca tca acc     528
Pro Gly Arg Asn Gly Ser Thr Tyr Pro Tyr Gly Ser Val Thr Ser Thr
65                  70                  75                  80 cgc tat ttc atc ccg tca ggc tat cga agc gga aat tcg aat tac gac     576
Arg Tyr Phe Ile Pro Ser Gly Tyr Arg Ser Gly Asn Ser Asn Tyr Asp
                85                  90                  95 tac gga gcc ata gag ctc agc cag ccg atc ggc aac acc gtc ggg tat     624
Tyr Gly Ala Ile Glu Leu Ser Gln Pro Ile Gly Asn Thr Val Gly Tyr
            100                 105                 110 ttc gga tat tcc tac acc acc tcg tct ctc gtt ggg tca agc gtt acc     672
Phe Gly Tyr Ser Tyr Thr Thr Ser Ser Leu Val Gly Ser Ser Val Thr
        115                 120                 125 atc atc gga tat cca ggc gac aaa aca tcg ggc acc caa tgg cag atg     720
Ile Ile Gly Tyr Pro Gly Asp Lys Thr Ser Gly Thr Gln Trp Gln Met
130                 135                 140 tcc gga aat atc gcc gtc tca gaa aca tat aaa ctg caa tat gcg atc     768
Ser Gly Asn Ile Ala Val Ser Glu Thr Tyr Lys Leu Gln Tyr Ala Ile
145                 150                 155                 160 gac aca tac gga ggg cag agc ggc tct ccc gta tat gag gcg agc agc     816
Asp Thr Tyr Gly Gly Gln Ser Gly Ser Pro Val Tyr Glu Ala Ser Ser
                165                 170                 175 tcc aga acg aat tgc agc ggc cca tgt tcg ctg gcc gtt cat acg aat     864
Ser Arg Thr Asn Cys Ser Gly Pro Cys Ser Leu Ala Val His Thr Asn
            180                 185                 190
```

```
ggg gtg tac gga gga tct tca tac aac aga ggc acc cgg att aca aaa      912
Gly Val Tyr Gly Gly Ser Ser Tyr Asn Arg Gly Thr Arg Ile Thr Lys
        195                 200                 205 gaa gta ttc gat aat ttg aca aac tgg aaa aac agc gcc caa              954
Glu Val Phe Asp Asn Leu Thr Asn Trp Lys Asn Ser Ala Gln
    210                 215                 220

<210> SEQ ID NO 10
<211> LENGTH: 318
<212> TYPE: PRT
<213> ORGANISM: Bacillus licheniformis CDJ31

<400> SEQUENCE: 10

Met Lys Lys Ser Val Thr Arg Val Leu Met Ala Gly Leu Ile Gly Ile
    -95                 -90                 -85

Ser Ile Tyr Ser Met Gly Ile Asp Ser Ala Gln Ala Ala Ser Ser Pro
-80                 -75                 -70                 -65

His Thr Pro Val Ser Ser Asp Pro Ser Tyr Lys Pro Asp Ser Ser Ala
                -60                 -55                 -50

Ser Tyr Asp Pro Ala Ile Lys Thr Asn Lys Asn Gly Ala Tyr Ser Lys
            -45                 -40                 -35

Ala Phe Glu Gly Thr Gly Lys Leu Asp Ala Pro Leu Tyr Gln Glu Lys
        -30                 -25                 -20

Ser Lys Pro Thr Lys Lys Ser Pro Ala Gly Pro Arg Tyr Ser Pro Lys
    -15                 -10                  -5                  -1

Ser Val Ile Gly Ser Asp Glu Arg Thr Arg Val Thr Asn Thr Thr Ala
1                   5                   10                  15

Tyr Pro Tyr Arg Ala Ile Val His Ile Ser Ser Ser Ile Gly Ser Cys
                20                  25                  30

Thr Gly Ser Leu Ile Gly Pro Lys Thr Val Ala Thr Ala Gly His Cys
            35                  40                  45

Ile Tyr Asp Thr Ala Ser Gly Ser Phe Ala Gly Thr Ala Thr Val Ser
50                  55                  60

Pro Gly Arg Asn Gly Ser Thr Tyr Pro Tyr Gly Ser Val Thr Ser Thr
65                  70                  75                  80

Arg Tyr Phe Ile Pro Ser Gly Tyr Arg Ser Gly Asn Ser Asn Tyr Asp
                85                  90                  95

Tyr Gly Ala Ile Glu Leu Ser Gln Pro Ile Gly Asn Thr Val Gly Tyr
                100                 105                 110

Phe Gly Tyr Ser Tyr Thr Thr Ser Ser Leu Val Gly Ser Ser Val Thr
            115                 120                 125

Ile Ile Gly Tyr Pro Gly Asp Lys Thr Ser Gly Thr Gln Trp Gln Met
130                 135                 140

Ser Gly Asn Ile Ala Val Ser Glu Thr Tyr Lys Leu Gln Tyr Ala Ile
145                 150                 155                 160

Asp Thr Tyr Gly Gly Gln Ser Gly Ser Pro Val Tyr Glu Ala Ser Ser
                165                 170                 175

Ser Arg Thr Asn Cys Ser Gly Pro Cys Ser Leu Ala Val His Thr Asn
            180                 185                 190

Gly Val Tyr Gly Gly Ser Ser Tyr Asn Arg Gly Thr Arg Ile Thr Lys
        195                 200                 205

Glu Val Phe Asp Asn Leu Thr Asn Trp Lys Asn Ser Ala Gln
    210                 215                 220
```

```
<210> SEQ ID NO 11
<211> LENGTH: 906
<212> TYPE: DNA
<213> ORGANISM: Bacillus pumilus JA96
<220> FEATURE:
<221> NAME/KEY: CDS
<222> LOCATION: (1)..(906)
<220> FEATURE:
<221> NAME/KEY: sig_peptide
<222> LOCATION: (1)..(75)
<220> FEATURE:
<221> NAME/KEY: pro_peptide
<222> LOCATION: (76)..(261)
<220> FEATURE:
<221> NAME/KEY: mat_peptide
<222> LOCATION: (262)..(906)

<400> SEQUENCE: 11
```

| | | | | | | | | | | | | | | | | |
|---|---|---|---|---|---|---|---|---|---|---|---|---|---|---|---|---|
| atg | aaa | aag | gtg | aaa | aaa | tta | atc | cct | tct | cta | ctc | gtt | ttt | ggt | gct | 48 |
| Met | Lys | Lys | Val | Lys | Lys | Leu | Ile | Pro | Ser | Leu | Leu | Val | Phe | Gly | Ala | |
| | -85 | | | | -80 | | | | -75 | | | | | | | |
| tta | agt | gtg | cct | agt | ttt | gcc | cat | gca | gca | tct | gat | tca | gta | ctt | acg | 96 |
| Leu | Ser | Val | Pro | Ser | Phe | Ala | His | Ala | Ala | Ser | Asp | Ser | Val | Leu | Thr | |
| | -70 | | | | -65 | | | | -60 | | | | | | | |
| tct | gat | tat | gac | atg | gtg | act | tct | gac | gga | aag | gtg | att | tct | tca | gct | 144 |
| Ser | Asp | Tyr | Asp | Met | Val | Thr | Ser | Asp | Gly | Lys | Val | Ile | Ser | Ser | Ala | |
| -55 | | | | | -50 | | | | -45 | | | | | | -40 | |
| gac | ttc | cac | aac | gat | atg | aaa | acc | ccc | tca | tcc | ttt | gac | aaa | gtg | gat | 192 |
| Asp | Phe | His | Asn | Asp | Met | Lys | Thr | Pro | Ser | Ser | Phe | Asp | Lys | Val | Asp | |
| | | | -35 | | | | -30 | | | | | | -25 | | | |
| gat | ctc | tct | tct | act | att | ggc | gaa | aaa | gta | aaa | cca | ctc | aca | aca | tat | 240 |
| Asp | Leu | Ser | Ser | Thr | Ile | Gly | Glu | Lys | Val | Lys | Pro | Leu | Thr | Thr | Tyr | |
| | | -20 | | | | -15 | | | | | | -10 | | | | |
| tta | aaa | gac | ttt | caa | aca | aaa | gta | gtc | att | gga | gac | gat | ggt | aga | aca | 288 |
| Leu | Lys | Asp | Phe | Gln | Thr | Lys | Val | Val | Ile | Gly | Asp | Asp | Gly | Arg | Thr | |
| | -5 | | | | -1 | 1 | | | | 5 | | | | | | |
| aaa | gtg | acg | aat | aca | aga | gta | gca | ccc | tat | aat | tct | att | gct | tat | att | 336 |
| Lys | Val | Thr | Asn | Thr | Arg | Val | Ala | Pro | Tyr | Asn | Ser | Ile | Ala | Tyr | Ile | |
| 10 | | | | | 15 | | | | | 20 | | | | | 25 | |
| aca | ttt | ggt | gga | tct | agc | tgc | act | gga | aca | ctc | att | gct | cca | aac | aaa | 384 |
| Thr | Phe | Gly | Gly | Ser | Ser | Cys | Thr | Gly | Thr | Leu | Ile | Ala | Pro | Asn | Lys | |
| | | | | 30 | | | | | 35 | | | | | 40 | | |
| ata | ttg | aca | aac | gga | cac | tgc | gtc | tac | aat | aca | gcc | aca | aga | agt | tat | 432 |
| Ile | Leu | Thr | Asn | Gly | His | Cys | Val | Tyr | Asn | Thr | Ala | Thr | Arg | Ser | Tyr | |
| | | | 45 | | | | | 50 | | | | | 55 | | | |
| agt | gca | aaa | ggg | tct | gtc | tac | cca | ggc | atg | aat | gac | agc | acg | gct | gtg | 480 |
| Ser | Ala | Lys | Gly | Ser | Val | Tyr | Pro | Gly | Met | Asn | Asp | Ser | Thr | Ala | Val | |
| | | 60 | | | | | 65 | | | | | 70 | | | | |
| aac | ggc | tca | gca | aac | atg | acc | gaa | ttc | tat | gta | cca | agc | gga | tat | atc | 528 |
| Asn | Gly | Ser | Ala | Asn | Met | Thr | Glu | Phe | Tyr | Val | Pro | Ser | Gly | Tyr | Ile | |
| | 75 | | | | | 80 | | | | | 85 | | | | | |
| aac | acg | ggg | gcg | agt | caa | tat | gat | ttt | gcc | gtc | att | aaa | aca | gat | acg | 576 |
| Asn | Thr | Gly | Ala | Ser | Gln | Tyr | Asp | Phe | Ala | Val | Ile | Lys | Thr | Asp | Thr | |
| 90 | | | | | 95 | | | | | 100 | | | | | 105 | |
| aac | att | gga | aat | acg | gtc | ggc | tat | cgc | tct | att | cgt | caa | gtg | aca | aat | 624 |
| Asn | Ile | Gly | Asn | Thr | Val | Gly | Tyr | Arg | Ser | Ile | Arg | Gln | Val | Thr | Asn | |
| | | | | 110 | | | | | 115 | | | | | 120 | | |
| cta | aca | ggt | aca | acg | att | aaa | att | tct | gga | tat | cca | ggt | gat | aaa | atg | 672 |
| Leu | Thr | Gly | Thr | Thr | Ile | Lys | Ile | Ser | Gly | Tyr | Pro | Gly | Asp | Lys | Met | |
| | | | 125 | | | | | 130 | | | | | 135 | | | |
| aga | tcg | act | ggc | aaa | gtg | tca | caa | tgg | gaa | atg | tca | ggt | cca | gtc | acg | 720 |
| Arg | Ser | Thr | Gly | Lys | Val | Ser | Gln | Trp | Glu | Met | Ser | Gly | Pro | Val | Thr | |
| | | | 140 | | | | | 145 | | | | | 150 | | | |

```
aga gaa gat acg aat ctc gca tac tat acg atc gat aca ttt agc gga       768
Arg Glu Asp Thr Asn Leu Ala Tyr Tyr Thr Ile Asp Thr Phe Ser Gly
    155                 160                 165 aac tct ggc tct gcg atg cta gat cag aac caa caa atc gtc ggg gtc       816
Asn Ser Gly Ser Ala Met Leu Asp Gln Asn Gln Gln Ile Val Gly Val
170                 175                 180                 185 cat aat gcg ggt tat tca aat gga acg atc aac ggt gga cca aaa gcg       864
His Asn Ala Gly Tyr Ser Asn Gly Thr Ile Asn Gly Gly Pro Lys Ala
                190                 195                 200 act gct gcc ttt gtt gaa ttt atc aac tat gcg aag gcg caa               906
Thr Ala Ala Phe Val Glu Phe Ile Asn Tyr Ala Lys Ala Gln
                205                 210                 215

<210> SEQ ID NO 12
<211> LENGTH: 302
<212> TYPE: PRT
<213> ORGANISM: Bacillus pumilus JA96

<400> SEQUENCE: 12

Met Lys Lys Val Lys Lys Leu Ile Pro Ser Leu Leu Val Phe Gly Ala
        -85                 -80                 -75

Leu Ser Val Pro Ser Phe Ala His Ala Ala Ser Asp Ser Val Leu Thr
    -70                 -65                 -60

Ser Asp Tyr Asp Met Val Thr Ser Asp Gly Lys Val Ile Ser Ala
-55                 -50                 -45                 -40

Asp Phe His Asn Asp Met Lys Thr Pro Ser Ser Phe Asp Lys Val Asp
                -35                 -30                 -25

Asp Leu Ser Ser Thr Ile Gly Glu Lys Val Lys Pro Leu Thr Thr Tyr
            -20                 -15                 -10

Leu Lys Asp Phe Gln Thr Lys Val Val Ile Gly Asp Asp Gly Arg Thr
     -5                  -1   1                  5

Lys Val Thr Asn Thr Arg Val Ala Pro Tyr Asn Ser Ile Ala Tyr Ile
10                  15                  20                  25

Thr Phe Gly Gly Ser Ser Cys Thr Gly Thr Leu Ile Ala Pro Asn Lys
                30                  35                  40

Ile Leu Thr Asn Gly His Cys Val Tyr Asn Thr Ala Thr Arg Ser Tyr
                45                  50                  55

Ser Ala Lys Gly Ser Val Tyr Pro Gly Met Asn Asp Ser Thr Ala Val
            60                  65                  70

Asn Gly Ser Ala Asn Met Thr Glu Phe Tyr Val Pro Ser Gly Tyr Ile
75                  80                  85

Asn Thr Gly Ala Ser Gln Tyr Asp Phe Ala Val Ile Lys Thr Asp Thr
90                  95                  100                 105

Asn Ile Gly Asn Thr Val Gly Tyr Arg Ser Ile Arg Gln Val Thr Asn
                110                 115                 120

Leu Thr Gly Thr Thr Ile Lys Ile Ser Gly Tyr Pro Gly Asp Lys Met
                125                 130                 135

Arg Ser Thr Gly Lys Val Ser Gln Trp Glu Met Ser Gly Pro Val Thr
            140                 145                 150

Arg Glu Asp Thr Asn Leu Ala Tyr Tyr Thr Ile Asp Thr Phe Ser Gly
    155                 160                 165

Asn Ser Gly Ser Ala Met Leu Asp Gln Asn Gln Gln Ile Val Gly Val
170                 175                 180                 185

His Asn Ala Gly Tyr Ser Asn Gly Thr Ile Asn Gly Gly Pro Lys Ala
                190                 195                 200

Thr Ala Ala Phe Val Glu Phe Ile Asn Tyr Ala Lys Ala Gln
                205                 210                 215
```

<210> SEQ ID NO 13
<211> LENGTH: 939
<212> TYPE: DNA
<213> ORGANISM: Bacillus subtilis IS75
<220> FEATURE:
<221> NAME/KEY: CDS
<222> LOCATION: (1)..(939)
<220> FEATURE:
<221> NAME/KEY: sig_peptide
<222> LOCATION: (1)..(102)
<220> FEATURE:
<221> NAME/KEY: pro_peptide
<222> LOCATION: (103)..(279)
<220> FEATURE:
<221> NAME/KEY: mat_peptide
<222> LOCATION: (280)..(939)

<400> SEQUENCE: 13

```
atg aaa tta gtt cca aga ttc aga aaa caa tgg ttc gct tac tta acg      48
Met Lys Leu Val Pro Arg Phe Arg Lys Gln Trp Phe Ala Tyr Leu Thr
        -90                 -85                 -80 gtt ttg tgt ttg gct ttg gca gca gcg gtt tct ttt ggc gta ccg gca      96
Val Leu Cys Leu Ala Leu Ala Ala Ala Val Ser Phe Gly Val Pro Ala
    -75                 -70                 -65 aaa gcg gca gag aac ccg caa act tct gta tcg aat acc ggt aaa gaa     144
Lys Ala Ala Glu Asn Pro Gln Thr Ser Val Ser Asn Thr Gly Lys Glu
    -60                 -55                 -50 gct gat gct acg aaa aac caa acg tca aaa gca gat cag gtt tcc gcc     192
Ala Asp Ala Thr Lys Asn Gln Thr Ser Lys Ala Asp Gln Val Ser Ala
-45                 -40                 -35                 -30 cct tat gag gga acc gga aaa aca agt aaa tcg tta tac ggc ggc caa     240
Pro Tyr Glu Gly Thr Gly Lys Thr Ser Lys Ser Leu Tyr Gly Gly Gln
                -25                 -20                 -15 acg gaa ctg gaa aaa aac att caa acc tta cag cct tcg agc att atc     288
Thr Glu Leu Glu Lys Asn Ile Gln Thr Leu Gln Pro Ser Ser Ile Ile
        -10                  -5                  -1  1 gga act gat gaa cgc acc aga atc tcc agc acg aca tct ttt cca tat     336
Gly Thr Asp Glu Arg Thr Arg Ile Ser Ser Thr Thr Ser Phe Pro Tyr
  5                  10                  15 aga gca acc gtt caa ctg tca atc aag tat ccc aac act tca agc act     384
Arg Ala Thr Val Gln Leu Ser Ile Lys Tyr Pro Asn Thr Ser Ser Thr
 20                  25                  30                  35 tat gga tgt acc gga ttt tta gtc aat cca aat aca gtc gtc acg gct     432
Tyr Gly Cys Thr Gly Phe Leu Val Asn Pro Asn Thr Val Val Thr Ala
                 40                  45                  50 gga cat tgt gtg tac agc cag gat cat gga tgg gct tcg acg ata acc     480
Gly His Cys Val Tyr Ser Gln Asp His Gly Trp Ala Ser Thr Ile Thr
             55                  60                  65 gcc gcg ccg ggc cgc aat ggt tcg tca tat ccg tac ggt act tat tca     528
Ala Ala Pro Gly Arg Asn Gly Ser Ser Tyr Pro Tyr Gly Thr Tyr Ser
         70                  75                  80 ggc acg atg ttt tac tcc gtc aaa gga tgg acg gaa agc aaa gac acc     576
Gly Thr Met Phe Tyr Ser Val Lys Gly Trp Thr Glu Ser Lys Asp Thr
     85                  90                  95 aac tat gat tac gga gct att aaa tta aac ggt tct cct gga aac acg     624
Asn Tyr Asp Tyr Gly Ala Ile Lys Leu Asn Gly Ser Pro Gly Asn Thr
100                 105                 110                 115 gtt ggc tgg tac ggc tac cgg act aca aac agc agc agt ccc gtg ggc     672
Val Gly Trp Tyr Gly Tyr Arg Thr Thr Asn Ser Ser Ser Pro Val Gly
                120                 125                 130 ctt tcc tcg tca gtg aca gga ttc cca tgt gac aaa acc ttt ggc acg     720
Leu Ser Ser Ser Val Thr Gly Phe Pro Cys Asp Lys Thr Phe Gly Thr
            135                 140                 145
```

```
atg tgg tct gat aca aag ccg att cgc tcc gct gaa acg tat aag ctg      768
Met Trp Ser Asp Thr Lys Pro Ile Arg Ser Ala Glu Thr Tyr Lys Leu
        150                 155                 160 acc tat aca acc gat acg tac ggc tgc caa agc ggc tcg cct gtt tat      816
Thr Tyr Thr Thr Asp Thr Tyr Gly Cys Gln Ser Gly Ser Pro Val Tyr
165                 170                 175 cga aac tac agt gat aca ggg cag aca gct att gcc att cac acg aac      864
Arg Asn Tyr Ser Asp Thr Gly Gln Thr Ala Ile Ala Ile His Thr Asn
180                 185                 190                 195 gga gga tcg tca tat aac ttg gga aca agg gtg acg aac gat gta ttc      912
Gly Gly Ser Ser Tyr Asn Leu Gly Thr Arg Val Thr Asn Asp Val Phe
                200                 205                 210 aac aat att caa tat tgg gca aat caa                                  939
Asn Asn Ile Gln Tyr Trp Ala Asn Gln
            215                 220

<210> SEQ ID NO 14
<211> LENGTH: 313
<212> TYPE: PRT
<213> ORGANISM: Bacillus subtilis IS75

<400> SEQUENCE: 14

Met Lys Leu Val Pro Arg Phe Arg Lys Gln Trp Phe Ala Tyr Leu Thr
            -90                 -85                 -80

Val Leu Cys Leu Ala Leu Ala Ala Ala Val Ser Phe Gly Val Pro Ala
        -75                 -70                 -65

Lys Ala Ala Glu Asn Pro Gln Thr Ser Val Ser Asn Thr Gly Lys Glu
    -60                 -55                 -50

Ala Asp Ala Thr Lys Asn Gln Thr Ser Lys Ala Asp Gln Val Ser Ala
-45                 -40                 -35                 -30

Pro Tyr Glu Gly Thr Gly Lys Thr Ser Lys Ser Leu Tyr Gly Gly Gln
                -25                 -20                 -15

Thr Glu Leu Glu Lys Asn Ile Gln Thr Leu Gln Pro Ser Ser Ile Ile
            -10                  -5                  -1   1

Gly Thr Asp Glu Arg Thr Arg Ile Ser Ser Thr Thr Ser Phe Pro Tyr
        5                    10                  15

Arg Ala Thr Val Gln Leu Ser Ile Lys Tyr Pro Asn Thr Ser Ser Thr
20                  25                  30                  35

Tyr Gly Cys Thr Gly Phe Leu Val Asn Pro Asn Thr Val Val Thr Ala
                40                  45                  50

Gly His Cys Val Tyr Ser Gln Asp His Gly Trp Ala Ser Thr Ile Thr
            55                  60                  65

Ala Ala Pro Gly Arg Asn Gly Ser Ser Tyr Pro Tyr Gly Thr Tyr Ser
        70                  75                  80

Gly Thr Met Phe Tyr Ser Val Lys Gly Trp Thr Glu Ser Lys Asp Thr
    85                  90                  95

Asn Tyr Asp Tyr Gly Ala Ile Lys Leu Asn Gly Ser Pro Gly Asn Thr
100                 105                 110                 115

Val Gly Trp Tyr Gly Tyr Arg Thr Thr Asn Ser Ser Ser Pro Val Gly
                120                 125                 130

Leu Ser Ser Ser Val Thr Gly Phe Pro Cys Asp Lys Thr Phe Gly Thr
            135                 140                 145

Met Trp Ser Asp Thr Lys Pro Ile Arg Ser Ala Glu Thr Tyr Lys Leu
        150                 155                 160

Thr Tyr Thr Thr Asp Thr Tyr Gly Cys Gln Ser Gly Ser Pro Val Tyr
    165                 170                 175
```

```
Arg Asn Tyr Ser Asp Thr Gly Gln Thr Ala Ile Ala Ile His Thr Asn
180                 185                 190                 195

Gly Gly Ser Ser Tyr Asn Leu Gly Thr Arg Val Thr Asn Asp Val Phe
                200                 205                 210

Asn Asn Ile Gln Tyr Trp Ala Asn Gln
            215                 220

<210> SEQ ID NO 15
<211> LENGTH: 909
<212> TYPE: DNA
<213> ORGANISM: Bacillus intermedius
<220> FEATURE:
<221> NAME/KEY: CDS
<222> LOCATION: (1)..(909)
<220> FEATURE:
<221> NAME/KEY: sig_peptide
<222> LOCATION: (1)..(78)
<220> FEATURE:
<221> NAME/KEY: pro_peptide
<222> LOCATION: (79)..(264)
<220> FEATURE:
<221> NAME/KEY: mat_peptide
<222> LOCATION: (265)..(909)

<400> SEQUENCE: 15 atg atg aaa aag gtg aaa atg tta ctc cct tct cta ctc gtt ttt ggt      48
Met Met Lys Lys Val Lys Met Leu Leu Pro Ser Leu Leu Val Phe Gly
            -85                 -80                 -75 gct tta agt gtg cct agt ttt gcc cat gcc aca tcg gat tca gta cta      96
Ala Leu Ser Val Pro Ser Phe Ala His Ala Thr Ser Asp Ser Val Leu
        -70                 -65                 -60 acg tct gat tat gac atg gtg act tct gat gga aag gtg atc tct tca     144
Thr Ser Asp Tyr Asp Met Val Thr Ser Asp Gly Lys Val Ile Ser Ser
    -55                 -50                 -45 agt gat ttc cac aat gat acg aaa tcc ccc tca tcc ttt gac aaa gtg     192
Ser Asp Phe His Asn Asp Thr Lys Ser Pro Ser Ser Phe Asp Lys Val
-40                 -35                 -30                 -25 gat gat ctt tct tct act tct ggc gaa aaa gta aaa cca ctc tca aaa     240
Asp Asp Leu Ser Ser Thr Ser Gly Glu Lys Val Lys Pro Leu Ser Lys
                -20                 -15                 -10 tat tta aaa gac ttt caa aca aaa gtc gtc att gga gac gat gga ada     288
Tyr Leu Lys Asp Phe Gln Thr Lys Val Val Ile Gly Asp Asp Gly Xaa
            -5                  -1  1                   5 aca aaa gta gca aac aca aga gtg gca cca tat aat tca att gct tat     336
Thr Lys Val Ala Asn Thr Arg Val Ala Pro Tyr Asn Ser Ile Ala Tyr
        10                  15                  20 att aca ttt ggc ggc tca agc tgc acg ggg aca ctc att gcc cct aac     384
Ile Thr Phe Gly Gly Ser Ser Cys Thr Gly Thr Leu Ile Ala Pro Asn
25                  30                  35                  40 aaa att ttg aca aac ggg cac tgc gtg tac aat aca gca tcg aga agt     432
Lys Ile Leu Thr Asn Gly His Cys Val Tyr Asn Thr Ala Ser Arg Ser
                45                  50                  55 tat agt gca aaa gga tcg gtg tat cca ggc atg aac gat agt aca gcg     480
Tyr Ser Ala Lys Gly Ser Val Tyr Pro Gly Met Asn Asp Ser Thr Ala
            60                  65                  70 gtg aat ggc tca gca aac atg acg gag ttc tat gta cca agc gga tat     528
Val Asn Gly Ser Ala Asn Met Thr Glu Phe Tyr Val Pro Ser Gly Tyr
        75                  80                  85 atc aat aca ggc gcg agc caa tat gat ttt gcc gtg atc aaa aca gat     576
Ile Asn Thr Gly Ala Ser Gln Tyr Asp Phe Ala Val Ile Lys Thr Asp
    90                  95                  100 acg aac att ggc aat acg gtc ggt tac cgc tct atc cgt cag gtg aca     624
Thr Asn Ile Gly Asn Thr Val Gly Tyr Arg Ser Ile Arg Gln Val Thr
105                 110                 115                 120
```

-continued

```
aac tta act ggg aca acg att aaa att tct gga tat cca ggt gat aaa        672
Asn Leu Thr Gly Thr Thr Ile Lys Ile Ser Gly Tyr Pro Gly Asp Lys
            125                 130                 135 atg ada tcg act ggc aag gtg tcg cad tgg gag atg tca ggt tct gtg        720
Met Xaa Ser Thr Gly Lys Val Ser Xaa Trp Glu Met Ser Gly Ser Val
            140                 145                 150 aca aga gaa gat aca aat ctc gca tac tat acg att gat aca ttt agc        768
Thr Arg Glu Asp Thr Asn Leu Ala Tyr Tyr Thr Ile Asp Thr Phe Ser
            155                 160                 165 gga aat tca ggc tca gcg atg cta gat caa aat cad caa atc gtt ggg        816
Gly Asn Ser Gly Ser Ala Met Leu Asp Gln Asn Xaa Gln Ile Val Gly
        170                 175                 180 gtt cat aac gca ggg tat tca aac gga acg att aat ggc ggt cca aaa        864
Val His Asn Ala Gly Tyr Ser Asn Gly Thr Ile Asn Gly Gly Pro Lys
185                 190                 195                 200 gcg aca gct gcc ttt gtt gaa ttt atc aac tat gca aaa gcg caa            909
Ala Thr Ala Ala Phe Val Glu Phe Ile Asn Tyr Ala Lys Ala Gln
                205                 210                 215

<210> SEQ ID NO 16
<211> LENGTH: 303
<212> TYPE: PRT
<213> ORGANISM: Bacillus intermedius
<220> FEATURE:
<221> NAME/KEY: misc_feature
<222> LOCATION: (8)..(8)
<223> OTHER INFORMATION: The 'Xaa' at location 8 stands for Lys, Arg,
      or Ile.
<220> FEATURE:
<221> NAME/KEY: misc_feature
<222> LOCATION: (138)..(138)
<223> OTHER INFORMATION: The 'Xaa' at location 138 stands for Lys, Arg,
      or Ile.
<220> FEATURE:
<221> NAME/KEY: misc_feature
<222> LOCATION: (145)..(145)
<223> OTHER INFORMATION: The 'Xaa' at location 145 stands for Gln, or
      His.
<220> FEATURE:
<221> NAME/KEY: misc_feature
<222> LOCATION: (180)..(180)
<223> OTHER INFORMATION: The 'Xaa' at location 180 stands for Gln, or
      His.

<400> SEQUENCE: 16

Met Met Lys Lys Val Lys Met Leu Leu Pro Ser Leu Leu Val Phe Gly
            -85                 -80                 -75

Ala Leu Ser Val Pro Ser Phe Ala His Ala Thr Ser Asp Ser Val Leu
        -70                 -65                 -60

Thr Ser Asp Tyr Asp Met Val Thr Ser Asp Gly Lys Val Ile Ser Ser
    -55                 -50                 -45

Ser Asp Phe His Asn Asp Thr Lys Ser Pro Ser Ser Phe Asp Lys Val
-40                 -35                 -30                 -25

Asp Asp Leu Ser Ser Thr Ser Gly Glu Lys Val Lys Pro Leu Ser Lys
                -20                 -15                 -10

Tyr Leu Lys Asp Phe Gln Thr Lys Val Val Ile Gly Asp Asp Gly Xaa
            -5                  -1  1                 5

Thr Lys Val Ala Asn Thr Arg Val Ala Pro Tyr Asn Ser Ile Ala Tyr
    10                  15                  20

Ile Thr Phe Gly Gly Ser Ser Cys Thr Gly Thr Leu Ile Ala Pro Asn
25                  30                  35                  40

Lys Ile Leu Thr Asn Gly His Cys Val Tyr Asn Thr Ala Ser Arg Ser
                45                  50                  55
```

```
Tyr Ser Ala Lys Gly Ser Val Tyr Pro Gly Met Asn Asp Ser Thr Ala
            60              65                  70

Val Asn Gly Ser Ala Asn Met Thr Glu Phe Tyr Val Pro Ser Gly Tyr
        75              80              85

Ile Asn Thr Gly Ala Ser Gln Tyr Asp Phe Ala Val Ile Lys Thr Asp
    90              95                  100

Thr Asn Ile Gly Asn Thr Val Gly Tyr Arg Ser Ile Arg Gln Val Thr
105             110             115                         120

Asn Leu Thr Gly Thr Thr Ile Lys Ile Ser Gly Tyr Pro Gly Asp Lys
                125             130                 135

Met Xaa Ser Thr Gly Lys Val Ser Xaa Trp Glu Met Ser Gly Ser Val
        140             145                     150

Thr Arg Glu Asp Thr Asn Leu Ala Tyr Tyr Thr Ile Asp Thr Phe Ser
        155             160                 165

Gly Asn Ser Gly Ser Ala Met Leu Asp Gln Asn Xaa Gln Ile Val Gly
        170             175             180

Val His Asn Ala Gly Tyr Ser Asn Gly Thr Ile Asn Gly Gly Pro Lys
185             190             195                         200

Ala Thr Ala Ala Phe Val Glu Phe Ile Asn Tyr Ala Lys Ala Gln
                205             210             215

<210> SEQ ID NO 17
<211> LENGTH: 22
<212> TYPE: DNA
<213> ORGANISM: Artificial sequence
<220> FEATURE:
<223> OTHER INFORMATION: Primer

<400> SEQUENCE: 17
ctgtgccctt taaccgcaca gc                                          22

<210> SEQ ID NO 18
<211> LENGTH: 24
<212> TYPE: DNA
<213> ORGANISM: Artificial sequence
<220> FEATURE:
<223> OTHER INFORMATION: Primer

<400> SEQUENCE: 18
gcataagctt ttacaggtac cggc                                        24
```

PROTEASE VARIANTS

CROSS-REFERENCE TO RELATED APPLICATIONS

This application is a continuation of U.S. application Ser. No. 10/588,555 filed on Jun. 1, 2007 (now abandoned) which is a 35 U.S.C. 371 national application of PCT/DK2005/000097 filed Feb. 14, 2005 which claims priority or the benefit under 35 U.S.C. 119 of Danish Application no. PA 2004 00226 filed Feb. 13, 2004 and U.S. provisional application No. 60/558,191 filed Mar. 31, 2004, the contents of which are fully incorporated herein by reference.

FIELD OF THE INVENTION

The present invention relates to variants of proteases belonging to the RP-II or C-component type, and methods for the construction of such variants with altered properties, such as stability (e.g. thermostability or storage stability), $Ca^{2+}$ dependency, and pH dependent activity.

BACKGROUND OF THE INVENTION

Enzymes have been used within the detergent industry as part of washing formulations for more than 30 years. Proteases are from a commercial perspective the most relevant enzyme in such formulations, but other enzymes including lipases, amylases, cellulases, hemicellulases or mixtures of enzymes are also often used. Proteases are also used in other fields, such as production of diary products, processing of hides, feed processing, etc.

To improve the cost and/or the performance of proteases there is an ongoing search for proteases with altered properties, such as increased activity at low temperatures, increased thermostability, increased specific activity at a given pH, altered $Ca^{2+}$ dependency, increased stability in the presence of other detergent ingredients (e.g. bleach, surfactants etc.), modified specificity in respect of substrates, etc.

The search for proteases with altered properties includes both discovery of naturally occurring proteases, i.e. so called wild-type proteases but also alteration of well-known proteases by e.g. genetic manipulation of the nucleic acid sequence encoding said proteases. Knowledge of the relationship between the three-dimensional structure and the function of a protein has improved the ability to evaluate which areas of a protein to alter to affect a specific property of the protein.

One group of proteases, which has been indicated for use in detergents, food processing, feed processing is the RP-II proteases or C-component proteases belonging to the protease family S1B, glutamic-acid-specific endopeptidases. This family has till now only received relatively minor attention and has not been further grouped into different sub-groups. However, from the amino acid identities of isolated RP-II proteases it is evident that subgroups exist. Bacillus proteases of the RP-II type are serine proteases that in primary structure are similar to chymotrypsin.

The first description of a protease of the RP-II family of Bacillus proteases was in U.S. Pat. No. 4,266,031 (Tang et al., Novo Industri A/S), where it was designated Component C and tentatively (and incorrectly) characterised as not being a serine protease or metallo protease. Component C was considered a contaminant in the production of the Bacillus licheniformis alkaline protease, subtilisin Carlsberg.

In EP 369 817 (Omnigene Bioproducts, Inc.) the B. subtilis member of the RP-II family was identified by its amino acid and DNA sequences. The enzyme was again stated not to be a serine protease, and the family name RP-II designated (Residual Protease II). The enzyme was characterized further as a metallo protease by the inventors of EP 369 817 (Rufo et al., 1990, J. Bacteriol. 2 1019-1023, and Sloma et al., 1990, J. Bacteriol. 172 1024-1029), designating the enzyme as mpr.

In WO 91/13553 (Novozymes A/S) the amino acid sequence of the C component was disclosed, stating that it is a serine protease specific for glutamic and aspartic acid, while EP 482 879 (Shionogi & Co. Ltd.) disclosed the enzyme and a DNA sequence encoding the C component from B. licheniformis ATCC No. 14580, naming the enzyme BLase. In EP 482 879 the protease is described as being specific for glutamic acid (see also Kakudo et al. "Purification, characterization, cloning, and expression of a glutamic acid-specific protease from Bacillus licheniformis ATCC 14580". J. Biol. Chem. 267:23782 (1992)).

In 1997 Okamoto et al. (Appl. Microbiol. Biotechnol. (1997) 48 27-33) found that the B. subtilis homologue of BLase, named BSase was identical to the above-mentioned enzyme, mpr/RP-II.

In 1999 Rebrikov et al. (Journal of Protein Chemistry, Vol. 18, No. 1, 1999) disclosed a Glu-specific protease from B. intermedius that also belongs to the RP-II family.

In WO 01/16285 a number of further RP-II protease were disclosed with DNA and amino acid sequences. These RP-II proteases were isolated from B. pumilus, B. halmapalus and B. licheniformis. WO 01/16285 also discloses a number of variants of RP-II proteases. These variants were based on various concepts relating to the primary structure of the RP-II proteases (amino acid sequences).

The homology matrix in Table 1 below clearly indicates that the RP-II proteases 1 to 8 are a distinct group of Glu-specific proteases that are clearly different from the other Glu-specific proteases in the Matrix

TABLE 1

| | 1 | 2 | 3 | 4 | 5 | 6 | 7 | 8 | 9 | 10 | 11 | 12 | 13 |
|---|---|---|---|---|---|---|---|---|---|---|---|---|---|
| 1 | 100 | 99 | 97 | 60 | 55 | 55 | 47 | 59 | 46 | 45 | 45 | 47 | 49 |
| 2 | | 100 | 99 | 60 | 60 | 59 | 50 | 61 | 50 | 44 | 45 | 46 | 52 |
| 3 | | | 100 | 60 | 57 | 54 | 47 | 60 | 47 | 45 | 45 | 44 | 49 |
| 4 | | | | 100 | 94 | 92 | 68 | 57 | 44 | 38 | 40 | 42 | 47 |
| 5 | | | | | 100 | 91 | 59 | 54 | 44 | 42 | 40 | 43 | 45 |
| 6 | | | | | | 100 | 63 | 53 | 39 | 42 | 46 | 41 | 45 |
| 7 | | | | | | | 100 | 48 | 41 | 41 | 40 | 36 | 44 |
| 8 | | | | | | | | 100 | 50 | 45 | 46 | 46 | 54 |
| 9 | | | | | | | | | 100 | 63 | 53 | *55* | *49* |
| 10 | | | | | | | | | | 100 | 53 | 56 | 52 |
| 11 | | | | | | | | | | | 100 | 78 | 54 |

TABLE 1-continued

| | 1 | 2 | 3 | 4 | 5 | 6 | 7 | 8 | 9 | 10 | 11 | 12 | 13 |
|---|---|---|---|---|---|---|---|---|---|---|---|---|---|
| 12 | | | | | | | | | | | | 100 | 53 |
| 13 | | | | | | | | | | | | | 100 |

In the matrix the sequences are identified by the patent publication in which first published or sequence database accession numbers.
1. *Bacillus* sp. JA96 glutamic-acid-specific endopeptidase, JA96, WO 01/16285
2. 1p3e *B. Intermedius*, glutamic-acid-specific endopeptidase, BIP, EMBL No. Y5136, Rebrikov et al., Journal of Protein Chemistry, Vol. 18, No. 1, 1999
3. *Bacillus* sp. BO32 glutamic-acid-specific endopeptidase, BO32, WO 01/16285
4. *Bacillus licheniformis*, BLC, WO 01/16285 (cf. U.S. Pat. No. 4,266,031)
5. *Bacillus* sp. CDJ31 glutamic-acid-specific endopeptidase, CDJ31, WO 01/16285
6. *Bacillus* sp. AC116 glutamic-acid-specific endopeptidase, AC116, WO 01/16285
7. mpr_bacsu *Bacillus subtilis* serine protease, MPR, EP 369 817
8. *Bacillus* sp. AA513 glutamic-acid-specific endopeptidase, AA513, WO 01/16285
9. eta_staau *Staphylococcus aureus* exfoliative toxin A (Lee et al. Sequence determination and comparison of the exfoliative toxin A and toxin B genes from *Staphylococcus aureus*; J. Bacteriol. 169: 3904 (1987))
10. etb_staau *Staphylococcus aureus* exfoliative toxin B (Jackson, M. P.; Iandolo, J. J.; Sequence of the exfoliative toxin B gene of *Staphylococcus aureus*; J. Bacteriol. 167: 726 (1986))
11. q53781 *Staphylococcus aureus* (strain Mu50/ATCC 700699) (Rieneck et al.; Submitted (June 1996) to the EMBL/GenBank/DDBJ databases)
12. q53782 *Staphylococcus aureus* (strain Mu50/ATCC 700699) (Rieneck et al., "Molecular cloning and expression of a novel *Staphylococcus aureus* antigen". Biochim. Biophys. Acta 1350: 128 (1997)
13. stsp_staau *Staphylococcal* serine endoproteinase V8 Glu-C (Gray, "Nucleotide sequence of the serine protease gene of *Staphylococcus aureus*, strain V8" Nucleic Acids Res. 15: 6757 (1987))

The three-dimensional structure of the protease Toxin A from *Staphylococcus aureus*. Belonging to the S1B family has been determined by Cavarelli, J., et al. Structure Vol. 5, p. 813 1997.

However, despite the sequence homology between the proteases belonging to the RP-II proteases and Toxin A from *Staphylococcus aureus*, modelling of the three-dimensional structure of RP-II proteases on the basis of the three-dimensional structure of Toxin A from *Staphylococcus aureus* may result in an incorrect three-dimensional structure because of structural differences, especially because the distinct difference in sequence homology to the RP-II proteases.

The inventors of the present invention have elucidated the three-dimensional structure of the C-component protease from *Bacillus licheniformis* and found that there are several differences between this and the three-dimensional structure of Toxin A from *Staphylococcus aureus* also belonging to the S1B subgroup of proteases. This surprising difference in structure makes it advantageous to use the BLC structure as basis for homology modelling of RP-II proteases, which, in turn, will improve the ability to obtain desired changes in functionality by protein engineering.

BRIEF DESCRIPTION OF THE INVENTION

The inventors have modified the amino acid sequence of a RP-II protease to obtain variants with improved properties, based on the three-dimensional structure of the C-component. The variants will have altered properties, such as increased activity at low temperatures, increased thermostability, increased specific activity at a given pH, altered $Ca^{2+}$ dependency, increased stability in the presence of other detergent ingredients (e.g. bleach, surfactants etc.) etc.

Accordingly, the object of the present invention is to provide a method for constructing RP-II proteases having altered properties, in particular to provide a method for constructing RP-II proteases having altered properties as described above.

Thus, in its broadest aspect, the present invention relates to a method for constructing a variant of a parent RP-II protease, wherein the variant has at least one altered property as compared to said parent RP-II protease, which method comprises:
i) analyzing the three-dimensional structure of the RP-II protease to identify, on the basis of an evaluation of structural considerations, at least one amino acid residue or at least one structural region of the RP-II protease, which is of relevance for altering said property;
ii) constructing a variant of the RP-II protease, which as compared to the parent RP-II protease, has been modified in the amino acid residue or structural part identified in i) so as to alter said property; and
iii) testing the resulting RP-II protease variant for said property.

Although it has been described in the following that modification of the parent RP-II protease in certain regions and/or positions is expected to confer a particular effect to the thus produced RP-II protease variant, it should be noted that modification of the parent RP-II protease in any of such regions may also give rise to any other of the above-mentioned effects. For example, any of the regions and/or positions mentioned as being of particular interest with respect to, e.g., improved thermostability, may also give rise to, e.g., higher activity at a lower pH, an altered pH optimum, or increased specific activity, such as increased peptidase activity.

Further aspects of the present invention relates to variants of a RP-II protease, the DNA encoding such variants and methods of preparing the variants. Still further aspects of the present invention relates to the use of the variants for various industrial purposes, in particular as an additive in detergent compositions. Other aspects of the present invention will be apparent from the below description as well as from the appended claims.

BRIEF DESCRIPTION OF DRAWINGS

FIG. 1 provides a schematic structure of the RP-II protease from *Bacillus licheniformis*, BLC (SEQ ID NO: 2).

FIG. 2 shows a 3D structure based alignment of the wild type RP-II proteases 1 to 8 of Table 1 (SEQ ID NOs: 2, 4, 6, 8, 10, 12, 14 and 16).

BRIEF DESCRIPTION OF APPENDICES

Figure 3:
FIG. 3 shows the BLC protease ribbon structure in black, with indication of active site residues, the bound peptide and the ion-binding site. The calcium ion is the sphere at the bottom of the Figure, the active site residues are in light grey and shown in stick model, and the bound peptide DAFE is in medium grey and shown in stick model.

APPENDIX 1 provides the structural coordinates for the solved crystal 3D structure of the BLC RP-II protease, in the standard pdb format. The residues are numbered from 1-217, the calcium ion is numbered 301, and the DAFE substrate is numbered 401-404.

DEFINITIONS

Prior to discussing this invention in further detail, the following terms and conventions will first be defined.

For a detailed description of the nomenclature of amino acids and nucleic acids and modifications introduced in a polypeptide or protein and especially in a RP-II protease by genetic manipulation, we refer to WO 01/16285 pages 5 to 15, hereby incorporated by reference.

The term "RP-II proteases" refers to a sub-group of serine protease, belonging to the protease family S1B, glutamic-acid-specific endopeptidases. Serine proteases or serine peptidases is a subgroup of proteases characterised by having a serine in the active site, which forms a covalent adduct with the substrate. Further the RP-II proteases (and the serine proteases) are characterised by having two active site amino acid residues apart from the serine, namely a histidine and an aspartic acid residue.

The RP-II proteases have a homology to the rest of the S1B protease family of around 50% (using the UWGCG version 8 software GAP program), or more preferred a homology higher than 55%. Table 1 demonstrate homologies between various S1B proteases. The RP-II proteases, nos. 1 to 8, are in Table 1 indicated in bold and the other S1B proteases, nos. 9 to 13, in bold italics. Table 1 shows that there is a clear distinction to the RP-II proteases from the other S1B proteases, but it is also clear that among the RP-II proteases there are subgroups. One subgroup comprises nos. 1, 2, and 3; and another subgroup comprises nos. 4, 5, and 6. The lengths of the listed RP-II proteases vary from 215 to 222 amino acid residues and experience within the subtilisin subgroups of subtilases indicates that such a variation in length probably has only little effect on the 3-dimensional structures of these and other RP-II protease subgroups.

Parent

The term "parent" is in the context of the present invention to be understood as a protein, which is modified to create a protein variant. The parent protein may be a naturally occurring (wild-type) polypeptide or it may be a variant thereof prepared by any suitable means. For instance, the parent protein may be a variant of a naturally occurring protein which has been modified by substitution, chemical modification, deletion or truncation of one or more amino acid residues, or by addition or insertion of one or more amino acid residues to the amino acid sequence, of a naturally-occurring polypeptide. Thus the term "parent RP-II protease" refers to a RP-II protease which is modified to create a RP-II protease variant.

Variant

The term "variant" is in the context of the present invention to be understood as a protein which has been modified as compared to a parent protein at one or more amino acid residues.

Modification

The term "modification(s)" or "modified" is in the context of the present invention to be understood as to include chemical modification of a protein as well as genetic manipulation of the DNA encoding a protein. The modification(s) may be replacement(s) of the amino acid side chain(s), substitution(s), deletion(s) and/or insertions in or at the amino acid(s) of interest. Thus the term "modified protein", e.g. "modified RP-II protease", is to be understood as a protein which contains modification(s) compared to a parent protein, e.g. RP-II protease.

Homology

"Homology" or "homologous to" is in the context of the present invention to be understood in its conventional meaning and the "homology" between two amino acid sequences should be determined by use of the "Similarity" parameter defined by the GAP program from the University of Wisconsin Genetics Computer Group (UWGCG) package using default settings for alignment parameters, comparison matrix, gap and gap extension penalties. Default values for GAP penalties, i.e. GAP creation penalty of 3.0 and GAP extension penalty of 0.1 (Program Manual for the Wisconsin Package, Version 8, August 1994, Genetics Computer Group, 575 Science Drive, Madison, Wis., USA 53711). The method is also described in S. B. Needleman and C. D. Wunsch, Journal of Molecular Biology, 48, 443-445 (1970). Identities can be extracted from the same calculation. The homology between two amino acid sequences can also be determined by "identity" or "similarity" using the GAP routine of the UWGCG package version 9.1 with default setting for alignment parameters, comparison matrix, gap and gap extension penalties can also be applied using the following parameters: gap creation penalty=8 and gap extension penalty=8 and all other parameters kept at their default values. The output from the routine is besides the amino acid alignment the calculation of the "Percent Identity" and the "Similarity" between the two sequences. The numbers calculated using UWGCG package version 9.1 is slightly different from the version 8.

Naming of RP-II Proteases

In describing the RP-II proteases of the invention the following abbreviations are used for ease of reference:

BLC=RP-II protease from *Bacillus licheniformis* (U.S. Pat. No. 4,266,031),

AA513=RP-II protease from *Bacillus* halmapalus AA513 (WO 01/16285),

AC116=RP-II protease from *Bacillus licheniformis* AC116 (WO 01/16285)

BO32=RP-II protease from *Bacillus pumilus* BO32 (WO 01/16285),

CDJ31=RP-II protease from *Bacillus licheniformis* CDJ31 (WO 01/16285),

JA96=RP-II protease from *Bacillus pumilus* JA96 (WO 01/16285),

MPR=RP-II protease from *Bacillus subtilis* IS75 (EP 369 817 B1)

BIP=RP-II protease from *B. intermedius* (Rebrikov et al., Journal of Protein Chemistry, Vol. 18, No. 1, 1999)

Sequence Listing

In the appended Sequence Listing the RP-II proteases are indicated as:

SEQ. ID. NO. 1=BLC (DNA), SEQ. ID. NO. 2=BLC (AA),
SEQ. ID. NO. 3=AA513 (DNA), SEQ. ID. NO. 4=AA513 (AA),
SEQ. ID. NO. 5=AC116 (DNA), SEQ. ID. NO. 6=AC116 (AA)
SEQ. ID. NO. 7=BO32 (DNA), SEQ. ID. NO. 8=BO32 (AA)
SEQ. ID. NO. 9=CDJ31 (DNA), SEQ. ID. NO. 10=CDJ31 (AA)
SEQ. ID. NO. 11=JA96 (DNA), SEQ. ID. NO. 12=JA96 (AA)
SEQ. ID. NO. 13=BSMPR (DNA), SEQ. ID. NO. 14=BSMPR (AA)
SEQ. ID. NO. 15=BIP (DNA), SEQ. ID. NO. 16=BIP (AA)

Position

The term "position" is in the context of the present invention to be understood as the number of an amino acid residue in a peptide, polypeptide or protein when counting from the N-terminal end of said peptide/polypeptide. The position numbers used here normally refer directly to different RP-II proteases.

The RP-II proteases are numbered individually according to each of SEQ ID NO: 2, 4, 6, 8, 10, 12, 14, and 16.

Corresponding Position

The invention, however, is not limited to variants of these particular RP-II proteases but extends to parent proteases containing amino acid residues at positions which are "equivalent" to the particular identified residues in *Bacillus licheniformis* RP-II protease. In some preferred embodiment of the present invention, the parent protease is JA96 or BIP RP-II protease and the substitutions are made at the equivalent amino acid residue positions in JA96 or BIP corresponding to those listed above.

A residue (amino acid) position of a RP-II protease is equivalent to a residue (position) of the *Bacillus licheniformis* RP-II protease if it is either homologous (i.e., corresponding in position in either primary or tertiary structure) or analogous to a specific residue or portion of that residue in *Bacillus licheniformis* RP-II protease (i.e., having the same or similar functional capacity to combine, react, or interact chemically).

In order to establish homology to primary structure, the amino acid sequence of a precursor protease is directly compared to the *Bacillus licheniformis* RP-II protease, BLC, primary sequence by aligning the amino acid sequence of an isolated or parent wild type enzyme with a suitable well-known enzyme of the same group or class of enzymes defines a frame of reference. This type of numbering was used in WO 01/16285.

If nothing else is indicated herein, in the present instance the *Bacillus licheniformis* RP-II protease, first designated component C and therefore here abbreviated BLC, has been chosen as standard.

In order to establish homology to the tertiary structure (3D structure) of BLC, the 3D structure based alignment in FIG. 2 has been provided. By using this alignment the amino acid sequence of a precursor RP-II protease may be directly correlated to the *Bacillus licheniformis* RP-II protease, BLC, primary sequence. For a novel RP-II protease sequence, the (3D based) position corresponding to a position in BLC is found by i) identifying the RP-II protease from the alignment of FIG. 2 that is most homologous to the novel sequence,
ii) aligning the novel sequence with the sequence identified to find the corresponding position in the RP-II protease from FIG. 2, and
iii) establishing from FIG. 2 the corresponding position in BLC.

For comparison and finding the most homologous sequence the GAP program from GCG package as described below are used.

The alignment can as indicated above be obtained by the GAP routine of the GCG package version 8 to number the variants using the following parameters: gap creation penalty=3 and gap extension penalty=0.1 and all other parameters kept at their default values.

The alignment of FIG. 2 defines a number of deletions and insertions in relation to the sequence of BLC. In the alignment deletions are indicated by asterixes (*) in the referenced sequence, and the referenced enzyme will be considered to have a gap at the position in question. Insertions are indicated by asterixes (*) in the BLC sequence, and the positions in the referenced enzyme are given as the position number of the last amino acid residue where a corresponding amino acid residue exists in the standard enzyme with a lower case letter appended in alphabetical order, e.g. 82a, 82b, 82c, 82d, see FIG. 2.

In case the referenced enzyme contains a N- or C-terminal extension in comparison to BLC; an N-terminal extension is given the position number 0a, 0b, etc. in the direction of the N-terminal; and a C-terminal extension will be given either the position number of the C-terminal amino acid residue of BLC with a lower case letter appended in alphabetical order, or simply a continued consecutive numbering.

Thus for comparisons RP-II proteases are numbered by reference to the positions of the BLC RP-II protease (SEQ ID NO: 2) as provided in FIG. 2. The position is then indicated as "corresponding to BLC".

DETAILED DESCRIPTION OF THE INVENTION

The inventors of the present invention have elucidated the three-dimensional structure of BLC, SEQ ID NO:2 by X-ray crystallography and found that there are several interesting features in the structure of this protease in comparison with the known structures of other proteases, such as the RP-II proteases. These features include both similarities and differences.

RP-II Proteases

As described above a RP-II protease is in the context of the present invention to be understood as a protease which has at least 50% homology to BLC (SEQ ID NO:2). In particular said protease may have at least 55% homology to BLC, i.e. to SEQ ID NO:2. The invention thus relates to variant RP-II proteases having at least 50% homology to BLC.

Specifically the variants of the invention may comprise RP-II proteases comprising a number of modifications or modifications in a number of positions ranging from at least one and up to 50, or from 1 to 45, or from 1 to 40, or from 1 to 35, or from 1 to 30, or from 1 to 25, or from 1 to 20, or from 1 to 15, or from 1 to 14, or from 1 to 13, or from 1 to 12, or from 1 to 11, or from 1 to 10, or from 1 to 9, or from 1 to 8, or from 1 to 7, or from 1 to 6, or from 1 to 5, or from 1 to 4, or from 1 to 3, or from 1 to 2 modifications or positions. Such modifications comprising substitutions, deletions and insertions in the indicated number or number of positions.

A RP-II protease variant of the present invention is encoded by an isolated polynucleotide, which nucleic acid sequence has at least 50% homology with the nucleic acid sequence shown in SEQ ID NO: 1, and where the polynucleotide encodes a variant RP-II protease in relation to a parent protease.

In a first embodiment of the present invention a RP-II protease suitable for the purpose described herein may be a RP-II protease homologous to the three-dimensional structure of BLC, i.e. it may be homologous to the three-dimensional structure defined by the structure coordinates in Appendix 1 by comprising the structural elements defined below.

It is well-known to a person skilled in the art that a set of structure coordinates for a protein or a portion thereof is a relative set of points that define a shape in three dimensions; it is possible that an entirely different set of coordinates defines an identical or a similar shape. Moreover, slight variations in the individual coordinates may have little or no effect on the overall shape.

These variations in coordinates may be generated because of mathematical manipulations of the structure coordinates. For example, the structure coordinates of Appendix 1 (BLC structure) may be manipulated by crystallographic permutations of the structure coordinates, fractionalization of the structure coordinates, integer additions or subtractions to sets of the structure coordinates, inversion of the structure coordinates or any combination of the above. Alternatively, said variations may be due to differences in the primary amino acid sequence.

When such variations are within an acceptable standard error as compared to the structure coordinates of Appendix 1 said three-dimensional structure is within the context of the present invention to be understood as being homologous to the structure of Appendix 1. The standard error may typically be measured as the root mean square deviation of e.g. conserved backbone residues, where the term "root mean square deviation" (RMS) means the square root of the arithmetic mean of the squares of the deviations from the mean.

It is also well-known to a person skilled in the art that within a group of proteins which have a homologous structure there may be variations in the three-dimensional structure in certain areas or domains of the structure, e.g. loops, which are not, or at least only of a small importance to the functional domains of the structure, but which may result in a big root mean square deviation of the conserved residue backbone atoms between said structures.

Thus it is well known that a set of structure coordinates is unique to the crystallised protein. No other three dimensional structure will have the exact same set of coordinates, be it a homologous structure or even the same protein crystallised in different manner. There are natural fluctuations in the coordinates. The overall structure and the inter-atomic relationship can be found to be similar. The similarity can be discussed in terms of root mean square deviation of each atom of a structure from each "homologous" atom of another structure. However, only identical proteins have the exact same number of atoms. Therefore, proteins having a similarity below 100% will often have a different number of atoms, and thus the root mean square deviation can not be calculated on all atoms, but only the ones that are considered "homologous". A precise description of the similarity based on the coordinates is thus difficult to describe and difficult to compute for homologous proteins. Regarding the present invention, similarities in 3D structure of different RP-II proteases can be described by the content of homologous structural elements, and/or the similarity in amino acid or DNA sequence Examples of BLC like RP-II proteases include the BLC=RP-II protease from *Bacillus licheniformis* (cf. U.S. Pat. No. 4,266,031), AA513=RP-II protease from *Bacillus halmapalus* AA513 (NP000368), AC116=RP-II protease from *Bacillus licheniformis* AC116 (NP000364), BO32=RP-II protease from *Bacillus pumilus* BO32 (NP000366), CDJ31=RP-II protease from *Bacillus licheniformis* CDJ31 (NP000365), JA96=RP-II protease from *Bacillus pumilus* JA96 (NP000367), MPR=RP-II protease from *Bacillus subtilis* IS75 (cf. EP 369 817 B1), BIP=RP-II protease from *B. intermedius* (EMBL No. Y5136, Rebrikov et al., Journal of Protein Chemistry, Vol. 18, No. 1, 1999)

Accordingly, a preferred embodiment of the present invention is a variant of a parent RP-II protease or a RP-II protease variant which is at least 50% homologous to the sequence of SEQ ID NO 2 preferably at least 55%, preferably at least 65%, at least 70%, at least 74%, at least 80%, at least 83%, at least 90%, at least 91%, at least 92%, at least 93%, at least 94%, at least 95%, at least 96%, at least 97%, at least 98% or at least 99% homologous to the sequence of SEQ ID NO:2, 4, 6, 8, 10, 12, 14 or 16.

A further embodiment of the invention is a RP-II protease variant comprising the following structural characteristics:

a) two beta-barrel domains each comprising six long strands in antiparallel organisation,
b) three alpha helices,
c) at least one ion-binding site,
d) an active site comprising the amino acid residues His, Asp and Ser.

The potential ion binding site is defined as similar coordination or arrangement of the coordinates as in the 3D structure of BLC having one calcium ion coordinated by the Ile 3 carbonyl atom O, the Ser 5 carbonyl atom O and bidendate by the Asp 161 Carboxyl acid group and the further coordination made by waters. The calcium may be substituted in the structure by water but then having the same coordination.

The RP-II protease variants of the present invention are encoded by isolated polynucleotides, which nucleic acid sequence has at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% homology with the nucleic acid sequence shown in SEQ ID NO:1, 3, 5, 7, 9, 11, 13, or 15, and where the polynucleotide encodes a variant RP-II protease in relation to a parent protease.

Further the isolated nucleic acid sequence encoding a RP-II protease variant of the invention hybridizes with a complementary strand of the nucleic acid sequence shown in SEQ ID NO: 1 preferably under low stringency conditions, at least under medium stringency conditions, at least under medium/high stringency conditions, at least under high stringency conditions, at least under very high stringency conditions.

Suitable experimental conditions for determining hybridization at low, medium, or high stringency between a nucleotide probe and a homologous DNA or RNA sequence involves presoaking of the filter containing the DNA fragments or RNA to hybridize in 5×SSC (Sodium chloride/Sodium citrate, Sambrook et al. 1989) for 10 min, and pre-hybridization of the filter in a solution of 5×SSC, 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) *Anal. Biochem.* 132:6-13), $^{32}$P-dCTP-labeled (specific activity>1×10$^9$ cpm/µg) probe for 12 hours at ca. 45° C. The filter is then washed twice for 30 minutes in 2×SSC, 0.5% SDS at least 55° C. (low stringency), more preferably at least 60° C. (medium stringency), still more preferably at least 65° C. (medium/high stringency), even more preferably at least 70° C. (high stringency), and even more preferably at least 75° C. (very high stringency).

Three-Dimensional Structure of RP-II Proteases

The BLC RP-II protease was used to elucidate the three-dimensional structure forming the basis for the present invention.

The structure of BLC was solved in accordance with the principle for x-ray crystallographic methods, for example, as given in X-Ray Structure Determination, Stout, G. K. and Jensen, L. H., John Wiley & Sons, Inc. NY, 1989.

The structural coordinates for the solved crystal structure of BLC are given in standard PDB format (Protein Data Bank, Brookhaven National Laboratory, Brookhaven, Conn.) as set forth in Appendix 1. It is to be understood that Appendix 1 forms part of the present application. In the context of Appendix 1, the following abbreviations are used: CA refers to c-alpha (carbon atoms) or to calcium ions, (however to avoid misunderstandings we normally use the full names "c-alpha atoms", "calcium" "Ca" or "ion" in the present specification).

Amino acid residues are given in their standard three-letter code or the standard one-letter code. The structural coordinates in Appendix 1 contain the protease structure wherein the active serine was replaced by alanine and a complex formed with the peptide DAFE (=Asp-Ala-Phe-Glu) as well as water molecules. The protease coordinates has a chain identification called A, whereas the peptide is called B, the calcium ion is called C, and the water is W. In the following the positions of the mentioned residues refer to the sequence of BLC as disclosed in SEQ ID NO: 2.

The overall structure of BLC falls into the SI group of the proteases (MEROPS). The structure is a trypsin type of fold with two beta-barrel domains. The beta-barrel's each consists of six antiparallel beta-sheets folded into a beta-barrel. The topology can be described as S1-S2-S3-S6-S5-S4 for the strands in both beta-barrels. It is assumed that all the RP-II proteases fall within the same general overall structure.

The 3D structure of C-component serine protease from *Bacillus licheniformis* has 16 strands of which the 12 bigger strands compose the two beta-barrels; and 3 helixes. The four very short strands are number 1, 5, 6 and 10 counting from the N-terminal and are composed of residue numbers 9-10, 50-51, 56-57 and 114-115. The other strands are residue numbers 22-26, 31-36, 41-44, 62-65, 77-83, 99-102, 126-131, 142-151, 156-159, 171-177, 182-192 and 201-205. One main helix C-terminal residue number 208-219. Two very small helices are composed of residues 86-90 and 106-110.

The active site consists of a triad involving the Ser in position 167, the His in position 47, and the Asp in position 96.

The 3D structure of BLC has one calcium ion coordinated by the carbonyl oxygen atom of Ile in position 3, the carbonyl oxygen atom of Ser in position 5, and bidendate by the Carboxylic acid group of Asp in position 161. Further coordinations are made by water molecules.

The calcium ion is placed in a distance from the CA atoms of the active site and Gly in position 168 as provided below:
Ser 167 CA atom to Ca ion: 16.07 Å
His 47 CA atom to Ca ion: 24.27 Å
Asp 96 CA atom to Ca ion: 23.72 Å
Gly 168 CA atom to Ca ion: 19.20 Å

The position of an ion-binding site can be defined by the distance to four specific atoms in the core structure. The distance from the ion-binding site to the c-alpha atoms of the three active site residues has been chosen. Throughout the RP-II proteases the residues Ser, His and Asp in the active site are highly conserved. In BLC they are Asp96, His47 and Ser167. The fourth distance chosen is the distance to the c-alpha atom of the amino acid residue coming first after the active site serine residue in the sequence (herein after called "next to Ser"); in the 3D structure of BLC it is Gly168.

In a preferred embodiment of the present invention, the distance between the ion-binding site and i) Asp c-alpha atom is 22.50-24.00 Å, ii) His c-alpha atom is 23.25-25.25 Å, iii) Ser c-alpha atom is 15.00-17.00 Å, iv) next to Ser c-alpha atom is 18.20-20.20 Å, However these distances may vary from one RP-II protease to the other, and as described above, the ion binding site may also bind to a sodium ion. The present distances are given with a calcium ion in the structure. If a sodium ion was bound instead the distances would be shifted a little bit. Generally the distances can vary ±0.8 Å, preferably ±0.7 Å, ±0.6 Å, ±0.5 Å, ±0.4 Å, or most preferably ±0.3 Å.

Further, in the RP-II proteases, the peptide structure circumscribing the ion-binding site is composed of the amino acid residues placed in positions 1-7, 159-162 and 143-145 with the coordinating atoms being the backbone carbonyl oxygen atom of residues 13, S5, D161 and water molecules.

3D structures of RP-II proteases can be modelled using the known structure of a related protease and general modelling tools as shown in Example 1. A prerequisite for obtaining a realistic 3D model structure is that the model is based on an adequate sequence homology higher than 50%, preferably higher than 55%, and even more preferred higher than 60% to the sequence of the protease for which the structure is known. RP-II Protease models can be constructed based on the 3D guided sequence alignments to BLC in FIG. 2.

Therefore 3D structure models of RP-II proteases could in principle be made by using the modelling tools and the known 3D structure of the toxin A protease from *Staphylococcus aureus* from the Exf family of proteases (Cavarelli et al. (1997) The Structure of *Staphylococcus aureus* Epidermolytic Toxin A, an atypic serine protease, at 1.7 Å resolution, Structure, Vol. 5, p. 813 (pdb name 1ARP).

If compared to the structure of the toxin A protease from *Staphylococcus aureus*, the structure of the RP-II proteases, as represented by BLC, can be divided into a "common protease" region, an "intermediate" region and a "nonhomologous" region.

The active site can be found in the common protease region, which is structurally closely related to the Toxin A structure. The common protease region is composed of residues 58, 70-83. The common protease region has an RMS lower than 1.2.

Outside the common protease region the structure of the RP-II protease BLC differs from the Toxin A structure to a greater extent.

The intermediate region consists of residues 14-28, 29-51, 94-104, 155-175. The intermediate region has an RMS bigger than 1.2 and less than 1.8. Any relationships between the three-dimensional structure and functionality based on modelling from the *S. aureus* 3D structure are potentially difficult to predict in this region of the RP-II proteases.

The common region and the intermediate region consist of the majority of the two central beta-barrels, especially the strands of the beta-barrels.

The nonhomologous region consists of residues 1-6, 7-13, 52-57, 59-69, 84-88, 89-93, 105-153. The nonhomologous region has a RMS higher than 1.5. Any relationships between the three-dimensional structure and functionality based on modelling from the *S. aureus* 3D structure are very difficult to predict in this region of the RP-II proteases.

Inferred structure-function relationships based on model building of a RP-II protease 3D structure on the 3D structure of *S. aureus* Toxin A would thus be very uncertain and speculative.

Homology Building of RP-II Proteases

A model structure of a RP-II protease can be built using the BLC structure in Appendix 1, or a structure similar to the BLC structure comprising the structural elements (a) two beta-barrel domains each comprising six long strands in antiparallel organisation, (b) three alpha helices, (c) at least one low affinity ion-binding site, and (d) an active site comprising the amino acid residues His, Asp and Ser, or other 3D RP-II protease structures, e.g. established by X-ray structure determination, that may become available in the future, and the Homology™ program or a comparable program, e.g., Modeller™ (both from Molecular Simulations, Inc., San Diego, Calif.). The principle is to align the amino acid sequence of a protein for which the 3D structure is known with the amino acid sequence of a protein for which a model 3D structure has to be constructed. The structurally conserved regions can then be built on the basis of consensus sequences. In areas lacking homology, loop structures can be inserted, or sequences can be deleted with subsequent bonding of the necessary residues using, e.g., the program Homology. Subsequent relaxation and optimization of the structure should be done using either Homology or another molecular simulation program, e.g., CHARMm™ from Molecular Simulations.

Methods for Designing BLC and RP-II or Sib Family Protease Variants

Comparisons of the molecular dynamics of different proteins can give a hint as to which domains are important or connected to certain properties pertained by each protein.

The present invention comprises a method of producing a variant of a parent BLC like RP-II protease, the variant having at least one altered property as compared to the parent BLC like RP-II protease, the method comprising:
  a) producing a model structure of the parent BLC like RP-II protease on the three-dimensional structure of BLC,
  b) comparing the model three-dimensional structure of the parent BLC like RP-II protease to the BLC structure by superimposing the structures through matching the active residues CA, CB, C, O, and N atoms,
  c) identifying on the basis of the comparison in step a) at least one structural part of the parent BLC like RP-II protease, wherein an alteration in said structural part is predicted to result in an altered property;
  d) modifying the nucleic acid sequence encoding the parent BLC like RP-II protease to produce a nucleic acid sequence encoding deletion or substitution of one or more amino acids at a position corresponding to said structural part, or an insertion of one or more amino acid residues in positions corresponding to said structural part;
  e) expressing the modified nucleic acid sequence in a host cell to produce the variant RP-II protease;
  f) isolating the produced protease;
  g) purifying the isolated protease and
  h) recovering the purified RP-II protease.

Stability—Alteration of Ion-Binding Site

An ion-binding site is a significant feature of an enzyme. Therefore alterations of the amino acid residues close to the ion-binding site are likely to result in alterations of the stability of the enzyme. Especially modifications affecting the charge distribution and/or the electrostatic field strength at or in the vicinity of the site are important.

Improved Stability

Stabilisation of the ion-binding site of RP-II proteases may be obtained by modifications in positions close to the ion binding site.

Such modifications may comprise the substitution of a positively charged amino acid residue with a neutral or negatively charged residue, or the substitution of a neutral residue with a negatively charged residue or the deletion of a positively charged or neutral residue in positions close to the ion binding site.

Positions located at a distance of 10 Å or less to the ion-binding site of BLC are: 1, 2, 3, 4, 5, 6, 7, 8, 143, 144, 145, 146, 158, 159, 160, 161, 162, 194, 199, 200, and 201. Especially positions 2, 3, 4, 5, 6, 7, 144, 159, 160, 161 located at a distance of 6 Å or less from the ion binding site are important.

Corresponding positions in other RP-II proteases may be identified using FIG. 2 herein.

The modifications D7E and D7Q in BLC are examples of suitable modifications in one of these positions.

Removal of Ion-Binding Site in BLC

By removing the ion-binding site it is possible to alter the dependency of the enzyme on calcium or other ions in the solution.

Removal of the Calcium site in BLC can be done by the substitutions H144R and/or D161R,K+H144Q,N (SEQ ID NO: 2). Similar modifications may be made in structurally corresponding residues in other RP-II proteases.

Alteration of Thermostability

A variant with improved stability (typically increased thermostability) may be obtained by modification of the mobility of identified regions, such as by introduction of disulfide bond(s), substitution with proline, alteration of hydrogen bond contact(s), altering charge distribution, introduction of salt bridge(s), filling in internal structural cavities with one or more amino acids with bulkier side groups (in e.g. regions which are structurally mobile), substitution of histidine residues with other amino acids, removal of a deamidation sites, or by helix capping.

Regions with Increased Mobility:

The below indicated regions of BLC have an increased mobility in the crystal structure of the enzyme, and it is presently believed that these regions can be responsible for stability or activity of BLC and the other RP-II proteases. Especially thermostabilisation may be obtained by altering the highly mobile regions. Generally, thermostability may be improved by making these regions less mobile. Improvements of the enzyme may be obtained by making modifications in the regions and positions identified below. Introducing e.g. larger residues or residues having more atoms in the side chain could increase the stability, or, e.g., introduction of residues having fewer atoms in the side chain could be important for the mobility and thus the activity profile of the enzyme. The regions can be found by analysing the B-factors taken from the coordinate file in Appendix 1, and/or from molecular dynamics calculations of the isotropic fluctuations. These can be obtained by using the program CHARMm from MSI (Molecular Simulations Inc.).

Molecular dynamics simulation at 300K and 400K of BLC reveals the following highly mobile regions:

26-31, 50-55, 89-91, and 193-198, and 4-5, 11-12, 26-31, 50-55, 69-70, 89-91, 178-183, 195-199 and 216-221, respectively.

It is contemplated that modifications in these regions may influence the thermostability of RP-II proteases. Modifications are preferably made in the regions 26-31 (26, 27, 28, 29, 30, 31); 89-91 (89, 90, 91); 216-221 (216, 217, 218, 219, 220, 221), and especially in BLC the substitutions G30A and G91A. Similar modifications may be made in structurally corresponding residues in other RP-II proteases.

Also B-factors (see "in X-Ray Structure Determination, Stout, G. K. and Jensen, L. H., John Wiley & Sons, Inc. NY, 1989") from crystallographic data indicate the following more mobile regions in the BLC (RP-II protease) structure:

51-56, (i.e. 51, 52, 53, 54, 55, 56)
88-94, (i.e. 88, 89, 90, 91, 92, 93, 94)
118-122 (I.e. 118, 119, 120, 121, 122)
173-183 (i.e. 173, 174, 175, 176, 177, 178, 179, 180, 181, 182, 183)

It is contemplated that modifications in these regions may influence the thermostability of RP-II proteases. Modifications are preferably made in the regions 51-56 and 118-122.

Disulfide Bonds:

A RP-II protease variant of the present invention with improved stability, e.g. thermostability, as compared to the parent RP-II protease may be obtained by introducing new interdomain or intra-domain bonds to provide a more rigid and stable structure, such as by establishing inter- or intra-domain disulfide bridges. This is done by introducing cysteines in appropriate positions in the RP-II molecule by substitution(s) or insertion(s).

According to the guidelines mentioned above the below mentioned amino acid residues identified in the amino acid sequence of SEQ ID NO: 2 are contemplated as being suitable for cysteine replacement. With one or more of these substitutions with cysteine, disulfide bridges may form in a variant of BLC. A stabilising disulfide bridge may be constructed through the substitutions: S145C and T128C Surface Charge Distribution A variant with improved stability (typically improved thermostability or storage stability) as compared to the parent RP-II protease may be obtained by changing the surface charge distribution of the RP-II protease. For example, when the pH is lowered to about 5 or below, histidine residues typically become positively charged and, consequently, unfavorable electrostatic interactions on the protein surface may occur. By engineering the surface charge of the RP-II protease one may avoid such unfavorable electrostatic interactions that in turn may lead to a higher stability of the RP-II protease.

Charged amino acid residues are (a) positively charged: Lys, Arg, His (pH<5), Tyr (pH>9) and Cys (pH>10) and (b) negatively charged: Asp and Glu.

The surface charge distribution may be modified by (a) removing charged residues from the surface through deletion of a charged residue or substituting an uncharged residue for a charged residue, (b) adding charged residues to the surface through insertion of a charged residue or substituting a charged residue for an uncharged residue, or (c) by reverting the charge at a residue through substituting a positively charged residue for a negatively charged residue or substituting a negatively charged residue for a positively charged residue.

Therefore, a further aspect of the present invention relates to a method for constructing a variant of a parent RP-II protease having a modified surface charge distribution, the method comprising:
   a) identifying, on the surface of the parent RP-II protease, at least one charged amino acid residue;
   b) modifying the charged residue identified in step (a) through deletion or substitution with an uncharged amino acid residue;
   c) optionally repeating steps a) and b) recursively;
   d) preparing the variant resulting from steps a)-c);
   e) testing the stability of said variant; and
   f) optionally repeating steps a)-e) recursively; and
   g) selecting a RP-II protease variant having increased stability as compared to the parent RP-II protease.

As will be understood by the skilled person it may also, in some cases, be advantageous to substitute an uncharged amino acid residue with an amino acid residue bearing a charge or, alternatively, it may in some cases be advantageous to substitute an amino acid residue bearing a charge with an amino acid residue bearing a charge of opposite sign. Thus, the above-mentioned method may be employed by the skilled person also for these purposes. In the case of substituting an uncharged amino acid residue with an amino acid residue bearing a charge the above-mentioned method may be employed the only difference being steps a) and b) which will then read:
   a) identifying, on the surface of the parent RP-II protease, at least one position being occupied by an uncharged amino acid residue;
   b) modifying the charge in that position by substituting the uncharged amino acid residue with a charged amino acid residue or by insertion of a charged amino acid residue at the position.

Also in the case of changing the sign of an amino acid residue present on the surface of the RP-II protease the above method may be employed. Again, compared to the above method, the only difference being steps a) and b) which, in this case, read:
   a) identifying, on the surface of the parent RP-II protease, at least one charged amino acid residue;
   b) substituting the charged amino acid residue identified in step (a) with an amino acid residue having an opposite charge.

In order to determine the amino acid residues of a protease, which are present on the surface of the enzyme, the surface accessible area are measured using the DSSP program (Kabsch and Sander, *Biopolymers* (1983), 22, 2577-2637). All residues having a surface accessibility higher than 0, 0.10, 0.20, 0.30, 0.35, 0.40, 0.45, 0.50, 0.55 or 0.60 are regarded a surface residue.

An amino acid residue found on the surface of BLC using the above method is T109 and it is contemplated that the substitutions T109R, K, H are of particular interest.

Similar substitutions may be introduced in equivalent positions of other RP-II proteases.

For the purpose of providing RP-II protease variants exhibiting improved wash performance it is possible to modify the pI of the RP-II protease through modification of the surface charge as indicated in WO 91/00345 (Novozymes A/S) and/or WO 99/20771 (Genencor International, Inc.)

Especially changing the pI of the RP-II protease is of interest

Changes in BLC:
T109R, K, H
Q143R, K, H
E209Q, N
D7N, S, T
Q174R, K, H
N216R, K, H
Y17R, K, H
Y95R, K, H Corresponding modifications may be performed in corresponding positions of other RP-II proteases.

Substitution with Proline Residues

Improved thermostability of a RP-II protease can be obtained by subjecting the RP-II protease in question to analysis for secondary structure, identifying residues in the RP-II protease having dihedral angles $\phi$ (phi) and $\psi$ (psi) confined to the intervals [$-90°<\phi<-40°$ and $-180°<\psi<180°$], preferably the intervals [$-90°<\phi<-40°$ and $120°<\psi<180°$] or [$-90°<\phi<-40°$ and $-50°<\psi<10°$] and excluding residues located in regions in which the RP-II protease is characterized by possessing α-helical or β-sheet structure.

After the dihedral angles $\phi$ (phi) and $\psi$ (psi) for the amino acids have been calculated, based on the atomic structure in the crystalline RP-II proteases, it is possible to select position(s) which has/have dihedral phi and psi angles favourable for substitution with a proline residue. The aliphatic side chain of proline residues is bonded covalently to the nitrogen atom of the peptide group. The resulting cyclic five-membered ring consequently imposes a rigid constraint on the rotation about the N—$C_\alpha$ bond of the peptide backbone and simultaneously prevents the formation of hydrogen bonding to the backbone N-atom. For these structural reasons, proline residues are generally not compatible with α-helical and β-sheet secondary conformations.

If a proline residue is not already at the identified position(s), the naturally occurring amino acid residue is substituted with a proline residue, preferably by site directed mutagenesis applied on a gene encoding the RP-II protease in question.

In the group of BLC-like proteases proline residues can be introduced at positions 18, 115, 185, 269 and 293. Accordingly, a preferred BLC variant has one or more of the substitutions: T60P, S221P, G193P, and V194P.

Alteration of Activity:

Amino acid residues at a distance of less than 10 Å from the active site residues are most likely to influence the specificity and activity of the RP-II proteases, therefore variants comprising modifications in positions 1, 8, 22-35 (22, 23, 24, 25, 26, 27, 28, 29, 30, 31, 32, 33, 34, 35), 42-58 (42, 43, 44, 45, 46, 47, 48, 49, 50, 51, 52, 53, 54, 55, 56, 57, 58), 82-100 (82, 83, 84, 85, 86, 87, 88, 89, 90, 91, 92, 93, 94, 95, 96, 97, 98, 99, 100), 129-135 (1129, 130, 131, 132, 133, 134, 135), 141-142, 153-156 (153, 154, 155, 156), 158, 161-171 (161, 162, 163, 164, 165, 166, 167, 168, 169, 170, 171), 188-193 (188, 189, 190, 191, 192, 193), 195, 201-207 (201, 202, 203, 204, 205, 206, 207), 210, 213-214, 217 may provide a change in activity and/or specificity of the RP-II protease variant.

Substrate Binding Site

The substrate binding site is identified by the residues in contact with a substrate model, such as the DAFE. The 3D structure coordinates of the BLC protease with DAFE bound in the active site can be found in Appendix 1. Without being limited to any theory, it is presently believed that binding between a substrate and an enzyme is supported by favorable interactions found within a sphere 10 Å from the substrate molecule, in particular within a sphere of 6 Å from the substrate molecule. Examples of such favorable bonds are hydrogen bonds, strong electrostatic interaction and/or hydrophobic interactions.

The following residues of the BLC protease (SEQ ID NO:1), are within a distance of 10 Å from the peptide DAFE and thus believed to be involved in interactions with said substrate: 1, 2, 3, 8, 25, 29, 30, 31, 32, 33, 34, 44, 45, 46, 47, 48, 49, 50, 51, 52, 53, 90, 91, 92, 93, 94, 95, 96, 97, 129, 131, 132, 133, 134, 135, 155, 157, 158, 159, 160, 161, 162, 163, 164, 165, 166, 167, 168, 169, 171, 189, 190, 191, 192, 193, 194, 195, 196, 197, 198, 200 and 204.

The following residues of the BLC protease (SEQ ID NO: 1), are within a distance of 6 Å from the peptide DAFE and thus believed to be involved in interactions with said substrate: 1, 2, 31, 32, 47, 48, 88, 91, 93, 96, 162, 163, 164, 165, 166, 167, 168, 190, 191, 192, 193, 194, 195, and 201.

Helix Capping:

For the RP-II proteases helix capping may be obtained by modifying the position structurally corresponding to position 221 in BLC, and specifically in BLC by the modification A221N,T Removal of Deamidation Sites For the RP-II proteases, removal of deamidation sites may be obtained by modifying the positions structurally corresponding to positions 213, 216, and 222 of BLC, and specifically in BLC by the modifications.

N213A,C,D,E,F,G,H,I,K,L,P,Q,R,S,T,V,Y,M,W preferably N213L,T,S

N216A,C,D,E,F,G,H,I,K,L,P,Q,R,S,T,V,Y,M,W preferably N216L,T,S

N222A,C,D,E,F,G,H,I,K,L,P,Q,R,S,T,V,Y,M,W preferably N222L,T,S

Combined Modifications

The present invention also encompasses any of the above mentioned RP-II protease variants in combination with any other modification to the amino acid sequence thereof. Especially combinations with other modifications known in the art to provide improved properties to the enzyme are envisaged. Such modifications to be combined with any of the above indicated modifications are exemplified in the following.

Removal of Critical Oxidation Sites

In order to increase the stability of the RP-II protease it may be advantageous to substitute or delete critical oxidation sites, such as methionines, with other amino acid residues which are not subject to oxidation.

Accordingly, in a further embodiment the present invention relates to an RP-II protease variant, in which one or more amino acid residues susceptible to oxidation, especially methionine residues exposed to the surface of the molecule, is/are deleted or replaced with another amino acid residue less susceptible to oxidation. The amino acid residue less susceptible to oxidation may for instance be selected from the group consisting of A, E, N, Q, I, L, S and K.

Specific such variants comprises at least one of the deletions or substitutions M36{*,S,A,N,Q,K}; M160{*,S,A,N,Q,K} of the BLC protease; M144{*,S,A,N,Q,K} of the AC116 and CDJ31 proteases; M67{*,S,A,N,Q,K}, M79{*,S,A,N,Q,K}, M137{*,S,A,N,Q,K}, M144{*,S,A,N,Q,K}, and M171{*,S,A,N,Q,K} of the BO32, BIP and JA96 proteases; M159{*,S,A,N,Q,K} of the BO32 protease; M81{*,S,A,N,Q,K}, and M141{*,S,A,N,Q,K} in the MPR protease; and M17{*,S,A,N,Q,K}, M67{*,S,A,N,Q,K}, M144{*,S,A,N,Q,K}, M160{*,S,A,N,Q,K}, M186{*,S,A,N,Q,K}, and M217{*,S,A,N,Q,K} of the AA513 protease (positions are indicated in relation to the BLC protease as indicated in FIG. 2).

Modification of Asn-Gly Sequences in the Protease

It is known that at alkaline pH, the side chain of Asn may interact with the NH group of a sequential neighboring amino acid to form an isoAsp residue where the backbone goes through the Asp side chain. This will leave the backbone more vulnerable to proteolysis. The deamidation is much more likely to occur if the residue that follows is a Gly. Changing the Asn in front of the Gly or the Gly will prevent this from happening and thus improve the stability, especially as concerns thermo- and storage stability.

The invention consequently further relates to an RP-II protease variant, in which either or both residues of any of the Asn-Gly sequence appearing in the amino acid sequence of the parent RP-II protease is/are deleted or substituted with a residue of a different amino acid.

The Asn and/or Gly residue may, for instance, be substituted with a residue of an amino acid selected from the group consisting of A, Q, S, P, T and Y.

More specifically, any of the Asn or Gly residues of the Asn-Gly occupying positions 68-69, 182-183 and/or 192-193 of the BLC protease; positions 68-69 and/or 192-193 of the AC116 and CDJ-31 proteases, positions 45-46, 74-75, 196-197, and/or 201-202 of the BO32, JA96 and BIP proteases, positions 68-69, 103-104 and/or 192-196 of the MPR protease; and positions 90-91 and/or 201-202 of the AA513 protease, may be deleted or substituted with a residue of an amino acid selected from the group consisting of A, Q, S, P, T and Y. (positions are indicated in relation to the BLC protease as indicated in FIG. 2)

Specific Variants of BLC are:

N68{*,A,Q,S,P,T,Y}; G69{*,A,Q,S,P,T,Y}
N68{*,A,Q,S,P,T,Y}+G69{*,A,Q,S,P,T,Y}
N182{*,A,Q,S,P,T,Y}; G183{*,A,Q,S,P,T,Y}
N182{*,A,Q,S,P,T,Y}+G183{*,A,Q,S,P,T,Y}
N192{*,A,Q,S,P,T,Y}; G193{*,A,Q,S,P,T,Y}
N192{*,A,Q,S,P,T,Y}+G193{*,A,Q,S,P,T,Y}
and combinations thereof.

Specific Variants of the AC116 and CDJ-31 Proteases are:
N68{*,A,Q,S,P,T,Y}; G69{*,A,Q,S,P,T,Y}
N68{*,A,Q,S,P,T,Y}+G69{*,A,Q,S,P,T,Y}
N192{*,A,Q,S,P,T,Y}; G193{*,A,Q,S,P,T,Y}
N192{*,A,Q,S,P,T,Y}+G193{*,A,Q,S,P,T,Y}
N68{*,A,Q,S,P,T,Y}+N192{*,A,Q,S,P,T,Y}
and combinations thereof.
Specific Variants of BO32, JA96 and BIP Proteases are:
N45{*,A,Q,S,P,T,Y}; G46{*,A,Q,S,P,T,Y}
N45{*,A,Q,S,P,T,Y}+G46{*,A,Q,S,P,T,Y}
N74{*,A,Q,S,P,T,Y}; G75{*,A,Q,S,P,T,Y}
N74{*,A,Q,S,P,T,Y}+G75{*,A,Q,S,P,T,Y}
N196{*,A,Q,S,P,T,Y}; G197{*,A,Q,S,P,T,Y}
N196{*,A,Q,S,P,T,Y}+G197{*,A,Q,S,P,T,Y}
N201{*,A,Q,S,P,T,Y}; G202{*,A,Q,S,P,T,Y}
N201{*,A,Q,S,P,T,Y}+G202{*,A,Q,S,P,T,Y}
N45{*,A,Q,S,P,T,Y}+N74{*,A,Q,S,P,T,Y}
N45{*,A,Q,S,P,T,Y}+N196{*,A,Q,S,P,T,Y}
N45{*,A,Q,S,P,T,Y}+N201{*,A,Q,S,P,T,Y}
N74{*,A,Q,S,P,T,Y}+N196{*,A,Q,S,P,T,Y}
N74{*,A,Q,S,P,T,Y}+N201{*,A,Q,S,P,T,Y}
N196{*,A,Q,S,P,T,Y}+N201{*,A,Q,S,P,T,Y}
N45{*,A,Q,S,P,T,Y}+N74{*,A,Q,S,P,T,Y}+N196{*,A,Q,S,P,T,Y}
N45{*,A,Q,S,P,T,Y}+N74{*,A,Q,S,P,T,Y}+N201{*,A,Q,S,P,T,Y}
N45{*,A,Q,S,P,T,Y}+N196{*,A,Q,S,P,T,Y}+N201{*,A,Q,S,P,T,Y}
N74{*,A,Q,S,P,T,Y}+N196{*,A,Q,S,P,T,Y}+N201{*,A,Q,S,P,T,Y}
N45{*,A,Q,S,P,T,Y}+N74{*,A,Q,S,P,T,Y}+N196{*,A,Q,S,P,T,Y}+N201{*,A,Q,S,P,T,Y}
and combinations thereof.
Specific Variants of AA513 are:
N90{*,A,Q,S,P,T,Y}; G91{*,A,Q,S,P,T,Y}
N90{*,A,Q,S,P,T,Y}+G91{*,A,Q,S,P,T,Y}
N201{*,A,Q,S,P,T,Y}; G202{*,A,Q,S,P,T,Y}
N201{*,A,Q,S,P,T,Y}+G202{*,A,Q,S,P,T,Y}
N90{*,A,Q,S,P,T,Y}+N201{*,A,Q,S,P,T,Y}
and combinations thereof.
Specific Variants of MPR are:
N68{*,A,Q,S,P,T,Y}; G69{*,A,Q,S,P,T,Y}
N68{*,A,Q,S,P,T,Y}+G69{*,A,Q,S,P,T,Y}
N103{*,A,Q,S,P,T,Y}; G104{*,A,Q,S,P,T,Y}
N103{*,A,Q,S,P,T,Y}+G104{*,A,Q,S,P,T,Y}
N192{*,A,Q,S,P,T,Y}; G196{*,A,Q,S,P,T,Y}
N192{*,A,Q,S,P,T,Y}+G196{*,A,Q,S,P,T,Y}
N68{*,A,Q,S,P,T,Y}+N103{*,A,Q,S,P,T,Y}
N68{*,A,Q,S,P,T,Y}+N192{*,A,Q,S,P,T,Y}
N103{*,A,Q,S,P,T,Y}+N192{*,A,Q,S,P,T,Y}
N68{*,A,Q,S,P,T,Y}+N103{*,A,Q,S,P,T,Y}+N192{*,A,Q,S,P,T,Y}
and combinations thereof.
Removal of Autoproteolysis Sites According to a further aspect of the invention autoproteolysis sites may be removed by changing the amino acids at an autoproteolysis site. Since the RP-II proteases cleaves at Glu and Asp residues it is preferred to modify such residues of a parent RP-II protease having the same or a similar specificity, preferably by substituting with any other amino acid except Glu.

The parent RP-II proteases are mostly specific towards Glu and to a minor extent towards Asp residues. Therefore the modification of the parent (trypsin-like) RP-II protease may preferably be made by changing Glu to another amino acid residue (including Asp). Experiments have indicated that the substitution of Ala for Glu or Asp provides good results.

Glu and Asp residue are in the BLC, CDJ31 and AC116 proteases found in positions E101, E152, E173, E209, D6, D51, D96, D135, D161, and D212. BLC has a further Glu in position E104 and Asp in D7.

Specific BLC, CDJ31 and AC116 variants are thus E101A, E152A, E173A, E209A, D6A, D51A, D135A, D161A, D212A, and double, triple, quadruple, etc. combinations thereof. Further specific BLC variants are E104A and D7A.

In JA96, BO32 and BIP Glu and Asp are found at positions E81, E143, E151, E209, D5, D6, D69, D96, D103, D135, D152, D161, and D173.

Specific JA96, BO32 and BIP variants are thus E81A, E143A, E151A, E202A, D5A, D6A, D69A, D96A, D103A, D135A, D152A, D161A, D173A, and double, triple, quadruple, etc. combinations thereof.

In MPR Glu and Asp are found at positions E7, E89a, E152, D6, D54, D92, D96, D135, D144, D161, D177 and D209

Specific MPR variants are thus E7A, E89aA, E152A, D6A, D54A, D92A, D96A, D135A, D144A, D161A, D177A and D209A, and double, triple, quadruple, etc. combinations thereof.

In AA513 Glu and Asp are found at positions E26, E55, E94, E117, E123, E137b, E199, D40, D96, D103b, D103d, D135, D149, D154, D161, D184 and D209

Specific AA513 variants are thus E26A, E55A, E94A, E117A, E123A, E137bA, E199A, D40A, D96A, D103bA, D103dA, D135A, D149A, D154A, D161A, D184A and D209A, and double, triple, quadruple, etc. combinations thereof.

Corresponding variants are easily identified in any other RP-II protease.

Alternatively autoproteolysis can be prevented by changing the amino acid residue occupying the 1st and/or 2nd position following the Glu or Asp residue in question to Pro. For instance, this may in BLC, CDJ31 and AC116 be done in the positions 174 and/or 175 as follows:

Q174P; S175P; Q174P+5175P or in a similar manner in JA96, BO32 or BIP at positions 152 and/or 153 as D152P; T153P; or D152P+T153P.

Corresponding variants are easily identified in these and any other RP-II protease.

Modification of Tryptophan Residues

In order to stabilize the protein it may be advantageous to replace or delete tryptophan residues at the surface of the protein, e.g., as described in U.S. Pat. No. 5,118,623. The tryptophan residues may advantageously be substituted for F, T, Q or G. Thus, in a further embodiment the invention relates to an RP-II variant comprising one or more of the following substitutions:

BLC and AC116:
W35{F,T,Q,G}; W88{F,T,Q,G}; W142{F,T,Q,G}; W217{F,T,Q,G}
CDJ31:
W142{F,T,Q,G}; W217{F,T,Q,G};
BO32, JA96 and BIP:
W142{F,T,Q,G};
AA513:
W30{F,T,Q,G}; W72{F,T,Q,G}; W142{F,T,Q,G}
MPR:
W57{F,T,Q,G}; W88{F,T,Q,G}; W112{F,T,Q,G}; W142{F,T,Q,G}; W217{F,T,Q,G}
Modification of Tyrosines In relation to wash performance it has been found that the modification of certain tyrosine residues to phenylalanine provides an improved wash performance. Without being bound by any specific theory, it is believed that titration of these Tyr residues in the alkaline wash liquor has negative effects that are alleviated by replacing the Tyr residues with other residues, especially Phe or Trp, particularly Phe.

In the BLC, AC116 and CDJ31 parent RP-II proteases, the following tyrosine residues may be modified:
19, 50, 72, 74, 82, 95, 97, 112, 115, 117, 132, 154, 163, 195, 200. In BLC and CDJ31 the tyrosines in positions 17 and 158 may also be modified, and in AC116 and CDJ31 the tyrosines in position 172

Examples of specific variants comprise one or more of the following substitutions:
Y17{F,W}, Y19{F,W}, Y50{F,W}, Y72{F,W}, Y74{F,W}, Y82{F,W}, Y88{F,W}, Y95{F,W}, Y97{F,W}, Y112{F,W}, Y115{F,W}, Y117{F,W}, Y132{F,W}, Y154{F,W}, Y158{F,W}, Y163{F,W}, Y172{F,W}, Y195{F,W}, Y200{F,W}

In the JA96, BO32 and BIP parent RP-II proteases, the following tyrosine residues may be modified:
19, 24, 50, 57, 64, 83, 88, 95, 112, 132, 157, 158, 195, 216

Examples of specific JA96, BO32 and BIP variants comprises one or more of the following substitutions:
Y19{F,W}, Y24{F,W}, Y50{F,W}, Y57{F,W}, Y64{F,W}, Y83{F,W}, Y88{F,W}, Y95{F,W}, Y112{F,W}, Y132{F,W}, Y157{F,W}, Y158{F,W}, Y195{F,W} and Y216{F,W}

In the AA513 parent RP-II protease, the following tyrosine residues may be modified:
24, 74, 77, 84, 88, 97, 130, 132, 158, 163, 193a Examples of specific AA513 variants comprises one or more of the following substitutions:
Y24{F,W}, Y74{F,W}, Y77{F,W}, Y84{F,W}, Y88{F,W}, Y97{F,W}, Y130{F,W}, Y132{F,W}, Y158{F,W}, Y163{F,W}, Y193A{F,W}

In the MPR parent RP-II protease, the following tyrosine residues may be modified:
19, 28a, 30, 50, 72, 74, 77, 83, 95, 97, 113, 115, 154, 158, 163, 172, 175, 200, 216

Examples of specific MPR variants comprises one or more of the following substitutions:
Y19{F,W}, Y28Ad{F,W}, Y30{F,W}, Y50{F,W}, Y72{F,W}, Y74{F,W}, Y77{F,W}, Y83{F,W}, Y95{F,W}, Y97{F,W}, Y113{F,W}, 115{F,W}, Y154{F,W}, Y158{F,W}, Y163{F,W}, Y172{F,W}, Y175{F,W}, Y200{F,W}, Y216{F,W}

Other Modifications for Combination

Examples of specific BLC variants comprises one or more of the following substitutions:
E152{A,R,K,G}
E173A
E209A
E152G+G164R Methods of Preparing RP-II Protease Variants The RP-II protease variants of the present invention may be produced by any known method within the art. The invention also relates to polynucleotides encoding the RP-II protease variants of the present invention, DNA constructs comprising such polynucleotides and host cells comprising such constructs or polynucleotides.

In general natural occurring proteins may be produced by culturing the organism expressing the protein and subsequently purifying the protein, or recombinantly by cloning a polynucleotide, e.g. genomic DNA or cDNA, encoding the protein into an expression vector, introducing said expression vector into a host cell, culturing the host cell and purifying the expressed protein.

Site-Directed Mutagenesis

Typically protein variants may be produced by site-directed mutagenesis of the gene encoding a parent protein, introduction of the mutated gene into an expression vector, host cell etc. The gene encoding the parent protein may be cloned from a strain producing the polypeptide or from an expression library, i.e. it may be isolated from genomic DNA or prepared from cDNA, or a combination thereof. The gene may even be a fully synthetically produced gene.

In general standard procedures for cloning of genes and/or introducing mutations (random and/or site directed) into said genes may be used in order to obtain a parent RP-II protease, or RP-II protease variant of the invention. For further description of suitable techniques reference is made to Molecular cloning: A laboratory manual (Sambrook et al. (1989), Cold Spring Harbor lab., Cold Spring Harbor, N.Y.; Ausubel, F. M. et al. (eds.)); Current protocols in Molecular Biology (John Wiley and Sons, 1995; Harwood, C. R., and Cutting, S. M. (eds.)); Molecular Biological Methods for *Bacillus* (John Wiley and Sons, 1990); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); A Practical Guide To Molecular Cloning (B. Perbal, (1984)) and WO 96/34946.

Localized and Region Specific Random Mutagenesis

Random mutagenesis is suitably performed either as localized or region-specific random mutagenesis in at least three parts of the gene translating to the amino acid sequence shown in question, or within the whole gene.

The random mutagenesis of a DNA sequence encoding a parent RP-II protease may be conveniently performed by use of any method known in the art.

In relation to the above, a further aspect of the present invention relates to a method for generating a variant of a parent RP-II protease wherein the variant exhibits an altered property, such as increased thermostability, increased stability at low pH and at low calcium concentration, relative to the parent RP-II protease, the method comprising:

a) subjecting a DNA sequence encoding the parent protease to localized or region-specific random mutagenesis, b) expressing the mutated DNA sequence obtained in step (a) in a host cell, and c) screening for host cells expressing a RP-II protease variant which has an altered property relative to the parent RP-II protease.

Step (a) of the above method of the invention is preferably performed using doped primers.

When the mutagenesis is performed by the use of an oligonucleotide, the oligonucleotide may be doped or spiked with the three non-parent nucleotides during the synthesis of the oligonucleotide at the positions that are to be changed. The doping or spiking may be done so that codons for unwanted amino acids are avoided. The doped or spiked oligonucleotide can be incorporated into the DNA encoding the RP-II protease by any published technique, using, e.g., PCR, LCR or any DNA polymerase and ligase as deemed appropriate.

Preferably, the doping is carried out using "constant random doping", in which the percentage of wild-type and modification in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% modifications in each position. An additional consideration in the choice of a doping scheme is based on genetic as well as protein-structural constraints. The doping scheme may be made by using the DOPE program which, inter alia, ensures that introduction of stop codons is avoided (L. J. Jensen et al. *Nucleic Acid Research*, 26, 697-702 (1998).

The DNA sequence to be mutagenized may conveniently be present in a genomic or cDNA library prepared from an organism expressing the parent RP-II protease. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulants, Bacillus circulans, Bacillus lautus, Bacillus megaterium, Bacillus thuringiensis, Streptomyces lividans* or *Streptomyces murinus*; and gram negative bacteria such as *E. coli*.

The mutated DNA sequence may further comprise a DNA sequence encoding functions permitting expression of the mutated DNA sequence.

Localised Random Mutagenesis

The random mutagenesis may be advantageously localised to a part of the parent RP-II protease in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localised or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

General Method for Localised Random Mutagenesis by Use of the DOPE Program

The localised random mutagenesis may be carried out by the following steps:

1. Select regions of interest for modification in the parent enzyme
2. Decide on mutation sites and non-mutated sites in the selected region
3. Decide on which kind of mutations should be carried out, e.g. with respect to the desired stability and/or performance of the variant to be constructed
4. Select structurally based mutations
5. Adjust the residues selected in step 3 with regard to step 4.
6. Analyse by use of a suitable dope algorithm the nucleotide distribution.
7. If necessary, adjust the wanted residues to genetic code realism, e.g. taking into account constraints resulting from the genetic code, e.g. in order to avoid introduction of stop codons; the skilled person will be aware that some codon combinations cannot be used in practice and will need to be adapted
8. Make primers
9. Perform localised random mutagenesis by use of the primers
10. Select resulting RP-II protease variants by screening for the desired improved properties.

Suitable dope algorithms for use in step 6 are well known in the art. One such algorithm is described by Tomandl, D. et al., 1997, Journal of Computer-Aided Molecular Design 11:29-38. Another algorithm is DOPE (Jensen, L J, Andersen, K V, Svendsen, A, and Kretzschmar, T (1998) Nucleic Acids Research 26:697-702).

Expression Vectors

A recombinant expression vector comprising a nucleic acid sequence encoding a RP-II protease variant of the invention may be any vector that may conveniently be subjected to recombinant DNA procedures and which may bring about the expression of the nucleic acid sequence.

The choice of vector will often depend on the host cell into which it is to be introduced. Examples of a suitable vector include a linear or closed circular plasmid or a virus. The vector may be an autonomously replicating vector, i.e., a vector which exists as an extra-chromosomal entity, the replication of which is independent of chromosomal replication, e.g., a plasmid, an extra-chromosomal element, a mini chromosome, or an artificial chromosome. The vector may contain any means for assuring self-replication. Examples of bacterial origins of replication are the origins of replication of plasmids pBR322, pUC19, pACYC177, pACYC184, pUB110, pE194, pTA1060, and pAMβ1. Examples of origin of replications for use in a yeast host cell are the 2 micron origin of replication, the combination of CEN6 and ARS4, and the combination of CEN3 and ARS1. The origin of replication may be one having a mutation which makes it function as temperature-sensitive in the host cell (see, e.g., Ehrlich, 1978, Proceedings of the National Academy of Sciences USA 75:1433).

Alternatively, the vector may be one which, when introduced into the host cell, is integrated into the genome and replicated together with the chromosome(s) into which it has been integrated. Vectors which are integrated into the genome of the host cell may contain any nucleic acid sequence enabling integration into the genome; in particular it may contain nucleic acid sequences facilitating integration into the genome by homologous or non-homologous re-combination. The vector system may be a single vector, e.g. plasmid or virus, or two or more vectors, e.g. plasmids or virus', which together contain the total DNA to be introduced into the genome of the host cell, or a transposon.

The vector may in particular be an expression vector in which the DNA sequence encoding the RP-II protease variant of the invention is operably linked to additional segments or control sequences required for transcription of the DNA. The term, "operably linked" indicates that the segments are arranged so that they function in concert for their intended purposes, e.g. transcription initiates in a promoter and proceeds through the DNA sequence encoding the RP-II protease variant. Additional segments or control sequences include a promoter, a polyadenylation sequence, a propeptide sequence, a signal sequence and a transcription terminator. At a minimum the control sequences include a promoter and transcriptional and translational stop signals.

The promoter may be any DNA sequence that shows transcriptional activity in the host cell of choice and may be derived from genes encoding proteins either homologous or heterologous to the host cell.

Examples of suitable promoters for use in bacterial host cells include the promoter of the *Bacillus subtilis* levansucrase gene (sacB), the *Bacillus stearothermophilus* maltogenic amylase gene (amyM), the *Bacillus licheniformis* alpha-amylase gene (amyL), the *Bacillus amyloliquefaciens* alpha-amylase gene (amyQ), the *Bacillus subtilis* alkaline protease gene, or the *Bacillus pumilus* xylosidase gene, the *Bacillus amyloliquefaciens* BAN amylase gene, the *Bacillus licheniformis* penicillinase gene (penP), the *Bacillus subtilis* xylA and xylB genes, and the prokaryotic beta-lactamase gene (Villa-Kamaroff et al., 1978, Proceedings of the National Academy of Sciences USA 75:3727-3731). Other examples include the phage Lambda $P_R$ or $P_L$ promoters or the *E. coli* lac, trp or tac promoters or the *Streptomyces coelicolor* agarase gene (dagA). Further promoters are described in "Useful proteins from recombinant bacteria" in Scientific American, 1980, 242:74-94; and in Sambrook et al., 1989, supra.

Examples of suitable promoters for use in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (as described in U.S. Pat. No. 4,288,627, which is incorporated herein by reference), and hybrids thereof. Particularly preferred promoters for use in filamentous fungal host cells are the TAKA amylase, NA2-tpi (a hybrid of the promoters from the genes encoding *Aspergillus niger* neutral (-amylase and *Aspergillus oryzae* triose phosphate isomerase), and glaA promoters. Further suitable promoters for use in filamentous fungus host cells are the ADH3 promoter (McKnight et al., The EMBO J. 4 (1985), 2093-2099) or the tpiA promoter.

Examples of suitable promoters for use in yeast host cells include promoters from yeast glycolytic genes (Hitzeman et al., J. Biol. Chem. 255 (1980), 12073-12080; Alber and Kawasaki, J. Mol. Appl. Gen. 1 (1982), 419-434) or alcohol dehydrogenase genes (Young et al., in Genetic Engineering of Microorganisms for Chemicals (Hollaender et al, eds.), Plenum Press, New York, 1982), or the TPI1 (U.S. Pat. No. 4,599,311) or ADH2-4-c (Russell et al., Nature 304 (1983), 652-654) promoters.

Further useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8:423-488. In a mammalian host cell, useful promoters include viral promoters such as those from Simian Virus 40 (SV40), Rous sarcoma virus (RSV), adenovirus, and bovine papilloma virus (BPV).

Examples of suitable promoters for use in mammalian cells are the SV40 promoter (Subramani et al., Mol. Cell. Biol. 1 (1981), 854-864), the MT-1 (metallothionein gene) promoter (Palmiter et al., Science 222 (1983), 809-814) or the adenovirus 2 major late promoter.

An example of a suitable promoter for use in insect cells is the polyhedrin promoter (U.S. Pat. No. 4,745,051; Vasuvedan et al., FEBS Lett. 311, (1992) 7-11), the P10 promoter (J. M. Vlak et al., J. Gen. Virology 69, 1988, pp. 765-776), the *Autographa californica* polyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

The DNA sequence encoding a RP-II protease variant of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like ampicillin, kanamycin, chloramphenicol, erythromycin, tetracycline, spectinomycine, neomycin, hygromycin, methotrexate, or resistance to heavy metals, virus or herbicides, or which provides for prototrophy or auxotrophs. Examples of bacterial selectable markers are the dal genes from *Bacillus subtilis* or *Bacillus licheniformis*, resistance. A frequently used mammalian marker is the dihydrofolate reductase gene (DHFR). Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Particularly, for use in an *Aspergillus* cell are the amdS and pyrG markers of *Aspergillus nidulans* or *Aspergillus oryzae* and the bar marker of *Streptomyces hygroscopicus*. Furthermore, selection may be accomplished by co-transformation, e.g., as described in WO 91/17243, where the selectable marker is on a separate vector.

To direct a RP-II protease variant of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme. The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al.).

More than one copy of a nucleic acid sequence encoding an enzyme of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The nucleic acid constructs of the present invention may also comprise one or more nucleic acid sequences which encode one or more factors that are advantageous in the expression of the polypeptide, e.g., an activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

Host Cells

The DNA sequence encoding a RP-II protease variant of the present invention may be either homologous or heterologous to the host cell into which it is introduced. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell that is capable of producing the present RP-II protease variants, such as prokaryotes, e.g. bacteria or eukaryotes, such as fungal cells, e.g. yeasts or filamentous fungi, insect cells, plant cells or mammalian cells.

Examples of bacterial host cells which, on cultivation, are capable of producing the RP-II protease variants of the invention are gram-positive bacteria such as strains of *Bacillus*, e.g. strains of *B. subtilis, B. licheniformis, B. lentus, B. brevis, B. stearothermophilus, B. alkalophilus, B. amyloliquefaciens, B. coagulans, B. circulans, B. lautus, B. megaterium* or *B. thuringiensis*, or strains of *Streptomyces*, such as *S. lividans* or *S. murinus*, or gram-negative bacteria such as *Escherichia coli* or *Pseudomonas* sp.

The transformation of the bacteria may be effected by protoplast transformation, electroporation, conjugation, or by using competent cells in a manner known per se (cf. Sambrook et al., supra).

When expressing the RP-II protease variant in bacteria such as *E. coli*, the enzyme may be retained in the cytoplasm, typically as insoluble granules (known as inclusion bodies), or it may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the RP-II protease variant in gram-positive bacteria such as *Bacillus* or *Streptomyces* strains, the enzyme may be retained in the cytoplasm, or it may be directed to the extracellular medium by a bacterial secretion sequence. In the latter case, the enzyme may be recovered from the medium as described below.

Examples of host yeast cells include cells of a species of *Candida, Kluyveromyces, Saccharomyces, Schizosaccharomyces, Pichia, Hansehula*, or *Yarrowia*. In a particular embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. Other useful yeast host cells are a *Kluyveromyces lactis, Kluyveromyces fragilis, Hansehula polymorpha, Pichia pastoris, Yarrowia lipolytica, Schizosaccharomyces pombe, Ustilgo maylis, Candida maltose, Pichia guillermondii* and *Pichia methanolio* cell (cf. Gleeson et al., J. Gen. Microbiol. 132, 1986, pp. 3459-3465; U.S. Pat. No. 4,882,279 and U.S. Pat. No. 4,879,231). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., Biochemistry and Genetics of Yeast, Bacil, M., Horecker, B. J., and Stopani, A. O. M., editors, 2nd edition, 1987; The Yeasts, Rose, A. H., and Harrison, J. S., editors, 2nd edition, 1987; and The Molecular Biology of the Yeast *Saccharomyces*, Strathern et al., editors, 1981). Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153:163; and Hinnen et al., 1978, Proceedings of the National Academy of Sciences USA 75:1920.

Examples of filamentous fungal cells include filamentous forms of the subdivision Eumycota and Oomycota (as defined by Hawksworth et al., 1995, supra), in particular it may of the a cell of a species of *Acremonium*, such as *A. chrysogenum*, *Aspergillus*, such as *A. awamori, A. foetidus, A. japonicus, A. niger, A. nidulans* or *A. oryzae*, *Fusarium*, such as *F. bactridioides, F. cerealis, F. crookwellense, F. culmorum, F. graminearum, F. graminum, F. heterosporum, F. negundi, F. reticulatum, F. roseum, F. sambucinum, F. sarcochroum, F. sulphureum, F. trichothecioides* or *F. oxysporum*, *Humicola*, such as *H. insolens* or *H. lanuginose*, *Mucor*, such as *M. miehei*, *Myceliophthora*, such as *M. thermophilum*, *Neurospora*, such as *N. crassa*, *Penicillium*, such as *P. purpurogenum*, *Thielavia*, such as *T. terrestris*, *Tolypocladium*, or *Trichoderma*, such as *T. harzianum, T. koningii, T. longibrachiatum, T. reesei* or *T. viride*, or a teleomorph or synonym thereof. The use of *Aspergillus* spp. for the expression of proteins is described in, e.g., EP 272 277, EP 230 023.

Examples of insect cells include a *Lepidoptera* cell line, such as *Spodoptera frugiperda* cells or *Trichoplusia ni* cells (cf. U.S. Pat. No. 5,077,214). Culture conditions may suitably be as described in WO 89/01029 or WO 89/01028. Transformation of insect cells and production of heterologous polypeptides therein may be performed as described in U.S. Pat. No. 4,745,051; U.S. Pat. No. 4,775,624; U.S. Pat. No. 4,879,236; U.S. Pat. No. 5,155,037; U.S. Pat. No. 5,162,222; EP 397,485).

Examples of mammalian cells include Chinese hamster ovary (CHO) cells, HeLa cells, baby hamster kidney (BHK) cells, COS cells, or any number of other immortalized cell lines available, e.g., from the American Type Culture Collection. Methods of transfecting mammalian cells and expressing DNA sequences introduced in the cells are described in e.g. Kaufman and Sharp, J. Mol. Biol. 159 (1982), 601-621;

Southern and Berg, J. Mol. Appl. Genet. 1 (1982), 327-341; Loyter et al., Proc. Natl. Acad. Sci. USA 79 (1982), 422-426; Wigler et al., Cell 14 (1978), 725; Corsaro and Pearson, Somatic Cell Genetics 7 (1981), 603, Ausubel et al., Current Protocols in Molecular Biology, John Wiley and Sons, Inc., N. Y., 1987, Hawley-Nelson et al., Focus 15 (1993), 73; Ciccarone et al., Focus 15 (1993), 80; Graham and van der Eb, Virology 52 (1973), 456; and Neumann et al., EMBO J. 1 (1982), 841-845. Mammalian cells may be transfected by direct uptake using the calcium phosphate precipitation method of Graham and Van der Eb (1978, Virology 52:546).

Methods for Expression and Isolation of Proteins

To express an enzyme of the present invention the above mentioned host cells trans-formed or transfected with a vector comprising a nucleic acid sequence encoding an enzyme of the present invention are typically cultured in a suitable nutrient medium under conditions permitting the production of the desired molecules, after which these are recovered from the cells, or the culture broth.

The medium used to culture the host cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media may be prepared using procedures known in the art (see, e.g., references for bacteria and yeast; Bennett, J. W. and LaSure, L., editors, More Gene Manipulations in Fungi, Academic Press, CA, 1991).

If the enzymes of the present invention are secreted into the nutrient medium, they may be recovered directly from the medium. If they are not secreted, they may be recovered from cell lysates. The enzymes of the present invention may be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the enzyme in question.

The enzymes of the invention may be detected using methods known in the art that are specific for these proteins. These detection methods include use of specific antibodies, formation of a product, or disappearance of a substrate. For example, an enzyme assay may be used to determine the activity of the molecule. Procedures for determining various kinds of activity are known in the art.

The enzymes of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J-C Janson and Lars Ryden, editors, VCH Publishers, New York, 1989).

When an expression vector comprising a DNA sequence encoding an enzyme of the present invention is transformed/transfected into a heterologous host cell it is possible to enable heterologous recombinant production of the enzyme. An advantage of using a heterologous host cell is that it is possible to make a highly purified enzyme composition, characterized in being free from homologous impurities, which are often present when a protein or peptide is expressed in a homologous host cell. In this context homologous impurities mean any impurity (e.g. other polypeptides than the enzyme of the invention) which originates from the homologous cell where the enzyme of the invention is originally obtained from.

Detergent Applications

The enzyme of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases:

Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 68, 76, 87, 97, 101, 104, 106, 120, 123, 167, 170, 194, 206, 218, 222, 224, 235, 245, 252 and 274.

Preferred commercially available protease enzymes include Alcalase™, Savinase™ Primase™, Duralase™, Esperase™, Coronase™ and Kannase™ (Novozymes A/S), Maxatase™, Maxacal™, Maxapem™, Properase™, Purafect™, Purafect OxP™, FN2™, and FN3™ (Genencor International Inc.).

Lipases:

Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas lipase*, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus lipase*, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™ and Lipex™ (Novozymes A/S).

Amylases:

Suitable amylases (α and/or β) include those of bacterial or fungal origin. Chemically modified or protein engineered mutants are included. Amylases include, for example, α-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Stainzyme™, Fungamyl™ and BAN™ (Novozymes A/S), Rapidase™ and Purastar™ (from Genencor International Inc.).

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Renozyme™, Celluzyme™, and Carezyme™ (Novozymes A/S), Clazinase™, and Puradax HA™ (Genencor International Inc.), and KAC-500(B)™ (Kao Corporation).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethylene glycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202 which is hereby incorporated as reference.

Food Processing Applications

The RP-II protease variants of the present invention may also be used in the processing of food, especially in the field of diary products, such as milk, cream and cheese, but also in the processing of meat and vegetables.

Feed Processing Application

The RP-II protease variants of the present invention may also be used in the processing of feed for cattle, poultry, and pigs and especially for pet food.

Treatment of Hides

The RP-II protease variants of the invention may also be used for the treatment of hides.

Decontamination of Possibly Infested Materials

The RP-II protease variants of the invention may also be used in processes for decontaminating instruments, surfaces, and other materials in hospitals, clinics, and meat processing plants, etc. in order to decompose prions or other infectious agents.

Materials and Methods

Strains:

*B. subtilis* DN1885: Disclosed in WO 01/16285

Plasmids:

pNM1003: Disclosed in WO 01/16285 pSX222: Disclosed in WO 96/34946 pNM1008: See Example 2

Method for Producing a Protease Variant

The present invention provides a method of producing an isolated enzyme according to the invention, wherein a suitable host cell, which has been transformed with a DNA sequence encoding the enzyme, is cultured under conditions permitting the production of the enzyme, and the resulting enzyme is recovered from the culture.

When an expression vector comprising a DNA sequence encoding the enzyme is trans-formed into a heterologous host cell it is possible to enable heterologous recombinant production of the enzyme of the invention. Thereby it is possible to make a highly purified RP-II protease composition, characterized in being free from homologous impurities.

The medium used to culture the transformed host cells may be any conventional medium suitable for growing the host cells in question. The expressed RP-II protease may conveniently be secreted into the culture medium and may be recovered there-from by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Proteolytic Activity

Enzyme activity can be measured using the PNA assay using succinyl-alanine-alanine-proline-glutamicacid-paranitroaniline as a substrate. The principle of the PNA assay is described in the Journal of American Oil Chemists Society, Rothgeb, T. M., Goodlander, B. D., Garrison, P. H., and Smith, L. A., (1988).

Textiles

Standard textile pieces are obtained from EMPA St. Gallen, Lerchfeldstrasse 5, CH-9014 St. Gallen, Switzerland. Especially type EMPA 116 (cotton textile stained with blood, milk and ink) and EMPA 117 (polyester/cotton textile stained with blood, milk and ink). The textile can be cut into a smaller textile piece of 5×3 cm or 13×3 cm Other relevant protease stain may be used as well, e.g. C-03, C-05, C-10 from CFT, Center For Testmaterials, Vlaardingen, Netherlands Wash Conditions

| Region | Latin America | Europe | North America | Japan |
| --- | --- | --- | --- | --- |
| Temperature | 20° C. | 30° C. | 20° C. | 20° C. |
| Washing time | 14 min | 20 min | 12 min | 15 min |
| Swatches | EMPA 117 | EMPA 116 | EMPA 117 | EMPA 117 |
| Water Hardness* | 9 or 12° dH | 15° dH | 6° dH | 3° dH |
| Detergent dosage | 1.5 or 2.5 g/l | 4, 6 or 8 g/l | HDL: 1.5 g/l | 0.5 or 0.7 |
| Washing pH | As is, or adjusted to 8, 9, 10 | As is, or adjusted to 8, 9, 10 | As is, or adjusted to 8, 9, 10 | As is, or adjusted to 8, 9, 10 |

*° dH: adjusted by adding $CaCl_2*2H_2O$; $MgCl_2*6H_2O$; $NaHCO_3$ (Ratio $Ca^{2+}$:$Mg^{2+}$:$HCO_3^-$ = 2:1:6) to milli-Q water.

Detergents

The enzymes of the invention may be tested in the detergent formulations disclosed in WO 97/07202 or in detergents formulations purchased from wfk testgewebe GmbH or similar supplier List of test detergents from wfk testgewebe IEC 60456 Type A* Base Detergent IEC 60456 Type B Base Detergent IEC 60456 Type C Detergent ECE Reference Detergent with Phosphate (1977)

ECE Reference Detergent without Phosphate (1998)

AHAM Standard Detergent

EU ECOLABEL (detergents) Light Duty Detergent

EU ECOLABEL (detergents) PVP

However, also one of the following commercial detergents may be used in the wash assay, e.g.

Omo Multi Acao HDP, Unilever, Brazil

Tide HDL, P&G, US

Wisk HDL, Unilever, US

TOP HDP, Lion, Japan

Attack HDP, Kao, Japan

Ariel Regular HDP, P&G, Europe

Ariel Compact HDPC, P&G, Europe

Persil Megaperls, Henkel, Germany

Persil, Unilever, UK

Furthermore, a brand extension or color/compact version for the above specified detergent could be used as well If the detergent contains enzymes, the detergent should be in-activated before use in order to eliminate the enzyme activity already present in the detergent. This is done by heating a detergent stock solution to 85° C. in 5 minutes in a micro wave oven. The concentration of the detergent stock solution in the micro wave oven is between 4-20 g/l Example 1

Modelling RP-II Proteases from the 3D Structure of BLC

The overall homology of *Bacillus licheniformis* protease BLC to other RP-II proteases is high. The similarity between the different RP-II proteases is provided in Table 1. Using the sequence alignment of FIG. 2 a model of the JA96 protease can be build using a suitable modelling tool like the Accellrys software Homology, or Modeller (also from Accellrys), or other software like Nest. These programs provide results as a first rough model, with some optimization in the Modeller and Nest programs.

The first rough model provides a close structural homology between the model of JA96 protease and the 3D structure of the BLC as there are no overlapping side chains in the model structure. To optimize the structure the protein can in silico be soaked in a box of water and subjected to energy minimization and further molecular dynamics simulations using e.g. the CHARMm™ software from Accelrys. The in silico soaking in water can conveniently be done by adding water in the Insight II program (from Accelrys) with a box size of 75*75*75 Å$^3$. The energy minimization can be done using settings of 300 Steepest descent (SD) and further 600 Conjugated gradients (CJ). The molecular dynamics simulations can conveniently be done using 1.2 ns run using the Verlet algorithm at 300K and standard parameters (see CHARMm manual). Other RP-II protease 3D models may be built in an analogous way.

Example 2

Construction of Library of RP-II Protease Variants

Construction and Expression of BLC

A *B. subtilis-E. coli* shuttle vector, pNM1003, suited to a gene coding for RP-II protease BLC and its mutants was constructed. It is derived from the *B. subtilis* expression vector pSX222 (Described in WO 96/34946) as described in WO 01/16285. To facilitate cloning pNM1008 was constructed introducing a kpnI restriction site downstream the HindIII site to facilitate the cloning of fragments inside the vector. For transformation in *Bacillus* pNM1008 was restricted with HindIII and a 4350 by DNA fragment was isolated and ligated. The ligation mixture was used to transform competent *B. subtilis* DN1885, selecting for protease activity, as described in WO 01/16285.

Site-Directed Mutagenesis

BLC site-directed variants of the invention comprising specific substitutions, insertions or deletions in the molecule are made by traditional cloning of PCR fragments (Sambrook et. al., Molecular Cloning: A Laboratory Manual, 2nd Ed., Cold Spring Harbor) produced by oligonucleotides containing the desired modification. As template pNM1008 is used. In a first PCR using a mutational primer (anti-sense) with a suitable opposite sense primer (e.g. 5"-CTGTGCCCTT-TAACCGCACAGC (SEQ ID No. 17)), downstream of the MluI site is used. The resulting DNA fragment is used as a sense primer in a second PCR together with a suitable anti-sense primer (e.g. 5'-GCATAAGCTTTTACAGGTACCGGC (SEQ ID No. 18)) upstream from the KpnI digestion site. This resulting PCR product is digested with KpnI and MluI and ligated in pNM1008 digested with the respective enzymes.

The ligation reaction is transformed into *E. coli* by well-known techniques and 5 randomly chosen colonies are sequenced to confirm the designed mutations.

In order to express a BLC variant of the invention, the pNM1008 derived plasmid comprising the variant is digested with HindIII, ligated and transformed into a competent *B. subtilis* strain, selecting for protease activity.

Example 3

Purification of Enzymes and Variants

This procedure relates to purification of 2 liter scale fermentation for the production of the RP-II proteases of the invention in a *Bacillus* host cell.

Approximately 1.6 liters of fermentation broth are centrifuged at 5000 rpm for 35 minutes in 1 liter beakers. The supernatants are adjusted to pH 7 using 10% acetic acid and filtered through a Seitz Supra S100 filter plate.

At room temperature, the filtrate is applied to a 100 ml Bacitracin affinity column equilibrated with 0.01M dimethylglutaric acid, 0.1 M boric acid and 0.002 M calcium chloride adjusted to pH 7 with sodium hydroxide (Buffer A). After washing the column with Buffer A to remove unbound protein, the protease is eluted from the Bacitracin column using Buffer A supplemented with 25% 2-propanol and 1 M sodium chloride.

The fractions with protease activity from the Bacitracin purification step are combined and applied to a 750 ml Sephadex G25 column (5 cm dia.) equilibrated with Buffer A.

Fractions with proteolytic activity from the Sephadex G25 column are combined and the pH was adjusted to pH 6 with 10% acetic acid and applied to a 150 ml CM Sepharose CL 6B cation exchange column (5 cm dia.) equilibrated with a buffer containing 0.01 M dimethylglutaric acid, 0.1 M boric acid, and 0.002 M calcium chloride adjusted to pH 6 with sodium hydroxide.

The protease is eluted using a linear gradient of 0-0.2 M sodium chloride in 2 liters of the same buffer.

Finally, the protease containing fractions from the CM Sepharose column are combined and filtered through a 0.2μ filter.

By using the techniques of Example 2 for the construction of variants and fermentation, and the above isolation procedure the following RP-II proteases and variants thereof may be produced and isolated:

Example 4

Wash Performance of Detergent Compositions Comprising Modified Enzymes

AMSA

The enzyme variants of the present application is tested using the Automatic Mechanical Stress Assay (AMSA). With the AMSA test the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress. For further description see WO 02/42740 especially the paragraph "Special method embodiments" at page 23-24.

The assay is conducted under the experimental conditions specified below. In respect of the detergent used, all the detergents listed above under "Materials and Methods" may be used:

| | |
|---|---|
| Detergent base | Example: Omo Acao |
| Detergent dosage | Example: 1.5 g/l |
| Test solution volume | 160 micro l |
| pH | Example: As is |

-continued

| | |
|---|---|
| Wash time | Example: 14 minutes |
| Temperature | Example: 20° C. |
| Water hardness | Example: 9° dH |
| Enzyme concentration in test solution | 5 nM, 10 nM and 30 nM |
| Test material | Example: EMPA 117 |

After washing the textile pieces is flushed in tap water and air-dried.

The performance of the enzyme variant is measured as the brightness of the colour of the textile samples washed with that specific enzyme variant. Brightness can also be expressed as the intensity of the light reflected from the textile sample when luminated with white light. When the textile is stained the intensity of the reflected light is lower, than that of a clean textile. Therefore the intensity of the reflected light can be used to measure wash performance of an enzyme variant.

Colour measurements are made with a professional flatbed scanner (PFU DL2400pro), which is used to capture an image of the washed textile samples. The scans are made with a resolution of 200 dpi and with an output colour dept of 24 bits. In order to get accurate results, the scanner is frequently calibrated with a Kodak reflective IT8 target.

To extract a value for the light intensity from the scanned images, a special designed software application is used (Novozymes Color Vector Analyzer). The program retrieves the 24 bit pixel values from the image and converts them into values for red, green and blue (RGB). The intensity value (Int) is calculated by adding the RGB values together as vectors and then taking the length of the resulting vector:

$$Int = \sqrt{r^2 + g^2 + b^2}.$$

The wash performance (P) of the variants is calculated in accordance with the below formula:

$$P = Int(v) - Int(r)$$

where
Int(v) is the light intensity value of textile surface washed with enzyme variant and
Int(r) is the light intensity value of textile surface washed with the reference enzyme BLC.

A performance score is given as the result of the miniwash in accordance with the definition:

Performance Scores (S) are summing up the performances (P) of the tested enzyme variants as:
S=2 which indicates that the variant performs better than the reference at all three concentrations (5, 10 and 30 nM) and
S=1 which indicates that the variant performs better than the reference at one or two concentrations.

A variant is considered to exhibit improved wash performance, if it performs better than the reference in at least one detergent composition.

Mini Wash Assay

The milliliter scale wash performance assay is conducted under the following conditions:

| | |
|---|---|
| Detergent base | Example: Omo Acao detergent powder |
| Detergent dose | Example: 1.5 g/l |
| pH | Example: "as is" in the current detergent solution and is not adjusted. |
| Wash time | Example: 14 min. |
| Temperature | Example: 20° C. |

| | |
|---|---|
| Water hardness | Example: 9° dH, adjusted by adding $CaCl_2 \cdot 2H_2O$; $MgCl_2 \cdot 6H_2O$; $NaHCO_3$ ($Ca^{2+}:Mg^{2+}:HCO^{3-}$ = 2:1:6) to milli-Q water. |
| Enzymes | Variants of BLC. BLC as reference enzyme |
| Enzyme conc. | 5 nM, 10 nM, 30 nM |
| Test system | 125 ml glass beakers. Textile dipped in test solution. Continuously lifted up and down into the detergent solution, 50 times per minute (up-time 0.4 sec, down-time 0.4 sec, lift time 0.2 sec) |
| Test solution volume | 50 ml |
| Test material | Example: EMPA 117 textile swatches (13 × 5 cm) |

After washing the textile piece is flushed in tap water and air-dried and the remission from the test material is measured at 460 nm using a Zeiss MCS 521 VIS spectrophotometer. The measurements are done according to the manufacturer's protocol.

A performance score is given as the result of the miniwash in accordance with the definition:

Performance Scores (S) are summing up the performances (P) of the tested enzyme variants as:
S=2 which indicates that the variant performs better than the reference at all three concentrations (5, 10 and 30 nM) and
S=1 which indicates that the variant performs better than the reference at one or two concentrations.

A Performance Score higher than 1 indicates better wash performance.

A variant is considered to exhibit improved wash performance, if it performs better than the reference in at least one detergent composition.

The following RP-II variants were constructed as indicated in Example 2 to be purified in accordance with Example 3 and tested as indicated above:

Ion-Binding Modification:
D7E; D7Q; H144R; D161R; D161K;
H144Q+D161R
Mobility Modification:
G30A; G91A
Cys-Bridge Formation:
S145C+T128C
Surface Charge Modification:
D7N,S,T; Y17R,K,H; Y95R,K,H; T109R,K,H; Q143R,K,H; Q174R,K,H; E209Q,N; N216R,K,H
Proline Stability:
T60P; S221 P; G193P; V194P Example 5

Storage Stability of Modified Enzymes

The storage stability of the variants of the invention is determined by measuring the "residual activity" of the parent and the variants at regular time intervals. The storage stability is often expressed as the half-life, $T_{1/2}$, the time lapsed till the activity is half the initial value.

Residual activity=(Activity at $t=i$)/((Activity at $t=0$)× 100)%

The Proteolytic activity is measured as described above (PNA assay).

Example 6

Thermostability of Modified Enzymes

The thermostability of the protease variant s of the invention is determine by Differential Scanning Calorimetry

Example 7

Autoproteolytic Stability Of Modified Enzymes

Comparative Fermentation Experiment

The RP-II variants of the invention are in a fermentation experiment compared to the parent RP-II protease.

Both the variants and the parent are cloned in a pNM1008 expression vector background and fermented in a suitable medium.

After 5 days fermentation 1.5 ml of the fermentation medium is centrifuged and the supernatant used to measure the Proteolytic activity (KPNU) as described above.

The variants providing an increased proteolytic activity in comparison to the activity of the parent are considered to posses an improved autoproteolytic stability relative to the parent.

Example 8

Oxidation Stability of Modified Enzymes

The variants are tested for their oxidation stability in 0.01 M peracetic acid after 20 minutes at 50° C. and pH 7. The parent protease is used as reference.

The results are presented by the residual proteolytic activity in the heat treated samples relative to samples untreated by oxidant or heat.

APPENDIX 1

| | | | | | | | | | | |
|---|---|---|---|---|---|---|---|---|---|---|
| ATOM | 3359 | N | SER | B | 1 | −2.987 | 12.370 | 17.565 | 1.00 | 7.82 N |
| ATOM | 3361 | CA | SER | B | 1 | −2.255 | 12.820 | 16.353 | 1.00 | 7.97 C |
| ATOM | 3363 | CB | SER | B | 1 | −3.233 | 12.933 | 15.188 | 1.00 | 8.69 C |
| ATOM | 3366 | OG | SER | B | 1 | −3.995 | 11.748 | 15.028 | 1.00 | 9.01 O |
| ATOM | 3368 | C | SER | B | 1 | −1.637 | 14.171 | 16.602 | 1.00 | 8.14 C |
| ATOM | 3369 | O | SER | B | 1 | −2.098 | 14.938 | 17.439 | 1.00 | 8.05 O |
| ATOM | 3372 | N | VAL | B | 2 | −0.592 | 14.472 | 15.848 | 1.00 | 8.60 N |
| ATOM | 3374 | CA | VAL | B | 2 | −0.039 | 15.812 | 15.824 | 1.00 | 10.11 C |
| ATOM | 3376 | CB | VAL | B | 2 | 1.432 | 15.811 | 15.404 | 1.00 | 11.81 C |
| ATOM | 3378 | CG1 | VAL | B | 2 | 1.949 | 17.239 | 15.233 | 1.00 | 13.46 C |
| ATOM | 3382 | CG2 | VAL | B | 2 | 2.255 | 15.065 | 16.421 | 1.00 | 14.12 C |
| ATOM | 3386 | C | VAL | B | 2 | −0.867 | 16.605 | 14.830 | 1.00 | 10.56 C |
| ATOM | 3387 | O | VAL | B | 2 | −0.928 | 16.250 | 13.660 | 1.00 | 12.81 O |
| ATOM | 3388 | N | ILE | B | 3 | −1.524 | 17.640 | 15.331 | 1.00 | 9.91 N |
| ATOM | 3390 | CA | ILE | B | 3 | −2.409 | 18.487 | 14.537 | 1.00 | 10.49 C |
| ATOM | 3392 | CB | ILE | B | 3 | −3.747 | 18.700 | 15.279 | 1.00 | 10.68 C |
| ATOM | 3394 | CG1 | ILE | B | 3 | −4.452 | 17.348 | 15.457 | 1.00 | 10.36 C |
| ATOM | 3397 | CD1 | ILE | B | 3 | −5.671 | 17.398 | 16.350 | 1.00 | 11.17 C |
| ATOM | 3401 | CG2 | ILE | B | 3 | −4.638 | 19.704 | 14.531 | 1.00 | 13.34 C |
| ATOM | 3405 | C | ILE | B | 3 | −1.683 | 19.796 | 14.299 | 1.00 | 10.96 C |
| ATOM | 3406 | O | ILE | B | 3 | −1.332 | 20.502 | 15.234 | 1.00 | 10.91 O |
| ATOM | 3407 | N | GLY | B | 4 | −1.433 | 20.141 | 13.043 | 1.00 | 12.22 N |
| ATOM | 3409 | CA | GLY | B | 4 | −0.702 | 21.359 | 12.748 | 1.00 | 12.69 C |
| ATOM | 3412 | C | GLY | B | 4 | 0.685 | 21.285 | 13.344 | 1.00 | 12.61 C |
| ATOM | 3413 | O | GLY | B | 4 | 1.324 | 20.239 | 13.303 | 1.00 | 13.40 O |
| ATOM | 3414 | N | SER | B | 5 | 1.162 | 22.383 | 13.913 | 1.00 | 11.93 N |
| ATOM | 3416 | CA | SER | B | 5 | 2.466 | 22.358 | 14.557 | 1.00 | 11.64 C |
| ATOM | 3418 | CB | SER | B | 5 | 2.900 | 23.757 | 14.975 | 1.00 | 11.92 C |
| ATOM | 3421 | OG | SER | B | 5 | 2.011 | 24.329 | 15.906 | 1.00 | 13.28 O |
| ATOM | 3423 | C | SER | B | 5 | 2.438 | 21.451 | 15.770 | 1.00 | 11.22 C |
| ATOM | 3424 | O | SER | B | 5 | 1.437 | 21.366 | 16.462 | 1.00 | 11.19 O |
| ATOM | 3425 | N | ASP | B | 6 | 3.551 | 20.779 | 16.028 | 1.00 | 10.41 N |
| ATOM | 3427 | CA | ASP | B | 6 | 3.704 | 19.951 | 17.230 | 1.00 | 10.02 C |
| ATOM | 3429 | CB | ASP | B | 6 | 4.700 | 18.839 | 16.981 | 1.00 | 10.75 C |
| ATOM | 3432 | CG | ASP | B | 6 | 4.838 | 17.886 | 18.144 | 1.00 | 10.38 C |
| ATOM | 3433 | OD1 | ASP | B | 6 | 4.132 | 18.013 | 19.178 | 1.00 | 10.80 O |
| ATOM | 3434 | OD2 | ASP | B | 6 | 5.685 | 16.961 | 18.055 | 1.00 | 11.46 O |
| ATOM | 3435 | C | ASP | B | 6 | 4.185 | 20.807 | 18.373 | 1.00 | 9.61 C |
| ATOM | 3436 | O | ASP | B | 6 | 5.353 | 21.229 | 18.410 | 1.00 | 11.09 O |
| ATOM | 3437 | N | ASP | B | 7 | 3.290 | 21.057 | 19.312 | 1.00 | 8.85 N |
| ATOM | 3439 | CA | ASP | B | 7 | 3.582 | 21.969 | 20.387 | 1.00 | 8.21 C |
| ATOM | 3441 | CB | ASP | B | 7 | 2.453 | 23.010 | 20.550 | 1.00 | 9.26 C |
| ATOM | 3444 | CG | ASP | B | 7 | 2.334 | 23.975 | 19.386 | 1.00 | 10.17 C |
| ATOM | 3445 | OD1 | ASP | B | 7 | 3.147 | 23.902 | 18.444 | 1.00 | 11.15 O |
| ATOM | 3446 | OD2 | ASP | B | 7 | 1.377 | 24.778 | 19.332 | 1.00 | 10.99 O |
| ATOM | 3447 | C | ASP | B | 7 | 3.856 | 21.237 | 21.712 | 1.00 | 8.24 C |
| ATOM | 3448 | O | ASP | B | 7 | 3.978 | 21.870 | 22.753 | 1.00 | 8.50 O |
| ATOM | 3449 | N | ARG | B | 8 | 4.016 | 19.918 | 21.677 | 1.00 | 7.90 N |
| ATOM | 3451 | CA | ARG | B | 8 | 4.429 | 19.187 | 22.872 | 1.00 | 7.81 C |
| ATOM | 3453 | CB | ARG | B | 8 | 4.444 | 17.681 | 22.634 | 1.00 | 7.75 C |
| ATOM | 3456 | CG | ARG | B | 8 | 3.068 | 17.077 | 22.470 | 1.00 | 7.65 C |
| ATOM | 3459 | CD | ARG | B | 8 | 3.090 | 15.631 | 22.015 | 1.00 | 7.89 C |
| ATOM | 3462 | NE | ARG | B | 8 | 3.673 | 15.554 | 20.679 | 1.00 | 8.24 N |
| ATOM | 3464 | CZ | ARG | B | 8 | 4.023 | 14.422 | 20.073 | 1.00 | 8.49 C |
| ATOM | 3465 | NH1 | ARG | B | 8 | 3.781 | 13.244 | 20.628 | 1.00 | 8.61 N |
| ATOM | 3468 | NH2 | ARG | B | 8 | 4.622 | 14.472 | 18.909 | 1.00 | 9.63 N |
| ATOM | 3471 | C | ARG | B | 8 | 5.812 | 19.628 | 23.321 | 1.00 | 8.24 C |
| ATOM | 3472 | O | ARG | B | 8 | 6.684 | 19.907 | 22.505 | 1.00 | 9.34 O |
| ATOM | 3473 | N | THR | B | 9 | 6.007 | 19.640 | 24.632 | 1.00 | 8.26 N |
| ATOM | 3475 | CA | THR | B | 9 | 7.315 | 19.897 | 25.226 | 1.00 | 8.75 C |

APPENDIX 1-continued

| ATOM | 3477 | CB | THR | B | 9 | 7.368 | 21.243 | 25.939 | 1.00 | 9.87 | C |
|---|---|---|---|---|---|---|---|---|---|---|---|
| ATOM | 3479 | OG1 | THR | B | 9 | 6.296 | 21.350 | 26.880 | 1.00 | 10.91 | O |
| ATOM | 3481 | CG2 | THR | B | 9 | 7.191 | 22.375 | 24.936 | 1.00 | 11.78 | C |
| ATOM | 3485 | C | THR | B | 9 | 7.660 | 18.787 | 26.199 | 1.00 | 8.34 | C |
| ATOM | 3486 | O | THR | B | 9 | 6.793 | 18.176 | 26.835 | 1.00 | 8.22 | O |
| ATOM | 3487 | N | ARG | B | 10 | 8.954 | 18.535 | 26.340 | 1.00 | 8.65 | N |
| ATOM | 3489 | CA | ARG | B | 10 | 9.413 | 17.459 | 27.194 | 1.00 | 8.98 | C |
| ATOM | 3491 | CB | ARG | B | 10 | 10.873 | 17.096 | 26.927 | 1.00 | 10.45 | C |
| ATOM | 3494 | CG | ARG | B | 10 | 11.309 | 15.787 | 27.587 | 1.00 | 11.25 | C |
| ATOM | 3497 | CD | ARG | B | 10 | 12.701 | 15.396 | 27.212 | 1.00 | 12.23 | C |
| ATOM | 3500 | NE | ARG | B | 10 | 13.213 | 14.299 | 28.025 | 1.00 | 12.62 | N |
| ATOM | 3502 | CZ | ARG | B | 10 | 14.465 | 13.868 | 27.967 | 1.00 | 14.40 | C |
| ATOM | 3503 | NH1 | ARG | B | 10 | 15.328 | 14.413 | 27.114 | 1.00 | 16.93 | N |
| ATOM | 3506 | NH2 | ARG | B | 10 | 14.855 | 12.884 | 28.743 | 1.00 | 14.13 | N |
| ATOM | 3509 | C | ARG | B | 10 | 9.237 | 17.885 | 28.642 | 1.00 | 8.65 | C |
| ATOM | 3510 | O | ARG | B | 10 | 9.534 | 19.027 | 29.025 | 1.00 | 9.59 | O |
| ATOM | 3511 | N | VAL | B | 11 | 8.771 | 16.952 | 29.453 | 1.00 | 8.69 | N |
| ATOM | 3513 | CA | VAL | B | 11 | 8.751 | 17.118 | 30.893 | 1.00 | 9.52 | C |
| ATOM | 3515 | CB | VAL | B | 11 | 7.810 | 16.080 | 31.532 | 1.00 | 9.21 | C |
| ATOM | 3517 | CG1 | VAL | B | 11 | 7.862 | 16.145 | 33.047 | 1.00 | 10.41 | C |
| ATOM | 3521 | CG2 | VAL | B | 11 | 6.381 | 16.257 | 31.015 | 1.00 | 9.54 | C |
| ATOM | 3525 | C | VAL | B | 11 | 10.207 | 16.954 | 31.390 | 1.00 | 10.62 | C |
| ATOM | 3526 | O | VAL | B | 11 | 10.777 | 15.869 | 31.301 | 1.00 | 12.34 | O |
| ATOM | 3527 | N | THR | B | 12 | 10.795 | 18.048 | 31.884 | 1.00 | 12.38 | N |
| ATOM | 3529 | CA | THR | B | 12 | 12.217 | 18.113 | 32.253 | 1.00 | 13.55 | C |
| ATOM | 3531 | CB | THR | B | 12 | 12.790 | 19.543 | 32.093 | 1.00 | 14.37 | C |
| ATOM | 3533 | OG1 | THR | B | 12 | 12.035 | 20.449 | 32.902 | 1.00 | 17.60 | O |
| ATOM | 3535 | CG2 | THR | B | 12 | 12.611 | 20.030 | 30.671 | 1.00 | 16.03 | C |
| ATOM | 3539 | C | THR | B | 12 | 12.507 | 17.657 | 33.666 | 1.00 | 13.34 | C |
| ATOM | 3540 | O | THR | B | 12 | 13.669 | 17.515 | 34.032 | 1.00 | 14.60 | O |
| ATOM | 3541 | N | ASN | B | 13 | 11.472 | 17.465 | 34.469 | 1.00 | 12.04 | N |
| ATOM | 3543 | CA | ASN | B | 13 | 11.646 | 16.901 | 35.800 | 1.00 | 11.12 | C |
| ATOM | 3545 | CB | ASN | B | 13 | 11.713 | 17.962 | 36.894 | 1.00 | 11.74 | C |
| ATOM | 3548 | CG | ASN | B | 13 | 11.935 | 17.344 | 38.252 | 1.00 | 12.29 | C |
| ATOM | 3549 | OD1 | ASN | B | 13 | 12.166 | 16.141 | 38.356 | 1.00 | 12.18 | O |
| ATOM | 3550 | ND2 | ASN | B | 13 | 11.868 | 18.153 | 39.302 | 1.00 | 15.45 | N |
| ATOM | 3553 | C | ASN | B | 13 | 10.502 | 15.940 | 36.074 | 1.00 | 10.21 | C |
| ATOM | 3554 | O | ASN | B | 13 | 9.450 | 16.321 | 36.578 | 1.00 | 10.60 | O |
| ATOM | 3555 | N | THR | B | 14 | 10.714 | 14.678 | 35.743 | 1.00 | 9.43 | N |
| ATOM | 3557 | CA | THR | B | 14 | 9.671 | 13.680 | 35.934 | 1.00 | 9.11 | C |
| ATOM | 3559 | CB | THR | B | 14 | 9.887 | 12.455 | 35.046 | 1.00 | 9.24 | C |
| ATOM | 3561 | OG1 | THR | B | 14 | 11.122 | 11.827 | 35.409 | 1.00 | 9.63 | O |
| ATOM | 3563 | CG2 | THR | B | 14 | 9.958 | 12.808 | 33.561 | 1.00 | 10.29 | C |
| ATOM | 3567 | C | THR | B | 14 | 9.556 | 13.227 | 37.385 | 1.00 | 9.62 | C |
| ATOM | 3568 | O | THR | B | 14 | 8.730 | 12.361 | 37.672 | 1.00 | 10.68 | O |
| ATOM | 3569 | N | THR | B | 15 | 10.357 | 13.804 | 38.295 | 1.00 | 10.09 | N |
| ATOM | 3571 | CA | THR | B | 15 | 10.147 | 13.593 | 39.725 | 1.00 | 10.57 | C |
| ATOM | 3573 | CB | THR | B | 15 | 11.456 | 13.495 | 40.553 | 1.00 | 11.89 | C |
| ATOM | 3575 | OG1 | THR | B | 15 | 12.124 | 14.763 | 40.616 | 1.00 | 12.96 | O |
| ATOM | 3577 | CG2 | THR | B | 15 | 12.432 | 12.491 | 39.954 | 1.00 | 12.96 | C |
| ATOM | 3581 | C | THR | B | 15 | 9.244 | 14.638 | 40.367 | 1.00 | 10.41 | C |
| ATOM | 3582 | O | THR | B | 15 | 8.911 | 14.514 | 41.540 | 1.00 | 12.03 | O |
| ATOM | 3583 | N | ALA | B | 16 | 8.832 | 15.656 | 39.622 | 1.00 | 10.32 | N |
| ATOM | 3585 | CA | ALA | B | 16 | 7.900 | 16.643 | 40.148 | 1.00 | 10.73 | C |
| ATOM | 3587 | CB | ALA | B | 16 | 7.927 | 17.897 | 39.301 | 1.00 | 11.48 | C |
| ATOM | 3591 | C | ALA | B | 16 | 6.488 | 16.060 | 40.161 | 1.00 | 10.05 | C |
| ATOM | 3592 | O | ALA | B | 16 | 6.059 | 15.433 | 39.198 | 1.00 | 9.80 | O |
| ATOM | 3593 | N | TYR | B | 17 | 5.755 | 16.284 | 41.237 | 1.00 | 10.35 | N |
| ATOM | 3595 | CA | TYR | B | 17 | 4.338 | 15.962 | 41.260 | 1.00 | 10.36 | C |
| ATOM | 3597 | CB | TYR | B | 17 | 3.838 | 16.018 | 42.706 | 1.00 | 10.90 | C |
| ATOM | 3600 | CG | TYR | B | 17 | 2.379 | 15.675 | 42.858 | 1.00 | 10.77 | C |
| ATOM | 3601 | CD1 | TYR | B | 17 | 1.436 | 16.674 | 42.985 | 1.00 | 11.41 | C |
| ATOM | 3603 | CE1 | TYR | B | 17 | 0.086 | 16.386 | 43.118 | 1.00 | 11.35 | C |
| ATOM | 3605 | CZ | TYR | B | 17 | −0.338 | 15.081 | 43.139 | 1.00 | 11.51 | C |
| ATOM | 3606 | OH | TYR | B | 17 | −1.690 | 14.831 | 43.268 | 1.00 | 13.22 | O |
| ATOM | 3608 | CE2 | TYR | B | 17 | 0.579 | 14.051 | 42.988 | 1.00 | 11.13 | C |
| ATOM | 3610 | CD2 | TYR | B | 17 | 1.940 | 14.358 | 42.861 | 1.00 | 11.24 | C |
| ATOM | 3612 | C | TYR | B | 17 | 3.588 | 16.946 | 40.363 | 1.00 | 10.06 | C |
| ATOM | 3613 | O | TYR | B | 17 | 3.857 | 18.150 | 40.452 | 1.00 | 11.57 | O |
| ATOM | 3614 | N | PRO | B | 18 | 2.609 | 16.510 | 39.557 | 1.00 | 10.05 | N |
| ATOM | 3615 | CA | PRO | B | 18 | 2.080 | 15.145 | 39.436 | 1.00 | 9.55 | C |
| ATOM | 3617 | CB | PRO | B | 18 | 0.606 | 15.412 | 39.151 | 1.00 | 10.69 | C |
| ATOM | 3620 | CG | PRO | B | 18 | 0.646 | 16.604 | 38.275 | 1.00 | 11.31 | C |
| ATOM | 3623 | CD | PRO | B | 18 | 1.772 | 17.460 | 38.810 | 1.00 | 10.99 | C |
| ATOM | 3626 | C | PRO | B | 18 | 2.667 | 14.326 | 38.287 | 1.00 | 8.62 | C |
| ATOM | 3627 | O | PRO | B | 18 | 2.189 | 13.217 | 38.035 | 1.00 | 8.43 | O |
| ATOM | 3628 | N | TYR | B | 19 | 3.695 | 14.844 | 37.616 | 1.00 | 8.36 | N |
| ATOM | 3630 | CA | TYR | B | 19 | 4.343 | 14.126 | 36.531 | 1.00 | 8.21 | C |
| ATOM | 3632 | CB | TYR | B | 19 | 5.389 | 15.034 | 35.875 | 1.00 | 8.56 | C |
| ATOM | 3635 | CG | TYR | B | 19 | 4.722 | 16.277 | 35.304 | 1.00 | 8.70 | C |

APPENDIX 1-continued

| | | | | | | | | | | |
|---|---|---|---|---|---|---|---|---|---|---|
| ATOM | 3636 | CD1 | TYR | B | 19 | 4.072 | 16.231 | 34.070 | 1.00 | 8.24 C |
| ATOM | 3638 | CE1 | TYR | B | 19 | 3.424 | 17.343 | 33.553 | 1.00 | 9.10 C |
| ATOM | 3640 | CZ | TYR | B | 19 | 3.374 | 18.496 | 34.286 | 1.00 | 9.96 C |
| ATOM | 3641 | OH | TYR | B | 19 | 2.725 | 19.608 | 33.802 | 1.00 | 11.01 O |
| ATOM | 3643 | CE2 | TYR | B | 19 | 3.987 | 18.565 | 35.519 | 1.00 | 10.79 C |
| ATOM | 3645 | CD2 | TYR | B | 19 | 4.660 | 17.462 | 36.020 | 1.00 | 10.02 C |
| ATOM | 3647 | C | TYR | B | 19 | 4.951 | 12.801 | 36.969 | 1.00 | 7.80 C |
| ATOM | 3648 | O | TYR | B | 19 | 4.984 | 11.860 | 36.180 | 1.00 | 8.04 O |
| ATOM | 3649 | N | ARG | B | 20 | 5.385 | 12.701 | 38.224 | 1.00 | 7.62 N |
| ATOM | 3651 | CA | ARG | B | 20 | 5.919 | 11.452 | 38.741 | 1.00 | 7.92 C |
| ATOM | 3653 | CB | ARG | B | 20 | 6.659 | 11.679 | 40.056 | 1.00 | 8.70 C |
| ATOM | 3656 | CG | ARG | B | 20 | 5.865 | 12.292 | 41.176 | 1.00 | 9.58 C |
| ATOM | 3659 | CD | ARG | B | 20 | 6.640 | 12.228 | 42.469 | 1.00 | 10.61 C |
| ATOM | 3662 | NE | ARG | B | 20 | 5.937 | 12.768 | 43.620 | 1.00 | 12.27 N |
| ATOM | 3664 | CZ | ARG | B | 20 | 6.343 | 13.830 | 44.332 | 1.00 | 14.55 C |
| ATOM | 3665 | NH1 | ARG | B | 20 | 7.433 | 14.528 | 44.011 | 1.00 | 15.43 N |
| ATOM | 3668 | NH2 | ARG | B | 20 | 5.641 | 14.205 | 45.395 | 1.00 | 15.98 N |
| ATOM | 3671 | C | ARG | B | 20 | 4.833 | 10.398 | 38.938 | 1.00 | 7.88 C |
| ATOM | 3672 | O | ARG | B | 20 | 5.142 | 9.210 | 39.062 | 1.00 | 8.74 O |
| ATOM | 3673 | N | ALA | B | 21 | 3.573 | 10.834 | 38.989 | 1.00 | 7.67 N |
| ATOM | 3675 | CA | ALA | B | 21 | 2.436 | 9.931 | 39.101 | 1.00 | 7.77 C |
| ATOM | 3677 | CB | ALA | B | 21 | 1.355 | 10.545 | 40.004 | 1.00 | 8.33 C |
| ATOM | 3681 | C | ALA | B | 21 | 1.860 | 9.554 | 37.740 | 1.00 | 7.49 C |
| ATOM | 3682 | O | ALA | B | 21 | 0.883 | 8.813 | 37.670 | 1.00 | 8.24 O |
| ATOM | 3683 | N | ILE | B | 22 | 2.451 | 10.077 | 36.668 | 1.00 | 7.07 N |
| ATOM | 3685 | CA | ILE | B | 22 | 2.180 | 9.629 | 35.315 | 1.00 | 7.15 C |
| ATOM | 3687 | CB | ILE | B | 22 | 2.239 | 10.805 | 34.320 | 1.00 | 7.19 C |
| ATOM | 3689 | CG1 | ILE | B | 22 | 1.204 | 11.861 | 34.727 | 1.00 | 7.74 C |
| ATOM | 3692 | CD1 | ILE | B | 22 | 1.150 | 13.060 | 33.823 | 1.00 | 7.78 C |
| ATOM | 3696 | CG2 | ILE | B | 22 | 2.012 | 10.301 | 32.895 | 1.00 | 7.55 C |
| ATOM | 3700 | C | ILE | B | 22 | 3.192 | 8.540 | 35.014 | 1.00 | 7.08 C |
| ATOM | 3701 | O | ILE | B | 22 | 4.376 | 8.686 | 35.297 | 1.00 | 8.15 O |
| ATOM | 3702 | N | VAL | B | 23 | 2.708 | 7.426 | 34.477 | 1.00 | 7.33 N |
| ATOM | 3704 | CA | VAL | B | 23 | 3.505 | 6.221 | 34.384 | 1.00 | 7.49 C |
| ATOM | 3706 | CB | VAL | B | 23 | 2.933 | 5.092 | 35.284 | 1.00 | 7.65 C |
| ATOM | 3708 | CG1 | VAL | B | 23 | 2.619 | 5.599 | 36.672 | 1.00 | 8.69 C |
| ATOM | 3712 | CG2 | VAL | B | 23 | 1.690 | 4.436 | 34.682 | 1.00 | 8.21 C |
| ATOM | 3716 | C | VAL | B | 23 | 3.625 | 5.760 | 32.939 | 1.00 | 6.99 C |
| ATOM | 3717 | O | VAL | B | 23 | 2.710 | 5.912 | 32.130 | 1.00 | 7.44 O |
| ATOM | 3718 | N | HIS | B | 24 | 4.788 | 5.194 | 32.623 | 1.00 | 7.09 N |
| ATOM | 3720 | CA | HIS | B | 24 | 5.005 | 4.494 | 31.375 | 1.00 | 7.24 C |
| ATOM | 3722 | CB | HIS | B | 24 | 6.484 | 4.596 | 30.984 | 1.00 | 7.56 C |
| ATOM | 3725 | CG | HIS | B | 24 | 6.810 | 3.808 | 29.779 | 1.00 | 8.11 C |
| ATOM | 3726 | ND1 | HIS | B | 24 | 7.112 | 2.467 | 29.831 | 1.00 | 9.52 N |
| ATOM | 3728 | CE1 | HIS | B | 24 | 7.263 | 2.022 | 28.599 | 1.00 | 10.58 C |
| ATOM | 3730 | NE2 | HIS | B | 24 | 7.090 | 3.026 | 27.757 | 1.00 | 11.37 N |
| ATOM | 3732 | CD2 | HIS | B | 24 | 6.804 | 4.156 | 28.474 | 1.00 | 10.43 C |
| ATOM | 3734 | C | HIS | B | 24 | 4.599 | 3.027 | 31.568 | 1.00 | 7.57 C |
| ATOM | 3735 | O | HIS | B | 24 | 4.949 | 2.409 | 32.577 | 1.00 | 8.17 O |
| ATOM | 3736 | N | ILE | B | 25 | 3.848 | 2.485 | 30.615 | 1.00 | 7.37 N |
| ATOM | 3738 | CA | ILE | B | 25 | 3.381 | 1.108 | 30.652 | 1.00 | 7.87 C |
| ATOM | 3740 | CB | ILE | B | 25 | 1.842 | 1.058 | 30.651 | 1.00 | 8.18 C |
| ATOM | 3742 | CG1 | ILE | B | 25 | 1.257 | 1.843 | 31.824 | 1.00 | 9.00 C |
| ATOM | 3745 | CD1 | ILE | B | 25 | −0.242 | 2.093 | 31.705 | 1.00 | 8.99 C |
| ATOM | 3749 | CG2 | ILE | B | 25 | 1.356 | −0.398 | 30.666 | 1.00 | 9.66 C |
| ATOM | 3753 | C | ILE | B | 25 | 3.899 | 0.364 | 29.441 | 1.00 | 8.15 C |
| ATOM | 3754 | O | ILE | B | 25 | 3.755 | 0.843 | 28.315 | 1.00 | 8.94 O |
| ATOM | 3755 | N | SER | B | 26 | 4.486 | −0.806 | 29.669 | 1.00 | 8.77 N |
| ATOM | 3757 | CA | SER | B | 26 | 4.773 | −1.727 | 28.581 | 1.00 | 9.89 C |
| ATOM | 3759 | CB | BSER | B | 26 | 6.238 | −1.804 | 28.196 | 0.35 | 10.66 C |
| ATOM | 3760 | CB | ASER | B | 26 | 6.305 | −1.864 | 28.514 | 0.65 | 11.47 C |
| ATOM | 3765 | OG | BSER | B | 26 | 6.986 | −2.328 | 29.246 | 0.35 | 11.77 O |
| ATOM | 3766 | OG | ASER | B | 26 | 6.755 | −2.916 | 27.701 | 0.65 | 12.82 O |
| ATOM | 3769 | C | SER | B | 26 | 4.177 | −3.089 | 28.889 | 1.00 | 9.15 C |
| ATOM | 3770 | O | SER | B | 26 | 4.245 | −3.579 | 30.017 | 1.00 | 9.90 O |
| ATOM | 3771 | N | SER | B | 27 | 3.579 | −3.695 | 27.878 | 1.00 | 8.91 N |
| ATOM | 3773 | CA | SER | B | 27 | 3.049 | −5.042 | 27.993 | 1.00 | 9.24 C |
| ATOM | 3775 | CB | SER | B | 27 | 1.609 | −5.020 | 28.523 | 1.00 | 9.75 C |
| ATOM | 3778 | OG | SER | B | 27 | 0.701 | −4.659 | 27.498 | 1.00 | 10.07 O |
| ATOM | 3780 | C | SER | B | 27 | 3.045 | −5.686 | 26.626 | 1.00 | 9.09 C |
| ATOM | 3781 | O | SER | B | 27 | 3.418 | −5.071 | 25.633 | 1.00 | 9.64 O |
| ATOM | 3782 | N | SER | B | 28 | 2.555 | −6.913 | 26.573 | 1.00 | 9.24 N |
| ATOM | 3784 | CA | SER | B | 28 | 2.448 | −7.620 | 25.319 | 1.00 | 9.63 C |
| ATOM | 3786 | CB | SER | B | 28 | 1.950 | −9.034 | 25.569 | 1.00 | 10.05 C |
| ATOM | 3789 | OG | SER | B | 28 | 0.663 | −9.022 | 26.149 | 1.00 | 11.00 O |
| ATOM | 3791 | C | SER | B | 28 | 1.551 | −6.906 | 24.309 | 1.00 | 9.09 C |
| ATOM | 3792 | O | SER | B | 28 | 1.683 | −7.141 | 23.109 | 1.00 | 10.26 O |
| ATOM | 3793 | N | ILE | B | 29 | 0.612 | −6.081 | 24.765 | 1.00 | 9.01 N |
| ATOM | 3795 | CA | ILE | B | 29 | −0.230 | −5.322 | 23.829 | 1.00 | 9.45 C |
| ATOM | 3797 | CB | ILE | B | 29 | −1.528 | −4.860 | 24.527 | 1.00 | 9.84 C |

APPENDIX 1-continued

| | | | | | | | | | | |
|---|---|---|---|---|---|---|---|---|---|---|
| ATOM | 3799 | CG1 | ILE | B | 29 | −2.467 | −6.054 | 24.687 | 1.00 | 10.68 C |
| ATOM | 3802 | CD1 | ILE | B | 29 | −3.749 | −5.729 | 25.407 | 1.00 | 11.23 C |
| ATOM | 3806 | CG2 | ILE | B | 29 | −2.209 | −3.738 | 23.755 | 1.00 | 10.93 C |
| ATOM | 3810 | C | ILE | B | 29 | 0.520 | −4.165 | 23.182 | 1.00 | 9.75 C |
| ATOM | 3811 | O | ILE | B | 29 | 0.298 | −3.856 | 22.009 | 1.00 | 10.61 O |
| ATOM | 3812 | N | GLY | B | 30 | 1.392 | −3.519 | 23.936 | 1.00 | 9.50 N |
| ATOM | 3814 | CA | GLY | B | 30 | 2.104 | −2.366 | 23.439 | 1.00 | 10.18 C |
| ATOM | 3817 | C | GLY | B | 30 | 2.498 | −1.451 | 24.564 | 1.00 | 8.93 C |
| ATOM | 3818 | O | GLY | B | 30 | 2.432 | −1.827 | 25.728 | 1.00 | 10.65 O |
| ATOM | 3819 | N | SER | B | 31 | 2.926 | −0.258 | 24.195 | 1.00 | 9.21 N |
| ATOM | 3821 | CA | SER | B | 31 | 3.322 | 0.746 | 25.151 | 1.00 | 9.76 C |
| ATOM | 3823 | CB | BSER | B | 31 | 4.627 | 1.413 | 24.672 | 0.35 | 10.79 C |
| ATOM | 3824 | CB | ASER | B | 31 | 4.636 | 1.385 | 24.762 | 0.65 | 11.07 C |
| ATOM | 3829 | OG | BSER | B | 31 | 5.007 | 2.545 | 25.442 | 0.35 | 12.74 O |
| ATOM | 3830 | OG | ASER | B | 31 | 5.642 | 0.393 | 24.813 | 0.65 | 12.96 O |
| ATOM | 3833 | C | SER | B | 31 | 2.236 | 1.796 | 25.263 | 1.00 | 8.79 C |
| ATOM | 3834 | O | SER | B | 31 | 1.624 | 2.194 | 24.261 | 1.00 | 10.03 O |
| ATOM | 3835 | N | CYS | B | 32 | 2.006 | 2.249 | 26.481 | 1.00 | 8.21 N |
| ATOM | 3837 | CA | CYS | B | 32 | 0.981 | 3.237 | 26.755 | 1.00 | 8.25 C |
| ATOM | 3839 | CB | BCYS | B | 32 | −0.398 | 2.638 | 26.853 | 0.35 | 9.91 C |
| ATOM | 3840 | CB | ACYS | B | 32 | −0.338 | 2.497 | 27.106 | 0.65 | 8.79 C |
| ATOM | 3845 | SG | BCYS | B | 32 | −0.604 | 1.615 | 28.261 | 0.35 | 14.50 S |
| ATOM | 3846 | SG | ACYS | B | 32 | −1.274 | 1.895 | 25.659 | 0.65 | 7.95 S |
| ATOM | 3847 | C | CYS | B | 32 | 1.399 | 4.076 | 27.956 | 1.00 | 7.16 C |
| ATOM | 3848 | O | CYS | B | 32 | 2.526 | 3.975 | 28.467 | 1.00 | 8.13 O |
| ATOM | 3849 | N | THR | B | 33 | 0.491 | 4.947 | 28.359 | 1.00 | 6.54 N |
| ATOM | 3851 | CA | THR | B | 33 | 0.647 | 5.783 | 29.522 | 1.00 | 6.41 C |
| ATOM | 3853 | CB | THR | B | 33 | 0.515 | 7.251 | 29.080 | 1.00 | 6.34 C |
| ATOM | 3855 | OG1 | THR | B | 33 | 1.515 | 7.524 | 28.079 | 1.00 | 6.92 O |
| ATOM | 3857 | CG2 | THR | B | 33 | 0.761 | 8.237 | 30.220 | 1.00 | 6.68 C |
| ATOM | 3861 | C | THR | B | 33 | −0.451 | 5.417 | 30.520 | 1.00 | 6.49 C |
| ATOM | 3862 | O | THR | B | 33 | −1.496 | 4.893 | 30.137 | 1.00 | 6.80 O |
| ATOM | 3863 | N | GLY | B | 34 | −0.228 | 5.715 | 31.793 | 1.00 | 6.76 N |
| ATOM | 3865 | CA | GLY | B | 34 | −1.290 | 5.682 | 32.779 | 1.00 | 6.72 C |
| ATOM | 3868 | C | GLY | B | 34 | −1.039 | 6.736 | 33.827 | 1.00 | 6.52 C |
| ATOM | 3869 | O | GLY | B | 34 | −0.075 | 7.493 | 33.760 | 1.00 | 6.78 O |
| ATOM | 3870 | N | TRP | B | 35 | −1.887 | 6.753 | 34.838 | 1.00 | 6.86 N |
| ATOM | 3872 | CA | TRP | B | 35 | −1.766 | 7.724 | 35.904 | 1.00 | 7.26 C |
| ATOM | 3874 | CB | TRP | B | 35 | −2.492 | 9.043 | 35.563 | 1.00 | 7.82 C |
| ATOM | 3877 | CG | TRP | B | 35 | −3.831 | 8.901 | 34.906 | 1.00 | 8.11 C |
| ATOM | 3878 | CD1 | TRP | B | 35 | −4.066 | 8.555 | 33.608 | 1.00 | 8.12 C |
| ATOM | 3880 | NE1 | TRP | B | 35 | −5.414 | 8.580 | 33.339 | 1.00 | 8.93 N |
| ATOM | 3882 | CE2 | TRP | B | 35 | −6.079 | 8.965 | 34.473 | 1.00 | 8.81 C |
| ATOM | 3883 | CD2 | TRP | B | 35 | −5.111 | 9.181 | 35.475 | 1.00 | 7.96 C |
| ATOM | 3884 | CE3 | TRP | B | 35 | −5.542 | 9.590 | 36.735 | 1.00 | 8.75 C |
| ATOM | 3886 | CZ3 | TRP | B | 35 | −6.887 | 9.760 | 36.966 | 1.00 | 9.89 C |
| ATOM | 3888 | CH2 | TRP | B | 35 | −7.814 | 9.526 | 35.963 | 1.00 | 10.09 C |
| ATOM | 3890 | CZ2 | TRP | B | 35 | −7.432 | 9.140 | 34.705 | 1.00 | 10.05 C |
| ATOM | 3892 | C | TRP | B | 35 | −2.265 | 7.119 | 37.203 | 1.00 | 7.17 C |
| ATOM | 3893 | O | TRP | B | 35 | −3.305 | 6.444 | 37.247 | 1.00 | 7.48 O |
| ATOM | 3894 | N | MET | B | 36 | −1.514 | 7.324 | 38.276 | 1.00 | 7.22 N |
| ATOM | 3896 | CA | MET | B | 36 | −1.884 | 6.750 | 39.562 | 1.00 | 7.60 C |
| ATOM | 3898 | CB | MET | B | 36 | −0.790 | 6.983 | 40.601 | 1.00 | 8.12 C |
| ATOM | 3901 | CG | MET | B | 36 | 0.593 | 6.429 | 40.265 | 1.00 | 8.68 C |
| ATOM | 3904 | SD | MET | B | 36 | 0.683 | 4.684 | 39.895 | 1.00 | 9.14 S |
| ATOM | 3905 | CE | MET | B | 36 | 0.098 | 4.015 | 41.440 | 1.00 | 9.93 C |
| ATOM | 3909 | C | MET | B | 36 | −3.173 | 7.378 | 40.084 | 1.00 | 7.70 C |
| ATOM | 3910 | O | MET | B | 36 | −3.339 | 8.603 | 40.029 | 1.00 | 8.47 O |
| ATOM | 3911 | N | ILE | B | 37 | −4.055 | 6.534 | 40.632 | 1.00 | 7.60 N |
| ATOM | 3913 | CA | ILE | B | 37 | −5.248 | 6.992 | 41.337 | 1.00 | 8.62 C |
| ATOM | 3915 | CB | ILE | B | 37 | −6.553 | 6.614 | 40.591 | 1.00 | 8.72 C |
| ATOM | 3917 | CG1 | ILE | B | 37 | −6.723 | 5.099 | 40.438 | 1.00 | 9.33 C |
| ATOM | 3920 | CD1 | ILE | B | 37 | −8.120 | 4.724 | 39.928 | 1.00 | 9.73 C |
| ATOM | 3924 | CG2 | ILE | B | 37 | −6.607 | 7.330 | 39.261 | 1.00 | 9.21 C |
| ATOM | 3928 | C | ILE | B | 37 | −5.294 | 6.519 | 42.789 | 1.00 | 8.85 C |
| ATOM | 3929 | O | ILE | B | 37 | −6.214 | 6.872 | 43.524 | 1.00 | 10.47 O |
| ATOM | 3930 | N | GLY | B | 38 | −4.311 | 5.739 | 43.210 | 1.00 | 9.34 N |
| ATOM | 3932 | CA | GLY | B | 38 | −4.205 | 5.289 | 44.585 | 1.00 | 9.66 C |
| ATOM | 3935 | C | GLY | B | 38 | −2.837 | 4.675 | 44.794 | 1.00 | 9.97 C |
| ATOM | 3936 | O | GLY | B | 38 | −1.986 | 4.723 | 43.900 | 1.00 | 10.35 O |
| ATOM | 3937 | N | PRO | B | 39 | −2.597 | 4.131 | 45.975 | 1.00 | 9.86 N |
| ATOM | 3938 | CA | PRO | B | 39 | −1.304 | 3.498 | 46.274 | 1.00 | 10.14 C |
| ATOM | 3940 | CB | PRO | B | 39 | −1.552 | 2.839 | 47.634 | 1.00 | 10.75 C |
| ATOM | 3943 | CG | PRO | B | 39 | −2.545 | 3.766 | 48.271 | 1.00 | 11.80 C |
| ATOM | 3946 | CD | PRO | B | 39 | −3.486 | 4.139 | 47.149 | 1.00 | 10.25 C |
| ATOM | 3949 | C | PRO | B | 39 | −0.830 | 2.487 | 45.238 | 1.00 | 9.69 C |
| ATOM | 3950 | O | PRO | B | 39 | 0.366 | 2.411 | 44.978 | 1.00 | 10.04 O |
| ATOM | 3951 | N | LYS | B | 40 | −1.734 | 1.687 | 44.702 | 1.00 | 9.60 N |
| ATOM | 3953 | CA | LYS | B | 40 | −1.328 | 0.634 | 43.791 | 1.00 | 9.71 C |
| ATOM | 3955 | CB | LYS | B | 40 | −1.113 | −0.678 | 44.529 | 1.00 | 11.09 C |

APPENDIX 1-continued

| | | | | | | | | | | |
|---|---|---|---|---|---|---|---|---|---|---|
| ATOM | 3958 | CG | LYS | B | 40 | −2.335 | −1.186 | 45.229 | 1.00 | 11.94 C |
| ATOM | 3961 | CD | LYS | B | 40 | −2.132 | −2.615 | 45.726 | 1.00 | 13.45 C |
| ATOM | 3964 | CE | LYS | B | 40 | −0.996 | −2.749 | 46.704 | 1.00 | 14.20 C |
| ATOM | 3967 | NZ | LYS | B | 40 | −0.976 | −4.121 | 47.344 | 1.00 | 15.10 N |
| ATOM | 3971 | C | LYS | B | 40 | −2.284 | 0.467 | 42.617 | 1.00 | 8.70 C |
| ATOM | 3972 | O | LYS | B | 40 | −2.366 | −0.617 | 42.060 | 1.00 | 9.87 O |
| ATOM | 3973 | N | THR | B | 41 | −2.985 | 1.532 | 42.227 | 1.00 | 8.11 N |
| ATOM | 3975 | CA | THR | B | 41 | −3.939 | 1.455 | 41.125 | 1.00 | 8.14 C |
| ATOM | 3977 | CB | THR | B | 41 | −5.375 | 1.586 | 41.663 | 1.00 | 8.25 C |
| ATOM | 3979 | OG1 | THR | B | 41 | −5.572 | 0.652 | 42.741 | 1.00 | 9.37 O |
| ATOM | 3981 | CG2 | THR | B | 41 | −6.399 | 1.262 | 40.576 | 1.00 | 9.16 C |
| ATOM | 3985 | C | THR | B | 41 | −3.641 | 2.556 | 40.130 | 1.00 | 7.63 C |
| ATOM | 3986 | O | THR | B | 41 | −3.476 | 3.711 | 40.515 | 1.00 | 8.27 O |
| ATOM | 3987 | N | VAL | B | 42 | −3.590 | 2.160 | 38.861 | 1.00 | 7.48 N |
| ATOM | 3989 | CA | VAL | B | 42 | −3.271 | 3.007 | 37.732 | 1.00 | 7.56 C |
| ATOM | 3991 | CB | VAL | B | 42 | −2.122 | 2.378 | 36.911 | 1.00 | 7.80 C |
| ATOM | 3993 | CG1 | VAL | B | 42 | −1.745 | 3.260 | 35.729 | 1.00 | 8.94 C |
| ATOM | 3997 | CG2 | VAL | B | 42 | −0.914 | 2.085 | 37.763 | 1.00 | 9.62 C |
| ATOM | 4001 | C | VAL | B | 42 | −4.491 | 3.072 | 36.818 | 1.00 | 7.34 C |
| ATOM | 4002 | O | VAL | B | 42 | −5.024 | 2.044 | 36.433 | 1.00 | 9.14 O |
| ATOM | 4003 | N | ALA | B | 43 | −4.918 | 4.274 | 36.432 | 1.00 | 7.37 N |
| ATOM | 4005 | CA | ALA | B | 43 | −5.911 | 4.442 | 35.377 | 1.00 | 7.20 C |
| ATOM | 4007 | CB | ALA | B | 43 | −6.711 | 5.713 | 35.603 | 1.00 | 7.51 C |
| ATOM | 4011 | C | ALA | B | 43 | −5.214 | 4.503 | 34.017 | 1.00 | 7.00 C |
| ATOM | 4012 | O | ALA | B | 43 | −4.129 | 5.081 | 33.886 | 1.00 | 7.26 O |
| ATOM | 4013 | N | THR | B | 44 | −5.836 | 3.904 | 33.019 | 1.00 | 6.97 N |
| ATOM | 4015 | CA | THR | B | 44 | −5.286 | 3.897 | 31.670 | 1.00 | 7.04 C |
| ATOM | 4017 | CB | THR | B | 44 | −4.160 | 2.834 | 31.570 | 1.00 | 7.41 C |
| ATOM | 4019 | OG1 | THR | B | 44 | −3.485 | 2.938 | 30.303 | 1.00 | 7.54 O |
| ATOM | 4021 | CG2 | THR | B | 44 | −4.692 | 1.413 | 31.698 | 1.00 | 7.72 C |
| ATOM | 4025 | C | THR | B | 44 | −6.413 | 3.683 | 30.656 | 1.00 | 6.99 C |
| ATOM | 4026 | O | THR | B | 44 | −7.596 | 3.731 | 30.998 | 1.00 | 7.52 O |
| ATOM | 4027 | N | ALA | B | 45 | −6.048 | 3.485 | 29.395 | 1.00 | 7.00 N |
| ATOM | 4029 | CA | ALA | B | 45 | −7.003 | 3.149 | 28.349 | 1.00 | 7.12 C |
| ATOM | 4031 | CB | ALA | B | 45 | −6.479 | 3.579 | 26.979 | 1.00 | 7.53 C |
| ATOM | 4035 | C | ALA | B | 45 | −7.281 | 1.644 | 28.351 | 1.00 | 7.28 C |
| ATOM | 4036 | O | ALA | B | 45 | −6.370 | 0.833 | 28.543 | 1.00 | 8.36 O |
| ATOM | 4037 | N | GLY | B | 46 | −8.529 | 1.256 | 28.120 | 1.00 | 7.41 N |
| ATOM | 4039 | CA | GLY | B | 46 | −8.874 | −0.156 | 28.014 | 1.00 | 7.78 C |
| ATOM | 4042 | C | GLY | B | 46 | −8.106 | −0.884 | 26.933 | 1.00 | 7.87 C |
| ATOM | 4043 | O | GLY | B | 46 | −7.669 | −2.017 | 27.135 | 1.00 | 8.48 O |
| ATOM | 4044 | N | HIS | B | 47 | −7.940 | −0.234 | 25.783 | 1.00 | 7.88 N |
| ATOM | 4046 | CA | HIS | B | 47 | −7.288 | −0.893 | 24.672 | 1.00 | 8.40 C |
| ATOM | 4048 | CB | HIS | B | 47 | −7.524 | −0.133 | 23.362 | 1.00 | 8.56 C |
| ATOM | 4051 | CG | HIS | B | 47 | −6.718 | 1.122 | 23.182 | 1.00 | 7.89 C |
| ATOM | 4052 | ND1 | HIS | B | 47 | −7.280 | 2.381 | 23.233 | 1.00 | 8.37 N |
| ATOM | 4054 | CE1 | HIS | B | 47 | −6.356 | 3.284 | 22.954 | 1.00 | 8.17 C |
| ATOM | 4056 | NE2 | HIS | B | 47 | −5.209 | 2.668 | 22.753 | 1.00 | 8.05 N |
| ATOM | 4058 | CD2 | HIS | B | 47 | −5.409 | 1.313 | 22.884 | 1.00 | 7.79 C |
| ATOM | 4060 | C | HIS | B | 47 | −5.808 | −1.162 | 24.909 | 1.00 | 8.34 C |
| ATOM | 4061 | O | HIS | B | 47 | −5.198 | −1.909 | 24.160 | 1.00 | 9.86 O |
| ATOM | 4062 | N | CYS | B | 48 | −5.235 | −0.537 | 25.933 | 1.00 | 7.91 N |
| ATOM | 4064 | CA | CYS | B | 48 | −3.850 | −0.803 | 26.311 | 1.00 | 8.43 C |
| ATOM | 4066 | CB | CYS | B | 48 | −3.317 | 0.340 | 27.164 | 1.00 | 9.43 C |
| ATOM | 4069 | SG | CYS | B | 48 | −3.197 | 1.908 | 26.286 | 1.00 | 11.14 S |
| ATOM | 4070 | C | CYS | B | 48 | −3.671 | −2.102 | 27.099 | 1.00 | 8.41 C |
| ATOM | 4071 | O | CYS | B | 48 | −2.553 | −2.599 | 27.197 | 1.00 | 9.30 O |
| ATOM | 4072 | N | ILE | B | 49 | −4.758 | −2.622 | 27.679 | 1.00 | 8.25 N |
| ATOM | 4074 | CA | ILE | B | 49 | −4.680 | −3.771 | 28.589 | 1.00 | 8.11 C |
| ATOM | 4076 | CB | ILE | B | 49 | −4.931 | −3.327 | 30.049 | 1.00 | 8.38 C |
| ATOM | 4078 | CG1 | ILE | B | 49 | −6.349 | −2.791 | 30.254 | 1.00 | 8.89 C |
| ATOM | 4081 | CD1 | ILE | B | 49 | −6.631 | −2.365 | 31.696 | 1.00 | 9.33 C |
| ATOM | 4085 | CG2 | ILE | B | 49 | −3.871 | −2.314 | 30.454 | 1.00 | 9.04 C |
| ATOM | 4089 | C | ILE | B | 49 | −5.574 | −4.945 | 28.224 | 1.00 | 8.36 C |
| ATOM | 4090 | O | ILE | B | 49 | −5.385 | −6.015 | 28.774 | 1.00 | 8.42 O |
| ATOM | 4091 | N | TYR | B | 50 | −6.527 | −4.765 | 27.313 | 1.00 | 8.78 N |
| ATOM | 4093 | CA | TYR | B | 50 | −7.397 | −5.847 | 26.876 | 1.00 | 9.04 C |
| ATOM | 4095 | CB | TYR | B | 50 | −8.752 | −5.812 | 27.602 | 1.00 | 9.41 C |
| ATOM | 4098 | CG | TYR | B | 50 | −9.689 | −6.905 | 27.142 | 1.00 | 10.04 C |
| ATOM | 4099 | CD1 | TYR | B | 50 | −10.686 | −6.650 | 26.211 | 1.00 | 10.86 C |
| ATOM | 4101 | CE1 | TYR | B | 50 | −11.534 | −7.668 | 25.770 | 1.00 | 11.77 C |
| ATOM | 4103 | CZ | TYR | B | 50 | −11.372 | −8.951 | 26.279 | 1.00 | 11.98 C |
| ATOM | 4104 | OH | TYR | B | 50 | −12.188 | −9.993 | 25.878 | 1.00 | 14.06 O |
| ATOM | 4106 | CE2 | TYR | B | 50 | −10.394 | −9.208 | 27.210 | 1.00 | 11.89 C |
| ATOM | 4108 | CD2 | TYR | B | 50 | −9.549 | −8.200 | 27.615 | 1.00 | 10.91 C |
| ATOM | 4110 | C | TYR | B | 50 | −7.585 | −5.731 | 25.363 | 1.00 | 9.64 C |
| ATOM | 4111 | O | TYR | B | 50 | −8.007 | −4.678 | 24.858 | 1.00 | 10.03 O |
| ATOM | 4112 | N | ASP | B | 51 | −7.221 | −6.802 | 24.663 | 1.00 | 10.47 N |
| ATOM | 4114 | CA | ASP | B | 51 | −7.291 | −6.906 | 23.220 | 1.00 | 12.23 C |
| ATOM | 4116 | CB | BASP | B | 51 | −6.107 | −7.742 | 22.729 | 0.35 | 12.66 C |

APPENDIX 1-continued

| ATOM | 4117 | CB | AASP | B | 51 | −6.122 | −7.695 | 22.640 | 0.65 | 13.16 | C |
|---|---|---|---|---|---|---|---|---|---|---|---|
| ATOM | 4122 | CG | BASP | B | 51 | −6.080 | −7.888 | 21.234 | 0.35 | 13.82 | C |
| ATOM | 4123 | CG | AASP | B | 51 | −6.149 | −7.713 | 21.131 | 0.65 | 15.14 | C |
| ATOM | 4124 | OD1 | BASP | B | 51 | −6.122 | −9.033 | 20.747 | 0.35 | 14.80 | O |
| ATOM | 4125 | OD1 | AASP | B | 51 | −5.098 | −7.505 | 20.497 | 0.65 | 16.90 | O |
| ATOM | 4126 | OD2 | BASP | B | 51 | −6.018 | −6.909 | 20.468 | 0.35 | 15.44 | O |
| ATOM | 4127 | OD2 | AASP | B | 51 | −7.200 | −7.900 | 20.492 | 0.65 | 16.43 | O |
| ATOM | 4128 | C | ASP | B | 51 | −8.601 | −7.577 | 22.843 | 1.00 | 11.68 | C |
| ATOM | 4129 | O | ASP | B | 51 | −8.809 | −8.770 | 23.089 | 1.00 | 12.14 | O |
| ATOM | 4130 | N | THR | B | 52 | −9.484 | −6.811 | 22.224 | 1.00 | 12.82 | N |
| ATOM | 4132 | CA | THR | B | 52 | −10.821 | −7.311 | 21.944 | 1.00 | 14.29 | C |
| ATOM | 4134 | CB | THR | B | 52 | −11.794 | −6.158 | 21.621 | 1.00 | 15.31 | C |
| ATOM | 4136 | OG1 | THR | B | 52 | −11.342 | −5.436 | 20.473 | 1.00 | 17.85 | O |
| ATOM | 4138 | CG2 | THR | B | 52 | −11.813 | −5.133 | 22.748 | 1.00 | 15.84 | C |
| ATOM | 4142 | C | THR | B | 52 | −10.849 | −8.374 | 20.842 | 1.00 | 15.07 | C |
| ATOM | 4143 | O | THR | B | 52 | −11.736 | −9.221 | 20.836 | 1.00 | 16.91 | O |
| ATOM | 4144 | N | SER | B | 53 | −9.900 | −8.338 | 19.911 | 1.00 | 15.21 | N |
| ATOM | 4146 | CA | SER | B | 53 | −9.869 | −9.326 | 18.824 | 1.00 | 15.87 | C |
| ATOM | 4148 | CB | BSER | B | 53 | −8.908 | −8.886 | 17.708 | 0.35 | 16.21 | C |
| ATOM | 4149 | CB | ASER | B | 53 | −8.859 | −8.903 | 17.756 | 0.65 | 16.72 | C |
| ATOM | 4154 | OG | BSER | B | 53 | −7.569 | −8.772 | 18.157 | 0.35 | 17.00 | O |
| ATOM | 4155 | OG | ASER | B | 53 | −8.752 | −9.892 | 16.748 | 0.65 | 18.99 | O |
| ATOM | 4158 | C | SER | B | 53 | −9.530 | −10.736 | 19.309 | 1.00 | 15.03 | C |
| ATOM | 4159 | O | SER | B | 53 | −10.178 | −11.722 | 18.919 | 1.00 | 14.93 | O |
| ATOM | 4160 | N | SER | B | 54 | −8.511 | −10.836 | 20.153 | 1.00 | 14.11 | N |
| ATOM | 4162 | CA | SER | B | 54 | −8.082 | −12.117 | 20.691 | 1.00 | 13.76 | C |
| ATOM | 4164 | CB | SER | B | 54 | −6.585 | −12.082 | 20.984 | 1.00 | 14.63 | C |
| ATOM | 4167 | OG | SER | B | 54 | −6.302 | −11.212 | 22.069 | 1.00 | 15.48 | O |
| ATOM | 4169 | C | SER | B | 54 | −8.830 | −12.497 | 21.955 | 1.00 | 12.67 | C |
| ATOM | 4170 | O | SER | B | 54 | −8.716 | −13.624 | 22.416 | 1.00 | 13.34 | O |
| ATOM | 4171 | N | GLY | B | 55 | −9.564 | −11.539 | 22.518 | 1.00 | 12.60 | N |
| ATOM | 4173 | CA | GLY | B | 55 | −10.337 | −11.766 | 23.724 | 1.00 | 12.43 | C |
| ATOM | 4176 | C | GLY | B | 55 | −9.474 | −11.987 | 24.936 | 1.00 | 11.80 | C |
| ATOM | 4177 | O | GLY | B | 55 | −9.834 | −12.737 | 25.833 | 1.00 | 12.09 | O |
| ATOM | 4178 | N | SER | B | 56 | −8.333 | −11.313 | 24.993 | 1.00 | 12.30 | N |
| ATOM | 4180 | CA | SER | B | 56 | −7.404 | −11.563 | 26.071 | 1.00 | 12.22 | C |
| ATOM | 4182 | CB | SER | B | 56 | −6.277 | −12.470 | 25.600 | 1.00 | 13.33 | C |
| ATOM | 4185 | OG | SER | B | 56 | −5.511 | −11.840 | 24.607 | 1.00 | 17.47 | O |
| ATOM | 4187 | C | SER | B | 56 | −6.813 | −10.288 | 26.619 | 1.00 | 10.81 | C |
| ATOM | 4188 | O | SER | B | 56 | −6.567 | −9.310 | 25.907 | 1.00 | 10.50 | O |
| ATOM | 4189 | N | PHE | B | 57 | −6.573 | −10.325 | 27.916 | 1.00 | 9.99 | N |
| ATOM | 4191 | CA | PHE | B | 57 | −5.790 | −9.301 | 28.562 | 1.00 | 9.43 | C |
| ATOM | 4193 | CB | PHE | B | 57 | −5.887 | −9.455 | 30.080 | 1.00 | 10.07 | C |
| ATOM | 4196 | CG | PHE | B | 57 | −7.232 | −9.069 | 30.620 | 1.00 | 10.41 | C |
| ATOM | 4197 | CD1 | PHE | B | 57 | −7.527 | −7.744 | 30.869 | 1.00 | 10.08 | C |
| ATOM | 4199 | CE1 | PHE | B | 57 | −8.774 | −7.363 | 31.333 | 1.00 | 11.19 | C |
| ATOM | 4201 | CZ | PHE | B | 57 | −9.751 | −8.313 | 31.532 | 1.00 | 12.88 | C |
| ATOM | 4203 | CE2 | PHE | B | 57 | −9.476 | −9.645 | 31.264 | 1.00 | 13.00 | C |
| ATOM | 4205 | CD2 | PHE | B | 57 | −8.230 | −10.020 | 30.810 | 1.00 | 12.20 | C |
| ATOM | 4207 | C | PHE | B | 57 | −4.347 | −9.410 | 28.102 | 1.00 | 9.19 | C |
| ATOM | 4208 | O | PHE | B | 57 | −3.877 | −10.475 | 27.678 | 1.00 | 10.24 | O |
| ATOM | 4209 | N | ALA | B | 58 | −3.643 | −8.288 | 28.189 | 1.00 | 9.20 | N |
| ATOM | 4211 | CA | ALA | B | 58 | −2.202 | −8.292 | 28.075 | 1.00 | 9.09 | C |
| ATOM | 4213 | CB | ALA | B | 58 | −1.664 | −6.887 | 28.322 | 1.00 | 9.63 | C |
| ATOM | 4217 | C | ALA | B | 58 | −1.601 | −9.247 | 29.090 | 1.00 | 9.25 | C |
| ATOM | 4218 | O | ALA | B | 58 | −2.213 | −9.573 | 30.105 | 1.00 | 9.38 | O |
| ATOM | 4219 | N | GLY | B | 59 | −0.371 | −9.666 | 28.838 | 1.00 | 9.59 | N |
| ATOM | 4221 | CA | GLY | B | 59 | 0.444 | −10.276 | 29.857 | 1.00 | 9.95 | C |
| ATOM | 4224 | C | GLY | B | 59 | 0.793 | −9.242 | 30.908 | 1.00 | 9.76 | C |
| ATOM | 4225 | O | GLY | B | 59 | 0.308 | −8.099 | 30.891 | 1.00 | 10.29 | O |
| ATOM | 4226 | N | THR | B | 60 | 1.637 | −9.646 | 31.834 | 1.00 | 10.02 | N |
| ATOM | 4228 | CA | THR | B | 60 | 2.060 | −8.759 | 32.898 | 1.00 | 10.25 | C |
| ATOM | 4230 | CB | THR | B | 60 | 3.107 | −9.463 | 33.740 | 1.00 | 11.48 | C |
| ATOM | 4232 | OG1 | THR | B | 60 | 2.519 | −10.662 | 34.262 | 1.00 | 13.35 | O |
| ATOM | 4234 | CG2 | THR | B | 60 | 3.526 | −8.622 | 34.941 | 1.00 | 12.09 | C |
| ATOM | 4238 | C | THR | B | 60 | 2.629 | −7.471 | 32.338 | 1.00 | 9.81 | C |
| ATOM | 4239 | O | THR | B | 60 | 3.465 | −7.498 | 31.441 | 1.00 | 10.64 | O |
| ATOM | 4240 | N | ALA | B | 61 | 2.176 | −6.351 | 32.884 | 1.00 | 9.32 | N |
| ATOM | 4242 | CA | ALA | B | 61 | 2.677 | −5.044 | 32.503 | 1.00 | 9.32 | C |
| ATOM | 4244 | CB | ALA | B | 61 | 1.568 | −3.981 | 32.587 | 1.00 | 9.62 | C |
| ATOM | 4248 | C | ALA | B | 61 | 3.837 | −4.632 | 33.385 | 1.00 | 8.92 | C |
| ATOM | 4249 | O | ALA | B | 61 | 3.876 | −4.954 | 34.567 | 1.00 | 10.09 | O |
| ATOM | 4250 | N | THR | B | 62 | 4.756 | −3.882 | 32.793 | 1.00 | 9.06 | N |
| ATOM | 4252 | CA | THR | B | 62 | 5.844 | −3.224 | 33.497 | 1.00 | 9.56 | C |
| ATOM | 4254 | CB | THR | B | 62 | 7.159 | −3.456 | 32.762 | 1.00 | 10.57 | C |
| ATOM | 4256 | OG1 | THR | B | 62 | 7.423 | −4.870 | 32.721 | 1.00 | 11.83 | O |
| ATOM | 4258 | CG2 | THR | B | 62 | 8.326 | −2.808 | 33.497 | 1.00 | 12.14 | C |
| ATOM | 4262 | C | THR | B | 62 | 5.495 | −1.745 | 33.556 | 1.00 | 8.59 | C |
| ATOM | 4263 | O | THR | B | 62 | 5.334 | −1.089 | 32.521 | 1.00 | 9.17 | O |
| ATOM | 4264 | N | VAL | B | 63 | 5.359 | −1.225 | 34.771 | 1.00 | 8.26 | N |

APPENDIX 1-continued

| ATOM | 4266 | CA | VAL | B | 63 | 4.826 | 0.118 | 35.013 | 1.00 | 8.04 C |
|---|---|---|---|---|---|---|---|---|---|---|
| ATOM | 4268 | CB | VAL | B | 63 | 3.546 | 0.039 | 35.861 | 1.00 | 8.65 C |
| ATOM | 4270 | CG1 | VAL | B | 63 | 3.023 | 1.431 | 36.176 | 1.00 | 9.71 C |
| ATOM | 4274 | CG2 | VAL | B | 63 | 2.478 | −0.794 | 35.150 | 1.00 | 9.51 C |
| ATOM | 4278 | C | VAL | B | 63 | 5.891 | 0.959 | 35.693 | 1.00 | 7.95 C |
| ATOM | 4279 | O | VAL | B | 63 | 6.369 | 0.597 | 36.771 | 1.00 | 8.82 O |
| ATOM | 4280 | N | SER | B | 64 | 6.254 | 2.083 | 35.085 | 1.00 | 7.68 N |
| ATOM | 4282 | CA | SER | B | 64 | 7.393 | 2.863 | 35.515 | 1.00 | 8.03 C |
| ATOM | 4284 | CB | SER | B | 64 | 8.499 | 2.805 | 34.462 | 1.00 | 8.70 C |
| ATOM | 4287 | OG | SER | B | 64 | 8.898 | 1.469 | 34.228 | 1.00 | 9.66 O |
| ATOM | 4289 | C | SER | B | 64 | 6.965 | 4.306 | 35.757 | 1.00 | 7.95 C |
| ATOM | 4290 | O | SER | B | 64 | 6.893 | 5.116 | 34.823 | 1.00 | 7.83 O |
| ATOM | 4291 | N | PRO | B | 65 | 6.648 | 4.658 | 37.004 | 1.00 | 8.11 N |
| ATOM | 4292 | CA | PRO | B | 65 | 6.226 | 6.028 | 37.301 | 1.00 | 8.10 C |
| ATOM | 4294 | CB | PRO | B | 65 | 5.859 | 5.970 | 38.795 | 1.00 | 8.49 C |
| ATOM | 4297 | CG | PRO | B | 65 | 5.584 | 4.520 | 39.054 | 1.00 | 8.49 C |
| ATOM | 4300 | CD | PRO | B | 65 | 6.600 | 3.807 | 38.204 | 1.00 | 8.68 C |
| ATOM | 4303 | C | PRO | B | 65 | 7.344 | 7.027 | 37.057 | 1.00 | 8.00 C |
| ATOM | 4304 | O | PRO | B | 65 | 8.483 | 6.807 | 37.481 | 1.00 | 8.46 O |
| ATOM | 4305 | N | GLY | B | 66 | 7.038 | 8.127 | 36.383 | 1.00 | 7.75 N |
| ATOM | 4307 | CA | GLY | B | 66 | 8.034 | 9.166 | 36.186 | 1.00 | 8.40 C |
| ATOM | 4310 | C | GLY | B | 66 | 9.266 | 8.699 | 35.428 | 1.00 | 8.24 C |
| ATOM | 4311 | O | GLY | B | 66 | 10.346 | 9.265 | 35.586 | 1.00 | 8.86 O |
| ATOM | 4312 | N | ARG | B | 67 | 9.123 | 7.685 | 34.585 | 1.00 | 8.08 N |
| ATOM | 4314 | CA | ARG | B | 67 | 10.223 | 7.252 | 33.745 | 1.00 | 8.11 C |
| ATOM | 4316 | CB | ARG | B | 67 | 9.753 | 6.160 | 32.802 | 1.00 | 8.27 C |
| ATOM | 4319 | CG | ARG | B | 67 | 10.864 | 5.568 | 31.971 | 1.00 | 8.88 C |
| ATOM | 4322 | CD | ARG | B | 67 | 10.435 | 4.444 | 31.086 | 1.00 | 8.89 C |
| ATOM | 4325 | NE | ARG | B | 67 | 11.498 | 4.135 | 30.142 | 1.00 | 9.16 N |
| ATOM | 4327 | CZ | ARG | B | 67 | 11.404 | 3.282 | 29.149 | 1.00 | 10.30 C |
| ATOM | 4328 | NH1 | ARG | B | 67 | 12.410 | 3.169 | 28.296 | 1.00 | 11.25 N |
| ATOM | 4331 | NH2 | ARG | B | 67 | 10.320 | 2.541 | 29.004 | 1.00 | 12.36 N |
| ATOM | 4334 | C | ARG | B | 67 | 10.750 | 8.429 | 32.946 | 1.00 | 8.11 C |
| ATOM | 4335 | O | ARG | B | 67 | 9.983 | 9.254 | 32.462 | 1.00 | 8.22 O |
| ATOM | 4336 | N | ASN | B | 68 | 12.070 | 8.472 | 32.783 | 1.00 | 8.17 N |
| ATOM | 4338 | CA | ASN | B | 68 | 12.720 | 9.484 | 31.970 | 1.00 | 8.77 C |
| ATOM | 4340 | CB | ASN | B | 68 | 13.312 | 10.573 | 32.848 | 1.00 | 9.40 C |
| ATOM | 4343 | CG | ASN | B | 68 | 13.931 | 11.660 | 32.023 | 1.00 | 10.39 C |
| ATOM | 4344 | OD1 | ASN | B | 68 | 13.349 | 12.050 | 31.010 | 1.00 | 11.79 O |
| ATOM | 4345 | ND2 | ASN | B | 68 | 15.136 | 12.110 | 32.385 | 1.00 | 12.51 N |
| ATOM | 4348 | C | ASN | B | 68 | 13.812 | 8.863 | 31.104 | 1.00 | 9.03 C |
| ATOM | 4349 | O | ASN | B | 68 | 14.994 | 8.879 | 31.455 | 1.00 | 9.74 O |
| ATOM | 4350 | N | GLY | B | 69 | 13.405 | 8.293 | 29.977 | 1.00 | 9.60 N |
| ATOM | 4352 | CA | GLY | B | 69 | 14.329 | 7.682 | 29.037 | 1.00 | 9.82 C |
| ATOM | 4355 | C | GLY | B | 69 | 14.763 | 6.335 | 29.549 | 1.00 | 9.55 C |
| ATOM | 4356 | O | GLY | B | 69 | 13.946 | 5.419 | 29.628 | 1.00 | 10.48 O |
| ATOM | 4357 | N | THR | B | 70 | 16.040 | 6.194 | 29.885 | 1.00 | 9.50 N |
| ATOM | 4359 | CA | THR | B | 70 | 16.516 | 4.977 | 30.529 | 1.00 | 10.01 C |
| ATOM | 4361 | CB | THR | B | 70 | 17.775 | 4.427 | 29.839 | 1.00 | 10.64 C |
| ATOM | 4363 | OG1 | THR | B | 70 | 18.745 | 5.471 | 29.679 | 1.00 | 11.68 O |
| ATOM | 4365 | CG2 | THR | B | 70 | 17.437 | 3.934 | 28.436 | 1.00 | 11.69 C |
| ATOM | 4369 | C | THR | B | 70 | 16.747 | 5.185 | 32.024 | 1.00 | 10.48 C |
| ATOM | 4370 | O | THR | B | 70 | 17.362 | 4.357 | 32.689 | 1.00 | 11.63 O |
| ATOM | 4371 | N | SER | B | 71 | 16.214 | 6.274 | 32.558 | 1.00 | 10.58 N |
| ATOM | 4373 | CA | SER | B | 71 | 16.175 | 6.510 | 33.992 | 1.00 | 10.32 C |
| ATOM | 4375 | CB | SER | B | 71 | 16.437 | 7.969 | 34.309 | 1.00 | 10.45 C |
| ATOM | 4378 | OG | SER | B | 71 | 17.669 | 8.393 | 33.780 | 1.00 | 11.02 O |
| ATOM | 4380 | C | SER | B | 71 | 14.821 | 6.139 | 34.562 | 1.00 | 9.95 C |
| ATOM | 4381 | O | SER | B | 71 | 13.775 | 6.496 | 34.006 | 1.00 | 10.07 O |
| ATOM | 4382 | N | TYR | B | 72 | 14.853 | 5.470 | 35.710 | 1.00 | 9.77 N |
| ATOM | 4384 | CA | TYR | B | 72 | 13.665 | 4.953 | 36.370 | 1.00 | 9.83 C |
| ATOM | 4386 | CB | TYR | B | 72 | 13.637 | 3.420 | 36.298 | 1.00 | 10.11 C |
| ATOM | 4389 | CG | TYR | B | 72 | 13.491 | 2.884 | 34.890 | 1.00 | 10.38 C |
| ATOM | 4390 | CD1 | TYR | B | 72 | 12.261 | 2.467 | 34.422 | 1.00 | 10.73 C |
| ATOM | 4392 | CE1 | TYR | B | 72 | 12.112 | 1.963 | 33.142 | 1.00 | 11.24 C |
| ATOM | 4394 | CZ | TYR | B | 72 | 13.200 | 1.895 | 32.301 | 1.00 | 11.23 C |
| ATOM | 4395 | OH | TYR | B | 72 | 13.014 | 1.381 | 31.041 | 1.00 | 12.73 O |
| ATOM | 4397 | CE2 | TYR | B | 72 | 14.442 | 2.316 | 32.741 | 1.00 | 11.74 C |
| ATOM | 4399 | CD2 | TYR | B | 72 | 14.581 | 2.804 | 34.018 | 1.00 | 11.15 C |
| ATOM | 4401 | C | TYR | B | 72 | 13.739 | 5.443 | 37.815 | 1.00 | 10.00 C |
| ATOM | 4402 | O | TYR | B | 72 | 14.125 | 4.683 | 38.712 | 1.00 | 10.50 O |
| ATOM | 4403 | N | PRO | B | 73 | 13.426 | 6.715 | 38.070 | 1.00 | 10.19 N |
| ATOM | 4404 | CA | PRO | B | 73 | 13.605 | 7.254 | 39.425 | 1.00 | 10.57 C |
| ATOM | 4406 | CB | PRO | B | 73 | 13.195 | 8.719 | 39.285 | 1.00 | 10.64 C |
| ATOM | 4409 | CG | PRO | B | 73 | 12.351 | 8.766 | 38.059 | 1.00 | 10.69 C |
| ATOM | 4412 | CD | PRO | B | 73 | 12.927 | 7.742 | 37.134 | 1.00 | 10.07 C |
| ATOM | 4415 | C | PRO | B | 73 | 12.778 | 6.561 | 40.497 | 1.00 | 10.59 C |
| ATOM | 4416 | O | PRO | B | 73 | 13.139 | 6.627 | 41.664 | 1.00 | 12.17 O |
| ATOM | 4417 | N | TYR | B | 74 | 11.692 | 5.916 | 40.097 | 1.00 | 10.13 N |
| ATOM | 4419 | CA | TYR | B | 74 | 10.834 | 5.165 | 41.004 | 1.00 | 10.86 C |

APPENDIX 1-continued

| ATOM | 4421 | CB | TYR | B | 74 | 9.425 | 5.767 | 41.038 | 1.00 | 10.82 | C |
|---|---|---|---|---|---|---|---|---|---|---|---|
| ATOM | 4424 | CG | TYR | B | 74 | 9.500 | 7.222 | 41.399 | 1.00 | 10.36 | C |
| ATOM | 4425 | CD1 | TYR | B | 74 | 9.391 | 8.194 | 40.416 | 1.00 | 10.82 | C |
| ATOM | 4427 | CE1 | TYR | B | 74 | 9.519 | 9.518 | 40.701 | 1.00 | 11.59 | C |
| ATOM | 4429 | CZ | TYR | B | 74 | 9.748 | 9.915 | 41.996 | 1.00 | 11.91 | C |
| ATOM | 4430 | OH | TYR | B | 74 | 9.863 | 11.261 | 42.253 | 1.00 | 14.01 | O |
| ATOM | 4432 | CE2 | TYR | B | 74 | 9.864 | 8.972 | 43.005 | 1.00 | 12.35 | C |
| ATOM | 4434 | CD2 | TYR | B | 74 | 9.752 | 7.632 | 42.700 | 1.00 | 11.52 | C |
| ATOM | 4436 | C | TYR | B | 74 | 10.788 | 3.696 | 40.635 | 1.00 | 11.39 | C |
| ATOM | 4437 | O | TYR | B | 74 | 9.849 | 2.993 | 41.013 | 1.00 | 12.84 | O |
| ATOM | 4438 | N | GLY | B | 75 | 11.820 | 3.222 | 39.939 | 1.00 | 10.85 | N |
| ATOM | 4440 | CA | GLY | B | 75 | 11.872 | 1.851 | 39.479 | 1.00 | 10.79 | C |
| ATOM | 4443 | C | GLY | B | 75 | 10.764 | 1.505 | 38.505 | 1.00 | 10.56 | C |
| ATOM | 4444 | O | GLY | B | 75 | 10.129 | 2.370 | 37.891 | 1.00 | 10.85 | O |
| ATOM | 4445 | N | SER | B | 76 | 10.563 | 0.202 | 38.377 | 1.00 | 10.90 | N |
| ATOM | 4447 | CA | SER | B | 76 | 9.489 | −0.367 | 37.607 | 1.00 | 11.52 | C |
| ATOM | 4449 | CB | BSER | B | 76 | 10.053 | −1.085 | 36.386 | 0.35 | 11.19 | C |
| ATOM | 4450 | CB | ASER | B | 76 | 9.998 | −0.975 | 36.309 | 0.65 | 13.32 | C |
| ATOM | 4455 | OG | BSER | B | 76 | 10.704 | −0.188 | 35.508 | 0.35 | 7.99 | O |
| ATOM | 4456 | OG | ASER | B | 76 | 10.880 | −2.042 | 36.529 | 0.65 | 17.36 | O |
| ATOM | 4459 | C | SER | B | 76 | 8.802 | −1.393 | 38.474 | 1.00 | 11.22 | C |
| ATOM | 4460 | O | SER | B | 76 | 9.444 | −2.102 | 39.264 | 1.00 | 12.58 | O |
| ATOM | 4461 | N | VAL | B | 77 | 7.489 | −1.472 | 38.325 | 1.00 | 10.56 | N |
| ATOM | 4463 | CA | VAL | B | 77 | 6.668 | −2.352 | 39.116 | 1.00 | 10.65 | C |
| ATOM | 4465 | CB | BVAL | B | 77 | 5.793 | −1.531 | 40.080 | 0.35 | 10.56 | C |
| ATOM | 4466 | CB | AVAL | B | 77 | 5.843 | −1.555 | 40.151 | 0.65 | 11.99 | C |
| ATOM | 4469 | CG1 | BVAL | B | 77 | 4.837 | −2.397 | 40.810 | 0.35 | 8.39 | C |
| ATOM | 4470 | CG1 | AVAL | B | 77 | 6.704 | −0.441 | 40.775 | 0.65 | 12.64 | C |
| ATOM | 4477 | CG2 | BVAL | B | 77 | 6.661 | −0.843 | 41.119 | 0.35 | 11.33 | C |
| ATOM | 4478 | CG2 | AVAL | B | 77 | 4.627 | −0.943 | 39.578 | 0.65 | 12.49 | C |
| ATOM | 4485 | C | VAL | B | 77 | 5.801 | −3.183 | 38.174 | 1.00 | 9.91 | C |
| ATOM | 4486 | O | VAL | B | 77 | 5.303 | −2.699 | 37.163 | 1.00 | 12.13 | O |
| ATOM | 4487 | N | LYS | B | 78 | 5.596 | −4.440 | 38.500 | 1.00 | 11.93 | N |
| ATOM | 4489 | CA | LYS | B | 78 | 4.790 | −5.315 | 37.664 | 1.00 | 12.70 | C |
| ATOM | 4491 | CB | LYS | B | 78 | 5.236 | −6.767 | 37.809 | 1.00 | 13.36 | C |
| ATOM | 4494 | CG | LYS | B | 78 | 6.666 | −7.034 | 37.399 | 1.00 | 15.87 | C |
| ATOM | 4497 | CD | LYS | B | 78 | 6.906 | −6.736 | 35.938 | 1.00 | 17.52 | C |
| ATOM | 4500 | CE | LYS | B | 78 | 8.294 | −7.176 | 35.540 | 1.00 | 19.94 | C |
| ATOM | 4503 | NZ | LYS | B | 78 | 8.671 | −6.739 | 34.188 | 1.00 | 22.53 | N |
| ATOM | 4507 | C | LYS | B | 78 | 3.338 | −5.215 | 38.065 | 1.00 | 12.78 | C |
| ATOM | 4508 | O | LYS | B | 78 | 3.035 | −5.045 | 39.243 | 1.00 | 14.43 | O |
| ATOM | 4509 | N | SER | B | 79 | 2.436 | −5.360 | 37.098 | 1.00 | 12.03 | N |
| ATOM | 4511 | CA | SER | B | 79 | 1.017 | −5.509 | 37.378 | 1.00 | 11.74 | C |
| ATOM | 4513 | CB | SER | B | 79 | 0.196 | −5.437 | 36.090 | 1.00 | 11.51 | C |
| ATOM | 4516 | OG | SER | B | 79 | 0.508 | −6.477 | 35.178 | 1.00 | 10.77 | O |
| ATOM | 4518 | C | SER | B | 79 | 0.722 | −6.833 | 38.044 | 1.00 | 11.16 | C |
| ATOM | 4519 | O | SER | B | 79 | 1.441 | −7.826 | 37.856 | 1.00 | 12.07 | O |
| ATOM | 4520 | N | THR | B | 80 | −0.360 | −6.849 | 38.804 | 1.00 | 10.75 | N |
| ATOM | 4522 | CA | THR | B | 80 | −0.923 | −8.093 | 39.298 | 1.00 | 11.21 | C |
| ATOM | 4524 | CB | THR | B | 80 | −1.164 | −8.015 | 40.807 | 1.00 | 11.49 | C |
| ATOM | 4526 | OG1 | THR | B | 80 | −1.989 | −6.887 | 41.124 | 1.00 | 12.77 | O |
| ATOM | 4528 | CG2 | THR | B | 80 | 0.154 | −7.823 | 41.547 | 1.00 | 11.88 | C |
| ATOM | 4532 | C | THR | B | 80 | −2.196 | −8.485 | 38.578 | 1.00 | 11.33 | C |
| ATOM | 4533 | O | THR | B | 80 | −2.490 | −9.682 | 38.478 | 1.00 | 12.80 | O |
| ATOM | 4534 | N | ARG | B | 81 | −2.959 | −7.489 | 38.114 | 1.00 | 11.02 | N |
| ATOM | 4536 | CA | ARG | B | 81 | −4.210 | −7.752 | 37.427 | 1.00 | 10.96 | C |
| ATOM | 4538 | CB | ARG | B | 81 | −5.240 | −8.338 | 38.374 | 1.00 | 11.73 | C |
| ATOM | 4541 | CG | ARG | B | 81 | −5.626 | −7.375 | 39.459 | 1.00 | 11.26 | C |
| ATOM | 4544 | CD | ARG | B | 81 | −6.558 | −7.993 | 40.419 | 1.00 | 13.29 | C |
| ATOM | 4547 | NE | ARG | B | 81 | −6.874 | −7.102 | 41.525 | 1.00 | 14.74 | N |
| ATOM | 4549 | CZ | ARG | B | 81 | −7.891 | −7.291 | 42.357 | 1.00 | 13.37 | C |
| ATOM | 4550 | NH1 | ARG | B | 81 | −8.139 | −6.424 | 43.336 | 1.00 | 11.04 | N |
| ATOM | 4553 | NH2 | ARG | B | 81 | −8.704 | −8.320 | 42.185 | 1.00 | 16.83 | N |
| ATOM | 4556 | C | ARG | B | 81 | −4.748 | −6.458 | 36.824 | 1.00 | 9.86 | C |
| ATOM | 4557 | O | ARG | B | 81 | −4.234 | −5.348 | 37.074 | 1.00 | 10.32 | O |
| ATOM | 4558 | N | TYR | B | 82 | −5.781 | −6.619 | 36.013 | 1.00 | 9.05 | N |
| ATOM | 4560 | CA | TYR | B | 82 | −6.392 | −5.564 | 35.243 | 1.00 | 8.45 | C |
| ATOM | 4562 | CB | TYR | B | 82 | −6.236 | −5.882 | 33.761 | 1.00 | 8.46 | C |
| ATOM | 4565 | CG | TYR | B | 82 | −4.815 | −5.913 | 33.273 | 1.00 | 8.62 | C |
| ATOM | 4566 | CD1 | TYR | B | 82 | −4.012 | −4.791 | 33.367 | 1.00 | 9.06 | C |
| ATOM | 4568 | CE1 | TYR | B | 82 | −2.711 | −4.804 | 32.888 | 1.00 | 9.18 | C |
| ATOM | 4570 | CZ | TYR | B | 82 | −2.202 | −5.950 | 32.310 | 1.00 | 8.79 | C |
| ATOM | 4571 | OH | TYR | B | 82 | −0.907 | −5.894 | 31.850 | 1.00 | 9.78 | O |
| ATOM | 4573 | CE2 | TYR | B | 82 | −2.990 | −7.081 | 32.209 | 1.00 | 9.01 | C |
| ATOM | 4575 | CD2 | TYR | B | 82 | −4.284 | −7.053 | 32.688 | 1.00 | 9.11 | C |
| ATOM | 4577 | C | TYR | B | 82 | −7.886 | −5.476 | 35.560 | 1.00 | 8.75 | C |
| ATOM | 4578 | O | TYR | B | 82 | −8.513 | −6.470 | 35.949 | 1.00 | 9.58 | O |
| ATOM | 4579 | N | PHE | B | 83 | −8.447 | −4.290 | 35.362 | 1.00 | 8.61 | N |
| ATOM | 4581 | CA | PHE | B | 83 | −9.874 | −4.032 | 35.444 | 1.00 | 8.66 | C |
| ATOM | 4583 | CB | PHE | B | 83 | −10.228 | −3.092 | 36.585 | 1.00 | 9.00 | C |

APPENDIX 1-continued

| | | | | | | | | | | |
|---|---|---|---|---|---|---|---|---|---|---|
| ATOM | 4586 | CG | PHE | B | 83 | −9.748 | −3.516 | 37.936 | 1.00 | 9.24 C |
| ATOM | 4587 | CD1 | PHE | B | 83 | −8.475 | −3.177 | 38.366 | 1.00 | 10.26 C |
| ATOM | 4589 | CE1 | PHE | B | 83 | −8.059 | −3.502 | 39.639 | 1.00 | 11.44 C |
| ATOM | 4591 | CZ | PHE | B | 83 | −8.911 | −4.173 | 40.501 | 1.00 | 12.62 C |
| ATOM | 4593 | CE2 | PHE | B | 83 | −10.177 | −4.495 | 40.104 | 1.00 | 12.07 C |
| ATOM | 4595 | CD2 | PHE | B | 83 | −10.604 | −4.166 | 38.823 | 1.00 | 10.68 C |
| ATOM | 4597 | C | PHE | B | 83 | −10.298 | −3.339 | 34.160 | 1.00 | 8.76 C |
| ATOM | 4598 | O | PHE | B | 83 | −9.630 | −2.409 | 33.699 | 1.00 | 8.65 O |
| ATOM | 4599 | N | ILE | B | 84 | −11.421 | −3.768 | 33.598 | 1.00 | 8.84 N |
| ATOM | 4601 | CA | ILE | B | 84 | −12.048 | −3.068 | 32.478 | 1.00 | 9.12 C |
| ATOM | 4603 | CB | ILE | B | 84 | −11.734 | −3.740 | 31.118 | 1.00 | 9.53 C |
| ATOM | 4605 | CG1 | ILE | B | 84 | −12.103 | −5.225 | 31.124 | 1.00 | 10.28 C |
| ATOM | 4608 | CD1 | ILE | B | 84 | −11.973 | −5.909 | 29.791 | 1.00 | 12.10 C |
| ATOM | 4612 | CG2 | ILE | B | 84 | −10.281 | −3.522 | 30.746 | 1.00 | 10.12 C |
| ATOM | 4616 | C | ILE | B | 84 | −13.552 | −3.018 | 32.691 | 1.00 | 8.87 C |
| ATOM | 4617 | O | ILE | B | 84 | −14.134 | −3.904 | 33.327 | 1.00 | 9.55 O |
| ATOM | 4618 | N | PRO | B | 85 | −14.198 | −2.004 | 32.131 | 1.00 | 9.08 N |
| ATOM | 4619 | CA | PRO | B | 85 | −15.660 | −1.982 | 32.154 | 1.00 | 9.52 C |
| ATOM | 4621 | CB | PRO | B | 85 | −15.984 | −0.561 | 31.686 | 1.00 | 10.01 C |
| ATOM | 4624 | CG | PRO | B | 85 | −14.849 | −0.235 | 30.745 | 1.00 | 9.80 C |
| ATOM | 4627 | CD | PRO | B | 85 | −13.642 | −0.866 | 31.371 | 1.00 | 9.00 C |
| ATOM | 4630 | C | PRO | B | 85 | −16.212 | −3.010 | 31.176 | 1.00 | 10.10 C |
| ATOM | 4631 | O | PRO | B | 85 | −15.561 | −3.364 | 30.210 | 1.00 | 10.32 O |
| ATOM | 4632 | N | SER | B | 86 | −17.437 | −3.459 | 31.407 | 1.00 | 11.25 N |
| ATOM | 4634 | CA | SER | B | 86 | −18.073 | −4.415 | 30.502 | 1.00 | 12.53 C |
| ATOM | 4636 | CB | BSER | B | 86 | −19.506 | −4.715 | 30.963 | 0.35 | 13.18 C |
| ATOM | 4637 | CB | ASER | B | 86 | −19.476 | −4.789 | 30.986 | 0.65 | 13.91 C |
| ATOM | 4642 | OG | BSER | B | 86 | −19.544 | −5.098 | 32.327 | 0.35 | 14.94 O |
| ATOM | 4643 | OG | ASER | B | 86 | −20.279 | −3.644 | 31.135 | 0.65 | 17.06 O |
| ATOM | 4646 | C | SER | B | 86 | −18.116 | −3.886 | 29.071 | 1.00 | 12.33 C |
| ATOM | 4647 | O | SER | B | 86 | −17.957 | −4.654 | 28.127 | 1.00 | 13.62 O |
| ATOM | 4648 | N | GLY | B | 87 | −18.305 | −2.578 | 28.911 | 1.00 | 12.00 N |
| ATOM | 4650 | CA | GLY | B | 87 | −18.365 | −1.984 | 27.589 | 1.00 | 12.48 C |
| ATOM | 4653 | C | GLY | B | 87 | −17.076 | −2.129 | 26.808 | 1.00 | 12.31 C |
| ATOM | 4654 | O | GLY | B | 87 | −17.114 | −2.175 | 25.583 | 1.00 | 14.16 O |
| ATOM | 4655 | N | TRP | B | 88 | −15.931 | −2.192 | 27.495 | 1.00 | 11.78 N |
| ATOM | 4657 | CA | TRP | B | 88 | −14.658 | −2.408 | 26.804 | 1.00 | 11.93 C |
| ATOM | 4659 | CB | TRP | B | 88 | −13.432 | −1.778 | 27.501 | 1.00 | 11.63 C |
| ATOM | 4662 | CG | TRP | B | 88 | −12.253 | −1.984 | 26.598 | 1.00 | 10.61 C |
| ATOM | 4663 | CD1 | TRP | B | 88 | −11.202 | −2.843 | 26.769 | 1.00 | 10.04 C |
| ATOM | 4665 | NE1 | TRP | B | 88 | −10.404 | −2.843 | 25.652 | 1.00 | 10.00 N |
| ATOM | 4667 | CE2 | TRP | B | 88 | −10.932 | −1.976 | 24.733 | 1.00 | 9.81 C |
| ATOM | 4668 | CD2 | TRP | B | 88 | −12.106 | −1.434 | 25.292 | 1.00 | 10.13 C |
| ATOM | 4669 | CE3 | TRP | B | 88 | −12.838 | −0.519 | 24.539 | 1.00 | 11.31 C |
| ATOM | 4671 | CZ3 | TRP | B | 88 | −12.403 | −0.194 | 23.276 | 1.00 | 12.74 C |
| ATOM | 4673 | CH2 | TRP | B | 88 | −11.247 | −0.752 | 22.749 | 1.00 | 12.39 C |
| ATOM | 4675 | CZ2 | TRP | B | 88 | −10.504 | −1.659 | 23.451 | 1.00 | 11.10 C |
| ATOM | 4677 | C | TRP | B | 88 | −14.384 | −3.874 | 26.554 | 1.00 | 13.20 C |
| ATOM | 4678 | O | TRP | B | 88 | −13.795 | −4.228 | 25.544 | 1.00 | 14.61 O |
| ATOM | 4679 | N | ARG | B | 89 | −14.818 | −4.742 | 27.456 | 1.00 | 14.97 N |
| ATOM | 4681 | CA | ARG | B | 89 | −14.786 | −6.157 | 27.135 | 1.00 | 17.45 C |
| ATOM | 4683 | CB | ARG | B | 89 | −15.489 | −6.978 | 28.216 | 1.00 | 18.59 C |
| ATOM | 4686 | CG | ARG | B | 89 | −14.972 | −8.407 | 28.352 | 1.00 | 20.17 C |
| ATOM | 4689 | CD | ARG | B | 89 | −15.609 | −9.163 | 29.496 | 1.00 | 22.60 C |
| ATOM | 4692 | NE | ARG | B | 89 | −15.033 | −8.796 | 30.790 | 1.00 | 24.39 N |
| ATOM | 4694 | CZ | ARG | B | 89 | −13.948 | −9.349 | 31.330 | 1.00 | 25.64 C |
| ATOM | 4695 | NH1 | ARG | B | 89 | −13.279 | −10.314 | 30.701 | 1.00 | 26.15 N |
| ATOM | 4698 | NH2 | ARG | B | 89 | −13.524 | −8.931 | 32.516 | 1.00 | 26.48 N |
| ATOM | 4701 | C | ARG | B | 89 | −15.423 | −6.339 | 25.731 | 1.00 | 19.17 C |
| ATOM | 4702 | O | ARG | B | 89 | −15.043 | −7.254 | 24.999 | 1.00 | 20.41 O |
| ATOM | 4703 | N | SER | B | 90 | −16.345 | −5.436 | 25.357 | 1.00 | 20.72 N |
| ATOM | 4705 | CA | SER | B | 90 | −16.995 | −5.405 | 24.034 | 1.00 | 21.67 C |
| ATOM | 4707 | CB | SER | B | 90 | −18.412 | −4.837 | 24.189 | 1.00 | 22.17 C |
| ATOM | 4710 | OG | SER | B | 90 | −19.158 | −5.584 | 25.125 | 1.00 | 23.91 O |
| ATOM | 4712 | C | SER | B | 90 | −16.267 | −4.630 | 22.917 | 1.00 | 21.74 C |
| ATOM | 4713 | O | SER | B | 90 | −16.614 | −4.789 | 21.746 | 1.00 | 23.22 O |
| ATOM | 4714 | N | GLY | B | 91 | −15.307 | −3.771 | 23.253 | 1.00 | 21.01 N |
| ATOM | 4716 | CA | GLY | B | 91 | −14.547 | −3.027 | 22.258 | 1.00 | 20.45 C |
| ATOM | 4719 | C | GLY | B | 91 | −15.224 | −1.724 | 21.881 | 1.00 | 20.20 C |
| ATOM | 4720 | O | GLY | B | 91 | −14.868 | −1.062 | 20.893 | 1.00 | 20.84 O |
| ATOM | 4721 | N | ASN | B | 92 | −16.222 | −1.355 | 22.669 | 1.00 | 19.28 N |
| ATOM | 4723 | CA | ASN | B | 92 | −16.957 | −0.132 | 22.417 | 1.00 | 18.38 C |
| ATOM | 4725 | CB | ASN | B | 92 | −18.294 | −0.171 | 23.169 | 1.00 | 17.92 C |
| ATOM | 4728 | CG | ASN | B | 92 | −19.210 | 0.960 | 22.777 | 1.00 | 17.67 C |
| ATOM | 4729 | OD1 | ASN | B | 92 | −18.749 | 2.066 | 22.576 | 1.00 | 15.73 O |
| ATOM | 4730 | ND2 | ASN | B | 92 | −20.510 | 0.686 | 22.670 | 1.00 | 20.42 N |
| ATOM | 4733 | C | ASN | B | 92 | −16.081 | 1.052 | 22.845 | 1.00 | 17.91 C |
| ATOM | 4734 | O | ASN | B | 92 | −15.757 | 1.155 | 24.021 | 1.00 | 17.12 O |
| ATOM | 4735 | N | THR | B | 93 | −15.667 | 1.909 | 21.902 | 1.00 | 17.67 N |
| ATOM | 4737 | CA | THR | B | 93 | −14.789 | 3.068 | 22.178 | 1.00 | 17.77 C |

APPENDIX 1-continued

| ATOM | 4739 | CB  | THR | B | 93  | −14.457 | 3.902  | 20.885 | 1.00 | 18.92 | C |
| ---- | ---- | --- | --- | - | --- | ------- | ------ | ------ | ---- | ----- | - |
| ATOM | 4741 | OG1 | THR | B | 93  | −13.708 | 5.097  | 21.206 | 1.00 | 21.52 | O |
| ATOM | 4743 | CG2 | THR | B | 93  | −15.718 | 4.434  | 20.237 | 1.00 | 18.95 | C |
| ATOM | 4747 | C   | THR | B | 93  | −15.348 | 4.006  | 23.212 | 1.00 | 15.15 | C |
| ATOM | 4748 | O   | THR | B | 93  | −14.591 | 4.719  | 23.860 | 1.00 | 14.57 | O |
| ATOM | 4749 | N   | ASN | B | 94  | −16.676 | 4.042  | 23.349 | 1.00 | 13.37 | N |
| ATOM | 4751 | CA  | ASN | B | 94  | −17.263 | 4.874  | 24.369 | 1.00 | 11.96 | C |
| ATOM | 4753 | CB  | ASN | B | 94  | −18.767 | 5.001  | 24.180 | 1.00 | 12.29 | C |
| ATOM | 4756 | CG  | ASN | B | 94  | −19.122 | 5.919  | 23.041 | 1.00 | 14.50 | C |
| ATOM | 4757 | OD1 | ASN | B | 94  | −18.348 | 6.785  | 22.653 | 1.00 | 16.90 | O |
| ATOM | 4758 | ND2 | ASN | B | 94  | −20.312 | 5.739  | 22.508 | 1.00 | 17.07 | N |
| ATOM | 4761 | C   | ASN | B | 94  | −16.951 | 4.400  | 25.772 | 1.00 | 10.32 | C |
| ATOM | 4762 | O   | ASN | B | 94  | −17.229 | 5.130  | 26.707 | 1.00 | 10.75 | O |
| ATOM | 4763 | N   | TYR | B | 95  | −16.361 | 3.207  | 25.915 | 1.00 | 9.75  | N |
| ATOM | 4765 | CA  | TYR | B | 95  | −15.992 | 2.654  | 27.219 | 1.00 | 9.39  | C |
| ATOM | 4767 | CB  | TYR | B | 95  | −16.876 | 1.444  | 27.541 | 1.00 | 10.00 | C |
| ATOM | 4770 | CG  | TYR | B | 95  | −18.334 | 1.826  | 27.578 | 1.00 | 10.15 | C |
| ATOM | 4771 | CD1 | TYR | B | 95  | −19.127 | 1.734  | 26.446 | 1.00 | 11.72 | C |
| ATOM | 4773 | CE1 | TYR | B | 95  | −20.466 | 2.105  | 26.467 | 1.00 | 12.50 | C |
| ATOM | 4775 | CZ  | TYR | B | 95  | −21.008 | 2.602  | 27.625 | 1.00 | 13.24 | C |
| ATOM | 4776 | OH  | TYR | B | 95  | −22.332 | 2.984  | 27.661 | 1.00 | 14.96 | O |
| ATOM | 4778 | CE2 | TYR | B | 95  | −20.243 | 2.720  | 28.762 | 1.00 | 12.98 | C |
| ATOM | 4780 | CD2 | TYR | B | 95  | −18.911 | 2.333  | 28.733 | 1.00 | 11.90 | C |
| ATOM | 4782 | C   | TYR | B | 95  | −14.512 | 2.285  | 27.263 | 1.00 | 8.95  | C |
| ATOM | 4783 | O   | TYR | B | 95  | −14.114 | 1.400  | 28.010 | 1.00 | 8.99  | O |
| ATOM | 4784 | N   | ASP | B | 96  | −13.695 | 2.996  | 26.485 | 1.00 | 8.73  | N |
| ATOM | 4786 | CA  | ASP | B | 96  | −12.272 | 2.693  | 26.401 | 1.00 | 8.57  | C |
| ATOM | 4788 | CB  | ASP | B | 96  | −11.716 | 3.169  | 25.067 | 1.00 | 8.34  | C |
| ATOM | 4791 | CG  | ASP | B | 96  | −10.298 | 2.720  | 24.829 | 1.00 | 8.28  | C |
| ATOM | 4792 | OD1 | ASP | B | 96  | −9.773  | 3.069  | 23.732 | 1.00 | 8.57  | O |
| ATOM | 4793 | OD2 | ASP | B | 96  | −9.674  | 2.040  | 25.677 | 1.00 | 8.50  | O |
| ATOM | 4794 | C   | ASP | B | 96  | −11.510 | 3.314  | 27.580 | 1.00 | 7.91  | C |
| ATOM | 4795 | O   | ASP | B | 96  | −11.002 | 4.442  | 27.510 | 1.00 | 8.32  | O |
| ATOM | 4796 | N   | TYR | B | 97  | −11.479 | 2.567  | 28.671 | 1.00 | 8.03  | N |
| ATOM | 4798 | CA  | TYR | B | 97  | −10.719 | 2.910  | 29.860 | 1.00 | 7.75  | C |
| ATOM | 4800 | CB  | TYR | B | 97  | −11.386 | 3.992  | 30.707 | 1.00 | 7.83  | C |
| ATOM | 4803 | CG  | TYR | B | 97  | −12.688 | 3.607  | 31.371 | 1.00 | 8.16  | C |
| ATOM | 4804 | CD1 | TYR | B | 97  | −13.893 | 3.674  | 30.681 | 1.00 | 8.43  | C |
| ATOM | 4806 | CE1 | TYR | B | 97  | −15.092 | 3.350  | 31.297 | 1.00 | 8.51  | C |
| ATOM | 4808 | CZ  | TYR | B | 97  | −15.094 | 2.959  | 32.628 | 1.00 | 8.68  | C |
| ATOM | 4809 | OH  | TYR | B | 97  | −16.265 | 2.673  | 33.298 | 1.00 | 9.75  | O |
| ATOM | 4811 | CE2 | TYR | B | 97  | −13.906 | 2.878  | 33.321 | 1.00 | 8.95  | C |
| ATOM | 4813 | CD2 | TYR | B | 97  | −12.719 | 3.205  | 32.697 | 1.00 | 8.55  | C |
| ATOM | 4815 | C   | TYR | B | 97  | −10.531 | 1.625  | 30.653 | 1.00 | 7.47  | C |
| ATOM | 4816 | O   | TYR | B | 97  | −11.168 | 0.607  | 30.383 | 1.00 | 7.98  | O |
| ATOM | 4817 | N   | GLY | B | 98  | −9.659  | 1.684  | 31.647 | 1.00 | 7.59  | N |
| ATOM | 4819 | CA  | GLY | B | 98  | −9.409  | 0.542  | 32.502 | 1.00 | 7.74  | C |
| ATOM | 4822 | C   | GLY | B | 98  | −8.451  | 0.917  | 33.603 | 1.00 | 7.36  | C |
| ATOM | 4823 | O   | GLY | B | 98  | −8.061  | 2.082  | 33.748 | 1.00 | 7.93  | O |
| ATOM | 4824 | N   | ALA | B | 99  | −8.079  | −0.080 | 34.390 | 1.00 | 7.67  | N |
| ATOM | 4826 | CA  | ALA | B | 99  | −7.139  | 0.136  | 35.465 | 1.00 | 7.61  | C |
| ATOM | 4828 | CB  | ALA | B | 99  | −7.846  | 0.428  | 36.770 | 1.00 | 8.42  | C |
| ATOM | 4832 | C   | ALA | B | 99  | −6.207  | −1.042 | 35.626 | 1.00 | 8.10  | C |
| ATOM | 4833 | O   | ALA | B | 99  | −6.523  | −2.172 | 35.222 | 1.00 | 8.34  | O |
| ATOM | 4834 | N   | ILE | B | 100 | −5.045  | −0.762 | 36.211 | 1.00 | 8.17  | N |
| ATOM | 4836 | CA  | ILE | B | 100 | −4.042  | −1.770 | 36.490 | 1.00 | 8.36  | C |
| ATOM | 4838 | CB  | ILE | B | 100 | −2.709  | −1.485 | 35.749 | 1.00 | 8.61  | C |
| ATOM | 4840 | CG1 | ILE | B | 100 | −2.941  | −1.193 | 34.265 | 1.00 | 8.93  | C |
| ATOM | 4843 | CD1 | ILE | B | 100 | −1.682  | −0.873 | 33.485 | 1.00 | 10.13 | C |
| ATOM | 4847 | CG2 | ILE | B | 100 | −1.738  | −2.640 | 35.958 | 1.00 | 9.23  | C |
| ATOM | 4851 | C   | ILE | B | 100 | −3.764  | −1.741 | 37.982 | 1.00 | 8.16  | C |
| ATOM | 4852 | O   | ILE | B | 100 | −3.527  | −0.682 | 38.549 | 1.00 | 8.74  | O |
| ATOM | 4853 | N   | GLU | B | 101 | −3.784  | −2.903 | 38.627 | 1.00 | 8.55  | N |
| ATOM | 4855 | CA  | GLU | B | 101 | −3.315  | −3.015 | 40.003 | 1.00 | 8.71  | C |
| ATOM | 4857 | CB  | GLU | B | 101 | −4.160  | −4.001 | 40.797 | 1.00 | 9.18  | C |
| ATOM | 4860 | CG  | GLU | B | 101 | −3.907  | −3.943 | 42.293 | 1.00 | 10.20 | C |
| ATOM | 4863 | CD  | GLU | B | 101 | −5.020  | −4.604 | 43.089 | 1.00 | 10.31 | C |
| ATOM | 4864 | OE1 | GLU | B | 101 | −4.713  | −5.401 | 43.998 | 1.00 | 12.33 | O |
| ATOM | 4865 | OE2 | GLU | B | 101 | −6.210  | −4.354 | 42.782 | 1.00 | 11.03 | O |
| ATOM | 4866 | C   | GLU | B | 101 | −1.858  | −3.452 | 39.989 | 1.00 | 8.34  | C |
| ATOM | 4867 | O   | GLU | B | 101 | −1.466  | −4.253 | 39.161 | 1.00 | 9.30  | O |
| ATOM | 4868 | N   | LEU | B | 102 | −1.073  | −2.887 | 40.894 | 1.00 | 8.98  | N |
| ATOM | 4870 | CA  | LEU | B | 102 | 0.358   | −3.079 | 40.934 | 1.00 | 8.90  | C |
| ATOM | 4872 | CB  | LEU | B | 102 | 1.068   | −1.728 | 41.077 | 1.00 | 9.08  | C |
| ATOM | 4875 | CG  | LEU | B | 102 | 0.752   | −0.722 | 39.978 | 1.00 | 10.14 | C |
| ATOM | 4877 | CD1 | LEU | B | 102 | 1.517   | 0.561  | 40.225 | 1.00 | 10.89 | C |
| ATOM | 4881 | CD2 | LEU | B | 102 | 1.034   | −1.294 | 38.585 | 1.00 | 10.99 | C |
| ATOM | 4885 | C   | LEU | B | 102 | 0.807   | −3.976 | 42.080 | 1.00 | 9.48  | C |
| ATOM | 4886 | O   | LEU | B | 102 | 0.168   | −4.061 | 43.133 | 1.00 | 10.17 | O |
| ATOM | 4887 | N   | SER | B | 103 | 1.969   | −4.589 | 41.866 | 1.00 | 9.89  | N |

APPENDIX 1-continued

| ATOM | 4889 | CA | SER | B | 103 | 2.601 | −5.483 | 42.828 | 1.00 | 10.79 | C |
|---|---|---|---|---|---|---|---|---|---|---|---|
| ATOM | 4891 | CB | SER | B | 103 | 3.736 | −6.273 | 42.146 | 1.00 | 11.99 | C |
| ATOM | 4894 | OG | SER | B | 103 | 4.697 | −5.398 | 41.584 | 1.00 | 15.05 | O |
| ATOM | 4896 | C | SER | B | 103 | 3.183 | −4.776 | 44.053 | 1.00 | 10.53 | C |
| ATOM | 4897 | O | SER | B | 103 | 3.490 | −5.433 | 45.047 | 1.00 | 11.56 | O |
| ATOM | 4898 | N | GLU | B | 104 | 3.367 | −3.464 | 43.962 | 1.00 | 10.04 | N |
| ATOM | 4900 | CA | GLU | B | 104 | 3.968 | −2.672 | 45.021 | 1.00 | 10.08 | C |
| ATOM | 4902 | CB | GLU | B | 104 | 5.443 | −2.395 | 44.738 | 1.00 | 10.68 | C |
| ATOM | 4905 | CG | GLU | B | 104 | 6.259 | −3.644 | 44.449 | 1.00 | 11.66 | C |
| ATOM | 4908 | CD | GLU | B | 104 | 7.723 | −3.350 | 44.233 | 1.00 | 13.72 | C |
| ATOM | 4909 | OE1 | GLU | B | 104 | 8.329 | −2.659 | 45.084 | 1.00 | 14.76 | O |
| ATOM | 4910 | OE2 | GLU | B | 104 | 8.261 | −3.802 | 43.208 | 1.00 | 19.30 | O |
| ATOM | 4911 | C | GLU | B | 104 | 3.227 | −1.351 | 45.093 | 1.00 | 9.84 | C |
| ATOM | 4912 | O | GLU | B | 104 | 2.802 | −0.809 | 44.065 | 1.00 | 10.32 | O |
| ATOM | 4913 | N | PRO | B | 105 | 3.068 | −0.805 | 46.291 | 1.00 | 9.86 | N |
| ATOM | 4914 | CA | PRO | B | 105 | 2.283 | 0.420 | 46.478 | 1.00 | 10.40 | C |
| ATOM | 4916 | CB | PRO | B | 105 | 1.878 | 0.324 | 47.944 | 1.00 | 11.33 | C |
| ATOM | 4919 | CG | PRO | B | 105 | 3.053 | −0.322 | 48.587 | 1.00 | 11.44 | C |
| ATOM | 4922 | CD | PRO | B | 105 | 3.557 | −1.331 | 47.587 | 1.00 | 10.49 | C |
| ATOM | 4925 | C | PRO | B | 105 | 3.075 | 1.696 | 46.191 | 1.00 | 9.58 | C |
| ATOM | 4926 | O | PRO | B | 105 | 3.227 | 2.576 | 47.035 | 1.00 | 10.04 | O |
| ATOM | 4927 | N | ILE | B | 106 | 3.538 | 1.824 | 44.957 | 1.00 | 9.73 | N |
| ATOM | 4929 | CA | ILE | B | 106 | 4.421 | 2.908 | 44.586 | 1.00 | 9.44 | C |
| ATOM | 4931 | CB | ILE | B | 106 | 5.096 | 2.600 | 43.224 | 1.00 | 9.89 | C |
| ATOM | 4933 | CG1 | ILE | B | 106 | 6.252 | 3.566 | 42.933 | 1.00 | 10.25 | C |
| ATOM | 4936 | CD1 | ILE | B | 106 | 7.381 | 3.581 | 43.970 | 1.00 | 11.38 | C |
| ATOM | 4940 | CG2 | ILE | B | 106 | 4.082 | 2.599 | 42.085 | 1.00 | 10.23 | C |
| ATOM | 4944 | C | ILE | B | 106 | 3.729 | 4.271 | 44.620 | 1.00 | 9.14 | C |
| ATOM | 4945 | O | ILE | B | 106 | 4.382 | 5.305 | 44.734 | 1.00 | 9.49 | O |
| ATOM | 4946 | N | GLY | B | 107 | 2.407 | 4.287 | 44.541 | 1.00 | 9.13 | N |
| ATOM | 4948 | CA | GLY | B | 107 | 1.648 | 5.503 | 44.748 | 1.00 | 9.30 | C |
| ATOM | 4951 | C | GLY | B | 107 | 1.833 | 6.128 | 46.117 | 1.00 | 9.86 | C |
| ATOM | 4952 | O | GLY | B | 107 | 1.627 | 7.326 | 46.279 | 1.00 | 10.75 | O |
| ATOM | 4953 | N | ASN | B | 108 | 2.228 | 5.339 | 47.110 | 1.00 | 10.06 | N |
| ATOM | 4955 | CA | ASN | B | 108 | 2.578 | 5.915 | 48.400 | 1.00 | 11.08 | C |
| ATOM | 4957 | CB | ASN | B | 108 | 2.804 | 4.831 | 49.458 | 1.00 | 11.79 | C |
| ATOM | 4960 | CG | ASN | B | 108 | 1.518 | 4.133 | 49.862 | 1.00 | 13.13 | C |
| ATOM | 4961 | OD1 | ASN | B | 108 | 0.433 | 4.675 | 49.715 | 1.00 | 15.54 | O |
| ATOM | 4962 | ND2 | ASN | B | 108 | 1.649 | 2.941 | 50.428 | 1.00 | 15.52 | N |
| ATOM | 4965 | C | ASN | B | 108 | 3.799 | 6.809 | 48.340 | 1.00 | 11.38 | C |
| ATOM | 4966 | O | ASN | B | 108 | 3.968 | 7.676 | 49.192 | 1.00 | 13.40 | O |
| ATOM | 4967 | N | THR | B | 109 | 4.644 | 6.606 | 47.335 | 1.00 | 10.92 | N |
| ATOM | 4969 | CA | THR | B | 109 | 5.811 | 7.449 | 47.106 | 1.00 | 11.13 | C |
| ATOM | 4971 | CB | THR | B | 109 | 6.961 | 6.584 | 46.594 | 1.00 | 11.44 | C |
| ATOM | 4973 | OG1 | THR | B | 109 | 7.329 | 5.636 | 47.604 | 1.00 | 13.07 | O |
| ATOM | 4975 | CG2 | THR | B | 109 | 8.225 | 7.390 | 46.324 | 1.00 | 12.36 | C |
| ATOM | 4979 | C | THR | B | 109 | 5.521 | 8.572 | 46.123 | 1.00 | 10.67 | C |
| ATOM | 4980 | O | THR | B | 109 | 5.856 | 9.723 | 46.400 | 1.00 | 11.94 | O |
| ATOM | 4981 | N | VAL | B | 110 | 4.931 | 8.247 | 44.975 | 1.00 | 9.89 | N |
| ATOM | 4983 | CA | VAL | B | 110 | 4.771 | 9.245 | 43.921 | 1.00 | 9.99 | C |
| ATOM | 4985 | CB | VAL | B | 110 | 4.883 | 8.652 | 42.504 | 1.00 | 9.69 | C |
| ATOM | 4987 | CG1 | VAL | B | 110 | 6.238 | 8.008 | 42.291 | 1.00 | 10.32 | C |
| ATOM | 4991 | CG2 | VAL | B | 110 | 3.749 | 7.687 | 42.194 | 1.00 | 9.18 | C |
| ATOM | 4995 | C | VAL | B | 110 | 3.512 | 10.093 | 44.054 | 1.00 | 10.21 | C |
| ATOM | 4996 | O | VAL | B | 110 | 3.434 | 11.153 | 43.425 | 1.00 | 11.23 | O |
| ATOM | 4997 | N | GLY | B | 111 | 2.543 | 9.644 | 44.840 | 1.00 | 10.22 | N |
| ATOM | 4999 | CA | GLY | B | 111 | 1.265 | 10.314 | 44.904 | 1.00 | 10.24 | C |
| ATOM | 5002 | C | GLY | B | 111 | 0.334 | 9.866 | 43.803 | 1.00 | 9.73 | C |
| ATOM | 5003 | O | GLY | B | 111 | 0.623 | 8.938 | 43.039 | 1.00 | 10.12 | O |
| ATOM | 5004 | N | TYR | B | 112 | −0.815 | 10.522 | 43.733 | 1.00 | 9.97 | N |
| ATOM | 5006 | CA | TYR | B | 112 | −1.832 | 10.140 | 42.768 | 1.00 | 9.95 | C |
| ATOM | 5008 | CB | BTYR | B | 112 | −2.648 | 8.897 | 43.221 | 0.35 | 10.43 | C |
| ATOM | 5009 | CB | ATYR | B | 112 | −2.598 | 8.884 | 43.221 | 0.65 | 10.39 | C |
| ATOM | 5014 | CG | BTYR | B | 112 | −2.791 | 8.641 | 44.714 | 0.35 | 11.58 | C |
| ATOM | 5015 | CG | ATYR | B | 112 | −3.133 | 8.921 | 44.615 | 0.65 | 11.41 | C |
| ATOM | 5016 | CD1 | BTYR | B | 112 | −1.797 | 7.973 | 45.428 | 0.35 | 12.47 | C |
| ATOM | 5017 | CD1 | ATYR | B | 112 | −2.406 | 8.376 | 45.672 | 0.65 | 13.18 | C |
| ATOM | 5020 | CE1 | BTYR | B | 112 | −1.935 | 7.713 | 46.789 | 0.35 | 13.56 | C |
| ATOM | 5021 | CE1 | ATYR | B | 112 | −2.905 | 8.381 | 46.970 | 0.65 | 15.52 | C |
| ATOM | 5024 | CZ | BTYR | B | 112 | −3.085 | 8.100 | 47.449 | 0.35 | 14.96 | C |
| ATOM | 5025 | CZ | ATYR | B | 112 | −4.144 | 8.931 | 47.209 | 0.65 | 16.29 | C |
| ATOM | 5026 | OH | BTYR | B | 112 | −3.215 | 7.838 | 48.796 | 0.35 | 16.64 | O |
| ATOM | 5027 | OH | ATYR | B | 112 | −4.641 | 8.940 | 48.492 | 0.65 | 18.51 | O |
| ATOM | 5030 | CE2 | BTYR | B | 112 | −4.097 | 8.743 | 46.766 | 0.35 | 14.31 | C |
| ATOM | 5031 | CE2 | ATYR | B | 112 | −4.894 | 9.467 | 46.174 | 0.65 | 14.98 | C |
| ATOM | 5034 | CD2 | BTYR | B | 112 | −3.951 | 9.007 | 45.400 | 0.35 | 12.89 | C |
| ATOM | 5035 | CD2 | ATYR | B | 112 | −4.382 | 9.459 | 44.880 | 0.65 | 13.02 | C |
| ATOM | 5038 | C | TYR | B | 112 | −2.745 | 11.327 | 42.440 | 1.00 | 9.75 | C |
| ATOM | 5039 | O | TYR | B | 112 | −2.730 | 12.363 | 43.110 | 1.00 | 10.71 | O |
| ATOM | 5040 | N | PHE | B | 113 | −3.495 | 11.159 | 41.355 | 1.00 | 9.55 | N |

APPENDIX 1-continued

| ATOM | 5042 | CA | PHE | B | 113 | −4.382 | 12.182 | 40.822 | 1.00 | 9.90 | C |
|---|---|---|---|---|---|---|---|---|---|---|---|
| ATOM | 5044 | CB | PHE | B | 113 | −4.592 | 11.952 | 39.321 | 1.00 | 9.79 | C |
| ATOM | 5047 | CG | PHE | B | 113 | −3.437 | 12.384 | 38.452 | 1.00 | 8.75 | C |
| ATOM | 5048 | CD1 | PHE | B | 113 | −3.520 | 13.562 | 37.714 | 1.00 | 9.30 | C |
| ATOM | 5050 | CE1 | PHE | B | 113 | −2.467 | 13.968 | 36.912 | 1.00 | 10.00 | C |
| ATOM | 5052 | CZ | PHE | B | 113 | −1.321 | 13.222 | 36.851 | 1.00 | 8.88 | C |
| ATOM | 5054 | CE2 | PHE | B | 113 | −1.220 | 12.060 | 37.566 | 1.00 | 8.70 | C |
| ATOM | 5056 | CD2 | PHE | B | 113 | −2.271 | 11.633 | 38.372 | 1.00 | 8.97 | C |
| ATOM | 5058 | C | PHE | B | 113 | −5.772 | 12.106 | 41.441 | 1.00 | 10.47 | C |
| ATOM | 5059 | O | PHE | B | 113 | −6.262 | 11.022 | 41.775 | 1.00 | 11.47 | O |
| ATOM | 5060 | N | GLY | B | 114 | −6.409 | 13.267 | 41.550 | 1.00 | 10.79 | N |
| ATOM | 5062 | CA | GLY | B | 114 | −7.854 | 13.333 | 41.663 | 1.00 | 11.39 | C |
| ATOM | 5065 | C | GLY | B | 114 | −8.481 | 13.125 | 40.293 | 1.00 | 10.67 | C |
| ATOM | 5066 | O | GLY | B | 114 | −7.801 | 13.207 | 39.265 | 1.00 | 10.78 | O |
| ATOM | 5067 | N | TYR | B | 115 | −9.781 | 12.875 | 40.278 | 1.00 | 10.57 | N |
| ATOM | 5069 | CA | TYR | B | 115 | −10.524 | 12.763 | 39.030 | 1.00 | 10.75 | C |
| ATOM | 5071 | CB | TYR | B | 115 | −10.346 | 11.382 | 38.379 | 1.00 | 10.71 | C |
| ATOM | 5074 | CG | TYR | B | 115 | −10.685 | 10.219 | 39.275 | 1.00 | 10.79 | C |
| ATOM | 5075 | CD1 | TYR | B | 115 | −11.988 | 9.716 | 39.338 | 1.00 | 10.63 | C |
| ATOM | 5077 | CE1 | TYR | B | 115 | −12.311 | 8.658 | 40.183 | 1.00 | 10.32 | C |
| ATOM | 5079 | CZ | TYR | B | 115 | −11.313 | 8.093 | 40.968 | 1.00 | 10.91 | C |
| ATOM | 5080 | OH | TYR | B | 115 | −11.581 | 7.056 | 41.831 | 1.00 | 12.42 | O |
| ATOM | 5082 | CE2 | TYR | B | 115 | −10.021 | 8.585 | 40.921 | 1.00 | 11.68 | C |
| ATOM | 5084 | CD2 | TYR | B | 115 | −9.715 | 9.638 | 40.074 | 1.00 | 11.40 | C |
| ATOM | 5086 | C | TYR | B | 115 | −11.983 | 13.069 | 39.319 | 1.00 | 10.14 | C |
| ATOM | 5087 | O | TYR | B | 115 | −12.466 | 12.866 | 40.448 | 1.00 | 11.11 | O |
| ATOM | 5088 | N | SER | B | 116 | −12.696 | 13.556 | 38.315 | 1.00 | 10.15 | N |
| ATOM | 5090 | CA | SER | B | 116 | −14.058 | 14.032 | 38.525 | 1.00 | 11.05 | C |
| ATOM | 5092 | CB | SER | B | 116 | −14.047 | 15.464 | 39.061 | 1.00 | 12.22 | C |
| ATOM | 5095 | OG | SER | B | 116 | −15.261 | 15.741 | 39.743 | 1.00 | 15.63 | O |
| ATOM | 5097 | C | SER | B | 116 | −14.881 | 13.963 | 37.258 | 1.00 | 10.80 | C |
| ATOM | 5098 | O | SER | B | 116 | −14.333 | 13.881 | 36.155 | 1.00 | 11.34 | O |
| ATOM | 5099 | N | TYR | B | 117 | −16.198 | 13.964 | 37.448 | 1.00 | 11.27 | N |
| ATOM | 5101 | CA | TYR | B | 117 | −17.167 | 14.054 | 36.366 | 1.00 | 11.28 | C |
| ATOM | 5103 | CB | TYR | B | 117 | −18.098 | 12.834 | 36.354 | 1.00 | 11.24 | C |
| ATOM | 5106 | CG | TYR | B | 117 | −19.039 | 12.746 | 37.533 | 1.00 | 11.74 | C |
| ATOM | 5107 | CD1 | TYR | B | 117 | −20.343 | 13.212 | 37.431 | 1.00 | 13.27 | C |
| ATOM | 5109 | CE1 | TYR | B | 117 | −21.221 | 13.145 | 38.509 | 1.00 | 15.32 | C |
| ATOM | 5111 | CZ | TYR | B | 117 | −20.788 | 12.637 | 39.708 | 1.00 | 15.51 | C |
| ATOM | 5112 | OH | TYR | B | 117 | −21.659 | 12.576 | 40.774 | 1.00 | 18.16 | O |
| ATOM | 5114 | CE2 | TYR | B | 117 | −19.494 | 12.174 | 39.841 | 1.00 | 15.41 | C |
| ATOM | 5116 | CD2 | TYR | B | 117 | −18.626 | 12.229 | 38.758 | 1.00 | 13.41 | C |
| ATOM | 5118 | C | TYR | B | 117 | −17.976 | 15.325 | 36.528 | 1.00 | 12.11 | C |
| ATOM | 5119 | O | TYR | B | 117 | −18.090 | 15.880 | 37.624 | 1.00 | 13.00 | O |
| ATOM | 5120 | N | THR | B | 118 | −18.546 | 15.790 | 35.430 | 1.00 | 12.32 | N |
| ATOM | 5122 | CA | THR | B | 118 | −19.471 | 16.915 | 35.476 | 1.00 | 13.14 | C |
| ATOM | 5124 | CB | BTHR | B | 118 | −18.839 | 18.242 | 34.989 | 0.35 | 13.58 | C |
| ATOM | 5125 | CB | ATHR | B | 118 | −18.853 | 18.174 | 34.815 | 0.65 | 13.85 | C |
| ATOM | 5128 | OG1 | BTHR | B | 118 | −17.607 | 18.487 | 35.674 | 0.35 | 14.98 | O |
| ATOM | 5129 | OG1 | ATHR | B | 118 | −18.864 | 18.025 | 33.391 | 0.65 | 12.42 | O |
| ATOM | 5132 | CG2 | BTHR | B | 118 | −19.688 | 19.435 | 35.421 | 0.35 | 13.29 | C |
| ATOM | 5133 | CG2 | ATHR | B | 118 | −17.368 | 18.339 | 35.127 | 0.65 | 14.99 | C |
| ATOM | 5140 | C | THR | B | 118 | −20.722 | 16.573 | 34.714 | 1.00 | 13.65 | C |
| ATOM | 5141 | O | THR | B | 118 | −20.751 | 15.691 | 33.870 | 1.00 | 14.93 | O |
| ATOM | 5142 | N | THR | B | 119 | −21.782 | 17.313 | 35.018 | 1.00 | 14.79 | N |
| ATOM | 5144 | CA | THR | B | 119 | −23.087 | 17.127 | 34.387 | 1.00 | 16.50 | C |
| ATOM | 5146 | CB | THR | B | 119 | −24.192 | 17.090 | 35.473 | 1.00 | 17.34 | C |
| ATOM | 5148 | OG1 | THR | B | 119 | −24.184 | 18.319 | 36.209 | 1.00 | 19.76 | O |
| ATOM | 5150 | CG2 | THR | B | 119 | −23.906 | 16.005 | 36.521 | 1.00 | 18.20 | C |
| ATOM | 5154 | C | THR | B | 119 | −23.412 | 18.233 | 33.389 | 1.00 | 16.89 | C |
| ATOM | 5155 | O | THR | B | 119 | −24.581 | 18.446 | 33.065 | 1.00 | 18.39 | O |
| ATOM | 5156 | N | SER | B | 120 | −22.392 | 18.945 | 32.932 | 1.00 | 15.85 | N |
| ATOM | 5158 | CA | SER | B | 120 | −22.568 | 20.023 | 31.976 | 1.00 | 15.52 | C |
| ATOM | 5160 | CB | SER | B | 120 | −22.688 | 21.348 | 32.714 | 1.00 | 17.29 | C |
| ATOM | 5163 | OG | SER | B | 120 | −21.566 | 21.555 | 33.538 | 1.00 | 19.16 | O |
| ATOM | 5165 | C | SER | B | 120 | −21.385 | 20.044 | 31.015 | 1.00 | 13.69 | C |
| ATOM | 5166 | O | SER | B | 120 | −20.433 | 19.256 | 31.151 | 1.00 | 13.49 | O |
| ATOM | 5167 | N | SER | B | 121 | −21.450 | 20.938 | 30.037 | 1.00 | 13.50 | N |
| ATOM | 5169 | CA | SER | B | 121 | −20.440 | 20.977 | 28.999 | 1.00 | 13.20 | C |
| ATOM | 5171 | CB | SER | B | 121 | −20.823 | 22.004 | 27.943 | 1.00 | 13.58 | C |
| ATOM | 5174 | OG | SER | B | 121 | −19.822 | 22.072 | 26.951 | 1.00 | 14.79 | O |
| ATOM | 5176 | C | SER | B | 121 | −19.065 | 21.321 | 29.561 | 1.00 | 12.29 | C |
| ATOM | 5177 | O | SER | B | 121 | −18.936 | 22.162 | 30.445 | 1.00 | 13.82 | O |
| ATOM | 5178 | N | LEU | B | 122 | −18.034 | 20.659 | 29.042 | 1.00 | 11.06 | N |
| ATOM | 5180 | CA | LEU | B | 122 | −16.653 | 20.994 | 29.362 | 1.00 | 10.63 | C |
| ATOM | 5182 | CB | LEU | B | 122 | −15.870 | 19.715 | 29.679 | 1.00 | 10.33 | C |
| ATOM | 5185 | CG | LEU | B | 122 | −16.152 | 19.154 | 31.076 | 1.00 | 11.02 | C |
| ATOM | 5187 | CD1 | LEU | B | 122 | −15.645 | 17.729 | 31.205 | 1.00 | 11.81 | C |
| ATOM | 5191 | CD2 | LEU | B | 122 | −15.557 | 20.038 | 32.139 | 1.00 | 12.56 | C |
| ATOM | 5195 | C | LEU | B | 122 | −15.968 | 21.775 | 28.238 | 1.00 | 10.13 | C |

APPENDIX 1-continued

| ATOM | 5196 | O | LEU | B | 122 | −14.775 | 22.042 | 28.324 | 1.00 | 10.57 | O |
|---|---|---|---|---|---|---|---|---|---|---|---|
| ATOM | 5197 | N | VAL | B | 123 | −16.708 | 22.183 | 27.209 | 1.00 | 10.64 | N |
| ATOM | 5199 | CA | VAL | B | 123 | −16.101 | 22.935 | 26.115 | 1.00 | 10.83 | C |
| ATOM | 5201 | CB | VAL | B | 123 | −17.123 | 23.312 | 25.017 | 1.00 | 11.49 | C |
| ATOM | 5203 | CG1 | VAL | B | 123 | −16.511 | 24.290 | 24.006 | 1.00 | 12.60 | C |
| ATOM | 5207 | CG2 | VAL | B | 123 | −17.603 | 22.060 | 24.288 | 1.00 | 12.49 | C |
| ATOM | 5211 | C | VAL | B | 123 | −15.439 | 24.192 | 26.669 | 1.00 | 10.32 | C |
| ATOM | 5212 | O | VAL | B | 123 | −16.057 | 24.936 | 27.431 | 1.00 | 11.74 | O |
| ATOM | 5213 | N | GLY | B | 124 | −14.189 | 24.416 | 26.283 | 1.00 | 10.03 | N |
| ATOM | 5215 | CA | GLY | B | 124 | −13.431 | 25.575 | 26.714 | 1.00 | 10.35 | C |
| ATOM | 5218 | C | GLY | B | 124 | −12.591 | 25.362 | 27.954 | 1.00 | 9.90 | C |
| ATOM | 5219 | O | GLY | B | 124 | −11.707 | 26.170 | 28.220 | 1.00 | 11.28 | O |
| ATOM | 5220 | N | THR | B | 125 | −12.851 | 24.311 | 28.726 | 1.00 | 9.67 | N |
| ATOM | 5222 | CA | THR | B | 125 | −12.062 | 24.049 | 29.919 | 1.00 | 9.49 | C |
| ATOM | 5224 | CB | THR | B | 125 | −12.709 | 22.900 | 30.695 | 1.00 | 10.53 | C |
| ATOM | 5226 | OG1 | THR | B | 125 | −13.998 | 23.310 | 31.178 | 1.00 | 13.20 | O |
| ATOM | 5228 | CG2 | THR | B | 125 | −11.907 | 22.498 | 31.922 | 1.00 | 10.73 | C |
| ATOM | 5232 | C | THR | B | 125 | −10.635 | 23.689 | 29.511 | 1.00 | 8.89 | C |
| ATOM | 5233 | O | THR | B | 125 | −10.437 | 22.872 | 28.619 | 1.00 | 9.49 | O |
| ATOM | 5234 | N | THR | B | 126 | −9.646 | 24.285 | 30.170 | 1.00 | 9.07 | N |
| ATOM | 5236 | CA | THR | B | 126 | −8.254 | 23.992 | 29.867 | 1.00 | 9.38 | C |
| ATOM | 5238 | CB | THR | B | 126 | −7.368 | 25.212 | 30.064 | 1.00 | 10.46 | C |
| ATOM | 5240 | OG1 | THR | B | 126 | −7.532 | 25.706 | 31.393 | 1.00 | 12.73 | O |
| ATOM | 5242 | CG2 | THR | B | 126 | −7.790 | 26.346 | 29.130 | 1.00 | 11.44 | C |
| ATOM | 5246 | C | THR | B | 126 | −7.731 | 22.819 | 30.679 | 1.00 | 8.61 | C |
| ATOM | 5247 | O | THR | B | 126 | −8.035 | 22.654 | 31.874 | 1.00 | 9.84 | O |
| ATOM | 5248 | N | VAL | B | 127 | −6.951 | 21.996 | 29.987 | 1.00 | 8.18 | N |
| ATOM | 5250 | CA | VAL | B | 127 | −6.403 | 20.764 | 30.520 | 1.00 | 8.03 | C |
| ATOM | 5252 | CB | VAL | B | 127 | −7.290 | 19.529 | 30.187 | 1.00 | 8.26 | C |
| ATOM | 5254 | CG1 | VAL | B | 127 | −8.635 | 19.599 | 30.912 | 1.00 | 9.66 | C |
| ATOM | 5258 | CG2 | VAL | B | 127 | −7.486 | 19.389 | 28.694 | 1.00 | 9.04 | C |
| ATOM | 5262 | C | VAL | B | 127 | −5.001 | 20.543 | 29.961 | 1.00 | 7.96 | C |
| ATOM | 5263 | O | VAL | B | 127 | −4.625 | 21.117 | 28.935 | 1.00 | 9.12 | O |
| ATOM | 5264 | N | THR | B | 128 | −4.259 | 19.675 | 30.630 | 1.00 | 7.81 | N |
| ATOM | 5266 | CA | THR | B | 128 | −2.953 | 19.208 | 30.209 | 1.00 | 7.75 | C |
| ATOM | 5268 | CB | THR | B | 128 | −1.953 | 19.374 | 31.362 | 1.00 | 8.07 | C |
| ATOM | 5270 | OG1 | THR | B | 128 | −1.843 | 20.762 | 31.705 | 1.00 | 9.24 | O |
| ATOM | 5272 | CG2 | THR | B | 128 | −0.549 | 18.864 | 31.006 | 1.00 | 8.88 | C |
| ATOM | 5276 | C | THR | B | 128 | −3.052 | 17.735 | 29.857 | 1.00 | 7.12 | C |
| ATOM | 5277 | O | THR | B | 128 | −3.715 | 16.967 | 30.556 | 1.00 | 7.80 | O |
| ATOM | 5278 | N | ILE | B | 129 | −2.385 | 17.340 | 28.775 | 1.00 | 6.77 | N |
| ATOM | 5280 | CA | ILE | B | 129 | −2.233 | 15.940 | 28.421 | 1.00 | 6.79 | C |
| ATOM | 5282 | CB | ILE | B | 129 | −2.874 | 15.613 | 27.062 | 1.00 | 7.12 | C |
| ATOM | 5284 | CG1 | ILE | B | 129 | −4.328 | 16.098 | 27.046 | 1.00 | 7.95 | C |
| ATOM | 5287 | CD1 | ILE | B | 129 | −5.076 | 15.825 | 25.764 | 1.00 | 8.74 | C |
| ATOM | 5291 | CG2 | ILE | B | 129 | −2.766 | 14.141 | 26.789 | 1.00 | 8.17 | C |
| ATOM | 5295 | C | ILE | B | 129 | −0.739 | 15.639 | 28.412 | 1.00 | 6.77 | C |
| ATOM | 5296 | O | ILE | B | 129 | 0.001 | 16.217 | 27.603 | 1.00 | 7.27 | O |
| ATOM | 5297 | N | SER | B | 130 | −0.298 | 14.761 | 29.305 | 1.00 | 6.76 | N |
| ATOM | 5299 | CA | SER | B | 130 | 1.112 | 14.417 | 29.438 | 1.00 | 6.68 | C |
| ATOM | 5301 | CB | SER | B | 130 | 1.694 | 15.022 | 30.710 | 1.00 | 7.29 | C |
| ATOM | 5304 | OG | SER | B | 130 | 3.097 | 14.906 | 30.734 | 1.00 | 8.01 | O |
| ATOM | 5306 | C | SER | B | 130 | 1.250 | 12.911 | 29.453 | 1.00 | 6.73 | C |
| ATOM | 5307 | O | SER | B | 130 | 0.517 | 12.224 | 30.158 | 1.00 | 6.79 | O |
| ATOM | 5308 | N | GLY | B | 131 | 2.187 | 12.390 | 28.665 | 1.00 | 6.62 | N |
| ATOM | 5310 | CA | GLY | B | 131 | 2.425 | 10.958 | 28.637 | 1.00 | 6.73 | C |
| ATOM | 5313 | C | GLY | B | 131 | 3.640 | 10.604 | 27.804 | 1.00 | 6.56 | C |
| ATOM | 5314 | O | GLY | B | 131 | 4.554 | 11.409 | 27.661 | 1.00 | 7.16 | O |
| ATOM | 5315 | N | TYR | B | 132 | 3.652 | 9.381 | 27.288 | 1.00 | 6.84 | N |
| ATOM | 5317 | CA | TYR | B | 132 | 4.858 | 8.737 | 26.740 | 1.00 | 7.12 | C |
| ATOM | 5319 | CB | TYR | B | 132 | 5.165 | 7.463 | 27.555 | 1.00 | 7.14 | C |
| ATOM | 5322 | CG | TYR | B | 132 | 5.728 | 7.832 | 28.917 | 1.00 | 7.14 | C |
| ATOM | 5323 | CD1 | TYR | B | 132 | 7.087 | 8.103 | 29.060 | 1.00 | 7.37 | C |
| ATOM | 5325 | CE1 | TYR | B | 132 | 7.614 | 8.520 | 30.265 | 1.00 | 7.89 | C |
| ATOM | 5327 | CZ | TYR | B | 132 | 6.781 | 8.669 | 31.364 | 1.00 | 7.57 | C |
| ATOM | 5328 | OH | TYR | B | 132 | 7.269 | 9.112 | 32.573 | 1.00 | 8.04 | O |
| ATOM | 5330 | CE2 | TYR | B | 132 | 5.438 | 8.389 | 31.262 | 1.00 | 7.67 | C |
| ATOM | 5332 | CD2 | TYR | B | 132 | 4.908 | 7.980 | 30.035 | 1.00 | 7.29 | C |
| ATOM | 5334 | C | TYR | B | 132 | 4.676 | 8.424 | 25.250 | 1.00 | 6.94 | C |
| ATOM | 5335 | O | TYR | B | 132 | 4.361 | 7.295 | 24.880 | 1.00 | 8.05 | O |
| ATOM | 5336 | N | PRO | B | 133 | 4.874 | 9.411 | 24.378 | 1.00 | 7.25 | N |
| ATOM | 5337 | CA | PRO | B | 133 | 4.670 | 9.185 | 22.944 | 1.00 | 7.42 | C |
| ATOM | 5339 | CB | PRO | B | 133 | 4.628 | 10.594 | 22.368 | 1.00 | 8.13 | C |
| ATOM | 5342 | CG | PRO | B | 133 | 5.503 | 11.387 | 23.285 | 1.00 | 8.21 | C |
| ATOM | 5345 | CD | PRO | B | 133 | 5.210 | 10.826 | 24.655 | 1.00 | 7.47 | C |
| ATOM | 5348 | C | PRO | B | 133 | 5.786 | 8.400 | 22.267 | 1.00 | 7.76 | C |
| ATOM | 5349 | O | PRO | B | 133 | 6.974 | 8.597 | 22.533 | 1.00 | 8.78 | O |
| ATOM | 5350 | N | GLY | B | 134 | 5.389 | 7.581 | 21.300 | 1.00 | 8.21 | N |
| ATOM | 5352 | CA | GLY | B | 134 | 6.306 | 6.749 | 20.548 | 1.00 | 9.26 | C |
| ATOM | 5355 | C | GLY | B | 134 | 7.046 | 7.440 | 19.418 | 1.00 | 9.69 | C |

APPENDIX 1-continued

| | | | | | | | | | | |
|---|---|---|---|---|---|---|---|---|---|---|
| ATOM | 5356 | O | GLY | B | 134 | 7.926 | 6.828 | 18.819 | 1.00 | 12.46 O |
| ATOM | 5357 | N | ASP | B | 135 | 6.718 | 8.697 | 19.134 | 1.00 | 8.82 N |
| ATOM | 5359 | CA | ASP | B | 135 | 7.459 | 9.489 | 18.154 | 1.00 | 9.23 C |
| ATOM | 5361 | CB | ASP | B | 135 | 6.533 | 10.305 | 17.243 | 1.00 | 8.88 C |
| ATOM | 5364 | CG | ASP | B | 135 | 5.732 | 11.364 | 17.966 | 1.00 | 8.72 C |
| ATOM | 5365 | OD1 | ASP | B | 135 | 5.506 | 11.238 | 19.200 | 1.00 | 8.57 O |
| ATOM | 5366 | OD2 | ASP | B | 135 | 5.290 | 12.341 | 17.292 | 1.00 | 9.32 O |
| ATOM | 5367 | C | ASP | B | 135 | 8.523 | 10.368 | 18.796 | 1.00 | 9.65 C |
| ATOM | 5368 | O | ASP | B | 135 | 9.102 | 11.216 | 18.121 | 1.00 | 11.42 O |
| ATOM | 5369 | N | LYS | B | 136 | 8.768 | 10.161 | 20.088 | 1.00 | 9.77 N |
| ATOM | 5371 | CA | LYS | B | 136 | 9.873 | 10.781 | 20.812 | 1.00 | 10.15 C |
| ATOM | 5373 | CB | LYS | B | 136 | 9.349 | 11.647 | 21.958 | 1.00 | 9.99 C |
| ATOM | 5376 | CG | LYS | B | 136 | 8.378 | 12.734 | 21.523 | 1.00 | 10.04 C |
| ATOM | 5379 | CD | LYS | B | 136 | 9.008 | 13.792 | 20.637 | 1.00 | 11.86 C |
| ATOM | 5382 | CE | LYS | B | 136 | 8.014 | 14.925 | 20.392 | 1.00 | 13.11 C |
| ATOM | 5385 | NZ | LYS | B | 136 | 8.453 | 15.910 | 19.384 | 1.00 | 15.13 N |
| ATOM | 5389 | C | LYS | B | 136 | 10.756 | 9.670 | 21.376 | 1.00 | 10.43 C |
| ATOM | 5390 | O | LYS | B | 136 | 10.432 | 8.491 | 21.280 | 1.00 | 11.37 O |
| ATOM | 5391 | N | THR | B | 137 | 11.881 | 10.042 | 21.976 | 1.00 | 11.03 N |
| ATOM | 5393 | CA | THR | B | 137 | 12.777 | 9.068 | 22.582 | 1.00 | 11.49 C |
| ATOM | 5395 | CB | THR | B | 137 | 13.887 | 9.813 | 23.343 | 1.00 | 12.46 C |
| ATOM | 5397 | OG1 | THR | B | 137 | 14.687 | 10.558 | 22.415 | 1.00 | 14.16 O |
| ATOM | 5399 | CG2 | THR | B | 137 | 14.865 | 8.837 | 24.040 | 1.00 | 13.85 C |
| ATOM | 5403 | C | THR | B | 137 | 12.010 | 8.169 | 23.536 | 1.00 | 10.34 C |
| ATOM | 5404 | O | THR | B | 137 | 11.257 | 8.654 | 24.378 | 1.00 | 9.84 O |
| ATOM | 5405 | N | ALA | B | 138 | 12.240 | 6.868 | 23.428 | 1.00 | 10.82 N |
| ATOM | 5407 | CA | ALA | B | 138 | 11.524 | 5.900 | 24.232 | 1.00 | 10.91 C |
| ATOM | 5409 | CB | ALA | B | 138 | 12.055 | 4.511 | 23.995 | 1.00 | 11.85 C |
| ATOM | 5413 | C | ALA | B | 138 | 11.631 | 6.256 | 25.702 | 1.00 | 10.45 C |
| ATOM | 5414 | O | ALA | B | 138 | 12.694 | 6.552 | 26.218 | 1.00 | 11.32 O |
| ATOM | 5415 | N | GLY | B | 139 | 10.503 | 6.194 | 26.378 | 1.00 | 10.16 N |
| ATOM | 5417 | CA | GLY | B | 139 | 10.468 | 6.419 | 27.800 | 1.00 | 9.75 C |
| ATOM | 5420 | C | GLY | B | 139 | 10.535 | 7.861 | 28.250 | 1.00 | 8.52 C |
| ATOM | 5421 | O | GLY | B | 139 | 10.669 | 8.089 | 29.441 | 1.00 | 9.08 O |
| ATOM | 5422 | N | THR | B | 140 | 10.421 | 8.829 | 27.340 | 1.00 | 8.37 N |
| ATOM | 5424 | CA | THR | B | 140 | 10.416 | 10.238 | 27.729 | 1.00 | 8.32 C |
| ATOM | 5426 | CB | THR | B | 140 | 11.318 | 11.119 | 26.843 | 1.00 | 9.11 C |
| ATOM | 5428 | OG1 | THR | B | 140 | 10.877 | 11.095 | 25.476 | 1.00 | 9.56 O |
| ATOM | 5430 | CG2 | THR | B | 140 | 12.768 | 10.611 | 26.900 | 1.00 | 10.40 C |
| ATOM | 5434 | C | THR | B | 140 | 8.987 | 10.774 | 27.783 | 1.00 | 7.64 C |
| ATOM | 5435 | O | THR | B | 140 | 8.120 | 10.378 | 26.991 | 1.00 | 8.11 O |
| ATOM | 5436 | N | GLN | B | 141 | 8.736 | 11.644 | 28.753 | 1.00 | 7.31 N |
| ATOM | 5438 | CA | GLN | B | 141 | 7.405 | 12.176 | 28.997 | 1.00 | 7.20 C |
| ATOM | 5440 | CB | GLN | B | 141 | 7.108 | 12.226 | 30.513 | 1.00 | 7.37 C |
| ATOM | 5443 | CG | GLN | B | 141 | 5.617 | 12.242 | 30.802 | 1.00 | 7.74 C |
| ATOM | 5446 | CD | GLN | B | 141 | 5.238 | 12.460 | 32.256 | 1.00 | 7.09 C |
| ATOM | 5447 | OE1 | GLN | B | 141 | 4.394 | 13.318 | 32.560 | 1.00 | 8.12 O |
| ATOM | 5448 | NE2 | GLN | B | 141 | 5.812 | 11.669 | 33.171 | 1.00 | 7.80 N |
| ATOM | 5451 | C | GLN | B | 141 | 7.284 | 13.551 | 28.353 | 1.00 | 7.04 C |
| ATOM | 5452 | O | GLN | B | 141 | 8.177 | 14.384 | 28.523 | 1.00 | 7.62 O |
| ATOM | 5453 | N | TRP | B | 142 | 6.180 | 13.771 | 27.652 | 1.00 | 7.07 N |
| ATOM | 5455 | CA | TRP | B | 142 | 5.912 | 14.982 | 26.902 | 1.00 | 7.12 C |
| ATOM | 5457 | CB | TRP | B | 142 | 6.063 | 14.717 | 25.387 | 1.00 | 7.52 C |
| ATOM | 5460 | CG | TRP | B | 142 | 7.481 | 14.449 | 24.987 | 1.00 | 7.95 C |
| ATOM | 5461 | CD1 | TRP | B | 142 | 8.205 | 13.342 | 25.263 | 1.00 | 7.71 C |
| ATOM | 5463 | NE1 | TRP | B | 142 | 9.486 | 13.476 | 24.796 | 1.00 | 8.83 N |
| ATOM | 5465 | CE2 | TRP | B | 142 | 9.612 | 14.702 | 24.206 | 1.00 | 8.82 C |
| ATOM | 5466 | CD2 | TRP | B | 142 | 8.363 | 15.342 | 24.303 | 1.00 | 8.41 C |
| ATOM | 5467 | CE3 | TRP | B | 142 | 8.227 | 16.617 | 23.758 | 1.00 | 9.13 C |
| ATOM | 5469 | CZ3 | TRP | B | 142 | 9.321 | 17.200 | 23.122 | 1.00 | 9.87 C |
| ATOM | 5471 | CH2 | TRP | B | 142 | 10.538 | 16.541 | 23.048 | 1.00 | 10.47 C |
| ATOM | 5473 | CZ2 | TRP | B | 142 | 10.703 | 15.288 | 23.568 | 1.00 | 10.08 C |
| ATOM | 5475 | C | TRP | B | 142 | 4.492 | 15.441 | 27.166 | 1.00 | 6.82 C |
| ATOM | 5476 | O | TRP | B | 142 | 3.594 | 14.623 | 27.352 | 1.00 | 7.54 O |
| ATOM | 5477 | N | GLN | B | 143 | 4.282 | 16.757 | 27.146 | 1.00 | 6.91 N |
| ATOM | 5479 | CA | GLN | B | 143 | 2.998 | 17.337 | 27.499 | 1.00 | 6.91 C |
| ATOM | 5481 | CB | GLN | B | 143 | 3.012 | 17.856 | 28.938 | 1.00 | 7.31 C |
| ATOM | 5484 | CG | GLN | B | 143 | 3.928 | 19.058 | 29.162 | 1.00 | 8.18 C |
| ATOM | 5487 | CD | GLN | B | 143 | 3.867 | 19.564 | 30.570 | 1.00 | 8.88 C |
| ATOM | 5488 | OE1 | GLN | B | 143 | 2.792 | 19.555 | 31.173 | 1.00 | 10.18 O |
| ATOM | 5489 | NE2 | GLN | B | 143 | 4.988 | 20.039 | 31.087 | 1.00 | 10.86 N |
| ATOM | 5492 | C | GLN | B | 143 | 2.599 | 18.460 | 26.561 | 1.00 | 7.08 C |
| ATOM | 5493 | O | GLN | B | 143 | 3.427 | 19.104 | 25.928 | 1.00 | 7.42 O |
| ATOM | 5494 | N | HIS | B | 144 | 1.296 | 18.711 | 26.521 | 1.00 | 7.02 N |
| ATOM | 5496 | CA | HIS | B | 144 | 0.706 | 19.829 | 25.804 | 1.00 | 7.09 C |
| ATOM | 5498 | CB | HIS | B | 144 | 0.457 | 19.463 | 24.342 | 1.00 | 7.49 C |
| ATOM | 5501 | CG | HIS | B | 144 | 0.061 | 20.617 | 23.491 | 1.00 | 7.31 C |
| ATOM | 5502 | ND1 | HIS | B | 144 | −0.682 | 20.454 | 22.350 | 1.00 | 8.42 N |
| ATOM | 5504 | CE1 | HIS | B | 144 | −0.861 | 21.643 | 21.800 | 1.00 | 8.61 C |
| ATOM | 5506 | NE2 | HIS | B | 144 | −0.286 | 22.564 | 22.557 | 1.00 | 8.06 N |

APPENDIX 1-continued

| ATOM | 5508 | CD2 | HIS | B | 144 | 0.319 | 21.942 | 23.610 | 1.00 | 8.23 C |
|---|---|---|---|---|---|---|---|---|---|---|
| ATOM | 5510 | C | HIS | B | 144 | −0.604 | 20.173 | 26.496 | 1.00 | 6.98 C |
| ATOM | 5511 | O | HIS | B | 144 | −1.362 | 19.276 | 26.890 | 1.00 | 8.41 O |
| ATOM | 5512 | N | SER | B | 145 | −0.878 | 21.463 | 26.640 | 1.00 | 7.81 N |
| ATOM | 5514 | CA | SER | B | 145 | −2.093 | 21.946 | 27.290 | 1.00 | 7.65 C |
| ATOM | 5516 | CB | SER | B | 145 | −1.755 | 22.780 | 28.522 | 1.00 | 8.72 C |
| ATOM | 5519 | OG | SER | B | 145 | −1.027 | 22.028 | 29.472 | 1.00 | 9.99 O |
| ATOM | 5521 | C | SER | B | 145 | −2.927 | 22.764 | 26.315 | 1.00 | 7.50 C |
| ATOM | 5522 | O | SER | B | 145 | −2.406 | 23.304 | 25.338 | 1.00 | 8.51 O |
| ATOM | 5523 | N | GLY | B | 146 | −4.218 | 22.863 | 26.598 | 1.00 | 7.67 N |
| ATOM | 5525 | CA | GLY | B | 146 | −5.132 | 23.637 | 25.793 | 1.00 | 7.84 C |
| ATOM | 5528 | C | GLY | B | 146 | −6.563 | 23.318 | 26.170 | 1.00 | 7.50 C |
| ATOM | 5529 | O | GLY | B | 146 | −6.830 | 22.629 | 27.148 | 1.00 | 8.13 O |
| ATOM | 5530 | N | PRO | B | 147 | −7.503 | 23.835 | 25.402 | 1.00 | 7.99 N |
| ATOM | 5531 | CA | PRO | B | 147 | −8.924 | 23.707 | 25.733 | 1.00 | 8.42 C |
| ATOM | 5533 | CB | PRO | B | 147 | −9.524 | 24.935 | 25.053 | 1.00 | 8.99 C |
| ATOM | 5536 | CG | PRO | B | 147 | −8.686 | 25.096 | 23.804 | 1.00 | 9.17 C |
| ATOM | 5539 | CD | PRO | B | 147 | −7.290 | 24.658 | 24.195 | 1.00 | 8.66 C |
| ATOM | 5542 | C | PRO | B | 147 | −9.581 | 22.445 | 25.182 | 1.00 | 8.24 C |
| ATOM | 5543 | O | PRO | B | 147 | −9.216 | 21.930 | 24.128 | 1.00 | 8.60 O |
| ATOM | 5544 | N | ILE | B | 148 | −10.613 | 21.991 | 25.892 | 1.00 | 8.18 N |
| ATOM | 5546 | CA | ILE | B | 148 | −11.532 | 21.003 | 25.349 | 1.00 | 8.21 C |
| ATOM | 5548 | CB | ILE | B | 148 | −12.458 | 20.481 | 26.455 | 1.00 | 8.12 C |
| ATOM | 5550 | CG1 | ILE | B | 148 | −11.654 | 19.795 | 27.570 | 1.00 | 9.56 C |
| ATOM | 5553 | CD1 | ILE | B | 148 | −10.843 | 18.627 | 27.145 | 1.00 | 10.59 C |
| ATOM | 5557 | CG2 | ILE | B | 148 | −13.529 | 19.585 | 25.887 | 1.00 | 8.52 C |
| ATOM | 5561 | C | ILE | B | 148 | −12.338 | 21.662 | 24.222 | 1.00 | 8.21 C |
| ATOM | 5562 | O | ILE | B | 148 | −12.939 | 22.728 | 24.410 | 1.00 | 9.55 O |
| ATOM | 5563 | N | ALA | B | 149 | −12.348 | 21.019 | 23.064 | 1.00 | 8.67 N |
| ATOM | 5565 | CA | ALA | B | 149 | −13.055 | 21.532 | 21.896 | 1.00 | 9.10 C |
| ATOM | 5567 | CB | ALA | B | 149 | −12.286 | 21.197 | 20.632 | 1.00 | 9.84 C |
| ATOM | 5571 | C | ALA | B | 149 | −14.476 | 21.013 | 21.771 | 1.00 | 9.41 C |
| ATOM | 5572 | O | ALA | B | 149 | −15.352 | 21.743 | 21.301 | 1.00 | 10.63 O |
| ATOM | 5573 | N | ILE | B | 150 | −14.684 | 19.747 | 22.136 | 1.00 | 9.20 N |
| ATOM | 5575 | CA | ILE | B | 150 | −15.983 | 19.098 | 22.036 | 1.00 | 10.09 C |
| ATOM | 5577 | CB | ILE | B | 150 | −16.093 | 18.145 | 20.814 | 1.00 | 10.95 C |
| ATOM | 5579 | CG1 | ILE | B | 150 | −15.739 | 18.858 | 19.510 | 1.00 | 10.69 C |
| ATOM | 5582 | CD1 | ILE | B | 150 | −15.768 | 17.974 | 18.271 | 1.00 | 11.51 C |
| ATOM | 5586 | CG2 | ILE | B | 150 | −17.497 | 17.568 | 20.704 | 1.00 | 13.68 C |
| ATOM | 5590 | C | ILE | B | 150 | −16.183 | 18.306 | 23.320 | 1.00 | 9.44 C |
| ATOM | 5591 | O | ILE | B | 150 | −15.291 | 17.594 | 23.769 | 1.00 | 8.76 O |
| ATOM | 5592 | N | SER | B | 151 | −17.372 | 18.427 | 23.889 | 1.00 | 10.89 N |
| ATOM | 5594 | CA | SER | B | 151 | −17.765 | 17.741 | 25.101 | 1.00 | 11.77 C |
| ATOM | 5596 | CB | SER | B | 151 | −18.167 | 18.810 | 26.136 | 1.00 | 12.97 C |
| ATOM | 5599 | OG | SER | B | 151 | −18.512 | 18.242 | 27.381 | 1.00 | 15.09 O |
| ATOM | 5601 | C | SER | B | 151 | −18.973 | 16.866 | 24.767 | 1.00 | 11.59 C |
| ATOM | 5602 | O | SER | B | 151 | −20.087 | 17.374 | 24.707 | 1.00 | 14.34 O |
| ATOM | 5603 | N | GLU | B | 152 | −18.761 | 15.581 | 24.505 | 1.00 | 11.06 N |
| ATOM | 5605 | CA | GLU | B | 152 | −19.854 | 14.663 | 24.213 | 1.00 | 10.89 C |
| ATOM | 5607 | CB | BGLU | B | 152 | −19.631 | 13.897 | 22.888 | 0.35 | 11.93 C |
| ATOM | 5608 | CB | AGLU | B | 152 | −19.474 | 13.796 | 23.024 | 0.65 | 12.76 C |
| ATOM | 5613 | CG | BGLU | B | 152 | −20.041 | 14.715 | 21.652 | 0.35 | 12.04 C |
| ATOM | 5614 | CG | AGLU | B | 152 | −18.748 | 14.582 | 21.953 | 0.65 | 14.68 C |
| ATOM | 5619 | CD | BGLU | B | 152 | −20.198 | 13.882 | 20.388 | 0.35 | 13.76 C |
| ATOM | 5620 | CD | AGLU | B | 152 | −18.197 | 13.685 | 20.889 | 0.65 | 17.47 C |
| ATOM | 5621 | OE1 | BGLU | B | 152 | −21.155 | 14.126 | 19.613 | 0.35 | 15.60 O |
| ATOM | 5622 | OE1 | AGLU | B | 152 | −18.974 | 13.391 | 19.960 | 0.65 | 19.10 O |
| ATOM | 5623 | OE2 | BGLU | B | 152 | −19.369 | 12.976 | 20.169 | 0.35 | 15.01 O |
| ATOM | 5624 | OE2 | AGLU | B | 152 | −17.012 | 13.276 | 20.998 | 0.65 | 18.63 O |
| ATOM | 5625 | C | GLU | B | 152 | −20.076 | 13.771 | 25.417 | 1.00 | 10.28 C |
| ATOM | 5626 | O | GLU | B | 152 | −19.376 | 13.873 | 26.426 | 1.00 | 11.20 O |
| ATOM | 5627 | N | THR | B | 153 | −21.057 | 12.893 | 25.338 | 1.00 | 9.81 N |
| ATOM | 5629 | CA | THR | B | 153 | −21.430 | 12.101 | 26.492 | 1.00 | 10.13 C |
| ATOM | 5631 | CB | THR | B | 153 | −22.622 | 11.232 | 26.129 | 1.00 | 10.71 C |
| ATOM | 5633 | OG1 | THR | B | 153 | −23.706 | 12.086 | 25.751 | 1.00 | 12.66 O |
| ATOM | 5635 | CG2 | THR | B | 153 | −23.106 | 10.417 | 27.332 | 1.00 | 11.52 C |
| ATOM | 5639 | C | THR | B | 153 | −20.286 | 11.246 | 27.012 | 1.00 | 9.76 C |
| ATOM | 5640 | O | THR | B | 153 | −20.065 | 11.197 | 28.214 | 1.00 | 10.41 O |
| ATOM | 5641 | N | TYR | B | 154 | −19.588 | 10.574 | 26.108 | 1.00 | 9.41 N |
| ATOM | 5643 | CA | TYR | B | 154 | −18.588 | 9.578 | 26.489 | 1.00 | 9.25 C |
| ATOM | 5645 | CB | TYR | B | 154 | −18.890 | 8.217 | 25.847 | 1.00 | 9.78 C |
| ATOM | 5648 | CG | TYR | B | 154 | −20.239 | 7.693 | 26.220 | 1.00 | 10.14 C |
| ATOM | 5649 | CD1 | TYR | B | 154 | −20.470 | 7.150 | 27.475 | 1.00 | 10.50 C |
| ATOM | 5651 | CE1 | TYR | B | 154 | −21.712 | 6.673 | 27.838 | 1.00 | 10.83 C |
| ATOM | 5653 | CZ | TYR | B | 154 | −22.755 | 6.754 | 26.930 | 1.00 | 11.01 C |
| ATOM | 5654 | OH | TYR | B | 154 | −24.016 | 6.299 | 27.224 | 1.00 | 12.69 O |
| ATOM | 5656 | CE2 | TYR | B | 154 | −22.535 | 7.282 | 25.686 | 1.00 | 11.61 C |
| ATOM | 5658 | CD2 | TYR | B | 154 | −21.293 | 7.762 | 25.344 | 1.00 | 11.24 C |
| ATOM | 5660 | C | TYR | B | 154 | −17.172 | 9.972 | 26.116 | 1.00 | 8.89 C |
| ATOM | 5661 | O | TYR | B | 154 | −16.233 | 9.282 | 26.532 | 1.00 | 9.04 O |

APPENDIX 1-continued

| ATOM | 5662 | N | LYS | B | 155 | −17.001 | 11.045 | 25.351 | 1.00 | 9.30 | N |
|---|---|---|---|---|---|---|---|---|---|---|---|
| ATOM | 5664 | CA | LYS | B | 155 | −15.694 | 11.445 | 24.860 | 1.00 | 9.53 | C |
| ATOM | 5666 | CB | BLYS | B | 155 | −15.479 | 11.009 | 23.401 | 0.35 | 10.42 | C |
| ATOM | 5667 | CB | ALYS | B | 155 | −15.521 | 11.057 | 23.393 | 0.65 | 10.60 | C |
| ATOM | 5672 | CG | BLYS | B | 155 | −15.714 | 9.526 | 23.080 | 0.35 | 11.44 | C |
| ATOM | 5673 | CG | ALYS | B | 155 | −15.446 | 9.579 | 23.102 | 0.65 | 11.66 | C |
| ATOM | 5678 | CD | BLYS | B | 155 | −14.796 | 8.573 | 23.861 | 0.35 | 11.42 | C |
| ATOM | 5679 | CD | ALYS | B | 155 | −14.096 | 8.991 | 23.466 | 0.65 | 9.69 | C |
| ATOM | 5684 | CE | BLYS | B | 155 | −13.424 | 8.327 | 23.221 | 0.35 | 11.05 | C |
| ATOM | 5685 | CE | ALYS | B | 155 | −14.129 | 7.489 | 23.408 | 0.65 | 12.11 | C |
| ATOM | 5690 | NZ | BLYS | B | 155 | −12.677 | 7.235 | 23.943 | 0.35 | 10.75 | N |
| ATOM | 5691 | NZ | ALYS | B | 155 | −12.784 | 6.834 | 23.478 | 0.65 | 10.75 | N |
| ATOM | 5698 | C | LYS | B | 155 | −15.565 | 12.944 | 24.954 | 1.00 | 9.70 | C |
| ATOM | 5699 | O | LYS | B | 155 | −16.531 | 13.686 | 24.765 | 1.00 | 11.39 | O |
| ATOM | 5700 | N | LEU | B | 156 | −14.365 | 13.388 | 25.280 | 1.00 | 8.75 | N |
| ATOM | 5702 | CA | LEU | B | 156 | −13.957 | 14.757 | 25.042 | 1.00 | 8.77 | C |
| ATOM | 5704 | CB | LEU | B | 156 | −13.188 | 15.313 | 26.238 | 1.00 | 9.34 | C |
| ATOM | 5707 | CG | LEU | B | 156 | −13.899 | 15.230 | 27.589 | 1.00 | 9.50 | C |
| ATOM | 5709 | CD1 | LEU | B | 156 | −13.075 | 15.921 | 28.641 | 1.00 | 10.29 | C |
| ATOM | 5713 | CD2 | LEU | B | 156 | −15.313 | 15.818 | 27.545 | 1.00 | 10.26 | C |
| ATOM | 5717 | C | LEU | B | 156 | −13.063 | 14.781 | 23.817 | 1.00 | 8.24 | C |
| ATOM | 5718 | O | LEU | B | 156 | −12.322 | 13.817 | 23.555 | 1.00 | 9.48 | O |
| ATOM | 5719 | N | GLN | B | 157 | −13.115 | 15.863 | 23.049 | 1.00 | 7.55 | N |
| ATOM | 5721 | CA | GLN | B | 157 | −12.210 | 16.040 | 21.931 | 1.00 | 7.62 | C |
| ATOM | 5723 | CB | GLN | B | 157 | −12.926 | 15.991 | 20.589 | 1.00 | 8.06 | C |
| ATOM | 5726 | CG | GLN | B | 157 | −13.830 | 14.779 | 20.448 | 1.00 | 8.73 | C |
| ATOM | 5729 | CD | GLN | B | 157 | −14.089 | 14.415 | 19.009 | 1.00 | 9.08 | C |
| ATOM | 5730 | OE1 | GLN | B | 157 | −13.254 | 14.641 | 18.152 | 1.00 | 11.00 | O |
| ATOM | 5731 | NE2 | GLN | B | 157 | −15.236 | 13.811 | 18.749 | 1.00 | 10.76 | N |
| ATOM | 5734 | C | GLN | B | 157 | −11.462 | 17.344 | 22.077 | 1.00 | 7.12 | C |
| ATOM | 5735 | O | GLN | B | 157 | −11.942 | 18.287 | 22.701 | 1.00 | 7.80 | O |
| ATOM | 5736 | N | TYR | B | 158 | −10.267 | 17.376 | 21.508 | 1.00 | 7.08 | N |
| ATOM | 5738 | CA | TYR | B | 158 | −9.332 | 18.471 | 21.731 | 1.00 | 7.13 | C |
| ATOM | 5740 | CB | TYR | B | 158 | −8.677 | 18.365 | 23.128 | 1.00 | 6.96 | C |
| ATOM | 5743 | CG | TYR | B | 158 | −8.393 | 16.941 | 23.559 | 1.00 | 7.06 | C |
| ATOM | 5744 | CD1 | TYR | B | 158 | −7.326 | 16.222 | 23.034 | 1.00 | 7.19 | C |
| ATOM | 5746 | CE1 | TYR | B | 158 | −7.108 | 14.901 | 23.404 | 1.00 | 7.09 | C |
| ATOM | 5748 | CZ | TYR | B | 158 | −7.946 | 14.281 | 24.320 | 1.00 | 7.18 | C |
| ATOM | 5749 | OH | TYR | B | 158 | −7.750 | 12.979 | 24.733 | 1.00 | 7.90 | O |
| ATOM | 5751 | CE2 | TYR | B | 158 | −9.012 | 14.992 | 24.839 | 1.00 | 7.53 | C |
| ATOM | 5753 | CD2 | TYR | B | 158 | −9.232 | 16.292 | 24.455 | 1.00 | 7.22 | C |
| ATOM | 5755 | C | TYR | B | 158 | −8.280 | 18.442 | 20.641 | 1.00 | 6.81 | C |
| ATOM | 5756 | O | TYR | B | 158 | −8.009 | 17.396 | 20.043 | 1.00 | 7.32 | O |
| ATOM | 5757 | N | ALA | B | 159 | −7.670 | 19.601 | 20.393 | 1.00 | 7.32 | N |
| ATOM | 5759 | CA | ALA | B | 159 | −6.629 | 19.703 | 19.374 | 1.00 | 7.78 | C |
| ATOM | 5761 | CB | ALA | B | 159 | −6.680 | 21.052 | 18.663 | 1.00 | 8.55 | C |
| ATOM | 5765 | C | ALA | B | 159 | −5.229 | 19.451 | 19.903 | 1.00 | 7.90 | C |
| ATOM | 5766 | O | ALA | B | 159 | −4.297 | 19.384 | 19.110 | 1.00 | 8.83 | O |
| ATOM | 5767 | N | MET | B | 160 | −5.055 | 19.302 | 21.220 | 1.00 | 7.36 | N |
| ATOM | 5769 | CA | MET | B | 160 | −3.713 | 19.139 | 21.772 | 1.00 | 7.42 | C |
| ATOM | 5771 | CB | MET | B | 160 | −3.733 | 18.986 | 23.293 | 1.00 | 8.13 | C |
| ATOM | 5774 | CG | MET | B | 160 | −4.060 | 20.269 | 24.029 | 1.00 | 8.32 | C |
| ATOM | 5777 | SD | MET | B | 160 | −5.812 | 20.754 | 24.003 | 1.00 | 8.06 | S |
| ATOM | 5778 | CE | MET | B | 160 | −6.418 | 19.818 | 25.409 | 1.00 | 8.63 | C |
| ATOM | 5782 | C | MET | B | 160 | −3.042 | 17.927 | 21.119 | 1.00 | 7.49 | C |
| ATOM | 5783 | O | MET | B | 160 | −3.660 | 16.882 | 20.868 | 1.00 | 7.73 | O |
| ATOM | 5784 | N | ASP | B | 161 | −1.756 | 18.098 | 20.866 | 1.00 | 7.41 | N |
| ATOM | 5786 | CA | ASP | B | 161 | −0.986 | 17.115 | 20.130 | 1.00 | 7.72 | C |
| ATOM | 5788 | CB | ASP | B | 161 | 0.316 | 17.758 | 19.654 | 1.00 | 8.40 | C |
| ATOM | 5791 | CG | ASP | B | 161 | 0.065 | 18.961 | 18.781 | 1.00 | 8.51 | C |
| ATOM | 5792 | OD1 | ASP | B | 161 | 0.577 | 20.072 | 19.078 | 1.00 | 9.92 | O |
| ATOM | 5793 | OD2 | ASP | B | 161 | −0.668 | 18.829 | 17.794 | 1.00 | 8.73 | O |
| ATOM | 5794 | C | ASP | B | 161 | −0.704 | 15.870 | 20.953 | 1.00 | 7.16 | C |
| ATOM | 5795 | O | ASP | B | 161 | −0.294 | 15.963 | 22.117 | 1.00 | 7.81 | O |
| ATOM | 5796 | N | THR | B | 162 | −0.901 | 14.722 | 20.319 | 1.00 | 7.20 | N |
| ATOM | 5798 | CA | THR | B | 162 | −0.669 | 13.420 | 20.924 | 1.00 | 7.17 | C |
| ATOM | 5800 | CB | THR | B | 162 | −1.969 | 12.811 | 21.499 | 1.00 | 7.29 | C |
| ATOM | 5802 | OG1 | THR | B | 162 | −2.905 | 12.578 | 20.436 | 1.00 | 7.90 | O |
| ATOM | 5804 | CG2 | THR | B | 162 | −2.645 | 13.727 | 22.509 | 1.00 | 8.12 | C |
| ATOM | 5808 | C | THR | B | 162 | −0.154 | 12.465 | 19.857 | 1.00 | 7.27 | C |
| ATOM | 5809 | O | THR | B | 162 | −0.332 | 12.693 | 18.664 | 1.00 | 7.57 | O |
| ATOM | 5810 | N | TYR | B | 163 | 0.414 | 11.350 | 20.298 | 1.00 | 7.74 | N |
| ATOM | 5812 | CA | TYR | B | 163 | 0.840 | 10.282 | 19.401 | 1.00 | 7.85 | C |
| ATOM | 5814 | CB | TYR | B | 163 | 2.316 | 10.465 | 19.013 | 1.00 | 8.00 | C |
| ATOM | 5817 | CG | TYR | B | 163 | 2.766 | 9.721 | 17.771 | 1.00 | 8.39 | C |
| ATOM | 5818 | CD1 | TYR | B | 163 | 2.621 | 10.309 | 16.533 | 1.00 | 10.58 | C |
| ATOM | 5820 | CE1 | TYR | B | 163 | 3.039 | 9.684 | 15.385 | 1.00 | 11.78 | C |
| ATOM | 5822 | CZ | TYR | B | 163 | 3.642 | 8.452 | 15.458 | 1.00 | 11.29 | C |
| ATOM | 5823 | OH | TYR | B | 163 | 4.037 | 7.861 | 14.280 | 1.00 | 14.10 | O |
| ATOM | 5825 | CE2 | TYR | B | 163 | 3.807 | 7.835 | 16.689 | 1.00 | 9.46 | C |

APPENDIX 1-continued

| | | | | | | | | | |
|---|---|---|---|---|---|---|---|---|---|
| ATOM | 5827 | CD2 | TYR | B | 163 | 3.390 | 8.484 | 17.833 | 1.00 | 8.33 C |
| ATOM | 5829 | C | TYR | B | 163 | 0.643 | 8.948 | 20.088 | 1.00 | 7.90 C |
| ATOM | 5830 | O | TYR | B | 163 | 0.537 | 8.870 | 21.310 | 1.00 | 8.15 O |
| ATOM | 5831 | N | GLY | B | 164 | 0.628 | 7.881 | 19.296 | 1.00 | 7.76 N |
| ATOM | 5833 | CA | GLY | B | 164 | 0.677 | 6.530 | 19.828 | 1.00 | 8.11 C |
| ATOM | 5836 | C | GLY | B | 164 | 1.667 | 6.417 | 20.964 | 1.00 | 7.49 C |
| ATOM | 5837 | O | GLY | B | 164 | 2.773 | 6.926 | 20.880 | 1.00 | 8.72 O |
| ATOM | 5838 | N | GLY | B | 165 | 1.262 | 5.708 | 22.009 | 1.00 | 7.45 N |
| ATOM | 5840 | CA | GLY | B | 165 | 1.988 | 5.644 | 23.269 | 1.00 | 7.27 C |
| ATOM | 5843 | C | GLY | B | 165 | 1.350 | 6.507 | 24.339 | 1.00 | 6.66 C |
| ATOM | 5844 | O | GLY | B | 165 | 1.461 | 6.214 | 25.531 | 1.00 | 7.23 O |
| ATOM | 5845 | N | GLN | B | 166 | 0.662 | 7.572 | 23.923 | 1.00 | 6.83 N |
| ATOM | 5847 | CA | GLN | B | 166 | −0.003 | 8.463 | 24.859 | 1.00 | 6.61 C |
| ATOM | 5849 | CB | GLN | B | 166 | 0.045 | 9.919 | 24.381 | 1.00 | 6.74 C |
| ATOM | 5852 | CG | GLN | B | 166 | 1.451 | 10.489 | 24.459 | 1.00 | 7.33 C |
| ATOM | 5855 | CD | GLN | B | 166 | 1.507 | 11.943 | 24.074 | 1.00 | 6.80 C |
| ATOM | 5856 | OE1 | GLN | B | 166 | 1.609 | 12.277 | 22.895 | 1.00 | 7.44 O |
| ATOM | 5857 | NE2 | GLN | B | 166 | 1.421 | 12.831 | 25.056 | 1.00 | 8.44 N |
| ATOM | 5860 | C | GLN | B | 166 | −1.429 | 8.054 | 25.211 | 1.00 | 6.58 C |
| ATOM | 5861 | O | GLN | B | 166 | −2.003 | 8.683 | 26.096 | 1.00 | 6.83 O |
| ATOM | 5862 | N | ALA | B | 167 | −2.023 | 7.043 | 24.587 | 1.00 | 6.87 N |
| ATOM | 5864 | CA | ALA | B | 167 | −3.285 | 6.550 | 25.133 | 1.00 | 6.77 C |
| ATOM | 5866 | CB | ALA | B | 167 | −3.854 | 5.379 | 24.386 | 1.00 | 7.55 C |
| ATOM | 5870 | C | ALA | B | 167 | −3.038 | 6.162 | 26.587 | 1.00 | 6.83 C |
| ATOM | 5871 | O | ALA | B | 167 | −1.998 | 5.619 | 26.939 | 1.00 | 7.16 O |
| ATOM | 5872 | N | GLY | B | 168 | −4.029 | 6.461 | 27.410 | 1.00 | 6.56 N |
| ATOM | 5874 | CA | GLY | B | 168 | −3.940 | 6.275 | 28.838 | 1.00 | 6.85 C |
| ATOM | 5877 | C | GLY | B | 168 | −3.482 | 7.506 | 29.584 | 1.00 | 6.95 C |
| ATOM | 5878 | O | GLY | B | 168 | −3.573 | 7.528 | 30.811 | 1.00 | 8.08 O |
| ATOM | 5879 | N | SER | B | 169 | −2.983 | 8.524 | 28.883 | 1.00 | 6.66 N |
| ATOM | 5881 | CA | SER | B | 169 | −2.522 | 9.730 | 29.550 | 1.00 | 6.73 C |
| ATOM | 5883 | CB | SER | B | 169 | −1.937 | 10.743 | 28.561 | 1.00 | 6.97 C |
| ATOM | 5886 | OG | SER | B | 169 | −0.786 | 10.274 | 27.893 | 1.00 | 7.01 O |
| ATOM | 5888 | C | SER | B | 169 | −3.682 | 10.418 | 30.252 | 1.00 | 6.37 C |
| ATOM | 5889 | O | SER | B | 169 | −4.809 | 10.457 | 29.735 | 1.00 | 7.00 O |
| ATOM | 5890 | N | PRO | B | 170 | −3.423 | 11.031 | 31.401 | 1.00 | 6.55 N |
| ATOM | 5891 | CA | PRO | B | 170 | −4.460 | 11.849 | 32.024 | 1.00 | 6.89 C |
| ATOM | 5893 | CB | PRO | B | 170 | −3.857 | 12.207 | 33.376 | 1.00 | 7.40 C |
| ATOM | 5896 | CG | PRO | B | 170 | −2.372 | 12.206 | 33.129 | 1.00 | 7.51 C |
| ATOM | 5899 | CD | PRO | B | 170 | −2.132 | 11.112 | 32.117 | 1.00 | 7.19 C |
| ATOM | 5902 | C | PRO | B | 170 | −4.681 | 13.102 | 31.183 | 1.00 | 6.85 C |
| ATOM | 5903 | O | PRO | B | 170 | −3.735 | 13.676 | 30.622 | 1.00 | 7.40 O |
| ATOM | 5904 | N | VAL | B | 171 | −5.937 | 13.524 | 31.132 | 1.00 | 7.09 N |
| ATOM | 5906 | CA | VAL | B | 171 | −6.348 | 14.785 | 30.543 | 1.00 | 7.34 C |
| ATOM | 5908 | CB | VAL | B | 171 | −7.465 | 14.557 | 29.506 | 1.00 | 7.54 C |
| ATOM | 5910 | CG1 | VAL | B | 171 | −7.909 | 15.888 | 28.901 | 1.00 | 8.25 C |
| ATOM | 5914 | CG2 | VAL | B | 171 | −7.031 | 13.593 | 28.430 | 1.00 | 7.81 C |
| ATOM | 5918 | C | VAL | B | 171 | −6.840 | 15.593 | 31.737 | 1.00 | 7.34 C |
| ATOM | 5919 | O | VAL | B | 171 | −7.955 | 15.357 | 32.214 | 1.00 | 8.22 O |
| ATOM | 5920 | N | PHE | B | 172 | −5.982 | 16.449 | 32.278 | 1.00 | 7.59 N |
| ATOM | 5922 | CA | PHE | B | 172 | −6.163 | 16.916 | 33.647 | 1.00 | 7.79 C |
| ATOM | 5924 | CB | PHE | B | 172 | −5.221 | 16.170 | 34.623 | 1.00 | 8.27 C |
| ATOM | 5927 | CG | PHE | B | 172 | −3.744 | 16.499 | 34.490 | 1.00 | 8.37 C |
| ATOM | 5928 | CD1 | PHE | B | 172 | −3.131 | 17.378 | 35.375 | 1.00 | 9.16 C |
| ATOM | 5930 | CE1 | PHE | B | 172 | −1.781 | 17.635 | 35.304 | 1.00 | 9.65 C |
| ATOM | 5932 | CZ | PHE | B | 172 | −1.013 | 17.033 | 34.328 | 1.00 | 9.66 C |
| ATOM | 5934 | CE2 | PHE | B | 172 | −1.601 | 16.164 | 33.436 | 1.00 | 9.16 C |
| ATOM | 5936 | CD2 | PHE | B | 172 | −2.958 | 15.881 | 33.524 | 1.00 | 8.25 C |
| ATOM | 5938 | C | PHE | B | 172 | −6.001 | 18.406 | 33.814 | 1.00 | 8.22 C |
| ATOM | 5939 | O | PHE | B | 172 | −5.216 | 19.061 | 33.133 | 1.00 | 8.32 O |
| ATOM | 5940 | N | GLU | B | 173 | −6.748 | 18.939 | 34.765 | 1.00 | 9.45 N |
| ATOM | 5942 | CA | GLU | B | 173 | −6.530 | 20.289 | 35.261 | 1.00 | 10.25 C |
| ATOM | 5944 | CB | GLU | B | 173 | −7.785 | 20.812 | 35.938 | 1.00 | 10.74 C |
| ATOM | 5947 | CG | GLU | B | 173 | −8.990 | 20.794 | 35.029 | 1.00 | 11.64 C |
| ATOM | 5950 | CD | GLU | B | 173 | −10.231 | 21.270 | 35.737 | 1.00 | 12.37 C |
| ATOM | 5951 | OE1 | GLU | B | 173 | −10.771 | 22.325 | 35.349 | 1.00 | 13.46 O |
| ATOM | 5952 | OE2 | GLU | B | 173 | −10.643 | 20.583 | 36.698 | 1.00 | 14.40 O |
| ATOM | 5953 | C | GLU | B | 173 | −5.379 | 20.263 | 36.258 | 1.00 | 11.18 C |
| ATOM | 5954 | O | GLU | B | 173 | −5.337 | 19.402 | 37.127 | 1.00 | 11.76 O |
| ATOM | 5955 | N | GLN | B | 174 | −4.454 | 21.209 | 36.145 | 1.00 | 12.69 N |
| ATOM | 5957 | CA | GLN | B | 174 | −3.289 | 21.244 | 37.026 | 1.00 | 14.03 C |
| ATOM | 5959 | CB | GLN | B | 174 | −2.344 | 22.376 | 36.616 | 1.00 | 14.32 C |
| ATOM | 5962 | CG | GLN | B | 174 | −1.682 | 22.176 | 35.261 | 1.00 | 14.57 C |
| ATOM | 5965 | CD | GLN | B | 174 | −0.500 | 21.229 | 35.272 | 1.00 | 13.85 C |
| ATOM | 5966 | OE1 | GLN | B | 174 | −0.120 | 20.709 | 34.207 | 1.00 | 14.35 O |
| ATOM | 5967 | NE2 | GLN | B | 174 | 0.089 | 20.999 | 36.440 | 1.00 | 13.83 N |
| ATOM | 5970 | C | GLN | B | 174 | −3.670 | 21.420 | 38.499 | 1.00 | 14.98 C |
| ATOM | 5971 | O | GLN | B | 174 | −3.055 | 20.828 | 39.382 | 1.00 | 15.06 O |
| ATOM | 5972 | N | SER | B | 175 | −4.688 | 22.232 | 38.754 | 1.00 | 16.64 N |
| ATOM | 5974 | CA | SER | B | 175 | −5.086 | 22.556 | 40.114 | 1.00 | 18.96 C |

APPENDIX 1-continued

| ATOM | 5976 | CB | SER | B | 175 | −4.237 | 23.718 | 40.627 | 1.00 | 19.69 | C |
| --- | --- | --- | --- | --- | --- | --- | --- | --- | --- | --- | --- |
| ATOM | 5979 | OG | SER | B | 175 | −4.601 | 24.095 | 41.945 | 1.00 | 22.47 | O |
| ATOM | 5981 | C | SER | B | 175 | −6.561 | 22.930 | 40.126 | 1.00 | 19.54 | C |
| ATOM | 5982 | O | SER | B | 175 | −6.933 | 24.006 | 39.666 | 1.00 | 20.78 | O |
| ATOM | 5983 | N | SER | B | 176 | −7.400 | 22.039 | 40.644 | 1.00 | 19.58 | N |
| ATOM | 5985 | CA | SER | B | 176 | −8.842 | 22.251 | 40.640 | 1.00 | 20.22 | C |
| ATOM | 5987 | CB | SER | B | 176 | −9.468 | 21.458 | 39.495 | 1.00 | 20.96 | C |
| ATOM | 5990 | OG | SER | B | 176 | −10.867 | 21.629 | 39.459 | 1.00 | 23.01 | O |
| ATOM | 5992 | C | SER | B | 176 | −9.475 | 21.805 | 41.947 | 1.00 | 20.01 | C |
| ATOM | 5993 | O | SER | B | 176 | −8.995 | 20.878 | 42.599 | 1.00 | 18.97 | O |
| ATOM | 5994 | N | SER | B | 177 | −10.560 | 22.486 | 42.311 | 1.00 | 20.67 | N |
| ATOM | 5996 | CA | SER | B | 177 | −11.457 | 22.038 | 43.368 | 1.00 | 21.82 | C |
| ATOM | 5998 | CB | SER | B | 177 | −11.738 | 23.164 | 44.369 | 1.00 | 22.03 | C |
| ATOM | 6001 | OG | SER | B | 177 | −12.180 | 24.343 | 43.719 | 1.00 | 24.65 | O |
| ATOM | 6003 | C | SER | B | 177 | −12.749 | 21.547 | 42.706 | 1.00 | 22.02 | C |
| ATOM | 6004 | O | SER | B | 177 | −13.563 | 22.340 | 42.230 | 1.00 | 23.51 | O |
| ATOM | 6005 | N | ARG | B | 178 | −12.881 | 20.226 | 42.622 | 1.00 | 21.68 | N |
| ATOM | 6007 | CA | ARG | B | 178 | −14.097 | 19.547 | 42.176 | 1.00 | 20.93 | C |
| ATOM | 6009 | CB | ARG | B | 178 | −13.937 | 18.996 | 40.745 | 1.00 | 20.43 | C |
| ATOM | 6012 | CG | ARG | B | 178 | −13.783 | 20.018 | 39.627 | 1.00 | 18.45 | C |
| ATOM | 6015 | CD | ARG | B | 178 | −13.677 | 19.382 | 38.238 | 1.00 | 16.30 | C |
| ATOM | 6018 | NE | ARG | B | 178 | −13.336 | 20.340 | 37.188 | 1.00 | 15.06 | N |
| ATOM | 6020 | CZ | ARG | B | 178 | −14.210 | 20.982 | 36.429 | 1.00 | 15.42 | C |
| ATOM | 6021 | NH1 | ARG | B | 178 | −15.520 | 20.830 | 36.599 | 1.00 | 16.79 | N |
| ATOM | 6024 | NH2 | ARG | B | 178 | −13.766 | 21.800 | 35.487 | 1.00 | 15.73 | N |
| ATOM | 6027 | C | ARG | B | 178 | −14.317 | 18.378 | 43.127 | 1.00 | 21.07 | C |
| ATOM | 6028 | O | ARG | B | 178 | −13.498 | 18.130 | 44.007 | 1.00 | 21.95 | O |
| ATOM | 6029 | N | THR | B | 179 | −15.409 | 17.643 | 42.952 | 1.00 | 20.41 | N |
| ATOM | 6031 | CA | THR | B | 179 | −15.601 | 16.424 | 43.723 | 1.00 | 20.45 | C |
| ATOM | 6033 | CB | THR | B | 179 | −16.934 | 15.754 | 43.349 | 1.00 | 21.16 | C |
| ATOM | 6035 | OG1 | THR | B | 179 | −18.030 | 16.605 | 43.717 | 1.00 | 22.79 | O |
| ATOM | 6037 | CG2 | THR | B | 179 | −17.156 | 14.483 | 44.160 | 1.00 | 22.10 | C |
| ATOM | 6041 | C | THR | B | 179 | −14.439 | 15.480 | 43.434 | 1.00 | 19.46 | C |
| ATOM | 6042 | O | THR | B | 179 | −14.150 | 15.185 | 42.267 | 1.00 | 19.41 | O |
| ATOM | 6043 | N | ASN | B | 180 | −13.759 | 15.050 | 44.493 | 1.00 | 18.57 | N |
| ATOM | 6045 | CA | ASN | B | 180 | −12.593 | 14.162 | 44.410 | 1.00 | 18.41 | C |
| ATOM | 6047 | CB | ASN | B | 180 | −12.948 | 12.851 | 43.684 | 1.00 | 18.60 | C |
| ATOM | 6050 | CG | ASN | B | 180 | −11.881 | 11.765 | 43.846 | 1.00 | 18.64 | C |
| ATOM | 6051 | OD1 | ASN | B | 180 | −11.492 | 11.110 | 42.874 | 1.00 | 17.95 | O |
| ATOM | 6052 | ND2 | ASN | B | 180 | −11.407 | 11.572 | 45.071 | 1.00 | 19.48 | N |
| ATOM | 6055 | C | ASN | B | 180 | −11.376 | 14.840 | 43.778 | 1.00 | 17.73 | C |
| ATOM | 6056 | O | ASN | B | 180 | −10.477 | 14.160 | 43.272 | 1.00 | 18.18 | O |
| ATOM | 6057 | N | CYS | B | 181 | −11.329 | 16.175 | 43.845 | 1.00 | 18.01 | N |
| ATOM | 6059 | CA | CYS | B | 181 | −10.170 | 16.955 | 43.412 | 1.00 | 17.47 | C |
| ATOM | 6061 | CB | CYS | B | 181 | −10.365 | 17.519 | 42.007 | 1.00 | 16.55 | C |
| ATOM | 6064 | SG | CYS | B | 181 | −10.449 | 16.203 | 40.788 | 1.00 | 14.03 | S |
| ATOM | 6065 | C | CYS | B | 181 | −9.864 | 18.092 | 44.372 | 1.00 | 18.41 | C |
| ATOM | 6066 | O | CYS | B | 181 | −10.756 | 18.845 | 44.780 | 1.00 | 19.23 | O |
| ATOM | 6067 | N | ASN | B | 182 | −8.595 | 18.188 | 44.734 | 1.00 | 19.10 | N |
| ATOM | 6069 | CA | ASN | B | 182 | −8.057 | 19.316 | 45.475 | 1.00 | 19.72 | C |
| ATOM | 6071 | CB | ASN | B | 182 | −8.215 | 19.085 | 46.989 | 1.00 | 20.52 | C |
| ATOM | 6074 | CG | ASN | B | 182 | −7.873 | 20.313 | 47.824 | 0.50 | 21.48 | C |
| ATOM | 6075 | OD1 | ASN | B | 182 | −7.469 | 20.192 | 48.983 | 0.50 | 23.03 | O |
| ATOM | 6076 | ND2 | ASN | B | 182 | −8.051 | 21.498 | 47.248 | 0.50 | 22.48 | N |
| ATOM | 6079 | C | ASN | B | 182 | −6.593 | 19.428 | 45.053 | 1.00 | 19.26 | C |
| ATOM | 6080 | O | ASN | B | 182 | −5.683 | 19.248 | 45.854 | 1.00 | 20.75 | O |
| ATOM | 6081 | N | GLY | B | 183 | −6.392 | 19.722 | 43.767 | 1.00 | 17.83 | N |
| ATOM | 6083 | CA | GLY | B | 183 | −5.102 | 19.586 | 43.106 | 1.00 | 16.31 | C |
| ATOM | 6086 | C | GLY | B | 183 | −5.308 | 19.065 | 41.691 | 1.00 | 15.03 | C |
| ATOM | 6087 | O | GLY | B | 183 | −6.328 | 19.348 | 41.063 | 1.00 | 15.07 | O |
| ATOM | 6088 | N | PRO | B | 184 | −4.353 | 18.300 | 41.168 | 1.00 | 13.71 | N |
| ATOM | 6089 | CA | PRO | B | 184 | −4.487 | 17.759 | 39.810 | 1.00 | 12.66 | C |
| ATOM | 6091 | CB | PRO | B | 184 | −3.241 | 16.889 | 39.651 | 1.00 | 13.12 | C |
| ATOM | 6094 | CG | PRO | B | 184 | −2.259 | 17.444 | 40.640 | 1.00 | 14.51 | C |
| ATOM | 6097 | CD | PRO | B | 184 | −3.077 | 17.925 | 41.800 | 1.00 | 14.52 | C |
| ATOM | 6100 | C | PRO | B | 184 | −5.769 | 16.941 | 39.671 | 1.00 | 11.46 | C |
| ATOM | 6101 | O | PRO | B | 184 | −6.076 | 16.141 | 40.565 | 1.00 | 12.12 | O |
| ATOM | 6102 | N | CYS | B | 185 | −6.500 | 17.154 | 38.581 | 1.00 | 10.93 | N |
| ATOM | 6104 | CA | CYS | B | 185 | −7.851 | 16.641 | 38.453 | 1.00 | 10.37 | C |
| ATOM | 6106 | CB | CYS | B | 185 | −8.838 | 17.758 | 38.780 | 1.00 | 11.29 | C |
| ATOM | 6109 | SG | CYS | B | 185 | −10.536 | 17.205 | 38.967 | 1.00 | 13.15 | S |
| ATOM | 6110 | C | CYS | B | 185 | −8.095 | 16.139 | 37.046 | 1.00 | 9.18 | C |
| ATOM | 6111 | O | CYS | B | 185 | −8.272 | 16.933 | 36.118 | 1.00 | 9.91 | O |
| ATOM | 6112 | N | SER | B | 186 | −8.075 | 14.824 | 36.874 | 1.00 | 9.10 | N |
| ATOM | 6114 | CA | SER | B | 186 | −8.312 | 14.244 | 35.555 | 1.00 | 8.73 | C |
| ATOM | 6116 | CB | SER | B | 186 | −7.828 | 12.808 | 35.521 | 1.00 | 9.22 | C |
| ATOM | 6119 | OG | SER | B | 186 | −6.445 | 12.784 | 35.662 | 1.00 | 10.95 | O |
| ATOM | 6121 | C | SER | B | 186 | −9.792 | 14.276 | 35.205 | 1.00 | 8.85 | C |
| ATOM | 6122 | O | SER | B | 186 | −10.631 | 13.896 | 36.021 | 1.00 | 9.47 | O |
| ATOM | 6123 | N | LEU | B | 187 | −10.070 | 14.716 | 33.981 | 1.00 | 8.48 | N |

APPENDIX 1-continued

| ATOM | 6125 | CA | LEU | B | 187 | −11.417 | 14.803 | 33.438 | 1.00 | 8.48 | C |
|---|---|---|---|---|---|---|---|---|---|---|---|
| ATOM | 6127 | CB | LEU | B | 187 | −11.672 | 16.220 | 32.909 | 1.00 | 8.73 | C |
| ATOM | 6130 | CG | LEU | B | 187 | −11.486 | 17.345 | 33.923 | 1.00 | 9.71 | C |
| ATOM | 6132 | CD1 | LEU | B | 187 | −11.768 | 18.686 | 33.266 | 1.00 | 10.15 | C |
| ATOM | 6136 | CD2 | LEU | B | 187 | −12.372 | 17.141 | 35.147 | 1.00 | 11.50 | C |
| ATOM | 6140 | C | LEU | B | 187 | −11.677 | 13.791 | 32.329 | 1.00 | 8.23 | C |
| ATOM | 6141 | O | LEU | B | 187 | −12.828 | 13.573 | 31.958 | 1.00 | 8.64 | O |
| ATOM | 6142 | N | ALA | B | 188 | −10.612 | 13.181 | 31.805 | 1.00 | 8.18 | N |
| ATOM | 6144 | CA | ALA | B | 188 | −10.694 | 12.216 | 30.727 | 1.00 | 7.99 | C |
| ATOM | 6146 | CB | ALA | B | 188 | −10.950 | 12.910 | 29.397 | 1.00 | 7.96 | C |
| ATOM | 6150 | C | ALA | B | 188 | −9.385 | 11.425 | 30.699 | 1.00 | 7.51 | C |
| ATOM | 6151 | O | ALA | B | 188 | −8.414 | 11.769 | 31.366 | 1.00 | 7.88 | O |
| ATOM | 6152 | N | VAL | B | 189 | −9.389 | 10.372 | 29.896 | 1.00 | 7.53 | N |
| ATOM | 6154 | CA | VAL | B | 189 | −8.217 | 9.552 | 29.624 | 1.00 | 7.68 | C |
| ATOM | 6156 | CB | BVAL | B | 189 | −8.268 | 8.135 | 30.229 | 0.35 | 8.28 | C |
| ATOM | 6157 | CB | AVAL | B | 189 | −8.511 | 8.063 | 29.995 | 0.65 | 8.30 | C |
| ATOM | 6160 | CG1 | BVAL | B | 189 | −9.551 | 7.453 | 29.930 | 0.35 | 9.36 | C |
| ATOM | 6161 | CG1 | AVAL | B | 189 | −7.306 | 7.209 | 29.742 | 0.65 | 9.65 | C |
| ATOM | 6168 | CG2 | BVAL | B | 189 | −7.113 | 7.296 | 29.717 | 0.35 | 10.02 | C |
| ATOM | 6169 | CG2 | AVAL | B | 189 | −8.970 | 7.917 | 31.433 | 0.65 | 8.62 | C |
| ATOM | 6176 | C | VAL | B | 189 | −7.982 | 9.584 | 28.117 | 1.00 | 7.27 | C |
| ATOM | 6177 | O | VAL | B | 189 | −8.890 | 9.267 | 27.338 | 1.00 | 7.48 | O |
| ATOM | 6178 | N | HIS | B | 190 | −6.793 | 9.991 | 27.673 | 1.00 | 6.91 | N |
| ATOM | 6180 | CA | HIS | B | 190 | −6.546 | 10.097 | 26.248 | 1.00 | 6.84 | C |
| ATOM | 6182 | CB | HIS | B | 190 | −5.167 | 10.736 | 25.956 | 1.00 | 6.94 | C |
| ATOM | 6185 | CG | HIS | B | 190 | −4.917 | 10.787 | 24.504 | 1.00 | 6.68 | C |
| ATOM | 6186 | ND1 | HIS | B | 190 | −5.791 | 11.423 | 23.659 | 1.00 | 7.50 | N |
| ATOM | 6188 | CE1 | HIS | B | 190 | −5.449 | 11.150 | 22.417 | 1.00 | 7.27 | C |
| ATOM | 6190 | NE2 | HIS | B | 190 | −4.369 | 10.394 | 22.428 | 1.00 | 7.70 | N |
| ATOM | 6192 | CD2 | HIS | B | 190 | −4.006 | 10.160 | 23.732 | 1.00 | 7.53 | C |
| ATOM | 6194 | C | HIS | B | 190 | −6.656 | 8.714 | 25.580 | 1.00 | 6.62 | C |
| ATOM | 6195 | O | HIS | B | 190 | −6.168 | 7.735 | 26.122 | 1.00 | 7.01 | O |
| ATOM | 6196 | N | THR | B | 191 | −7.271 | 8.655 | 24.402 | 1.00 | 6.90 | N |
| ATOM | 6198 | CA | THR | B | 191 | −7.429 | 7.367 | 23.723 | 1.00 | 7.18 | C |
| ATOM | 6200 | CB | THR | B | 191 | −8.815 | 6.739 | 23.986 | 1.00 | 7.59 | C |
| ATOM | 6202 | OG1 | THR | B | 191 | −9.845 | 7.700 | 23.751 | 1.00 | 9.16 | O |
| ATOM | 6204 | CG2 | THR | B | 191 | −8.974 | 6.296 | 25.430 | 1.00 | 8.33 | C |
| ATOM | 6208 | C | THR | B | 191 | −7.162 | 7.340 | 22.221 | 1.00 | 7.39 | C |
| ATOM | 6209 | O | THR | B | 191 | −6.635 | 6.336 | 21.746 | 1.00 | 8.24 | O |
| ATOM | 6210 | N | ASN | B | 192 | −7.589 | 8.362 | 21.472 | 1.00 | 7.54 | N |
| ATOM | 6212 | CA | ASN | B | 192 | −7.637 | 8.270 | 20.016 | 1.00 | 8.61 | C |
| ATOM | 6214 | CB | ASN | B | 192 | −9.084 | 8.158 | 19.500 | 1.00 | 10.14 | C |
| ATOM | 6217 | CG | ASN | B | 192 | −9.884 | 7.097 | 20.205 | 1.00 | 13.02 | C |
| ATOM | 6218 | OD1 | ASN | B | 192 | −9.925 | 5.949 | 19.768 | 1.00 | 17.47 | O |
| ATOM | 6219 | ND2 | ASN | B | 192 | −10.571 | 7.484 | 21.269 | 1.00 | 13.77 | N |
| ATOM | 6222 | C | ASN | B | 192 | −7.053 | 9.497 | 19.349 | 1.00 | 7.81 | C |
| ATOM | 6223 | O | ASN | B | 192 | −7.187 | 10.604 | 19.845 | 1.00 | 7.54 | O |
| ATOM | 6224 | N | GLY | B | 193 | −6.466 | 9.272 | 18.178 | 1.00 | 7.89 | N |
| ATOM | 6226 | CA | GLY | B | 193 | −6.097 | 10.347 | 17.282 | 1.00 | 7.94 | C |
| ATOM | 6229 | C | GLY | B | 193 | −7.269 | 10.780 | 16.424 | 1.00 | 7.68 | C |
| ATOM | 6230 | O | GLY | B | 193 | −8.434 | 10.495 | 16.712 | 1.00 | 8.59 | O |
| ATOM | 6231 | N | VAL | B | 194 | −6.934 | 11.448 | 15.329 | 1.00 | 7.94 | N |
| ATOM | 6233 | CA | VAL | B | 194 | −7.905 | 12.057 | 14.430 | 1.00 | 8.60 | C |
| ATOM | 6235 | CB | VAL | B | 194 | −7.210 | 13.166 | 13.608 | 1.00 | 9.21 | C |
| ATOM | 6237 | CG1 | VAL | B | 194 | −8.096 | 13.671 | 12.465 | 1.00 | 10.61 | C |
| ATOM | 6241 | CG2 | VAL | B | 194 | −6.800 | 14.308 | 14.504 | 1.00 | 9.07 | C |
| ATOM | 6245 | C | VAL | B | 194 | −8.484 | 10.982 | 13.518 | 1.00 | 9.30 | C |
| ATOM | 6246 | O | VAL | B | 194 | −7.749 | 10.269 | 12.840 | 1.00 | 10.19 | O |
| ATOM | 6247 | N | TYR | B | 195 | −9.806 | 10.861 | 13.489 | 1.00 | 9.47 | N |
| ATOM | 6249 | CA | TYR | B | 195 | −10.480 | 9.922 | 12.601 | 1.00 | 10.28 | C |
| ATOM | 6251 | CB | TYR | B | 195 | −10.327 | 8.471 | 13.092 | 1.00 | 11.06 | C |
| ATOM | 6254 | CG | TYR | B | 195 | −11.205 | 8.082 | 14.268 | 1.00 | 11.54 | C |
| ATOM | 6255 | CD1 | TYR | B | 195 | −10.850 | 8.436 | 15.562 | 1.00 | 11.78 | C |
| ATOM | 6257 | CE1 | TYR | B | 195 | −11.625 | 8.075 | 16.647 | 1.00 | 13.23 | C |
| ATOM | 6259 | CZ | TYR | B | 195 | −12.799 | 7.391 | 16.439 | 1.00 | 14.48 | C |
| ATOM | 6260 | OH | TYR | B | 195 | −13.573 | 7.033 | 17.518 | 1.00 | 17.11 | O |
| ATOM | 6262 | CE2 | TYR | B | 195 | −13.188 | 7.044 | 15.160 | 1.00 | 15.20 | C |
| ATOM | 6264 | CD2 | TYR | B | 195 | −12.393 | 7.385 | 14.082 | 1.00 | 13.19 | C |
| ATOM | 6266 | C | TYR | B | 195 | −11.953 | 10.279 | 12.489 | 1.00 | 10.34 | C |
| ATOM | 6267 | O | TYR | B | 195 | −12.463 | 11.132 | 13.209 | 1.00 | 10.36 | O |
| ATOM | 6268 | N | GLY | B | 196 | −12.644 | 9.603 | 11.582 | 1.00 | 11.32 | N |
| ATOM | 6270 | CA | GLY | B | 196 | −14.087 | 9.629 | 11.600 | 1.00 | 11.81 | C |
| ATOM | 6273 | C | GLY | B | 196 | −14.742 | 10.932 | 11.216 | 1.00 | 11.29 | C |
| ATOM | 6274 | O | GLY | B | 196 | −15.881 | 11.184 | 11.604 | 1.00 | 12.54 | O |
| ATOM | 6275 | N | GLY | B | 197 | −14.038 | 11.749 | 10.452 | 1.00 | 11.14 | N |
| ATOM | 6277 | CA | GLY | B | 197 | −14.556 | 13.043 | 10.072 | 1.00 | 11.40 | C |
| ATOM | 6280 | C | GLY | B | 197 | −14.354 | 14.124 | 11.118 | 1.00 | 10.86 | C |
| ATOM | 6281 | O | GLY | B | 197 | −14.712 | 15.268 | 10.864 | 1.00 | 11.89 | O |
| ATOM | 6282 | N | SER | B | 198 | −13.756 | 13.794 | 12.260 | 1.00 | 10.19 | N |
| ATOM | 6284 | CA | SER | B | 198 | −13.394 | 14.795 | 13.240 | 1.00 | 9.83 | C |

APPENDIX 1-continued

| ATOM | 6286 | CB | SER | B | 198 | −13.303 | 14.175 | 14.624 | 1.00 | 9.77 C |
|---|---|---|---|---|---|---|---|---|---|---|
| ATOM | 6289 | OG | SER | B | 198 | −12.942 | 15.156 | 15.567 | 1.00 | 9.88 O |
| ATOM | 6291 | C | SER | B | 198 | −12.066 | 15.428 | 12.891 | 1.00 | 10.01 C |
| ATOM | 6292 | O | SER | B | 198 | −11.212 | 14.812 | 12.266 | 1.00 | 12.17 O |
| ATOM | 6293 | N | SER | B | 199 | −11.898 | 16.664 | 13.339 | 1.00 | 9.97 N |
| ATOM | 6295 | CA | SER | B | 199 | −10.645 | 17.378 | 13.227 | 1.00 | 10.64 C |
| ATOM | 6297 | CB | SER | B | 199 | −10.911 | 18.863 | 12.962 | 1.00 | 11.88 C |
| ATOM | 6300 | OG | SER | B | 199 | −11.618 | 19.054 | 11.760 | 1.00 | 15.50 O |
| ATOM | 6302 | C | SER | B | 199 | −9.791 | 17.257 | 14.486 | 1.00 | 9.48 C |
| ATOM | 6303 | O | SER | B | 199 | −8.720 | 17.848 | 14.532 | 1.00 | 10.66 O |
| ATOM | 6304 | N | TYR | B | 200 | −10.239 | 16.495 | 15.480 | 1.00 | 8.05 N |
| ATOM | 6306 | CA | TYR | B | 200 | −9.643 | 16.523 | 16.805 | 1.00 | 7.75 C |
| ATOM | 6308 | CB | TYR | B | 200 | −10.654 | 17.084 | 17.810 | 1.00 | 7.69 C |
| ATOM | 6311 | CG | TYR | B | 200 | −11.101 | 18.490 | 17.511 | 1.00 | 8.31 C |
| ATOM | 6312 | CD1 | TYR | B | 200 | −10.287 | 19.570 | 17.798 | 1.00 | 9.21 C |
| ATOM | 6314 | CE1 | TYR | B | 200 | −10.680 | 20.867 | 17.534 | 1.00 | 10.29 C |
| ATOM | 6316 | CZ | TYR | B | 200 | −11.910 | 21.112 | 16.988 | 1.00 | 10.84 C |
| ATOM | 6317 | OH | TYR | B | 200 | −12.299 | 22.414 | 16.730 | 1.00 | 13.51 O |
| ATOM | 6319 | CE2 | TYR | B | 200 | −12.751 | 20.065 | 16.697 | 1.00 | 11.29 C |
| ATOM | 6321 | CD2 | TYR | B | 200 | −12.345 | 18.748 | 16.960 | 1.00 | 10.10 C |
| ATOM | 6323 | C | TYR | B | 200 | −9.217 | 15.133 | 17.266 | 1.00 | 7.26 C |
| ATOM | 6324 | O | TYR | B | 200 | −9.662 | 14.114 | 16.746 | 1.00 | 8.16 O |
| ATOM | 6325 | N | ASN | B | 201 | −8.348 | 15.125 | 18.274 | 1.00 | 7.06 N |
| ATOM | 6327 | CA | ASN | B | 201 | −8.042 | 13.952 | 19.084 | 1.00 | 7.16 C |
| ATOM | 6329 | CB | ASN | B | 201 | −6.680 | 14.153 | 19.748 | 1.00 | 7.15 C |
| ATOM | 6332 | CG | ASN | B | 201 | −5.554 | 14.230 | 18.742 | 1.00 | 7.21 C |
| ATOM | 6333 | OD1 | ASN | B | 201 | −5.516 | 13.447 | 17.803 | 1.00 | 7.69 O |
| ATOM | 6334 | ND2 | ASN | B | 201 | −4.644 | 15.175 | 18.926 | 1.00 | 7.72 N |
| ATOM | 6337 | C | ASN | B | 201 | −9.132 | 13.735 | 20.118 | 1.00 | 7.29 C |
| ATOM | 6338 | O | ASN | B | 201 | −9.912 | 14.647 | 20.394 | 1.00 | 7.53 O |
| ATOM | 6339 | N | ARG | B | 202 | −9.206 | 12.536 | 20.697 | 1.00 | 6.98 N |
| ATOM | 6341 | CA | ARG | B | 202 | −10.279 | 12.211 | 21.629 | 1.00 | 7.41 C |
| ATOM | 6343 | CB | ARG | B | 202 | −11.383 | 11.355 | 20.995 | 1.00 | 8.88 C |
| ATOM | 6346 | CG | ARG | B | 202 | −11.693 | 11.653 | 19.568 | 1.00 | 9.57 C |
| ATOM | 6349 | CD | ARG | B | 202 | −12.972 | 11.011 | 19.099 | 1.00 | 10.98 C |
| ATOM | 6352 | NE | ARG | B | 202 | −13.038 | 11.045 | 17.669 | 1.00 | 10.86 N |
| ATOM | 6354 | CZ | ARG | B | 202 | −14.060 | 10.645 | 16.946 | 1.00 | 10.42 C |
| ATOM | 6355 | NH1 | ARG | B | 202 | −15.207 | 10.244 | 17.495 | 1.00 | 11.93 N |
| ATOM | 6358 | NH2 | ARG | B | 202 | −13.935 | 10.652 | 15.633 | 1.00 | 11.59 N |
| ATOM | 6361 | C | ARG | B | 202 | −9.772 | 11.449 | 22.843 | 1.00 | 7.12 C |
| ATOM | 6362 | O | ARG | B | 202 | −8.800 | 10.686 | 22.775 | 1.00 | 7.24 O |
| ATOM | 6363 | N | GLY | B | 203 | −10.506 | 11.616 | 23.931 | 1.00 | 7.36 N |
| ATOM | 6365 | CA | GLY | B | 203 | −10.273 | 10.888 | 25.156 | 1.00 | 7.64 C |
| ATOM | 6368 | C | GLY | B | 203 | −11.594 | 10.478 | 25.782 | 1.00 | 7.46 C |
| ATOM | 6369 | O | GLY | B | 203 | −12.600 | 11.167 | 25.693 | 1.00 | 8.95 O |
| ATOM | 6370 | N | THR | B | 204 | −11.601 | 9.321 | 26.422 | 1.00 | 7.91 N |
| ATOM | 6372 | CA | THR | B | 204 | −12.766 | 8.862 | 27.169 | 1.00 | 7.85 C |
| ATOM | 6374 | CB | THR | B | 204 | −12.526 | 7.440 | 27.646 | 1.00 | 7.99 C |
| ATOM | 6376 | OG1 | THR | B | 204 | −12.283 | 6.626 | 26.490 | 1.00 | 9.14 O |
| ATOM | 6378 | CG2 | THR | B | 204 | −13.742 | 6.879 | 28.396 | 1.00 | 8.93 C |
| ATOM | 6382 | C | THR | B | 204 | −13.049 | 9.778 | 28.339 | 1.00 | 7.48 C |
| ATOM | 6383 | O | THR | B | 204 | −12.207 | 9.977 | 29.209 | 1.00 | 8.11 O |
| ATOM | 6384 | N | ARG | B | 205 | −14.246 | 10.340 | 28.347 | 1.00 | 7.64 N |
| ATOM | 6386 | CA | ARG | B | 205 | −14.673 | 11.241 | 29.393 | 1.00 | 8.00 C |
| ATOM | 6388 | CB | ARG | B | 205 | −15.976 | 11.911 | 28.965 | 1.00 | 8.79 C |
| ATOM | 6391 | CG | ARG | B | 205 | −16.504 | 12.958 | 29.902 | 1.00 | 8.59 C |
| ATOM | 6394 | CD | ARG | B | 205 | −17.749 | 13.634 | 29.351 | 1.00 | 9.13 C |
| ATOM | 6397 | NE | ARG | B | 205 | −18.197 | 14.685 | 30.247 | 1.00 | 9.66 N |
| ATOM | 6399 | CZ | ARG | B | 205 | −19.108 | 15.593 | 29.932 | 1.00 | 11.19 C |
| ATOM | 6400 | NH1 | ARG | B | 205 | −19.463 | 16.494 | 30.836 | 1.00 | 12.79 N |
| ATOM | 6403 | NH2 | ARG | B | 205 | −19.631 | 15.622 | 28.720 | 1.00 | 12.68 N |
| ATOM | 6406 | C | ARG | B | 205 | −14.893 | 10.499 | 30.697 | 1.00 | 8.17 C |
| ATOM | 6407 | O | ARG | B | 205 | −15.442 | 9.398 | 30.704 | 1.00 | 8.50 O |
| ATOM | 6408 | N | ILE | B | 206 | −14.511 | 11.107 | 31.803 | 1.00 | 7.90 N |
| ATOM | 6410 | CA | ILE | B | 206 | −14.857 | 10.543 | 33.102 | 1.00 | 8.22 C |
| ATOM | 6412 | CB | ILE | B | 206 | −13.888 | 10.984 | 34.205 | 1.00 | 8.53 C |
| ATOM | 6414 | CG1 | ILE | B | 206 | −12.479 | 10.503 | 33.832 | 1.00 | 10.37 C |
| ATOM | 6417 | CD1 | ILE | B | 206 | −11.395 | 10.782 | 34.838 | 1.00 | 11.44 C |
| ATOM | 6421 | CG2 | ILE | B | 206 | −14.335 | 10.417 | 35.576 | 1.00 | 8.96 C |
| ATOM | 6425 | C | ILE | B | 206 | −16.304 | 10.954 | 33.378 | 1.00 | 8.18 C |
| ATOM | 6426 | O | ILE | B | 206 | −16.577 | 12.055 | 33.837 | 1.00 | 9.63 O |
| ATOM | 6427 | N | THR | B | 207 | −17.221 | 10.054 | 33.053 | 1.00 | 8.48 N |
| ATOM | 6429 | CA | THR | B | 207 | −18.633 | 10.182 | 33.409 | 1.00 | 8.64 C |
| ATOM | 6431 | CB | THR | B | 207 | −19.500 | 9.287 | 32.520 | 1.00 | 9.02 C |
| ATOM | 6433 | OG1 | THR | B | 207 | −19.159 | 7.926 | 32.815 | 1.00 | 9.39 O |
| ATOM | 6435 | CG2 | THR | B | 207 | −19.290 | 9.543 | 31.017 | 1.00 | 9.86 C |
| ATOM | 6439 | C | THR | B | 207 | −18.829 | 9.725 | 34.857 | 1.00 | 8.82 C |
| ATOM | 6440 | O | THR | B | 207 | −17.906 | 9.220 | 35.505 | 1.00 | 9.18 O |
| ATOM | 6441 | N | LYS | B | 208 | −20.060 | 9.852 | 35.352 | 1.00 | 9.26 N |
| ATOM | 6443 | CA | LYS | B | 208 | −20.369 | 9.298 | 36.665 | 1.00 | 9.84 C |

APPENDIX 1-continued

| ATOM | 6445 | CB | LYS | B | 208 | −21.833 | 9.519 | 37.046 | 1.00 | 10.99 | C |
| ATOM | 6448 | CG | LYS | B | 208 | −22.087 | 9.129 | 38.528 | 1.00 | 14.71 | C |
| ATOM | 6451 | CD | LYS | B | 208 | −23.399 | 9.593 | 39.068 | 1.00 | 16.96 | C |
| ATOM | 6454 | CE | LYS | B | 208 | −23.489 | 9.258 | 40.552 | 1.00 | 19.57 | C |
| ATOM | 6457 | NZ | LYS | B | 208 | −23.241 | 7.822 | 40.859 | 1.00 | 20.47 | N |
| ATOM | 6461 | C | LYS | B | 208 | −20.034 | 7.814 | 36.745 | 1.00 | 9.27 | C |
| ATOM | 6462 | O | LYS | B | 208 | −19.537 | 7.336 | 37.761 | 1.00 | 10.16 | O |
| ATOM | 6463 | N | GLU | B | 209 | −20.331 | 7.079 | 35.694 | 1.00 | 9.18 | N |
| ATOM | 6465 | CA | GLU | B | 209 | −20.113 | 5.643 | 35.715 | 1.00 | 9.01 | C |
| ATOM | 6467 | CB | GLU | B | 209 | −20.903 | 4.935 | 34.624 | 1.00 | 9.53 | C |
| ATOM | 6470 | CG | GLU | B | 209 | −22.414 | 5.046 | 34.816 | 1.00 | 10.25 | C |
| ATOM | 6473 | CD | GLU | B | 209 | −22.978 | 6.405 | 34.428 | 1.00 | 10.76 | C |
| ATOM | 6474 | OE1 | GLU | B | 209 | −23.862 | 6.914 | 35.155 | 1.00 | 12.33 | O |
| ATOM | 6475 | OE2 | GLU | B | 209 | −22.549 | 6.961 | 33.386 | 1.00 | 11.21 | O |
| ATOM | 6476 | C | GLU | B | 209 | −18.624 | 5.295 | 35.653 | 1.00 | 8.78 | C |
| ATOM | 6477 | O | GLU | B | 209 | −18.183 | 4.353 | 36.318 | 1.00 | 9.54 | O |
| ATOM | 6478 | N | VAL | B | 210 | −17.843 | 6.052 | 34.878 | 1.00 | 8.31 | N |
| ATOM | 6480 | CA | VAL | B | 210 | −16.392 | 5.869 | 34.868 | 1.00 | 8.33 | C |
| ATOM | 6482 | CB | VAL | B | 210 | −15.715 | 6.782 | 33.835 | 1.00 | 8.11 | C |
| ATOM | 6484 | CG1 | VAL | B | 210 | −14.194 | 6.643 | 33.918 | 1.00 | 8.28 | C |
| ATOM | 6488 | CG2 | VAL | B | 210 | −16.207 | 6.468 | 32.427 | 1.00 | 8.18 | C |
| ATOM | 6492 | C | VAL | B | 210 | −15.835 | 6.162 | 36.264 | 1.00 | 8.18 | C |
| ATOM | 6493 | O | VAL | B | 210 | −15.034 | 5.400 | 36.807 | 1.00 | 8.46 | O |
| ATOM | 6494 | N | PHE | B | 211 | −16.257 | 7.285 | 36.828 | 1.00 | 8.80 | N |
| ATOM | 6496 | CA | PHE | B | 211 | −15.865 | 7.717 | 38.169 | 1.00 | 8.95 | C |
| ATOM | 6498 | CB | PHE | B | 211 | −16.632 | 8.996 | 38.522 | 1.00 | 9.38 | C |
| ATOM | 6501 | CG | PHE | B | 211 | −16.350 | 9.534 | 39.891 | 1.00 | 10.33 | C |
| ATOM | 6502 | CD1 | PHE | B | 211 | −17.036 | 9.054 | 40.992 | 1.00 | 12.42 | C |
| ATOM | 6504 | CE1 | PHE | B | 211 | −16.794 | 9.562 | 42.250 | 1.00 | 14.20 | C |
| ATOM | 6506 | CZ | PHE | B | 211 | −15.867 | 10.570 | 42.422 | 1.00 | 14.22 | C |
| ATOM | 6508 | CE2 | PHE | B | 211 | −15.184 | 11.071 | 41.328 | 1.00 | 12.56 | C |
| ATOM | 6510 | CD2 | PHE | B | 211 | −15.427 | 10.548 | 40.077 | 1.00 | 10.94 | C |
| ATOM | 6512 | C | PHE | B | 211 | −16.144 | 6.610 | 39.183 | 1.00 | 9.01 | C |
| ATOM | 6513 | O | PHE | B | 211 | −15.284 | 6.254 | 39.997 | 1.00 | 9.62 | O |
| ATOM | 6514 | N | ASP | B | 212 | −17.341 | 6.057 | 39.145 | 1.00 | 9.24 | N |
| ATOM | 6516 | CA | ASP | B | 212 | −17.719 | 5.020 | 40.091 | 1.00 | 9.38 | C |
| ATOM | 6518 | CB | ASP | B | 212 | −19.220 | 4.742 | 40.000 | 1.00 | 10.22 | C |
| ATOM | 6521 | CG | ASP | B | 212 | −20.081 | 5.866 | 40.585 | 1.00 | 10.96 | C |
| ATOM | 6522 | OD1 | ASP | B | 212 | −19.596 | 6.712 | 41.352 | 1.00 | 12.82 | O |
| ATOM | 6523 | OD2 | ASP | B | 212 | −21.294 | 5.924 | 40.326 | 1.00 | 14.21 | O |
| ATOM | 6524 | C | ASP | B | 212 | −16.920 | 3.730 | 39.883 | 1.00 | 9.20 | C |
| ATOM | 6525 | O | ASP | B | 212 | −16.558 | 3.075 | 40.860 | 1.00 | 9.67 | O |
| ATOM | 6526 | N | ASN | B | 213 | −16.642 | 3.364 | 38.646 | 1.00 | 8.79 | N |
| ATOM | 6528 | CA | ASN | B | 213 | −15.823 | 2.182 | 38.386 | 1.00 | 8.75 | C |
| ATOM | 6530 | CB | BASN | B | 213 | −15.892 | 1.765 | 36.925 | 0.35 | 8.75 | C |
| ATOM | 6531 | CB | AASN | B | 213 | −15.742 | 1.816 | 36.880 | 0.65 | 8.93 | C |
| ATOM | 6536 | CG | BASN | B | 213 | −17.240 | 1.173 | 36.556 | 0.35 | 9.22 | C |
| ATOM | 6537 | CG | AASN | B | 213 | −16.833 | 0.837 | 36.379 | 0.65 | 9.63 | C |
| ATOM | 6538 | OD1 | BASN | B | 213 | −17.635 | 1.198 | 35.396 | 0.35 | 11.25 | O |
| ATOM | 6539 | OD1 | AASN | B | 213 | −17.182 | 0.862 | 35.191 | 0.65 | 11.89 | O |
| ATOM | 6540 | ND2 | BASN | B | 213 | −17.948 | 0.634 | 37.537 | 0.35 | 8.61 | N |
| ATOM | 6541 | ND2 | AASN | B | 213 | −17.315 | −0.040 | 37.230 | 0.65 | 9.89 | N |
| ATOM | 6546 | C | ASN | B | 213 | −14.385 | 2.380 | 38.876 | 1.00 | 8.12 | C |
| ATOM | 6547 | O | ASN | B | 213 | −13.866 | 1.530 | 39.585 | 1.00 | 8.56 | O |
| ATOM | 6548 | N | LEU | B | 214 | −13.754 | 3.499 | 38.509 | 1.00 | 8.05 | N |
| ATOM | 6550 | CA | LEU | B | 214 | −12.388 | 3.756 | 38.975 | 1.00 | 8.09 | C |
| ATOM | 6552 | CB | LEU | B | 214 | −11.878 | 5.101 | 38.472 | 1.00 | 8.15 | C |
| ATOM | 6555 | CG | LEU | B | 214 | −11.645 | 5.232 | 36.974 | 1.00 | 8.61 | C |
| ATOM | 6557 | CD1 | LEU | B | 214 | −11.247 | 6.665 | 36.638 | 1.00 | 9.83 | C |
| ATOM | 6561 | CD2 | LEU | B | 214 | −10.596 | 4.247 | 36.475 | 1.00 | 9.91 | C |
| ATOM | 6565 | C | LEU | B | 214 | −12.321 | 3.712 | 40.498 | 1.00 | 8.01 | C |
| ATOM | 6566 | O | LEU | B | 214 | −11.378 | 3.153 | 41.070 | 1.00 | 8.50 | O |
| ATOM | 6567 | N | THR | B | 215 | −13.313 | 4.314 | 41.144 | 1.00 | 8.38 | N |
| ATOM | 6569 | CA | THR | B | 215 | −13.315 | 4.376 | 42.596 | 1.00 | 8.79 | C |
| ATOM | 6571 | CB | THR | B | 215 | −14.418 | 5.334 | 43.053 | 1.00 | 9.27 | C |
| ATOM | 6573 | OG1 | THR | B | 215 | −14.177 | 6.633 | 42.485 | 1.00 | 10.10 | O |
| ATOM | 6575 | CG2 | THR | B | 215 | −14.416 | 5.517 | 44.571 | 1.00 | 11.07 | C |
| ATOM | 6579 | C | THR | B | 215 | −13.481 | 2.979 | 43.209 | 1.00 | 8.80 | C |
| ATOM | 6580 | O | THR | B | 215 | −12.791 | 2.625 | 44.166 | 1.00 | 9.21 | O |
| ATOM | 6581 | N | ASN | B | 216 | −14.370 | 2.179 | 42.646 | 1.00 | 8.57 | N |
| ATOM | 6583 | CA | ASN | B | 216 | −14.557 | 0.818 | 43.115 | 1.00 | 8.67 | C |
| ATOM | 6585 | CB | ASN | B | 216 | −15.734 | 0.173 | 42.381 | 1.00 | 9.22 | C |
| ATOM | 6588 | CG | ASN | B | 216 | −15.982 | −1.271 | 42.786 | 1.00 | 8.90 | C |
| ATOM | 6589 | OD1 | ASN | B | 216 | −15.870 | −1.642 | 43.963 | 1.00 | 9.87 | O |
| ATOM | 6590 | ND2 | ASN | B | 216 | −16.303 | −2.099 | 41.811 | 1.00 | 10.95 | N |
| ATOM | 6593 | C | ASN | B | 216 | −13.273 | −0.002 | 42.920 | 1.00 | 8.34 | C |
| ATOM | 6594 | O | ASN | B | 216 | −12.861 | −0.759 | 43.806 | 1.00 | 8.95 | O |
| ATOM | 6595 | N | TRP | B | 217 | −12.626 | 0.156 | 41.771 | 1.00 | 8.60 | N |
| ATOM | 6597 | CA | TRP | B | 217 | −11.442 | −0.632 | 41.484 | 1.00 | 8.62 | C |
| ATOM | 6599 | CB | TRP | B | 217 | −11.051 | −0.484 | 40.025 | 1.00 | 8.99 | C |

APPENDIX 1-continued

| ATOM | 6602 | CG | TRP | B | 217 | −12.086 | −0.995 | 39.080 | 1.00 | 9.18 | C |
|---|---|---|---|---|---|---|---|---|---|---|---|
| ATOM | 6603 | CD1 | TRP | B | 217 | −13.046 | −1.934 | 39.324 | 1.00 | 10.15 | C |
| ATOM | 6605 | NE1 | TRP | B | 217 | −13.804 | −2.145 | 38.197 | 1.00 | 11.24 | N |
| ATOM | 6607 | CE2 | TRP | B | 217 | −13.350 | −1.320 | 37.207 | 1.00 | 10.18 | C |
| ATOM | 6608 | CD2 | TRP | B | 217 | −12.272 | −0.584 | 37.733 | 1.00 | 9.00 | C |
| ATOM | 6609 | CE3 | TRP | B | 217 | −11.640 | 0.346 | 36.907 | 1.00 | 9.73 | C |
| ATOM | 6611 | CZ3 | TRP | B | 217 | −12.074 | 0.488 | 35.602 | 1.00 | 11.01 | C |
| ATOM | 6613 | CH2 | TRP | B | 217 | −13.139 | −0.262 | 35.117 | 1.00 | 11.64 | C |
| ATOM | 6615 | CZ2 | TRP | B | 217 | −13.799 | −1.163 | 35.897 | 1.00 | 11.72 | C |
| ATOM | 6617 | C | TRP | B | 217 | −10.303 | −0.253 | 42.431 | 1.00 | 8.36 | C |
| ATOM | 6618 | O | TRP | B | 217 | −9.603 | −1.117 | 42.953 | 1.00 | 8.91 | O |
| ATOM | 6619 | N | LYS | B | 218 | −10.123 | 1.033 | 42.695 | 1.00 | 8.79 | N |
| ATOM | 6621 | CA | LYS | B | 218 | −9.100 | 1.444 | 43.625 | 1.00 | 9.20 | C |
| ATOM | 6623 | CB | LYS | B | 218 | −8.827 | 2.934 | 43.515 | 1.00 | 11.18 | C |
| ATOM | 6626 | CG | LYS | B | 218 | −9.737 | 3.843 | 44.197 | 1.00 | 15.17 | C |
| ATOM | 6629 | CD | LYS | B | 218 | −9.326 | 5.287 | 43.946 | 1.00 | 18.59 | C |
| ATOM | 6632 | CE | LYS | B | 218 | −10.240 | 6.273 | 44.642 | 1.00 | 20.56 | C |
| ATOM | 6635 | NZ | LYS | B | 218 | −9.920 | 6.379 | 46.090 | 1.00 | 23.12 | N |
| ATOM | 6639 | C | LYS | B | 218 | −9.431 | 0.985 | 45.054 | 1.00 | 9.00 | C |
| ATOM | 6640 | O | LYS | B | 218 | −8.543 | 0.568 | 45.790 | 1.00 | 10.38 | O |
| ATOM | 6641 | N | ASN | B | 219 | −10.709 | 1.008 | 45.430 | 1.00 | 8.68 | N |
| ATOM | 6643 | CA | ASN | B | 219 | −11.124 | 0.530 | 46.752 | 1.00 | 8.69 | C |
| ATOM | 6645 | CB | ASN | B | 219 | −12.545 | 1.004 | 47.075 | 1.00 | 9.62 | C |
| ATOM | 6648 | CG | ASN | B | 219 | −12.589 | 2.441 | 47.549 | 1.00 | 10.94 | C |
| ATOM | 6649 | OD1 | ASN | B | 219 | −11.678 | 2.906 | 48.223 | 1.00 | 14.01 | O |
| ATOM | 6650 | ND2 | ASN | B | 219 | −13.697 | 3.138 | 47.267 | 1.00 | 11.68 | N |
| ATOM | 6653 | C | ASN | B | 219 | −11.040 | −0.980 | 46.901 | 1.00 | 8.48 | C |
| ATOM | 6654 | O | ASN | B | 219 | −11.108 | −1.494 | 48.016 | 1.00 | 9.89 | O |
| ATOM | 6655 | N | SER | B | 220 | −10.884 | −1.688 | 45.792 | 1.00 | 8.99 | N |
| ATOM | 6657 | CA | SER | B | 220 | −10.799 | −3.141 | 45.786 | 1.00 | 8.99 | C |
| ATOM | 6659 | CB | SER | B | 220 | −11.517 | −3.693 | 44.555 | 1.00 | 9.46 | C |
| ATOM | 6662 | OG | SER | B | 220 | −12.907 | −3.416 | 44.600 | 1.00 | 9.93 | O |
| ATOM | 6664 | C | SER | B | 220 | −9.357 | −3.642 | 45.795 | 1.00 | 9.37 | C |
| ATOM | 6665 | O | SER | B | 220 | −9.124 | −4.844 | 45.742 | 1.00 | 10.44 | O |
| ATOM | 6666 | N | ALA | B | 221 | −8.377 | −2.741 | 45.851 | 1.00 | 9.78 | N |
| ATOM | 6668 | CA | ALA | B | 221 | −6.981 | −3.155 | 45.805 | 1.00 | 9.87 | C |
| ATOM | 6670 | CB | ALA | B | 221 | −6.068 | −1.948 | 45.804 | 1.00 | 10.44 | C |
| ATOM | 6674 | C | ALA | B | 221 | −6.632 | −4.065 | 46.968 | 1.00 | 11.09 | C |
| ATOM | 6675 | O | ALA | B | 221 | −7.064 | −3.848 | 48.094 | 1.00 | 12.58 | O |
| ATOM | 6676 | N | GLN | B | 222 | −5.824 | −5.080 | 46.664 | 1.00 | 11.56 | N |
| ATOM | 6678 | CA | GLN | B | 222 | −5.345 | −6.085 | 47.610 | 1.00 | 13.48 | C |
| ATOM | 6680 | CB | BGLN | B | 222 | −5.070 | −7.420 | 46.900 | 0.35 | 14.51 | C |
| ATOM | 6681 | CB | AGLN | B | 222 | −5.003 | −7.403 | 46.863 | 0.65 | 14.16 | C |
| ATOM | 6686 | CG | BGLN | B | 222 | −3.617 | −7.830 | 46.798 | 0.35 | 16.11 | C |
| ATOM | 6687 | CG | AGLN | B | 222 | −6.230 | −8.072 | 46.189 | 0.65 | 12.89 | C |
| ATOM | 6692 | CD | BGLN | B | 222 | −3.455 | −9.200 | 46.202 | 0.35 | 17.67 | C |
| ATOM | 6693 | CD | AGLN | B | 222 | −5.908 | −9.289 | 45.310 | 0.65 | 14.84 | C |
| ATOM | 6694 | OE1 | BGLN | B | 222 | −4.040 | −10.165 | 46.695 | 0.35 | 19.06 | O |
| ATOM | 6695 | OE1 | AGLN | B | 222 | −4.806 | −9.840 | 45.371 | 0.65 | 18.23 | O |
| ATOM | 6696 | NE2 | BGLN | B | 222 | −2.655 | −9.300 | 45.148 | 0.35 | 18.44 | N |
| ATOM | 6697 | NE2 | AGLN | B | 222 | −6.880 | −9.712 | 44.495 | 0.65 | 13.26 | N |
| ATOM | 6702 | C | GLN | B | 222 | −4.109 | −5.562 | 48.352 | 1.00 | 14.27 | C |
| ATOM | 6703 | O | GLN | B | 222 | −3.636 | −6.231 | 49.284 | 1.00 | 17.27 | O |
| ATOM | 6704 | OXT | GLN | B | 222 | −3.579 | −4.486 | 48.029 | 1.00 | 15.01 | O |
| ATOM | 6705 | CA | CA | B | 301 | −0.643 | 21.256 | 17.293 | 1.00 | 10.41 | CA |
| ATOM | 13398 | N | ASP | F | 401 | −10.088 | 3.418 | 14.402 | 1.00 | 20.15 | N |
| ATOM | 13400 | CA | ASP | F | 401 | −10.419 | 4.298 | 15.551 | 1.00 | 19.20 | C |
| ATOM | 13402 | CB | ASP | F | 401 | −11.005 | 3.471 | 16.700 | 1.00 | 20.61 | C |
| ATOM | 13405 | CG | ASP | F | 401 | −12.475 | 3.140 | 16.497 | 1.00 | 22.97 | C |
| ATOM | 13406 | OD1 | ASP | F | 401 | −13.045 | 2.395 | 17.327 | 1.00 | 26.18 | O |
| ATOM | 13407 | OD2 | ASP | F | 401 | −13.144 | 3.572 | 15.537 | 1.00 | 25.29 | O |
| ATOM | 13408 | C | ASP | F | 401 | −9.196 | 5.076 | 16.021 | 1.00 | 16.65 | C |
| ATOM | 13409 | O | ASP | F | 401 | −9.239 | 5.713 | 17.069 | 1.00 | 16.48 | O |
| ATOM | 13412 | N | ALA | F | 402 | −8.115 | 5.032 | 15.242 | 1.00 | 14.63 | N |
| ATOM | 13414 | CA | ALA | F | 402 | −6.897 | 5.780 | 15.549 | 1.00 | 12.75 | C |
| ATOM | 13416 | CB | ALA | F | 402 | −7.112 | 7.245 | 15.277 | 1.00 | 12.61 | C |
| ATOM | 13420 | C | ALA | F | 402 | −6.485 | 5.557 | 16.999 | 1.00 | 11.06 | C |
| ATOM | 13421 | O | ALA | F | 402 | −6.190 | 6.500 | 17.738 | 1.00 | 10.74 | O |
| ATOM | 13422 | N | PHE | F | 403 | −6.464 | 4.296 | 17.429 | 1.00 | 10.84 | N |
| ATOM | 13424 | CA | PHE | F | 403 | −6.076 | 4.009 | 18.798 | 1.00 | 10.34 | C |
| ATOM | 13426 | CB | PHE | F | 403 | −6.233 | 2.517 | 19.116 | 1.00 | 11.44 | C |
| ATOM | 13429 | CG | PHE | F | 403 | −7.671 | 2.025 | 19.183 | 1.00 | 12.38 | C |
| ATOM | 13430 | CD1 | PHE | F | 403 | −8.562 | 2.511 | 20.119 | 1.00 | 14.77 | C |
| ATOM | 13432 | CE1 | PHE | F | 403 | −9.880 | 2.048 | 20.187 | 1.00 | 17.09 | C |
| ATOM | 13434 | CZ | PHE | F | 403 | −10.309 | 1.064 | 19.322 | 1.00 | 18.48 | C |
| ATOM | 13436 | CE2 | PHE | F | 403 | −9.424 | 0.544 | 18.386 | 1.00 | 18.39 | C |
| ATOM | 13438 | CD2 | PHE | F | 403 | −8.109 | 1.018 | 18.324 | 1.00 | 16.19 | C |
| ATOM | 13440 | C | PHE | F | 403 | −4.626 | 4.428 | 19.018 | 1.00 | 10.00 | C |
| ATOM | 13441 | O | PHE | F | 403 | −3.748 | 4.110 | 18.209 | 1.00 | 12.25 | O |
| ATOM | 13442 | N | GLU | F | 404 | −4.372 | 5.130 | 20.116 | 1.00 | 8.64 | N |

APPENDIX 1-continued

| ATOM | 13444 | CA  | GLU | F | 404 | -3.025 | 5.588 | 20.427 | 1.00 | 8.12 | C |
| ATOM | 13446 | CB  | GLU | F | 404 | -2.992 | 7.120 | 20.524 | 1.00 | 7.95 | C |
| ATOM | 13449 | CG  | GLU | F | 404 | -3.122 | 7.705 | 19.117 | 1.00 | 8.08 | C |
| ATOM | 13452 | CD  | GLU | F | 404 | -3.043 | 9.212 | 19.009 | 1.00 | 7.71 | C |
| ATOM | 13453 | OE1 | GLU | F | 404 | -3.129 | 9.917 | 20.027 | 1.00 | 8.61 | O |
| ATOM | 13454 | OE2 | GLU | F | 404 | -2.901 | 9.672 | 17.856 | 1.00 | 8.80 | O |
| ATOM | 13455 | C   | GLU | F | 404 | -2.442 | 4.854 | 21.637 | 1.00 | 8.22 | C |
| ATOM | 13456 | O   | GLU | F | 404 | -2.865 | 3.708 | 21.892 | 1.00 | 8.82 | O |
| ATOM | 13457 | OXT | GLU | F | 404 | -1.513 | 5.394 | 22.258 | 1.00 | 8.53 | O |

The invention claimed is:

1. An isolated variant of the RP-II protease of SEQ ID NO: 2 having at least 92% identity to the amino acid sequence of SEQ ID NO: 2, wherein the variant comprises a substitution Gly$^{30}$Ala corresponding to the amino acid sequence of the mature polypeptide of SEQ ID NO: 2, and wherein the variant has the protease activity of SEQ ID NO: 2.

2. The variant of claim 1, having at least 95% identity to the amino acid sequence of SEQ ID NO: 2.

3. The variant of claim 1, having at least 97% identity to the amino acid sequence of SEQ ID NO: 2.

4. The variant of claim 1, having at least 98% identity to the amino acid sequence of SEQ ID NO: 2.

5. The variant of claim 1, having at least 99% identity to the amino acid sequence of SEQ ID NO: 2.

6. The variant of claim 1, further comprising a substitution in position 91 corresponding to the amino acid sequence of the mature polypeptide of SEQ ID NO: 2.

7. The variant of claim 6, further comprising the substitution G91A.

8. An isolated polynucleotide comprising a nucleic acid sequence, which encodes for a RP-II protease variant of claim 1.

9. The polynucleotide of claim 8, wherein the nucleic acid sequence has at least 90% identity to the nucleic acid sequence shown in SEQ ID NO: 1.

10. An isolated nucleic acid construct comprising the nucleic acid sequence of claim 8, operably linked to one or more control sequences capable of directing the expression of the polypeptide in a suitable expression host.

11. A recombinant host cell comprising the nucleic acid construct of claim 10.

12. A method for producing a variant of an RP-II protease, comprising:
  a) cultivating the recombinant host cell of claim 11 under conditions conducive to the production of the RP-II protease variant; and
  b) recovering the variant.

13. A detergent composition comprising the variant of an RP-II protease of claim 1.

* * * * *